US007704509B2

(12) United States Patent
Murphy et al.

(10) Patent No.: US 7,704,509 B2
(45) Date of Patent: Apr. 27, 2010

(54) RECOVERY OF RECOMBINANT HUMAN PARAINFLUENZA VIRUS TYPE 1 (HPIV1) FROM CDNA AND USE OF RECOMBINANT HPIV1 IN IMMUNOGENIC COMPOSITIONS AND AS VECTORS TO ELICIT IMMUNE RESPONSES AGAINST PIV AND OTHER HUMAN PATHOGENS

(75) Inventors: Brian R. Murphy, Bethesda, MD (US); Peter L. Collins, Kensington, MD (US); Mario H. Skiadopoulos, Potomac, MD (US); Jason T. Newman, Cranberry Township, PA (US)

(73) Assignee: United States of America, Washington, DC (US)

( * ) Notice: Subject to any disclaimer, the term of this patent is extended or adjusted under 35 U.S.C. 154(b) by 187 days.

(21) Appl. No.: 10/302,547

(22) Filed: Nov. 21, 2002

(65) Prior Publication Data

US 2004/0142448 A1 Jul. 22, 2004

Related U.S. Application Data

(60) Provisional application No. 60/331,961, filed on Nov. 21, 2001.

(51) Int. Cl.
*A61K 39/155* (2006.01)

(52) U.S. Cl. ................. 424/211.1; 424/199.1; 435/69.1

(58) Field of Classification Search .............. 424/184.1, 424/211.1, 212.1; 435/69.1, 69.3, 69.52
See application file for complete search history.

(56) References Cited

U.S. PATENT DOCUMENTS 5,993,824 A 11/1999 Murphy
6,410,023 B1 6/2002 Durbin
6,699,476 B1 3/2004 Collins

FOREIGN PATENT DOCUMENTS

WO WO 98/53078 11/1998

OTHER PUBLICATIONS

Ball et al., Phenotypic Consequences of Rearranging the P, M and G Genes of Vesicular Stomatitis Virus, Journal of Virology, Jun. 1999, vol. 73, No. 6, pp. 4705-4712.*
Skiadopoulos et al., Attenuation of the Recombinant Human Parainfluenza Virus Type 3 cp45 Candidate Vaccine Virus is Augmented by Imporation of the Respiratory Syncytial Virus cpts530 L polymerase mutation, Virology, 1999, vol. 260, pp. 125-135.*
Durbin et al., Mutations in the C, D and V Open Reading Frames of Human Parainfluenza Virus Type 3 Attenuate Replication in Rodents and Primates, Virology, 1999, vol. 261, pp. 319-330.*
McAuliffe et al., "Codon Substitution Mutations at Two Positions in the L Polymerase Protein of Human Parainfluenza Virus Type 1 Yield Viruses With a Spectrum of Attenuation in Vivo and Increased Phenotypic Stability in Vitro", J. Virol., Feb. 2004, vol. 78, No. 4, 2029-2036.
Newman et al., "Sequence Analysis of the Washington/1964 Strain of Human Parainfluenza Virus Type 1 (HPIV1) and Recovery and Characterization of Wild Type Recombinant HPIV1 Produced by Reverse Genetics", Virus Genes, 2002, vol. 24, No. 1, 77-92.

* cited by examiner

*Primary Examiner*—Stacy B Chen
(74) *Attorney, Agent, or Firm*—Woodcock Washburn LLP

(57) ABSTRACT

Recombinant human parainfluenza virus type 1 (HPIV1) compostions, formulations and methods are provided. The recombinant HPIV1 viruses and HPIV1 chimeric and chimeric vector viruses provided according to the invention are infectious and attenuated in permissive mammalian subjects, including humans, and are useful in immunogenic composition s for eliciting an immune responses against one or more PIVs, against one or more non-PIV pathogens, or against a PIV and a non-PIV pathogen. Also provided are isolated polynucleotide molecules and vectors incorporating a recombinant HPIV1 genome or antigenome.

270 Claims, 16 Drawing Sheets

FIG. 1

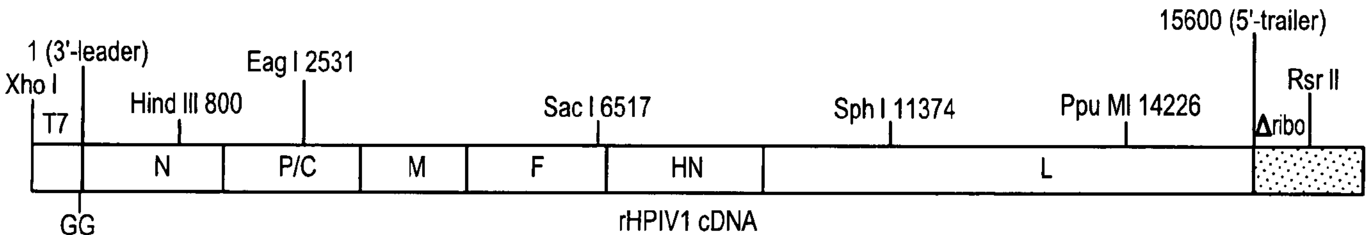

3' leader sequence — 1 … 55 … 79 — N-UTR — 96

```
HPIV1: 3'-UGGUUU GUUCUC CUUUUU GAACAA ACCUUA UAUAUU AUUAUA AUUUAU CAUAAA AUCCCA AUUUCA UUAUGA AAUUUC CCUGUU CAGUGU CUGUAA-5'
MPIV1: 3'-UGGUUU GUUCUC UUUUUU GUACAU ACCCUA UACAUU ACUUCA AUAUGU CCUAAA AUCCCA GUUUCA UAGGUG GGACUC CUCGUC CAAGGU CUGGGA-5'
HPIV3: 3'-UGGUUU GUUCUC UUCUUU GAACAG ACCCUU AUAUUU AAAUUG AAAUUU AAUUGA AUCCUA AUUUCU GUAACU GAUCUU CCAGUU CUUUUC CCUUGA-5'
BPIV3: 3'-UGGUUU GUUCUC UUCUCU GAACGA ACCCUU AUAAUU AAGUUU AUUUUU AAUUGA AUCCUA AUUUCU UGAAAU GGCUUU CCAUUC CCCUUU CUUUAG-5'
```

"IG" N gene-start

B.

96 — L-UTR — 79 — L gene-end — IG — 54 … 41 … 5' trailer sequence — 1

```
HPIV1: 3'- UUAGGG AAAUUG ACUGAG UAUUUU UGUAUC AUUCUU UUUGAA UGUUGU CUGUUC UCAUAA UUAUUA UAUAGC UAUAAA GAAUUU GAGAAC AGACCA -5'
MPIV1: 3'- CUUCAG AACCUG AAUAGG UAUACU GUUAUC AUUCUU UUUGAA UGUUCU UCUGUU CUUUUA AAUUUU CCUAUG UAUAGA GAAUUU GAGAAC AGACCA -5'
HPIV3: 3'- AUAUAG GAUUGG AAAUAG AAAUUC GGAUCC UUAUCU GUUUUU CAUUCU UUUUGU ACAUUA UAUAUA UAUGGU UUGUCU CAAGAA GAGAAC AAACCA -5'
BPIV3: 3'- UUUGUG GAUUAG GAGAGG GUAAGU GAAGGU UGUUUU ACUUUU CAUUCU UUUUGU AUAUUA UAUGUA UAUGGU UUGUCU CAAAAA GAGAAC AAACCA -5'
```

L gene-end "IG"

FIG. 3

| Strain | Gene-Start (3'-5') | Gene-End (3'-5') | Intergenic (3'-5') |
|---|---|---|---|
| PHIV1 Wash64 | UCCCAAUUUC | UUCAUUCUUUUU | GAA |
| MPIV1 Z | UCCCAGUUUC | AUCAUUCUUUUU | GAA |
| HPIV3 JS | UCCUAAUUUC | UUUAUUCUUUUU | GAA |
| BPIV3 KA | UCCUAAUUUC | UUCAUUCUUUUU | GAA |
| HPIV1 Wash64 | UCCCACUUAC | UUAAUUCUUUUU | GAA |
| MPIV1 Z | UCCCACUUUC | CUAAUUCUUUUU | GAA |
| HPIV3 JS | UCCUAAUUUC | UUUAUUCUUUUU | GAA |
| BPIV3 KA | UCCUAAUUAC | CUGAUUCUUUUU | GAA |
| HPIV1 Wash64 | UCCCAGUUUC | UUUAUUC -------- UUUUU | GCA |
| MPIV1 Z | UCCCACUUUC | UUUAUUC -------- UUUUU | GAA |
| HPIV3 JS | UCCUAAUUUC | UUUAUUUCCUAUUAGUUUUU | GAA |
| BPIV3 KA | UCCUACUUUC | UUUUUAG -------- UUUUU | GAA |
| HPIV1 Wash64 | UCCCUGUUUC | UUCAUUCUUUUU | GAA |
| MPIV1 Z | UCCCUAUUUC | AUUAUUCUUUUU | GAA |
| HPIV3 JS | UCCUGUUUUC | UUAAUAUUUUUU | GAA |
| BPIV3 KA | UCCUAGUUUC | UUCAUGUUUUUU | GAA |
| HPIV1 Wash64 | UCCCAAUUUC | CUUAUUCUUUUU | GAA |
| MPIV1 Z | UCCCACUUUC | AUAAUUCUUUUU | GGG |
| HPIV3 JS | UCCUCAUUUC | UUUAUAUUUUUU | GAA |
| BPIV3 KA | UCCUUGUUUC | UUAUUAUUUUUU | GAA |
| HPIV1 Wash64 | UCCCAAUUAC | AUCAUUCUUUUU | GAA |
| MPIV1 | UCCCACUUAC | AUCAUUCUUUUU | GAA |
| HPIV3 JS | UCCUCGUUUC | UUCAUUCUUUUU | GUA |
| BPIV3 KA | UCCUCUUUUC | UUCAUUCUUUUU | GUA |
| Consensus: | UCCYNNUUWC | HUNWUDBUUUUU | GNR |

FIG. 4
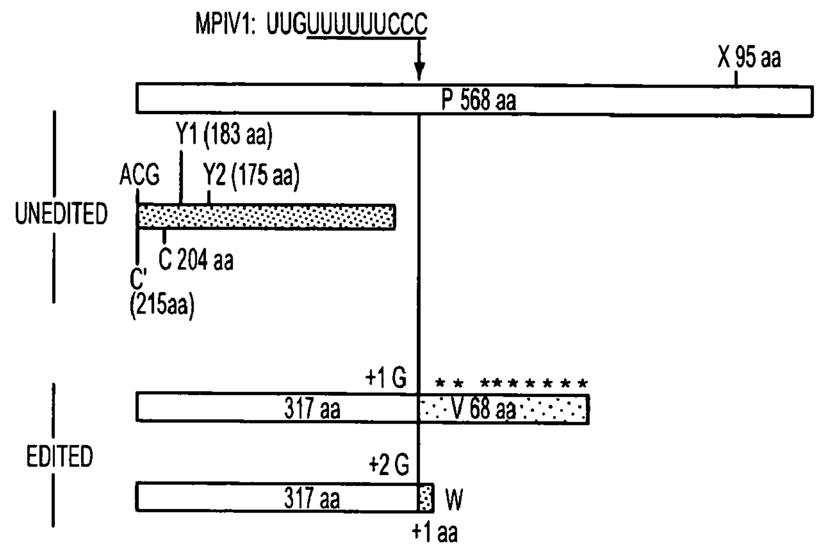
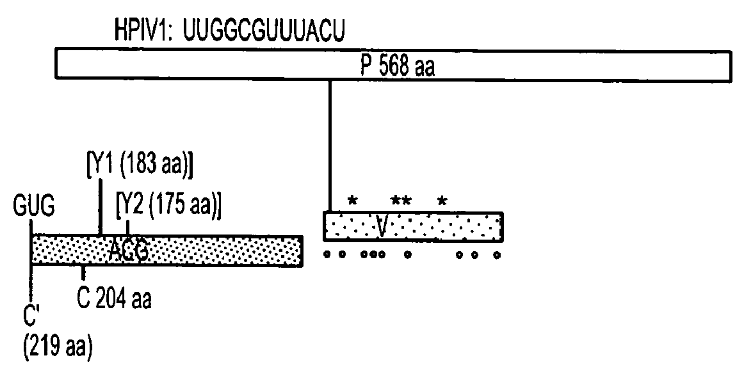
C
```
MPIV1:        GHRREHIIYERDGYIVDESWCNPVCSRIRIIPRRELCVCKICPKVCKLCRDDIQCMRPDPFCREIFRS
HPIV1 W/64:  •RGNQQHIGR-•DGQVISKSWCNEITT•I•II•ECKSCIC•AHVKICKLQRNDI•SLWYAYIS•KIT•E
HPIV1 C39:   •TGNQQHISR-•DGQIVSKSWCNEITT•I•II•KCKSCIC•AHVKICKLQRNDI•SLWYAYIS•KIT•E
```

```
                                         10706
WT  HPIV1   AA  AAU  GAA  UUC  AAA  GCU  GCU  GAC  UCA  UCA  AC
                 N    E    F    K    A    A    D    S    S
                                         10706
rHPIV1      AA  AAU  GAA  UUC  AAA  GCC  GCA  GAC  UCA  UCA  AC
                 N    E    F    K    A    A    D    S    S
```

B.

```
                                        14267
WT  HPIV1   UCA  GGU  GUU  AAU  UCU  UGU  GAU  CUC  AAC  GGA  C
             S    G    V    N    S    C    D    L    N    G
                                        14267
rHPIV1      UCA  GGU  GUU  AAU  UCU  UGU  GAU  CUC  AAC  GGA  C
             S    G    V    N    S    C    D    L    N    G
```

FIG. 6

```
MPIV1 Z          411  SEYQKEQNSLLMSNLSTLHIITDRGGKTDNTDSL 445
HPIV1 WASH/64:   411  SEYQKEQNSLMMANLSTLHIITDRGGKTGNPSDT 445
HPIV3 JS         446  IENQREQLSLITSLISNLKIMTERGGKKDQNESN 480
                      *  *.** **. . .*.*.*.*.****   .
```

5. Attenuating F170S mutation in MPIV1 C

```
HPIV1 C F170S:  (164)KTKLRDSQKRYEEVHPY(180)
HPIV1 WT:       (164)KTKLRDFQKRYEEVHPY(180)
MPIV1 WT:       (164)KTKLKDFQKRYEEVHPY(180)
MPIV1 C F170S:  (164)KTKLKDSQKRYEEVHPY(180)
```

9. Attenuating F21I mutation in RSV L (F456L in HPIV3)

```
HPIV1 L F456L:  (450)SFIGFKLLKFIEPQLDED(467)
HPIV1 WT:       (450)SFIGFKFLKFIEPQLDED(467)
HPIV3 WT:       (450)SFIGIKFNKFIEPQLDED(467)
HPIV3 L F456L:  (450)SFIGIKLNKFIEPQLDED(467)
```

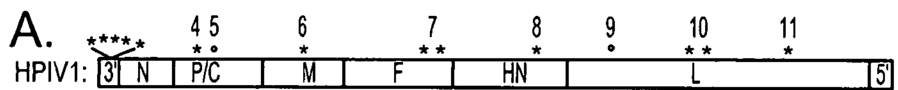

B.

1. cp45 3' leader mutations 22 28 45 62

HPIV1 3' mut: GCTTGGTATATATAATAATATTAAATAGTATTTTAGGGTTT
HPIV1 WT: GTTTGGAATATATAATAATATTAAATAGTATTTTAGGGTTA
HPIV3 WT: GTCTGGGAATATAAATTTAACTTTAAATTAACTTAGGATTA
HPIV3 cp45: GCTTGGTAATATAAATTTAACTTAAAATTAACTTAGGATTT 2. CP45 V96A mutation in HPIV1 N (V99A)

HPIV1 V99A: (92)TNGVNADAKYVIYN(105)
HPIV1 WT: (92)TNGVNADVKYVIYN(105)
HPIV3 WT: (89)TNGSNADVKYVIYM(102)
HPIV3 cp45: (89)TNGSNADAKYVIYM(102)

3. cp45 S389A: Already A in HPIV1 N (A390)

HPIV1 A389: (383)ELGVTDTAKERL(394)
HPIV1 WT: (383)ELGVTDTAKERL(394)
HPIV3 WT: (382)ELGVTHESKESL(393)
HPIV3 cp45: (382)ELGVTHEAKESL(393)

4. cp45 I96T mutation in HPIV1 C (S102T)

HPIV1 S102T: (95)KQRHMLETLINKVYTGPLGEE(115)
HPIV1 WT: (95)KQRHMLESLINKVYTGPLGEE(115)
HPIV3 WT: (89)QQKQKIEILIRKLYREDLGEE(109)
HPIV3 cp45: (89)QQKQKIETLIRKLYREDLGEE(109)

6. cp45 P199T mutation in HPIV1 M (P195T)

HPIV1 P195T: (188)TLADLALTNSISVNL(202)
HPIV1 WT: (188)TLADLALPNSISVNL(202)
HPIV3 WT: (192)SMASLSLPNTISINL(206)
HPIV3 cp45: (192)SMASLSLTNTISINL(206)

7. cp45 I420V and A450T mutations in HPIV1 F (I423V)

HPIV1 F mut: (420)CGLIGVNGI(428). . . .(488)VGPAVTIRPVDI(459)
HPIV1 WT: (420)CGLIGINGI(428). . . .(488)VGPAVSIRPVDI(459)
HPIV3 WT: (417)CSTIGINGM(425). . . .(455)LNNSVALDPIDI(456)
HPIV3 cp45: (417)CSTIGVNGM(425. . . .(455)LNNSVTLDPIDI(456)

8. cp45 V384A mutation in HPIV1 HN (R386A)

HPIV1 R386A: (377) RQVVNVLIAINNYL (390)
HPIV1 WT: (377) RQVVNVLIRINNYL (390)
HPIV3 WT: (375) RRMVNSIIVVDKGL (388)
HPIV3 cp45: (375) RRMVNSIIAVDKGL (388)

10. cp45 Y942H and L992F mutations in HPIV1 L (Y942H) and L992F)

HPIV1 L mut: (937) IGGFNHMSTARCF(949). . . .(986) PGDSSFFDWASDPY (999)
HPIV1 WT: (937) IGGFNYMSTARCF(949). . . .(986)PGDSSFLDWASDPY (999)
HPIV3 WT: (937) VGGFNYMAMSRCF(949). . . .(986)PGESSFLDWASDPY (999)
HPIV3 cp45: (937) VGGFNHMAMSRCF(949). . . .(986)PGESSFFDWASDPY (999)

11. cp45 T1558I mutation in HPIV1 L (L1558I)

HPIV1 L1558I: (1552) PVYGPNISNQDKI(1564)
HPIV1 WT: (1552) PVYGPNLSNQDKI(1564
HPIV3 WT: (1552) PIYGPNTASQDQI(1564)
HPIV3 cp45: (1552) PIYGPNIASQDQI(1564)

A.
3' leader
Mlu I
N
P
M
F
HN
L
5' trailer
B.
rHPIV1-HN2
rHPIV1-GA
rHPIV1-FA
ACGCGTA
Mlu I
ATG
HN2
GA
FA
TAA
TAAT
Gene-stop
AGTAAGAAAAA
CTT
Gene-start
AGGGTTAAAG
gctagc ACGCGT
Nhe I
Mlu I
AGGGTTAAAG
TAATACTTTAAAG
promoter element
GGACAA
GTCACA
GACATT
TGATCT TAGTATAAATACGCGTAATG
Mlu I
N ORF start A.
P ORF (568 aa)
GUG
C' (219aa)
C 204 aa
C ORF
Y1 (183 aa)
Y2 (175aa)
B.
P ORF (568 aa)
TAATAA
C'
C
Y1
Y2
ΔC'
1809 1814
WT : GTGGAT ....
ΔC' : TAATAA ....
TAATAA
TGA
C'
C
Y1
Y2
ΔC'C
1809 1814 1917 1924
WT : GTGGAT .....TCTCAGAT ...
ΔC'C : TAATAA .....TGAGCGAT ...
TAATAA
TGA
TAGTAG
TAGTAA
C'
C
Y1
Y2
ΔC' CY1Y2
1809 1814 1917 1924 1931 1940 1946 1954
WT : GTGGAT ....TCTCA...TCG...TTG...TCG...TATCC
ΔC' CY1Y2 : TAATAA....TGAGC...TAG...TAG...TAG...TAAGT

FIG. 10A-1

HPIV1_wash64
DNA sequence 15600 bp ACCAAACAAGAG . . . CTCTTGTCTGGT linear

```
          10          20          30          40          50          60          70          80          90         100
   1 ACCAAACAAG AGGAAAAACT TGTTTGGAAT ATATAATAAT ATTAAATAGT ATTTAGGGT TAAAGTAATA CTTTAAAGGG ACAAGTCACA GACATTTGAT 100
 101 CTTAGTATAA ATTTTTATAA TGGCCGGGCT ACTAAGTACT TTTGACACAT TTAGTTCCAG GAGAAGTGAG AGCATCAATA AGTCTGGCGG AGGAGCAATT 200
 201 ATACCTGGTC AAAGAAGTAC CGTTTCTGTC TTCACATTAG GCCCGAGTGT GACAGATGAT GCAGATAAAT TATTAATAGC AACCACTTTC TTAGCCCACT 300
 301 CATTGGACAC AGATAAACAA CACTCTCAAA GAGGAGGATT TTTAGTATCA CTCCTTGCAA TGGCCTACAG TAGTCCGGAG TTATATCTCA CTACAAACGG 400
 401 TGTCAATGCT GATGTCAAGT ATGTGATATA CAATATAGAG AGAGATCCTA AAAGAACAAA AACAGATGGG TTCATTGTCA AAACAAGAGA CATGGAGTAT 500
 501 GAAAGAACAA CAGAGTGGTT GTTTGGACCT ATGATCAACA AGAACCCATT GTTCCAAGGG CAAAGAGAGA ATGCGGATCT AGAGGCATTG CTTCAGACAT 600
 601 ATGGATATCC TGCATGTCTC GGAGCTATAA TAGTTCAAGT TTGGATAGTG TTGGTTAAAG CCATAACAAG TAGTGCTGGT CTAAGAAAAG GATTCTTCAA 700
 701 TAGATTAGAA GCATTCAGAC AGGATGGAAC CGTTAAAAGT GCCCTGGTCT TCACAGGAGA CACAGTTGAA GGTATTGGTG CAGTGATGAG GTCACAACAA 800
 801 AGCTTAGTAT CTCTTATGGT AGAAACTCTG GTGACTATGA ACACATCCAG GTCAGATTTA ACTACATTAG AGAAGAACAT TCAGATTGTA GGAAATTACA 900
 901 TAAGAGATGC AGGATTAGCA TCTTTCATGA ACACCATCAA GTATGGTGTA GAAACGAAGA TGGCCGCCCT GACACTATCA AATCTGAGAC CAGATATAAA 1000
1001 CAAATTGAGA AGCCTTGTTG ATATCTATCT ATCAAAGGGA GCCCGAGCCC CTTTTATATG TATACTCAGA GACCCAGTTC ATGGAGACTT TGCCCCTGGA 1100
1101 AACTATCCAG CACTGTGGAG CTACGCAATG GGCGTTGCTG TGGTACAAAA CAAAGCTATG CAACAGTATG TAACTGGAAG AACATATTTG GACATGGAAA 1200
1201 TGTTCCTACT TGGACAAGCT GTAGCTAAAG ATGCTGATTC CAAAATCAGC AGTGCTCTGG AGGAAGAACT AGGTGTGACA GATACAGCAA AAGAGAGACT 1300
1301 AAGACACCAT CTGACAAACC TTTCAGGAGG GGATGGTGCG TACCACAAGC CTACAGGTGG TGGAGCTATA GAAGTGGCAA TTGATCATAC AGACATAACA 1400
1401 TTTGGAGTCG AGGACACTGC TGATCGGGAC AACAAGAACT GGACAAATGA CAGCAATGAA AGATGGATGA ATCACTCGAT CAGCAACCAC ACAATCACGA 1500
1501 TTCGTGGTGC AGAAGAACTT GAAGAAGAGA CAAATGATGA AGACATCACT GATATAGAAA ACAAGATTGC ACGAAGGCTG GCCGACAGAA AACAGAGACT 1600
1601 AAGCCAGGCA AACAATAAAC GAGACACCAG CAGTGATGCT GACTATGAGA ATGATGATGA TGCTACAGCG GCTGCAGGGA TAGGAGGAAT TTAACAGGAT 1700
1701 ACTTGGACAA TAGAAGCCAG ATCAAAAGTA AGAAAAACTT AGGGTGAATG ACAATTCACA GATCAGCTCA ACCAGACACC ACCAGCATAC ACGAAACCAA 1800
1801 CCTTCACAGT GGATACCTCA GCATCCAAAA CTCTCCTTCC CGAATGGATC AGGATGCCTT CTTTTTTGAG AGGGATCCTG AAGCCGAAGG AGAGGCACCA 1900
1901 CGAAAACAAG AATCACTCTC AGATGTCATC GGACTCCTTG ACGTCGTCTT ATCCTACAAG CCCACAGAAA TTGGAGAAGA CAGAAGCTGG CTCCATGGTA 2000
2001 TCATCGACAA CCCAAAAGAA AACAAGCCAT CATGCAAAGC CGACGATAAC AACAAAGACA GAGCAATCTC AACGTCGACC CAAGATCATA GATCAAGTGA 2100
2101 GGGGAGTGGA ATCTCTAGGA GAACAAGTGA GTCAAAAACA GAGACACATG CTAGAATCCT TGATCAACAA GGTATACACA GGGCCTCTAG GCGAGGAACT 2200
2201 AGTCCAAACC CTCTACCTGA GAATATGGGC ATTGAAAGAA ACACCAGAAT CGACGAAGAT TCTCCAAATG AGAGAAGACA TCAGAGATCA GTACTTACGG 2300
2301 ATGAAGACAG AAAGATGGCT GAGAACTCTA ATAAGAGGGA AGAAGACCAA GTTGAGGGAT TTCCAGAAGA GGTACGAAGA AGTACACCCT TATCTGATGA 2400
2401 TGGAGAGGGT AGAACAAATA ATAATGGAAG AAGCATGGAA ACTAGCAGCA CACATAGTAC AAGAATAACT GATGTCATTA CCAACCCAAG TCCAGAGCTT 2500
2501 GAAGATGCCG TTCTACAAAG GAACAAAAGA CGGCCGACGA CCATCAAGCG TAACCAAACA AGATCAGAGA GAACACAGAG TTCAGAACTC CACAAATCAA 2600
2601 CAAGTGAAAA TAGCTCCAAC CTCGAAGACC ACAACACCAA AACCAGCCCA AAAGTTCCAC CGTCAAAGAA CGAAGAGTCA GCAGCCACTC CAAAGAACAA 2700
2701 CCACAACCAC AGAAAAACAA GATACACAAC AAACAATGCA AACAACAACA CAAAAAGTCC ACCAACTCCC GAACACGACG CAACCGCAAA TGAAGAGGAA 2800
2801 ACCAGCAACA CATCGGTCGA TGAGATGGCC AAGTTATTAG TAAGTCTTGG TGTAATGAAA TCACAACATG AATTTGAATT ATCTAGGAGT GCAAGTCATG 2900
```

FIG. 10A-2

```
2901 TATTTGCTAA GCGCATGTTA AAATCTGCAA ATTACAAAGA AATGACATTT AATCTCTGTG GTATGCTTAT ATCAGTTGAA AAATCACTTG AGAATAAAGT 3000
3001 AGAAGAAAAT AGAACATTAC TTAAACAAAT TCAAGAGGAA ATAAATTCAT CCAGGGATCT TCACAAACGG TTCTCGGAAT ACCAAAAAGA ACAGAACTCA 3100
3101 CTCATGATGG CCAATCTATC CACACTCCAT ATAATTACAG ATAGAGGCGG GAAAACGGGA AATCCCAGTG ATACTACAAG GTCACCATCA GTCTTCACAA 3200
3201 AAGGGAAAGA CAATAAGGTC AAAAAGACAA GGTTTGACCC CTCTATGGAA GCTCTAGGAG GTCAAGAGTT CAAGCCTGAC TTGATAAGAG AGGATGAACT 3300
3301 GAGAGATGAC ATCAAAAATC CGGTACTAGA AGAAAACAAC AATGAGCCTC AAGCATCCAA TGCATCACGC CTGATTCCGT CCACTGAAAA ACACACTCTG 3400
3401 CACTCACTCA AACTAGTTAT CGAAAACAGT CCTCTAAGCA GAGTAGAGAA GAAGGCTTAC ATCAAATCCC TTTATAAGTG TCGGACAAAC CAAGAGGTTA 3500
3501 AAAATGTAAT GGAGCTATTC GAGGAAGACA TAGATTCACT AACTAACTAA ACATGAATCT ACAATTTCAA CCAGCAATCA AAATCAATAT CCAGAGCCAA 3600
3601 CTCAAAAAGC TCCCTCAAAA CAATTAAGAA AAACTTAGGG TCAAAGAAAT TTTGCCCGGA GAAAGGAAAT GGCTGAAACA TACAGGTTCC CCAGATTCTC 3700
3701 ACACGAAGAA AATGGGACAG TAGAACCTCT CCCTCTCAAA ACAGGTCCTG ACAAAAAAGC AATCCCTCAC ATCAGAATAG TCAAGGTAGG AGATCCTCCA 3800
3801 AAACATGGAG TCAGGTATCT TGATGTGCTA CTATTGGGAT TCTTTGAAAC ACCTAAGCAA GGACCTCTAT CTGGCAGCAT ATCTGATCTC ACAGAATCAA 3900
3901 CCAGTTATTC AATCTGTGGA TCCGGATCCT TACCAATTGG CATAGCCAAG TATTACGGCA CAGATCAAGA ATTATTAAAA GCCTGCATTG ACCTCAAAAT 4000
4001 AACTGTACGA AGAACAGTTA GATCTGGAGA AATGATAGTA TACATGGTAG ATTCGATCCA TGCTCCTCTA CTACCATGGT CCAGCCGACT GAGACAAGGG 4100
4101 ATGATATATA ATGCCAATAA AGTAGCTCTA GCACCTCAAT GTCTCCCAGT CGACAAAGAC ATCAGATTCA GGGTTGTATT TGTCAATGGA ACATCACTAG 4200
4201 GTACAATTAC AATTGCTAAG GTCCCAGAAA CTCTTGCAGA TCTTGCATTA CCGAACTCAA TATCAGTGAA TCTGCTGGTT ACACTTAGGG CAGGAGTATC 4300
```

FIG. 10B-1

HPIV1_wash64

```
4301 AACGGAACAA AAAGGAATCC TCCCCGTTCT AGACGATGAT GGAGAAAAGA AGCTCAACTT CATGGTACAC CTAGGAATCA TAAGAAGAAA AGTTGGGAAG 4400
4401 ATATATTCAG TTGAATACTG CAAAAATAAA ATTGAGAAGA TGAAGCTAAT ATTCTCTCTC GGGCTTGTAG GTGGAATAAG TTTCCATGTA CATGCAACAG 4500
4501 GCACATTATC CAAAACTCTA ATGACCCAAC TTGCATGGAA AAAAGCAGTT TGCTATCCTT TAATGGATGT AAATCCACAT ATGAATCTAG TCATCTGGGC 4600
4601 AGCTTCAGTA GAAATCACAA GTGTAGATGC TGTGTTCCAA CCTGCAATTC CGAAAGAATT TCGCTATTAC CCAAATGTTG TTGCAAAAAG CATCGGGAAA 4700
4701 ATCAGGAGGA TATAAGTCTA CACTCCTCAA TAATGACACC CATTAGCTCT AAATCGTACC ATTAATCAAA TACAGATCAA TTCGATACAA TCAGTTCAAA 4800
4801 TAAGAAAAAC GTAGGGACAA AGTCCTCTAC CAACATCAAG GAAGACAAGA GTCTCAAAAA GCTCAGCCTA AGCAGAGAGA AAAACAACAA CACAAAGAAA 4900
4901 GAAAAGGACA AGATCACAAA CAAGAACAAA AGCAAAAACA AAAACAAGAA CAAAAAAGGG AAGAAAAACA AAGTATACA CAAAAACCAA AAAACAAAAA 5000
5001 AGGCCAGAGA CAAAAACGGA GGCAAGAACA AAAATTTAAA CAAAAACAGA ATTTAAATTC ATAATAAACA CCAAGATAGA GACAAAAATG CAAAAATCAG 5100
5101 AGATCCTCTT CTTAGTATAC TCAAGCTTGC TATTATCTTC ATCATTATGT CAAATTCCGG TAGAAAAACT TTCAAATGTA GGGGTTATAA TCAATGAGGG 5200
5201 CAAATTACTT AAAATAGCAG GATCTTATGA ATCTAGATAC ATAGTGTTAA GCTTGGTACC TTCAATTGAC CTACAAGATG GATGTGGAAC AACTCAAATT 5300
5301 ATTCAATACA AGAATTTATT AAATAGACTT CTAATTCCTC TGAAGGATGC CTTGGATCTT CAGGAATCCC TGATAACAAT AACTAATGAC ACCACTGTGA 5400
5401 CAAATGATAA TCCACAAACT AGATTCTTTG GTGCTGTCAT TGGTACCATA GCACTAGGAG TAGCCACAGC TGCTCAAATA ACTGCGGGCA TTGCATTAGC 5500
5501 TGAAGCACGA GAAGCCAGGA AGGACATAGC ACTAATAAAA GATTCCATAG TCAAGACACA CAATTCTGTA GAACTCATTC AAAGAGGTAT AGGAGAACAG 5600
5601 ATAATTGCAT TAAAGACATT ACAAGATTTT GTAAATGACG AGATAAGACC TGCAATAGGA GAACTAAGGT GTGAGACTAC GGCATTGAAA CTAGGGATCA 5700
5701 AGCTCACCCA ACACTACTCT GAATTAGCAA CAGCATTCAG CTCCAATCTT GGGACTATAG GAGAAAAAAG TCTTACCTTG CAGGCATTAT CATCTCTCTA 5800
5801 CTCTGCTAAT ATAACAGAAA TTCTAAGTAC AACTAAAAAG GATAAATCAG ATATATATGA CATCATTTAC ACTGAACAGG TTAAGGGAAC TGTGATAGAT 5900
5901 GTTGATTTGG AAAAATACAT GGTTACCCTC TTAGTTAAAA TACCAATTTT ATCAGAAATA CCAGGCGTGT TGATATACAG AGCTTCATCT ATATCTTATA 6000
6001 ATATTGAAGG AGAAGAATGG CATGTCGCAA TCCCAAATTA CATAATCAAT AAGGCATCAT CCTTAGGAGG TGCAGATGTC ACAAACTGTA TAGAATCAAA 6100
6101 ATTGGCATAT ATATGTCCTA GAGATCCTAC ACAATTAATA CCTGATAACC AACAGAAGTG TATACTCGGG GATGTATCAA AGTGCCCTGT GACTAAAGTA 6200
6201 ATAAACAATC TAGTACCAAA GTTCGCATTC ATCAATGGTG GTGTAGTGGC TAATTGCATT GCATCCACAT GTACATGCGG GACAAACAGA ATACCAGTGA 6300
6301 ATCAAGATCG CTCAAGAGGA GTTACATTCT TGACCTATAC CAATTGCGGT TTAATAGGTA TAAATGGAAT AGAACTATAT GCCAATAAAA GGGGACGAGA 6400
6401 CACTACTTGG GGGAATCAAA TCATCAAAGT GGGTCCAGCA GTCTCCATTA GACCTGTAGA CATTTCTTTA AATCTTGCAT CTGCCACAAA TTTCCTAGAG 6500
6501 GAATCCAAGA CAGAGCTCAT GAAGGCAAGG GCAATCATAT CAGCAGTTGG AGGATGGCAC AACACAGAGA GTACTCAGAT AATCATGATA ATAATTGTGT 6600
6601 GCATACTTAT AATAATCATA TGTGGTATAT TATACTATCT ATACAGGGTT AGAAGACTAT TAGTAATGAT TAATTCAACT CATAATTCAC CTGTTAATGC 6700
6701 TTATACTCTG GAGTCAAGAA TGAGAAATCC CTACATGGGT AACAACTCCA ATTAAAAAAT CAGATCAAGT ACATTGTAGC ATACATACAA CAATCAAATC 6800
6801 TATCCACAAC TTCACCAATC AGGTGTACAA CAAGTAAGAA AAACTTAGGG TTAAAGACAA TCCAGTCAAC CTATAAGGCA ACAGCATCCG ATTATACAAA 6900
6901 CGATGGCTGA AAAAGGGAAA ACAAATAGTT CATATTGGTC TACAACCCGA AATGACAATT CCACGGTAAA CACACACATT AATACACCAG CAGGAAGGAC 7000
7001 ACACATCTGG CTACTGATTG CAACAACAAT GCATACAGTA TTGTCCTTCA TTATCATGAT CCTATGCATT GACCTAATTA TAAAACAAGA CACTTGTATG 7100
7101 AAGACAAACA TCATGACAGT ATCCTCCATG AACGAAAGTG CCAAAAATAAT CAAAGAGACA ATCACAGAAT TAATCAGACA AGAAGTAATA TCAAGGACCA 7200
```

FIG. 10B-2

```
7201 TAAACATACA AAGTTCAGTA TCCCCGTTCT TCCCAATATT GTTAAACAAG CAAAGCAGAG ATCTCACACA ATTAATAGAG AAGTCATGCA ACAGACAGGA 7300
7301 ATTGGCTCAG ATATGCGAAA ACACCATTGC TATTCACCAT GCAGACGGCA TATCTCCTCT GGACCCACAC GATTTCTGGA GATGTCCCGT AGGGGAACCC 7400
7401 CTACTGAGCA ACAACCCCAA TATCTCATTA TTACCTGGAC CAAGTCTACT TTCTGGATCC ACCACAATTT CAGGATGTGT TAGACTACCT TCATTATCAA 7500
7501 TTGGTGATGC AATATATGCG TATTCATCAA ACTTAATCAC TCAAGGATGT GCAGATATAG GGAAGTCATA TCAGGTTTTA CAATTAGGTT ACATATCCTT 7600
7601 AAATTCAGAT ATGTATCCTG ATTTAAACCC GGTAATTTCT CATACCTATG ACATCAACGA CAACAGGAAA TCATGTTCTG TAATAGCTGC AGGAACAAGG 7700
7701 GGTTATCAGT TATGCTCCTT GCCCACTGTG AATGAGACTA CAGACTACTC GAGTGAAGGT ATAGAAGATT TAGTATTTGA CATATTAGAT CTCAAGGGAA 7800
7801 AGACCAAATC TCATCGATAC AAAAATGAAG ATATAACTTT TGACCATCCT TTTTCTGCAA TGTATCCGAG TGTAGGAAGT GGGATAAAAA TTGAAAATAC 7900
7901 ACTCATTTTC CTAGGGTACG GTGGCTTAAC AACTCCGCTC CAAGGCGACA CTAAGTGTGT GATAAACAGA TGTACCAATG TTAATCAGAG TGTTTGCAAT 8000
8001 GATGCTCTTA AGATAACTTG GCTAAAGAAA AGACAAGTTG TCAATGTCTT AATTCGTATC AATAATTATT TATCTGATAG GCCAAAGATT GTTGTCGAGA 8100
8101 CAATTCCAAT AACTCAAAAT TACTTAGGTG CCGAAGGTAG GCTACTTAAA CTAGGTAAAA AGATCTACAT ATATACTAGA TCTTCAGGTT GGCACTCCAA 8200
8201 CCTGCAAATA GGATCATTAG ATATCAACAA CCCCATGACC ATTAAATGGG CGCCTCATGA AGTCCTGTCT CGACCAGGAA ACCAAGACTG CAACTGGTAC 8300
8301 AACAGATGTC CGAGAGAATG CATATCAGGT GTATATACTG ATGCATATCC ACTATCTCCT GATGCAGTCA ATGTTGCTAC AACCACACTG TACGCAAACA 8400
8401 CATCACGTGT TAATCCCACC ATAATGTACT CAAATACCTC AGAAATTATC AACATGCTAA GACTCAAGAA TGTACAACTA GAGGCAGCAT ACACTACTAC 8500
8501 ATCATGTATC ACTCATTTCG GGAAGGGCTA CTGCTTCCAC ATTGTTGAAA TCAACCAAGC CAGCCTTAAT ACCTTACAAC CTATGTTGTT CAAGACAAGT 8600
8601 ATCCCTAAAA TATGTAAAAT CACATCTTGA GCAGATCAAG ACCCAACACT ATATCAATTA TGTGAAAACC AGATATGATG TATAAAAATT TAAAAACAAA 8700
8701 GCATGAATAG ACATTTATAT GACAAATAGA ATAAGAAAAA CTTAGGGTTA ATGCCTGCCT ATTTGTCAAA TATGGATAAA CAGGAGTCAA CTCAGAATTC 8800
8801 CTCAGACATC TTATATCCAG AATGTCACTT GAACTCTCCG ATTGTAAAAA GCAAGATTGC TCAACTTCAC GTTTTGCTAG ATATCAATCA ACCCTATGAT 8900
8901 TTAAAAGATA ACAGTATAAT AAATATCACC AAATACAAAA TCAGAAATGG AGGTTTATCG CCCCGGCAGA TCAAAATCAG ATCGCTAGGC AAAATCCTTA 9000
9001 AACAAGAAAT TAAGGATATT GATCGTTACA CTTTTGAACC TTATCCGATT TTCTCATTAG AGTTACTCAG ACTGGATATC CCAGAAATAT GTGACAAAAT 9100
9101 AAGATCCATT TTTTCAGTCT CTGATAGATT AATAAGAGAA CTATCATCTG GATTTCAAGA ATTGTGGTTA AATATTCTTA GACAATTAGG CTGTGTTGAA 9200
9201 GGGAAAGAGG GATTTGACTC ATTAAAGGAT GTAGATATCA TCCCAGATAT AACTGATAAA TATAATAAAA ACACATGGTA TCGCCCATTC TTAACATGGT 9300
```

FIG. 10C-1

HPIV1_wash64

```
9301 TTAGCATCAA ATATGATATG AGATGGATGC AAAAGAATAA GTCGGGGAAC CATTTAGATG TCTCAAATTC TCACAATTTT CTTGACTGTA AATCATATAT 9400
9401 TTTGATTATA TATAGAGATT TAGTGATAAT AATAAATAAA TTAAAATTAA CCGGTTATGT CCTTACACCT GAATTAGTAT TAATGTATTG TGATGTTGTC 9500
9501 GAAGGAAGAT GGAATATGTC TTCAGCTGGA CGACTCGATA AAAGGTCATC AAAAATAACA TGTAAGGGGG AAGAATTATG GGAGCTTATC GACTCTTTAT 9600
9601 TTCCCAATCT TGGTGAGGAT GTATATAATA TTATATCACT ACTAGAACCT TTATCACTTG CTTTAATACA GTTGGATGAC CCTGTAACTA ATTTAAAAGG 9700
9701 AGCTTTCATG AGACATGTTT TGACTGAGCT ACATACAATT TTAATAAAAG ATAATATATA CACAGATTCA GAAGCAGACA GCATAATGGA ATCATTGATA 9800
9801 AAGATTTTCA GAGAGACATC AATTGATGAA AAAGCAGAAA TTTTCTCCTT TTTTAGAACG TTTGGACATC CTAGCTTAGA AGCAATAACT GCTGCCGATA 9900
9901 AAGTAAGGAC ACATATGTAT TCCTCCAAAA AAATCATACT AAAGACACTA TATGAGTGTC ATGCAATCTT CTGTGCAATT ATAATAAACG GATATAGAGA 10000
10001 AAGACACGGT GGTCAATGGC CGCCATGCGA ATTCCCCAAT CATGTATGTC TTGAACTCAA GAATGCACAA GGATCCAACT CTGCAATTTC GTATGAATGT 10100
10101 GCCGTAGACA ATTATAGTAG TTTTATAGGA TTTAAATTTT TAAAATTTAT TGAGCCTCAA TTAGATGAAG ATTTGACAAT TTATATGAAG GATAAGGCTC 10200
10201 TATCACCTAG GAAAGCAGCA TGGGATTCAG TATATCCCGA CAGTAATTTA TATTACAAAG TCCCTGAATC AGAAGAGACT CGTAGGTTAA TCGAGGTTTT 10300
10301 TATAAATGAT AATAATTTTA ACCCTGCGGA TATTATTAAT TATGTAGAGT CAGGAGAATG GTTAAATGAC GATAGCTTCA ACATATCTTA CAGTCTCAAA 10400
10401 GAAAAAGAAA TTAAACAAGA GGGTCGACTC TTTGCCAAGA TGACATATAA GATGAGAGCA GTCCAGGTAT TAGCAGAAAC ACTACTAGCA AAAGGAGTAG 10500
10501 GTGAGTTATT CAGTGAAAAT GGGATGGTAA AGGGAGAAAT TGACCTACTA AAGAGACTGA CTACATTATC TGTCTCAGGT GTTCCAAGAT CCAACTCAGT 10600
10601 TTACAATAAT CCCATATTAC ATGAGAAATT GATCAAAAAT ATGAATAAGT GCAATTCAAA TGGGTATTGG GATGAAAGAA AGAAATCTAA AAATGAATTC 10700
10701 AAAGCTGCAG ACTCATCAAC CGAGGGGTAT GAGACTCTGA GCTGTTTTTT AACCACCGAT TTGAAAAAAT ACTGTCTCAA CTGGAGATTT GAAAGTACAG 10800
10801 CGTTGTTCGG TCAAAGATGT AATGAGATAT TCGGGTTTAA AACTTTCTTT AACTGGATGC ACCCTATTCT AGAAAAAAGT ACAATTTATG TAGGAGATCC 10900
10901 TTACTGTCCA GTACCTGATA GAATGCACAA AGAACTCCAA GATCATGATG ATACCGGAAT CTTTATCCAT AATCCAAGAG GGGGAATAGA GGGTTATTGC 11000
11001 CAGAAATTAT GGACACTAAT CTCTATTAGT GCAATCCATC TTGCAGCTGT TAAAGTTGGT GTCAGAGTGT CAGCAATGGT ACAAGGAGAC AATCAAGCTA 11100
11101 TAGCAGTGAC ATCCAGAGTT CCTGTCACAC AAACCTATAA GCAAAAAAAG ACTCACGTCT ATGAAGAAAT CACAAGATAT TTCGGTGCCT TGAGAGAAGT 11200
11201 TATGTTTGAT ATTGGACATG AATTAAAATT AAATGAGACC ATTATAAGTA GCAAAATGTT TGTATACAGC AAACGGATAT ATTATGATGG GAAAATCCTC 11300
11301 CCACAGTGCC TCAAAGCTTT AACAAGATGT GTATTTTGGT CAGAGACTCT TGTAGATGAA AACAGGTCAG CATGCTCAAA CATTGCAACA TCTATAGCCA 11400
11401 AAGCTATTGA GAATGGATAT TCACCTATCT TAGGCTATTG TATTGCTCTT TTTAAAACTT GCCAACAGGT ATGTATATCA TTAGGAATGA CCATTAATCC 11500
11501 TACTATTACG TCAACTATCA AAGATCAATA TTTTAAAGGG AAAAATTGGT TAAGATGTGC AATATTGATC CCAGCTAACA TAGGAGGGTT CAACTATATG 11600
11601 TCTACAGCTA GATGTTTTGT CAGAAATATA GGTGATCCAG CAGTTGCAGC TCTAGCAGAC TTAAAGAGAT TCATCAAAGC AGGTCTGTTA GATAAACAGG 11700
11701 TATTATATCG TGTGATGAAT CAAGAACCAG GAGACTCAAG CTTCTTAGAT TGGGCATCAG ACCCTTATTC ATGCAATCTC CCACACTCAC AAAGTATAAC 11800
11801 AACTATAATC AAAAATGTAA CAGCTAGATC AGTATTGCAG GAATCACCTA ATCCTCTCCT ATCAGGTCTC TTTTCAGAAT CAAGTAGTGA AGAAGATCTC 11900
11901 AACTTAGCAT CATTTTTGAT GGATAGGAAA GCCATATTGC CCAGAGTAGC TCACGAGATC TTAGATAACT CACTTACAGG TGTAAGAGAA GCTATAGCCG 12000
12001 GGATGCTTGA TACAACGAAA TCTCTAGTAA GAGCTAGTGT CAGGAGAGGA GGATTATCAT ATAGTATCTT AAGAAGACTT ATAAATTATG ATCTATTACA 12100
12101 ATATGAGACC TTAACAAGGA CACTCAGAAA ACCGGTTAAG GATAATATAG AATATGAGTA TATGTGTTCA GTAGAATTGG CAATAGGATT GAGGCAAAAA 12200
```

FIG. 10C-2

```
12201 ATGTGGTTTC ATCTAACTTA TGGAAGACCA ATCCACGGTT TAGAAACTCC AGACCCGTTA GAATTATTAA GAGGATCATT TATTGAAGGC TCAGAAATAT 12300
12301 GTAAATTTTG TAGATCAGAA GGGAATAACC CTATGTATAC TTGGTTCTAT CTTCCTGACA ACATCGACTT AGATACACTT AGCAATGGAA GTCCTGCCAT 12400
12401 ACGTATCCCT TATTTTGGTT CTGCTACTGA TGAAAGATCA GAGGCTCAAC TAGGTTATGT TAAGAACTTA AGCAAGCCGG CAAAAGCAGC AATAAGAATC 12500
12501 GCAATGGTTT ACACTTGGGC TTATGGAACT GATGAAATAT CATGGATGGA AGCAGCACTT ATAGCTCAAA CCAGGGCTAA CTTAAGTTTA GAGAATTTGA 12600
12601 AGTTACTCAC CCCTGTATCG ACTTCTACAA ATTTGTCCCA CAGATTGAGA GATACTGCTA CACAGATGAA ATTTTCAAGT GCTACTTTAG TTCGAGCGAG 12700
12701 TCGATTTATT ACCATATCTA ATGATAATAT GGCATTAAAA GAGGCAGGAG AGTCTAAAGA TACTAATTTA GTTTATCAAC AAATTATGTT AACCGGATTG 12800
12801 AGCTTATTTG AATTCAATAT GAGGTATAAA CAAGGATCAT TATCTAAACC TATGATATTA CACTTACATT TGAATAATAA ATGCTGTATC ATAGAATCTC 12900
12901 CTCAAGAATT GAATATTCCT CCTAGATCTA CATTGGACTT AGAGATCACT CAGGAAAATA ACAAGTTAAT CTATGATCCT GATCCTCTCA AGGACATAGA 13000
13001 TCTAGAGTTA TTTAGTAAGG TTAGGGATGT AGTACACACA ATTGATATGA ATTATTGGTC TGATGATGAA ATAATTAGAG CAACTAGTAT ATGTACAGCT 13100
13101 ATGACTATTG CAGACACAAT GTCTCAATTA GATAGAGACA ATCTTAAAGA AATGATAGCA CTGATAAATG ATGATGATAT AAATAGTTTA ATCACCGAAT 13200
13201 TTATGGTTAT TGATATACCC TTATTTTGTT CCACTTTCGG GGGTATTCTA ATCAATCAAT TTGCATATTC ACTTTACGGG TTAAACGTCA GAGGGAGGGA 13300
13301 TGAAATATGG GGATATGTGA TACGCATAAT TAAAGACACA TCACATGCAG TCCTAAAAGT ACTGTCCAAT GCATTATCAC ATCCTAAAAT ATTCAAACGA 13400
13401 TTCTGGGATG CAGGAGTTGT AGAGCCTGTT TATGGACCTA ACTTGTCCAA TCAAGACAAG ATACTGTTAG CCATTTCAGT ATGTGAATAC TCTGTTGACC 13500
13501 TCTTCATGCG TGATTGGCAA GAGGGCATAC CGCTTGAAAT ATTTATTTGT GATAACGACC CAAATATAGC AGAAATGAGA AAACTTTCAT TTTTAGCTAG 13600
13601 ACATCTAGCA TACTTGTGTA GTTTGGCAGA GATAGCTAAA GAGGGACCAA AATTGGAATC TATGACATCT CTCGAACGAC TCGAATCATT GAAAGAGTAT 13700
13701 CTAGAACTTA CTTTTTTAGA CGATCCTATA TTAAGATATA GTCAATTGAC AGGCTTAGTT ATTAAGATAT TCCCTTCAAC GTTAACTTAC ATCAGGAAAT 13800
13801 CTTCAATTAA GGTGTTGAGA GTAAGAGGTA TAGGGATACC AGAAGTCTTA GAGGACTGGG ATCCTGATGC CGATAGTATG CTACTAGATA ATATAACTGC 13900
13901 TGAGGTTCAA CACAATATAC CTTTAAAGAA GAACGAAAGA ACTCCCTTCT GGGGGTTAAG GGTATCAAAA TCACAAGTTC TGCGACTTAG AGGTTATGAA 14000
14001 GAGATAAAAA GGGAAGAAAG AGGAAGATCA GGTGTAGGAT TAACTCTACC TTTTGATGGG CGATATTTAT CACACCAATT GAGACTTTTC GGGATTAATA 14100
14101 GCACCAGTTG TTTGAAAGCA TTGGAACTTA CCTATTTACT GAATCCTCTA GTCAATAAGG ATAAAGATAG ATTATATCTC GGAGAAGGTG CAGGTGCAAT 14200
14201 GCTGTCTTGT TATGATGCTA CATTAGGACC CTGCATGAAC TATTATAATT CAGGTGTTAA TTCTTGTGAT CTCAACGGAC AAAGAGAATT AAATATTTAT 14300
```

FIG. 10D

HPIV1_wash64

```
14301 CCTTCAGAAG TGGCACTGGT AGGGAAGAAA TTGAATAATG TCACGAGTTT ATGTCAAAGA GTTAAGGTTT TATTCAATGG GAATCCTGGA TCAACTTGGA 14400
14401 TAGGGAATGA TGAATGTGAA ACACTAATCT GGAATGAATT ACAGAATAAT TCAATAGGGT TTATTCATTG TGACATGGAA GGTGGAGAAC ACAAATGTGA 14500
14501 TCAGGTGGTC TTACATGAAC ATTATAGTGT GATCAGGATT GCATACCTTG TTGGGGATAA GGACGTTATC TTAGTAAGCA AAATTGCACC AAGATTAGGT 14600
14601 ACAGACTGGA CAAAACAATT AAGTTTGTAT TTAAGATACT GGAGAGATGT CAGCTTAATA GTGTTGAAAA CATCTAACCC AGCCTCTACA GAAATGTATC 14700
14701 TGATATCAAA AGATCCTAAA TCTGATATTA TAGAGGATAG TAATACAGTA TTGGCAAACC TTCTTCCATT ATCTAAAGAG GATAGTATTA AGATAGAAAA 14800
14801 ATGGATTCTA GTTGAGAAAG CCAAAGTTCA TGATTGGATA GTTAGAGAAT TAAAGGAAGG GAGTGCATCG TCAGGTATGC TAAGACCTTA CCATCAAGCA 14900
14901 TTACAAATCT TCGGATTTGA GCCTAATTTA AACAAATTAT GTAGAGATTT CTTATCTACA CTAAATATAG TAGACACAAA AAATTGTATT ATCACATTTG 15000
15001 ATAGAGTATT AAGAGATACA ATCTTTGAGT GGACTCGGAT AAAAGACGCA GATAAGAAGC TAAGACTTAC AGGTAAATAT GATCTATATC CTCTTAGAGA 15100
15101 TTCAGGTAAG TTAAAAGTTA TTTCTAGAAG GCTTGTAATA TCTTGGATAG CATTGTCTAT GTCTACAAGA CTAGTAACAG GGTCATTTCC AGACATTAAA 15200
15201 TTTGAATCAA GACTCCAATT AGGTATAGTA TCAATATCCT CTCGTGAAAT CAAAAATCTT AGGGTTATAT CAAAGATTGT CATTGACAAA TTTGAAGATA 15300
15301 TTATACATAG TGTGACCTAT AGGTTCTTGA CTAAAGAAAT AAAAATATTG ATGAAAATTT TGGGAGCAGT CAAATTATTT GGGGCAAGAC AGAGCACATC 15400
15401 TGCTGATATC ACTAATATCG ATACATCGGA CTCCATACAA TGATCTTATA TCTTCTCATC TTTATTATCT AATTTGTTTA AAGAGATGAG TTAACAAGAT 15500
15501 AAGAAATCCC TTTAACTGAC TCATAAAAAC ATAGTAAGAA AAACTTACAA CAGACAAGAG TATTAATAAT ATATCGATAT TTCTTAAACT CTTGTCTGGT 15600
               |   10    |    20   |    30   |    40   |    50     |   60    |    70   |    80   |    90   |   100
```

FIG. 11

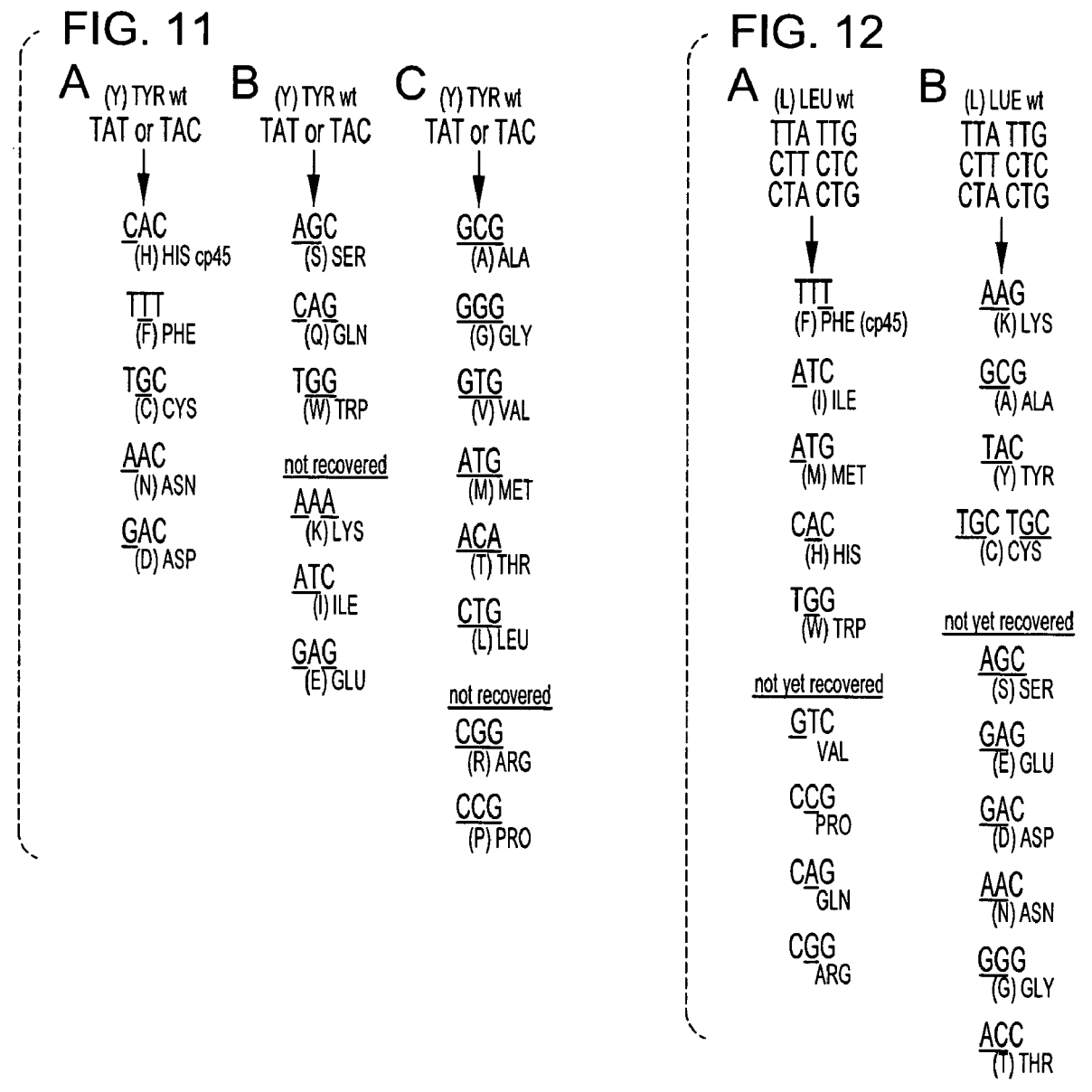

A (Y) TYR wt
TAT or TAC
↓
CAC (H) HIS cp45
TTT (F) PHE
TGC (C) CYS
AAC (N) ASN
GAC (D) ASP

B (Y) TYR wt
TAT or TAC
↓
AGC (S) SER
CAG (Q) GLN
TGG (W) TRP
not recovered
AAA (K) LYS
ATC (I) ILE
GAG (E) GLU C (Y) TYR wt
TAT or TAC
↓
GCG (A) ALA
GGG (G) GLY
GTG (V) VAL
ATG (M) MET
ACA (T) THR
CTG (L) LEU
not recovered
CGG (R) ARG
CCG (P) PRO

FIG. 12

A (L) LEU wt
TTA TTG
CTT CTC
CTA CTG
↓
TTT (F) PHE (cp45)
ATC (I) ILE
ATG (M) MET
CAC (H) HIS
TGG (W) TRP
not yet recovered
GTC VAL
CCG PRO
CAG GLN
CGG ARG B (L) LUE wt
TTA TTG
CTT CTC
CTA CTG
↓
AAG (K) LYS
GCG (A) ALA
TAC (Y) TYR
TGC TGC (C) CYS
not yet recovered
AGC (S) SER
GAG (E) GLU
GAC (D) ASP
AAC (N) ASN
GGG (G) GLY
ACC (T) THR

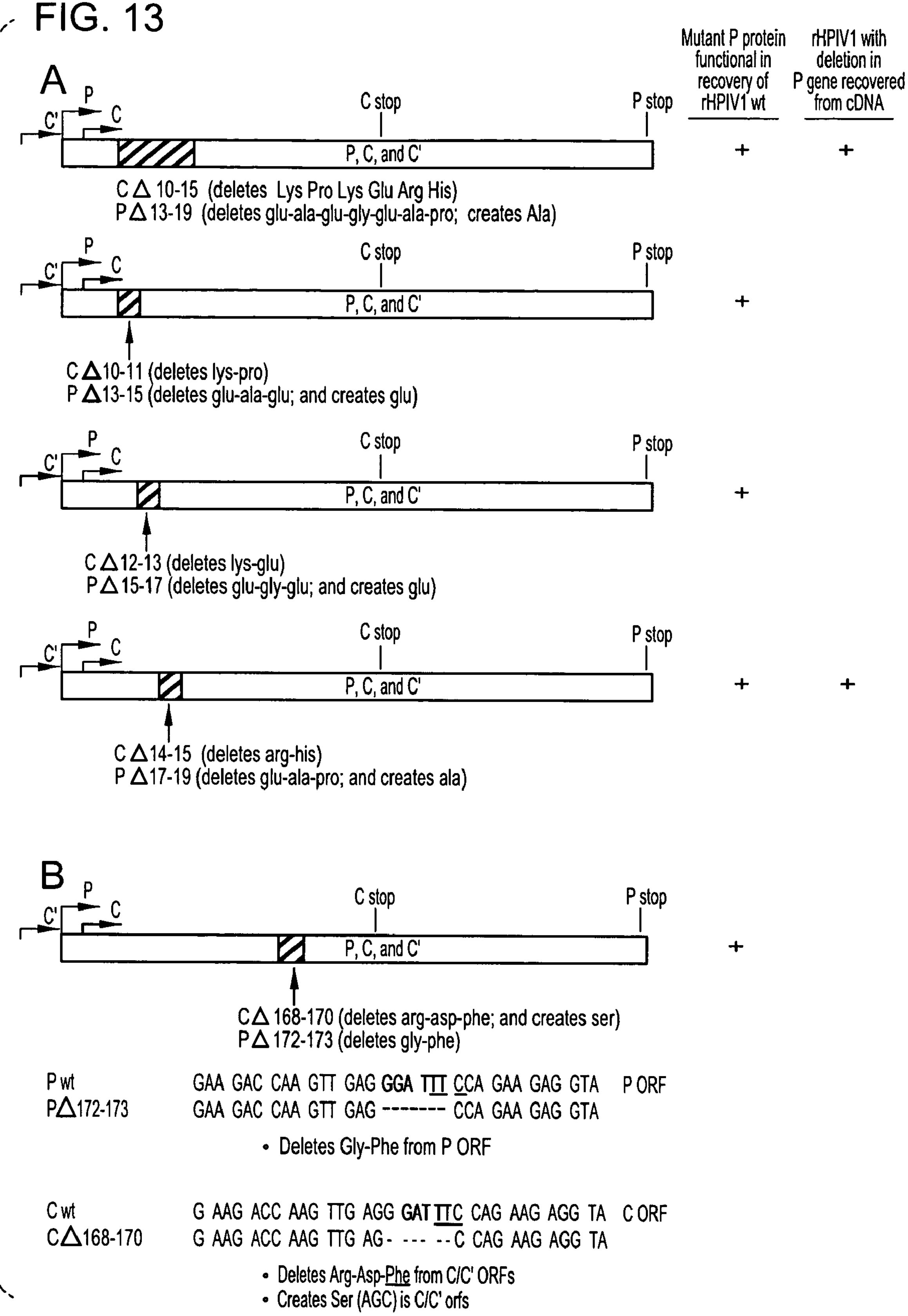
FIG. 13
A
Mutant P protein functional in recovery of rHPIV1 wt
rHPIV1 with deletion in P gene recovered from cDNA
P
C'
C
C stop
P stop
P, C, and C'
+
+
C Δ 10-15 (deletes Lys Pro Lys Glu Arg His)
P Δ 13-19 (deletes glu-ala-glu-gly-glu-ala-pro; creates Ala)
+
C Δ10-11 (deletes lys-pro)
P Δ13-15 (deletes glu-ala-glu; and creates glu)
+
C Δ12-13 (deletes lys-glu)
P Δ15-17 (deletes glu-gly-glu; and creates glu)
+
+
C Δ14-15 (deletes arg-his)
P Δ17-19 (deletes glu-ala-pro; and creates ala)
B
+
C Δ 168-170 (deletes arg-asp-phe; and creates ser)
P Δ 172-173 (deletes gly-phe)
P wt GAA GAC CAA GTT GAG GGA TTT CCA GAA GAG GTA P ORF
PΔ172-173 GAA GAC CAA GTT GAG -------- CCA GAA GAG GTA
• Deletes Gly-Phe from P ORF
C wt G AAG ACC AAG TTG AGG GAT TTC CAG AAG AGG TA C ORF
CΔ168-170 G AAG ACC AAG TTG AG- --- --C CAG AAG AGG TA
• Deletes Arg-Asp-Phe from C/C' ORFs
• Creates Ser (AGC) is C/C' orfs

SEQUENCE LISTING

```
<160> NUMBER OF SEQ ID NOS: 137

<210> SEQ ID NO 1
<211> LENGTH: 96
<212> TYPE: RNA
<213> ORGANISM: Human parainfluenza virus 1

<400> SEQUENCE: 1

aaugucugug acuugucccu uuaaaguauu acuuuaaccc uaaaauacua uuuaauauua      60

uuauauauuc caaacaaguu uuuccucuug uuuggu                                96


<210> SEQ ID NO 2
<211> LENGTH: 96
<212> TYPE: RNA
<213> ORGANISM: Murine parainfluenza virus 1

<400> SEQUENCE: 2

agggucugga accugcuccu cagggguggau acuuugaccc uaaaauccug uauaacuuca     60

uuacauaucc cauacauguu uuuucucuug uuuggu                                96


<210> SEQ ID NO 3
<211> LENGTH: 96
<212> TYPE: RNA
<213> ORGANISM: Human parainfluenza virus 3

<400> SEQUENCE: 3

aguucccuuu ucuugaccuu cuagucaaug ucuuuaaucc uaaguuaauu uaaaguuaaa      60

uuuauauucc cagacaaguu ucuucucuug uuuggu                                96


<210> SEQ ID NO 4
<211> LENGTH: 96
<212> TYPE: RNA
<213> ORGANISM: Bovine parainfluenza virus 3

<400> SEQUENCE: 4
```

-continued

```
gauuucuuuc cccuuaccuu ucgguaaagu ucuuuaaucc uaaguuaauu uuuauuugaa     60

uuaauauucc caagcaaguc ucuucucuug uuuggu                               96


<210> SEQ ID NO 5
<211> LENGTH: 96
<212> TYPE: RNA
<213> ORGANISM: Human parainfluenza virus 1

<400> SEQUENCE: 5

accagacaag aguuuaagaa auaucgauau auuauuaaua cucuugucug uuguaaguuu     60

uucuuacuau guuuuuauga gucaguuaaa gggauu                               96


<210> SEQ ID NO 6
<211> LENGTH: 96
<212> TYPE: RNA
<213> ORGANISM: Murine parainfluenza virus 1

<400> SEQUENCE: 6

accagacaag aguuuaagag auauguaucc uuuuaaauuu ucuugucuuc uuguaaguuu     60

uucuuacuau ugucauaugg auaaguccaa gacuuc                               96


<210> SEQ ID NO 7
<211> LENGTH: 96
<212> TYPE: RNA
<213> ORGANISM: Human parainfluenza virus 3

<400> SEQUENCE: 7

accaaacaag agaagaacuc uguuugguau auauauauua cauguuuuuc uuacuuuuug     60

ucuauuccua ggcuuaaaga uaaagguuag gauaua                               96


<210> SEQ ID NO 8
<211> LENGTH: 96
<212> TYPE: RNA
<213> ORGANISM: Bovine parainfluenza virus 3

<400> SEQUENCE: 8

accaaacaag agaaaaacuc uguuugguau auguauauua uauguuuuuc uuacuuuuca     60

uuuuguugga agugaauggg agaggauuag guguuu                               96


<210> SEQ ID NO 9
<211> LENGTH: 10
<212> TYPE: RNA
<213> ORGANISM: Human parainfluenza virus 1

<400> SEQUENCE: 9

cuuuaacccu                                                            10


<210> SEQ ID NO 10
<211> LENGTH: 12
<212> TYPE: RNA
<213> ORGANISM: Human parainfluenza virus 1

<400> SEQUENCE: 10

uuuuucuuac uu                                                         12


<210> SEQ ID NO 11
<211> LENGTH: 10
<212> TYPE: RNA
<213> ORGANISM: Murine parainfluenza virus 1
```

<400> SEQUENCE: 11
cuuugacccu 10

<210> SEQ ID NO 12
<211> LENGTH: 12
<212> TYPE: RNA
<213> ORGANISM: Murine parainfluenza virus 1

<400> SEQUENCE: 12
uuuuucuuac ua 12

<210> SEQ ID NO 13
<211> LENGTH: 10
<212> TYPE: RNA
<213> ORGANISM: Human parainfluenza virus 3

<400> SEQUENCE: 13
cuuuaauccu 10

<210> SEQ ID NO 14
<211> LENGTH: 12
<212> TYPE: RNA
<213> ORGANISM: Human parainfluenza virus 3

<400> SEQUENCE: 14
uuuuucuuau uu 12

<210> SEQ ID NO 15
<211> LENGTH: 10
<212> TYPE: RNA
<213> ORGANISM: Bovine parainfluenza virus 3

<400> SEQUENCE: 15
cuuuaauccu 10

<210> SEQ ID NO 16
<211> LENGTH: 12
<212> TYPE: RNA
<213> ORGANISM: Bovine parainfluenza virus 3

<400> SEQUENCE: 16
uuuuucuuac uu 12

<210> SEQ ID NO 17
<211> LENGTH: 10
<212> TYPE: RNA
<213> ORGANISM: Human parainfluenza virus 1

<400> SEQUENCE: 17
cauucacccu 10

<210> SEQ ID NO 18
<211> LENGTH: 12
<212> TYPE: RNA
<213> ORGANISM: Human parainfluenza virus 1

<400> SEQUENCE: 18
uuuuucuuaa uu 12

<210> SEQ ID NO 19
<211> LENGTH: 10
<212> TYPE: RNA
<213> ORGANISM: Murine parainfluenza virus 1

-continued

<400> SEQUENCE: 19
cuuucacccu 10

<210> SEQ ID NO 20
<211> LENGTH: 12
<212> TYPE: RNA
<213> ORGANISM: Murine parainfluenza virus 1

<400> SEQUENCE: 20
uuuuucuuaa uc 12

<210> SEQ ID NO 21
<211> LENGTH: 10
<212> TYPE: RNA
<213> ORGANISM: Human parainfluenza virus 3

<400> SEQUENCE: 21
cuuuaauccu 10

<210> SEQ ID NO 22
<211> LENGTH: 12
<212> TYPE: RNA
<213> ORGANISM: Human parainfluenza virus 3

<400> SEQUENCE: 22
uuuuucuuau uu 12

<210> SEQ ID NO 23
<211> LENGTH: 10
<212> TYPE: RNA
<213> ORGANISM: Bovine parainfluenza virus 3

<400> SEQUENCE: 23
cauuaauccu 10

<210> SEQ ID NO 24
<211> LENGTH: 12
<212> TYPE: RNA
<213> ORGANISM: Bovine parainfluenza virus 3

<400> SEQUENCE: 24
uuuuucuuag uc 12

<210> SEQ ID NO 25
<211> LENGTH: 10
<212> TYPE: RNA
<213> ORGANISM: Human parainfluenza virus 1

<400> SEQUENCE: 25
cuuugacccu 10

<210> SEQ ID NO 26
<211> LENGTH: 12
<212> TYPE: RNA
<213> ORGANISM: Human parainfluenza virus 1

<400> SEQUENCE: 26
uuuuucuuau uu 12

<210> SEQ ID NO 27
<211> LENGTH: 10
<212> TYPE: RNA

-continued

```
<213> ORGANISM: Murine parainfluenza virus 1

<400> SEQUENCE: 27

cuuucacccu                                                          10


<210> SEQ ID NO 28
<211> LENGTH: 12
<212> TYPE: RNA
<213> ORGANISM: Murine parainfluenza virus 1

<400> SEQUENCE: 28

uuuuucuuau uu                                                       12


<210> SEQ ID NO 29
<211> LENGTH: 10
<212> TYPE: RNA
<213> ORGANISM: Human parainfluenza virus 3

<400> SEQUENCE: 29

cuuuaauccu                                                          10


<210> SEQ ID NO 30
<211> LENGTH: 20
<212> TYPE: RNA
<213> ORGANISM: Human parainfluenza virus 3

<400> SEQUENCE: 30

uuuuugauua uccuuuauuu                                               20


<210> SEQ ID NO 31
<211> LENGTH: 10
<212> TYPE: RNA
<213> ORGANISM: Bovine parainfluenza virus 3

<400> SEQUENCE: 31

cuuucauccu                                                          10


<210> SEQ ID NO 32
<211> LENGTH: 12
<212> TYPE: RNA
<213> ORGANISM: Bovine parainfluenza virus 3

<400> SEQUENCE: 32

uuuuugauuu uu                                                       12


<210> SEQ ID NO 33
<211> LENGTH: 10
<212> TYPE: RNA
<213> ORGANISM: Human parainfluenza virus 1

<400> SEQUENCE: 33

cuuuguccu                                                           10


<210> SEQ ID NO 34
<211> LENGTH: 12
<212> TYPE: RNA
<213> ORGANISM: Human parainfluenza virus 1

<400> SEQUENCE: 34

uuuuucuuac uu                                                       12


<210> SEQ ID NO 35
<211> LENGTH: 10
```

-continued

<212> TYPE: RNA
<213> ORGANISM: Murine parainfluenza virus 1

<400> SEQUENCE: 35
cuuuaucccu 10

<210> SEQ ID NO 36
<211> LENGTH: 12
<212> TYPE: RNA
<213> ORGANISM: Murine parainfluenza virus 1

<400> SEQUENCE: 36
uuuuucuuau ua 12

<210> SEQ ID NO 37
<211> LENGTH: 10
<212> TYPE: RNA
<213> ORGANISM: Human parainfluenza virus 3

<400> SEQUENCE: 37
cuuuuguccu 10

<210> SEQ ID NO 38
<211> LENGTH: 12
<212> TYPE: RNA
<213> ORGANISM: Human parainfluenza virus 3

<400> SEQUENCE: 38
uuuuuuauaa uu 12

<210> SEQ ID NO 39
<211> LENGTH: 10
<212> TYPE: RNA
<213> ORGANISM: Bovine parainfluenza virus 3

<400> SEQUENCE: 39
cuuugauccu 10

<210> SEQ ID NO 40
<211> LENGTH: 12
<212> TYPE: RNA
<213> ORGANISM: Bovine parainfluenza virus 3

<400> SEQUENCE: 40
uuuuuuguac uu 12

<210> SEQ ID NO 41
<211> LENGTH: 10
<212> TYPE: RNA
<213> ORGANISM: Human parainfluenza virus 1

<400> SEQUENCE: 41
cuuuaacccu 10

<210> SEQ ID NO 42
<211> LENGTH: 12
<212> TYPE: RNA
<213> ORGANISM: Human parainfluenza virus 1

<400> SEQUENCE: 42
uuuuucuuau uc 12

<210> SEQ ID NO 43

-continued

```
<211> LENGTH: 10
<212> TYPE: RNA
<213> ORGANISM: Murine parainfluenza virus 1

<400> SEQUENCE: 43

cuuucacccu                                                            10


<210> SEQ ID NO 44
<211> LENGTH: 12
<212> TYPE: RNA
<213> ORGANISM: Murine parainfluenza virus 1

<400> SEQUENCE: 44

uuuuucuuaa ua                                                         12


<210> SEQ ID NO 45
<211> LENGTH: 10
<212> TYPE: RNA
<213> ORGANISM: Human parainfluenza virus 3

<400> SEQUENCE: 45

cuuuacuccu                                                            10


<210> SEQ ID NO 46
<211> LENGTH: 12
<212> TYPE: RNA
<213> ORGANISM: Human parainfluenza virus 3

<400> SEQUENCE: 46

uuuuuuauau uu                                                         12


<210> SEQ ID NO 47
<211> LENGTH: 10
<212> TYPE: RNA
<213> ORGANISM: Bovine parainfluenza virus 3

<400> SEQUENCE: 47

cuuuguuccu                                                            10


<210> SEQ ID NO 48
<211> LENGTH: 12
<212> TYPE: RNA
<213> ORGANISM: Bovine parainfluenza virus 3

<400> SEQUENCE: 48

uuuuuuauua uu                                                         12


<210> SEQ ID NO 49
<211> LENGTH: 10
<212> TYPE: RNA
<213> ORGANISM: Human parainfluenza virus 1

<400> SEQUENCE: 49

cauuaacccu                                                            10


<210> SEQ ID NO 50
<211> LENGTH: 12
<212> TYPE: RNA
<213> ORGANISM: Human parainfluenza virus 1

<400> SEQUENCE: 50

uuuuucuuac ua                                                         12
```

-continued

<210> SEQ ID NO 51
<211> LENGTH: 10
<212> TYPE: RNA
<213> ORGANISM: Murine parainfluenza virus 1

<400> SEQUENCE: 51
cauucacccu 10

<210> SEQ ID NO 52
<211> LENGTH: 12
<212> TYPE: RNA
<213> ORGANISM: Murine parainfluenza virus 1

<400> SEQUENCE: 52
uuuuucuuac ua 12

<210> SEQ ID NO 53
<211> LENGTH: 10
<212> TYPE: RNA
<213> ORGANISM: Human parainfluenza virus 3

<400> SEQUENCE: 53
cuuugcuccu 10

<210> SEQ ID NO 54
<211> LENGTH: 12
<212> TYPE: RNA
<213> ORGANISM: Human parainfluenza virus 3

<400> SEQUENCE: 54
uuuuucuuac uu 12

<210> SEQ ID NO 55
<211> LENGTH: 10
<212> TYPE: RNA
<213> ORGANISM: Bovine parainfluenza virus 3

<400> SEQUENCE: 55
cuuuucuccu 10

<210> SEQ ID NO 56
<211> LENGTH: 12
<212> TYPE: RNA
<213> ORGANISM: Bovine parainfluenza virus 3

<400> SEQUENCE: 56
uuuuucuuac uu 12

<210> SEQ ID NO 57
<211> LENGTH: 10
<212> TYPE: RNA
<213> ORGANISM: Artificial Sequence
<220> FEATURE:
<223> OTHER INFORMATION: Description of Artificial Sequence: Synthetic consensus sequence
<220> FEATURE:
<221> NAME/KEY: modified_base
<222> LOCATION: (5)..(6)
<223> OTHER INFORMATION: a, c, g or t

<400> SEQUENCE: 57 cwuunnyccu 10

<210> SEQ ID NO 58
<211> LENGTH: 12

```
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (10)
<223> OTHER INFORMATION: a, c, g or t

<400> SEQUENCE: 58

uuuuubduwn uh                                                          12


<210> SEQ ID NO 59
<211> LENGTH: 12
<212> TYPE: RNA
<213> ORGANISM: Murine parainfluenza virus 1

<400> SEQUENCE: 59

uuguuuuuuc cc                                                          12


<210> SEQ ID NO 60
<211> LENGTH: 12
<212> TYPE: RNA
<213> ORGANISM: Human parainfluenza virus 1

<400> SEQUENCE: 60

uuggcguuua cu                                                          12


<210> SEQ ID NO 61
<211> LENGTH: 68
<212> TYPE: PRT
<213> ORGANISM: Murine parainfluenza virus 1

<400> SEQUENCE: 61

Gly His Arg Arg Glu Met Ile Ile Tyr Glu Arg Asp Gly Tyr Ile Val
  1               5                  10                  15

Asp Glu Ser Trp Cys Asn Pro Val Cys Ser Arg Ile Arg Ile Ile Pro
             20                  25                  30

Arg Arg Glu Leu Cys Val Cys Lys Thr Cys Pro Lys Val Cys Lys Leu
         35                  40                  45

Cys Arg Asp Asp Ile Gln Cys Met Arg Pro Asp Pro Phe Cys Arg Glu
     50                  55                  60

Ile Phe Arg Ser
 65


<210> SEQ ID NO 62
<211> LENGTH: 59
<212> TYPE: PRT
<213> ORGANISM: Human parainfluenza virus 1

<400> SEQUENCE: 62

Arg Gly Asn Gln Gln Met Ile Gly Arg Asp Gly Gln Val Ile Ser Lys
  1               5                  10                  15

Ser Trp Cys Asn Glu Ile Thr Thr Ile Ile Ile Glu Cys Lys Ser Cys
             20                  25                  30

Ile Cys Ala His Val Lys Ile Cys Lys Leu Gln Arg Asn Asp Ile Ser
         35                  40                  45

Leu Trp Tyr Ala Tyr Ile Ser Lys Ile Thr Glu
     50                  55


<210> SEQ ID NO 63
```

<211> LENGTH: 59
<212> TYPE: PRT
<213> ORGANISM: Human parainfluenza virus 1

<400> SEQUENCE: 63

```
Thr Gly Asn Gln Gln Met Ile Ser Arg Asp Gly Gln Ile Val Ser Lys
  1               5                  10                  15

Ser Trp Cys Asn Glu Ile Thr Thr Ile Ile Ile Lys Cys Lys Ser Cys
             20                  25                  30

Ile Cys Ala His Val Lys Ile Cys Lys Leu Gln Arg Asn Asp Ile Ser
         35                  40                  45

Leu Trp Tyr Ala Tyr Ile Ser Lys Ile Thr Glu
     50                  55
```

<210> SEQ ID NO 64
<211> LENGTH: 31
<212> TYPE: RNA
<213> ORGANISM: Human parainfluenza virus 1
<220> FEATURE:
<221> NAME/KEY: CDS
<222> LOCATION: (3)..(29)

<400> SEQUENCE: 64

```
aa aau gaa uuc aaa gcu gcu gac uca uca ac                             31
   Asn Glu Phe Lys Ala Ala Asp Ser Ser
     1               5
```

<210> SEQ ID NO 65
<211> LENGTH: 9
<212> TYPE: PRT
<213> ORGANISM: Human parainfluenza virus 1

<400> SEQUENCE: 65

```
Asn Glu Phe Lys Ala Ala Asp Ser Ser
  1               5
```

<210> SEQ ID NO 66
<211> LENGTH: 31
<212> TYPE: RNA
<213> ORGANISM: Human parainfluenza virus 1
<220> FEATURE:
<221> NAME/KEY: CDS
<222> LOCATION: (3)..(29)

<400> SEQUENCE: 66

```
aa aau gaa uuc aaa gcc gca gac uca uca ac                             31
   Asn Glu Phe Lys Ala Ala Asp Ser Ser
     1               5
```

<210> SEQ ID NO 67
<211> LENGTH: 9
<212> TYPE: PRT
<213> ORGANISM: Human parainfluenza virus 1

<400> SEQUENCE: 67

```
Asn Glu Phe Lys Ala Ala Asp Ser Ser
  1               5
```

<210> SEQ ID NO 68
<211> LENGTH: 31
<212> TYPE: RNA
<213> ORGANISM: Human parainfluenza virus 1
<220> FEATURE:
<221> NAME/KEY: CDS
<222> LOCATION: (1)..(30)

-continued

```
<400> SEQUENCE: 68

uca ggu guu aau ucu ugu gau cuc aac gga c                          31
Ser Gly Val Asn Ser Cys Asp Leu Asn Gly
  1               5                  10


<210> SEQ ID NO 69
<211> LENGTH: 10
<212> TYPE: PRT
<213> ORGANISM: Human parainfluenza virus 1

<400> SEQUENCE: 69

Ser Gly Val Asn Ser Cys Asp Leu Asn Gly
  1               5                  10


<210> SEQ ID NO 70
<211> LENGTH: 31
<212> TYPE: RNA
<213> ORGANISM: Human parainfluenza virus 1
<220> FEATURE:
<221> NAME/KEY: CDS
<222> LOCATION: (1)..(30)

<400> SEQUENCE: 70

uca ggu guu aau ucu ugc gau cuc aac gga c                          31
Ser Gly Val Asn Ser Cys Asp Leu Asn Gly
  1               5                  10


<210> SEQ ID NO 71
<211> LENGTH: 10
<212> TYPE: PRT
<213> ORGANISM: Human parainfluenza virus 1

<400> SEQUENCE: 71

Ser Gly Val Asn Ser Cys Asp Leu Asn Gly
  1               5                  10


<210> SEQ ID NO 72
<211> LENGTH: 34
<212> TYPE: PRT
<213> ORGANISM: Murine parainfluenza virus 1

<400> SEQUENCE: 72

Ser Glu Tyr Gln Lys Glu Gln Asn Ser Leu Leu Met Ser Asn Leu Ser
  1               5                  10                  15

Thr Leu His Ile Ile Thr Asp Arg Gly Gly Lys Thr Asp Asn Thr Asp
             20                  25                  30

Ser Leu


<210> SEQ ID NO 73
<211> LENGTH: 34
<212> TYPE: PRT
<213> ORGANISM: Human parainfluenza virus 1

<400> SEQUENCE: 73

Ser Glu Tyr Gln Lys Glu Gln Asn Ser Leu Met Met Ala Asn Leu Ser
  1               5                  10                  15

Thr Leu His Ile Ile Thr Asp Arg Gly Gly Lys Thr Gly Asn Pro Ser
             20                  25                  30

Asp Thr


<210> SEQ ID NO 74
<211> LENGTH: 34
<212> TYPE: PRT
```

<213> ORGANISM: Human parainfluenza virus 3

<400> SEQUENCE: 74

Ile Glu Asn Gln Arg Glu Gln Leu Ser Leu Ile Thr Ser Leu Ile Ser
1 5 10 15

Asn Leu Lys Ile Met Thr Glu Arg Gly Gly Lys Lys Asp Gln Asn Glu
20 25 30

Ser Asn

<210> SEQ ID NO 75
<211> LENGTH: 41
<212> TYPE: DNA
<213> ORGANISM: Human parainfluenza virus 1

<400> SEQUENCE: 75
gcttggtata tataataata ttaaatagta ttttagggtt t 41

<210> SEQ ID NO 76
<211> LENGTH: 41
<212> TYPE: DNA
<213> ORGANISM: Human parainfluenza virus 1

<400> SEQUENCE: 76
gtttggaata tataataata ttaaatagta ttttagggtt a 41

<210> SEQ ID NO 77
<211> LENGTH: 41
<212> TYPE: DNA
<213> ORGANISM: Human parainfluenza virus 3

<400> SEQUENCE: 77
gtctgggaat ataaatttaa ctttaaatta acttaggatt a 41

<210> SEQ ID NO 78
<211> LENGTH: 41
<212> TYPE: DNA
<213> ORGANISM: Human parainfluenza virus 3

<400> SEQUENCE: 78
gcttggtaat ataaatttaa cttaaaatta acttaggatt t 41

<210> SEQ ID NO 79
<211> LENGTH: 14
<212> TYPE: PRT
<213> ORGANISM: Human parainfluenza virus 1

<400> SEQUENCE: 79

Thr Asn Gly Val Asn Ala Asp Ala Lys Tyr Val Ile Tyr Asn
1 5 10

<210> SEQ ID NO 80
<211> LENGTH: 14
<212> TYPE: PRT
<213> ORGANISM: Human parainfluenza virus 1

<400> SEQUENCE: 80

Thr Asn Gly Val Asn Ala Asp Val Lys Tyr Val Ile Tyr Asn
1 5 10

<210> SEQ ID NO 81
<211> LENGTH: 14
<212> TYPE: PRT
<213> ORGANISM: Human parainfluenza virus 3

-continued

<400> SEQUENCE: 81

```
Thr Asn Gly Ser Asn Ala Asp Val Lys Tyr Val Ile Tyr Met
  1               5                  10
```

<210> SEQ ID NO 82
<211> LENGTH: 14
<212> TYPE: PRT
<213> ORGANISM: Human parainfluenza virus 3

<400> SEQUENCE: 82

```
Thr Asn Gly Ser Asn Ala Asp Ala Lys Tyr Val Ile Tyr Met
  1               5                  10
```

<210> SEQ ID NO 83
<211> LENGTH: 12
<212> TYPE: PRT
<213> ORGANISM: Human parainfluenza virus 1

<400> SEQUENCE: 83

```
Glu Leu Gly Val Thr Asp Thr Ala Lys Glu Arg Leu
  1               5                  10
```

<210> SEQ ID NO 84
<211> LENGTH: 12
<212> TYPE: PRT
<213> ORGANISM: Human parainfluenza virus 1

<400> SEQUENCE: 84

```
Glu Leu Gly Val Thr Asp Thr Ala Lys Glu Arg Leu
  1               5                  10
```

<210> SEQ ID NO 85
<211> LENGTH: 12
<212> TYPE: PRT
<213> ORGANISM: Human parainfluenza virus 3

<400> SEQUENCE: 85

```
Glu Leu Gly Val Thr His Glu Ser Lys Glu Ser Leu
  1               5                  10
```

<210> SEQ ID NO 86
<211> LENGTH: 12
<212> TYPE: PRT
<213> ORGANISM: Human parainfluenza virus 3

<400> SEQUENCE: 86

```
Glu Leu Gly Val Thr His Glu Ala Lys Glu Ser Leu
  1               5                  10
```

<210> SEQ ID NO 87
<211> LENGTH: 21
<212> TYPE: PRT
<213> ORGANISM: Human parainfluenza virus 1

<400> SEQUENCE: 87

```
Lys Gln Arg His Met Leu Glu Thr Leu Ile Asn Lys Val Tyr Thr Gly
  1               5                  10                  15

Pro Leu Gly Glu Glu
             20
```

<210> SEQ ID NO 88
<211> LENGTH: 21
<212> TYPE: PRT

<213> ORGANISM: Human parainfluenza virus 1

<400> SEQUENCE: 88

Lys Gln Arg His Met Leu Glu Ser Leu Ile Asn Lys Val Tyr Thr Gly
1 5 10 15

Pro Leu Gly Glu Glu
20

<210> SEQ ID NO 89
<211> LENGTH: 21
<212> TYPE: PRT
<213> ORGANISM: Human parainfluenza virus 3

<400> SEQUENCE: 89

Gln Gln Lys Gln Lys Ile Glu Ile Leu Ile Arg Lys Leu Tyr Arg Glu
1 5 10 15

Asp Leu Gly Glu Glu
20

<210> SEQ ID NO 90
<211> LENGTH: 21
<212> TYPE: PRT
<213> ORGANISM: Human parainfluenza virus 3

<400> SEQUENCE: 90

Gln Gln Lys Gln Lys Ile Glu Thr Leu Ile Arg Lys Leu Tyr Arg Glu
1 5 10 15

Asp Leu Gly Glu Glu
20

<210> SEQ ID NO 91
<211> LENGTH: 15
<212> TYPE: PRT
<213> ORGANISM: Human parainfluenza virus 1

<400> SEQUENCE: 91

Thr Leu Ala Asp Leu Ala Leu Thr Asn Ser Ile Ser Val Asn Leu
1 5 10 15

<210> SEQ ID NO 92
<211> LENGTH: 15
<212> TYPE: PRT
<213> ORGANISM: Human parainfluenza virus 1

<400> SEQUENCE: 92

Thr Leu Ala Asp Leu Ala Leu Pro Asn Ser Ile Ser Val Asn Leu
1 5 10 15

<210> SEQ ID NO 93
<211> LENGTH: 15
<212> TYPE: PRT
<213> ORGANISM: Human parainfluenza virus 3

<400> SEQUENCE: 93

Ser Met Ala Ser Leu Ser Leu Pro Asn Thr Ile Ser Ile Asn Leu
1 5 10 15

<210> SEQ ID NO 94
<211> LENGTH: 15
<212> TYPE: PRT
<213> ORGANISM: Human parainfluenza virus 3

<400> SEQUENCE: 94

-continued

```
Ser Met Ala Ser Leu Ser Leu Thr Asn Thr Ile Ser Ile Asn Leu
  1               5                  10                  15


<210> SEQ ID NO 95
<211> LENGTH: 9
<212> TYPE: PRT
<213> ORGANISM: Human parainfluenza virus 1

<400> SEQUENCE: 95

Cys Gly Leu Ile Gly Val Asn Gly Ile
  1               5


<210> SEQ ID NO 96
<211> LENGTH: 12
<212> TYPE: PRT
<213> ORGANISM: Human parainfluenza virus 1

<400> SEQUENCE: 96

Val Gly Pro Ala Val Thr Ile Arg Pro Val Asp Ile
  1               5                  10


<210> SEQ ID NO 97
<211> LENGTH: 9
<212> TYPE: PRT
<213> ORGANISM: Human parainfluenza virus 1

<400> SEQUENCE: 97

Cys Gly Leu Ile Gly Ile Asn Gly Ile
  1               5


<210> SEQ ID NO 98
<211> LENGTH: 12
<212> TYPE: PRT
<213> ORGANISM: Human parainfluenza virus 1

<400> SEQUENCE: 98

Val Gly Pro Ala Val Ser Ile Arg Pro Val Asp Ile
  1               5                  10


<210> SEQ ID NO 99
<211> LENGTH: 9
<212> TYPE: PRT
<213> ORGANISM: Human parainfluenza virus 3

<400> SEQUENCE: 99

Cys Ser Thr Ile Gly Ile Asn Gly Met
  1               5


<210> SEQ ID NO 100
<211> LENGTH: 12
<212> TYPE: PRT
<213> ORGANISM: Human parainfluenza virus 3

<400> SEQUENCE: 100

Leu Asn Asn Ser Val Ala Leu Asp Pro Ile Asp Ile
  1               5                  10


<210> SEQ ID NO 101
<211> LENGTH: 9
<212> TYPE: PRT
<213> ORGANISM: Human parainfluenza virus 3

<400> SEQUENCE: 101

Cys Ser Thr Ile Gly Val Asn Gly Met
  1               5
```

<210> SEQ ID NO 102
<211> LENGTH: 12
<212> TYPE: PRT
<213> ORGANISM: Human parainfluenza virus 3

<400> SEQUENCE: 102

Leu Asn Asn Ser Val Thr Leu Asp Pro Ile Asp Ile
1 5 10

<210> SEQ ID NO 103
<211> LENGTH: 14
<212> TYPE: PRT
<213> ORGANISM: Human parainfluenza virus 1

<400> SEQUENCE: 103

Arg Gln Val Val Asn Val Leu Ile Ala Ile Asn Asn Tyr Leu
1 5 10

<210> SEQ ID NO 104
<211> LENGTH: 14
<212> TYPE: PRT
<213> ORGANISM: Human parainfluenza virus 1

<400> SEQUENCE: 104

Arg Gln Val Val Asn Val Leu Ile Arg Ile Asn Asn Tyr Leu
1 5 10

<210> SEQ ID NO 105
<211> LENGTH: 14
<212> TYPE: PRT
<213> ORGANISM: Human parainfluenza virus 3

<400> SEQUENCE: 105

Arg Arg Met Val Asn Ser Ile Ile Val Val Asp Lys Gly Leu
1 5 10

<210> SEQ ID NO 106
<211> LENGTH: 14
<212> TYPE: PRT
<213> ORGANISM: Human parainfluenza virus 3

<400> SEQUENCE: 106

Arg Arg Met Val Asn Ser Ile Ile Ala Val Asp Lys Gly Leu
1 5 10

<210> SEQ ID NO 107
<211> LENGTH: 13
<212> TYPE: PRT
<213> ORGANISM: Human parainfluenza virus 1

<400> SEQUENCE: 107

Ile Gly Gly Phe Asn His Met Ser Thr Ala Arg Cys Phe
1 5 10

<210> SEQ ID NO 108
<211> LENGTH: 14
<212> TYPE: PRT
<213> ORGANISM: Human parainfluenza virus 1

<400> SEQUENCE: 108

Pro Gly Asp Ser Ser Phe Phe Asp Trp Ala Ser Asp Pro Tyr
1 5 10

-continued

<210> SEQ ID NO 109
<211> LENGTH: 13
<212> TYPE: PRT
<213> ORGANISM: Human parainfluenza virus 1

<400> SEQUENCE: 109

Ile Gly Gly Phe Asn Tyr Met Ser Thr Ala Arg Cys Phe
1 5 10

<210> SEQ ID NO 110
<211> LENGTH: 14
<212> TYPE: PRT
<213> ORGANISM: Human parainfluenza virus 1

<400> SEQUENCE: 110

Pro Gly Asp Ser Ser Phe Leu Asp Trp Ala Ser Asp Pro Tyr
1 5 10

<210> SEQ ID NO 111
<211> LENGTH: 13
<212> TYPE: PRT
<213> ORGANISM: Human parainfluenza virus 3

<400> SEQUENCE: 111

Val Gly Gly Phe Asn Tyr Met Ala Met Ser Arg Cys Phe
1 5 10

<210> SEQ ID NO 112
<211> LENGTH: 14
<212> TYPE: PRT
<213> ORGANISM: Human parainfluenza virus 3

<400> SEQUENCE: 112

Pro Gly Glu Ser Ser Phe Leu Asp Trp Ala Ser Asp Pro Tyr
1 5 10

<210> SEQ ID NO 113
<211> LENGTH: 13
<212> TYPE: PRT
<213> ORGANISM: Human parainfluenza virus 3

<400> SEQUENCE: 113

Val Gly Gly Phe Asn His Met Ala Met Ser Arg Cys Phe
1 5 10

<210> SEQ ID NO 114
<211> LENGTH: 14
<212> TYPE: PRT
<213> ORGANISM: Human parainfluenza virus 3

<400> SEQUENCE: 114

Pro Gly Glu Ser Ser Phe Phe Asp Trp Ala Ser Asp Pro Tyr
1 5 10

<210> SEQ ID NO 115
<211> LENGTH: 13
<212> TYPE: PRT
<213> ORGANISM: Human parainfluenza virus 1

<400> SEQUENCE: 115

Pro Val Tyr Gly Pro Asn Ile Ser Asn Gln Asp Lys Ile
1 5 10

<210> SEQ ID NO 116
<211> LENGTH: 13

-continued

<212> TYPE: PRT
<213> ORGANISM: Human parainfluenza virus 1

<400> SEQUENCE: 116

Pro Val Tyr Gly Pro Asn Leu Ser Asn Gln Asp Lys Ile
1 5 10

<210> SEQ ID NO 117
<211> LENGTH: 13
<212> TYPE: PRT
<213> ORGANISM: Human parainfluenza virus 3

<400> SEQUENCE: 117

Pro Ile Tyr Gly Pro Asn Thr Ala Ser Gln Asp Gln Ile
1 5 10

<210> SEQ ID NO 118
<211> LENGTH: 13
<212> TYPE: PRT
<213> ORGANISM: Human parainfluenza virus 3

<400> SEQUENCE: 118

Pro Ile Tyr Gly Pro Asn Ile Ala Ser Gln Asp Gln Ile
1 5 10

<210> SEQ ID NO 119
<211> LENGTH: 17
<212> TYPE: PRT
<213> ORGANISM: Human parainfluenza virus 1

<400> SEQUENCE: 119

Lys Thr Lys Leu Arg Asp Ser Gln Lys Arg Tyr Glu Glu Val His Pro
1 5 10 15

Tyr

<210> SEQ ID NO 120
<211> LENGTH: 17
<212> TYPE: PRT
<213> ORGANISM: Human parainfluenza virus 1

<400> SEQUENCE: 120

Lys Thr Lys Leu Arg Asp Phe Gln Lys Arg Tyr Glu Glu Val His Pro
1 5 10 15

Tyr

<210> SEQ ID NO 121
<211> LENGTH: 17
<212> TYPE: PRT
<213> ORGANISM: Murine parainfluenza virus 1

<400> SEQUENCE: 121

Lys Thr Lys Leu Lys Asp Phe Gln Lys Arg Tyr Glu Glu Val His Pro
1 5 10 15

Tyr

<210> SEQ ID NO 122
<211> LENGTH: 17
<212> TYPE: PRT
<213> ORGANISM: Murine parainfluenza virus 1

<400> SEQUENCE: 122

Lys Thr Lys Leu Lys Asp Ser Gln Lys Arg Tyr Glu Glu Val His Pro
1 5 10 15

Tyr

<210> SEQ ID NO 123
<211> LENGTH: 18
<212> TYPE: PRT
<213> ORGANISM: Human parainfluenza virus 1

<400> SEQUENCE: 123

Ser Phe Ile Gly Phe Lys Leu Leu Lys Phe Ile Glu Pro Gln Leu Asp
1 5 10 15

Glu Asp

<210> SEQ ID NO 124
<211> LENGTH: 18
<212> TYPE: PRT
<213> ORGANISM: Human parainfluenza virus 1

<400> SEQUENCE: 124

Ser Phe Ile Gly Phe Lys Phe Leu Lys Phe Ile Glu Pro Gln Leu Asp
1 5 10 15

Glu Asp

<210> SEQ ID NO 125
<211> LENGTH: 18
<212> TYPE: PRT
<213> ORGANISM: Human parainfluenza virus 3

<400> SEQUENCE: 125

Ser Phe Ile Gly Ile Lys Phe Asn Lys Phe Ile Glu Pro Gln Leu Asp
1 5 10 15

Glu Asp

<210> SEQ ID NO 126
<211> LENGTH: 18
<212> TYPE: PRT
<213> ORGANISM: Human parainfluenza virus 3

<400> SEQUENCE: 126

Ser Phe Ile Gly Ile Lys Leu Asn Lys Phe Ile Glu Pro Gln Leu Asp
1 5 10 15

Glu Asp

<210> SEQ ID NO 127
<211> LENGTH: 10
<212> TYPE: DNA
<213> ORGANISM: Human parainfluenza virus 1

<400> SEQUENCE: 127
acgcgtaatg 10

<210> SEQ ID NO 128
<211> LENGTH: 44
<212> TYPE: DNA
<213> ORGANISM: Human parainfluenza virus 1

<400> SEQUENCE: 128
taataataag taagaaaaac ttagggttaa aggctagcac gcgt 44

<210> SEQ ID NO 129
<211> LENGTH: 67
<212> TYPE: DNA

-continued

<213> ORGANISM: Human parainfluenza virus 1

<400> SEQUENCE: 129
agggttaaag taatacttta aagggacaag tcacagacat ttgatcttag tataaatacg 60
cgtaatg 67

<210> SEQ ID NO 130
<211> LENGTH: 41
<212> TYPE: DNA
<213> ORGANISM: Human parainfluenza virus 1

<400> SEQUENCE: 130
taataagtaa gaaaaactta gggttaaagg ctagcacgcg t 41

<210> SEQ ID NO 131
<211> LENGTH: 15609
<212> TYPE: DNA
<213> ORGANISM: Human parainfluenza virus 1

<400> SEQUENCE: 131
accaaacaag aggaaaaact tgtttggaat atataataat attaaatagt attttagggt 60
taaagtaata ctttaaaggg acaagtcaca gacatttgat cttagtataa atttttataa 120
tggccgggct actaagtact tttgacacat ttagttccag gagaagtgag agcatcaata 180
agtctggcgg aggagcaatt atacctggtc aaagaagtac cgtttctgtc ttcacattag 240
gcccgagtgt gacagatgat gcagataaat tattaatagc aaccactttc ttagcccact 300
cattggacac agataaacaa cactctcaaa gaggaggatt tttagtatca ctccttgcaa 360
tggcctacag tagtccggag ttatatctca ctacaaacgg tgtcaatgct gatgtcaagt 420
atgtgatata caatatagag agagatccta aaagaacaaa aacagatggg ttcattgtca 480
aaacaagaga catggagtat gaaagaacaa cagagtggtt gtttggacct atgatcaaca 540
agaacccatt gttccaaggg caaagagaga atgcggatct agaggcattg cttcagacat 600
atggatatcc tgcatgtctc ggagctataa tagttcaagt ttggatagtg ttggttaaag 660
ccataacaag tagtgctggt ctaagaaaag gattcttcaa tagattagaa gcattcagac 720
aggatggaac cgttaaaagt gccctggtct tcacaggaga cacagttgaa ggtattggtg 780
cagtgatgag gtcacaacaa agcttagtat ctcttatggt agaaactctg gtgactatga 840
acacatccag gtcagattta actacattag agaagaacat tcagattgta ggaaattaca 900
taagagatgc aggattagca tctttcatga acaccatcaa gtatggtgta gaaacgaaga 960
tggccgccct gacactatca aatctgagac cagatataaa caaattgaga agccttgttg 1020
atatctatct atcaaaggga gcccgagccc cttttatatg tatactcaga gacccagttc 1080
atggagactt tgcccctgga aactatccag cactgtggag ctacgcaatg ggcgttgctg 1140
tggtacaaaa caaagctatg caacagtatg taactggaag aacatatttg gacatggaaa 1200
tgttcctact tggacaagct gtagctaaag atgctgattc caaaatcagc agtgctctgg 1260
aggaagaact aggtgtgaca gatacagcaa aagagagact aagacaccat ctgacaaacc 1320
tttcaggagg ggatggtgcg taccacaagc ctacaggtgg tggagctata gaagtggcaa 1380
ttgatcatac agacataaca tttggagtcg aggacactgc tgatcgggac aacaagaact 1440
ggacaaatga cagcaatgaa agatggatga atcactcgat cagcaaccac acaatcacga 1500
ttcgtggtgc agaagaactt gaagaagaga caaatgatga agacatcact gatatagaaa 1560
acaagattgc acgaaggctg gccgacagaa aacagagact aagccaggca aacaataaac 1620

```
gagacaccag cagtgatgct gactatgaga atgatgatga tgctacagcg gctgcaggga   1680
taggaggaat ttaacaggat acttggacaa tagaagccag atcaaaagta agaaaaactt   1740
agggtgaatg acaattcaca gatcagctca accagacacc accagcatac acgaaaccaa   1800
ccttcacagt ggatacctca gcatccaaaa ctctccttcc cgaatggatc aggatgcctt   1860
ctttttgag agggatcctg aagccgaagg agaggcacca cgaaaacaag aatcactctc    1920
agatgtcatc ggactccttg acgtcgtctt atcctacaag cccacagaaa ttggagaaga   1980
cagaagctgg ctccatggta tcatcgacaa cccaaaagaa aacaagccat catgcaaagc   2040
cgacgataac aacaaagaca gagcaatctc aacgtcgacc caagatcata gatcaagtga   2100
ggggagtgga atctctagga gaacaagtga gtcaaaaaca gagacacatg ctagaatcct   2160
tgatcaacaa ggtatacaca gggcctctag gcgaggaact agtccaaacc ctctacctga   2220
gaatatgggc aatgaaagaa acaccagaat cgacgaagat tctccaaatg agagaagaca   2280
tcagagatca gtacttacgg atgaagacag aaagatggct gagaactcta ataagaggga   2340
agaagaccaa gttgagggat ttccagaaga ggtacgaaga agtacaccct tatctgatga   2400
tggagagggt agaacaaata ataatggaag aagcatggaa actagcagca cacatagtac   2460
aagaataact gatgtcatta ccaacccaag tccagagctt gaagatgccg ttctacaaag   2520
gaacaaaaga cggccgacga ccatcaagcg taaccaaaca agatcagaga gaacacagag   2580
ttcagaactc cacaaatcaa caagtgaaaa tagctccaac ctcgaagacc acaacaccaa   2640
aaccagccca aaagttccac cgtcaaagaa cgaagagtca gcagccactc caaagaacaa   2700
ccacaaccac agaaaaacaa gatacacaac aaacaatgca aacaacaaca caaaaagtcc   2760
accaactccc gaacacgacg caaccgcaaa tgaagaggaa accagcaaca catcggtcga   2820
tgagatggcc aagttattag taagtcttgg tgtaatgaaa tcacaacatg aatttgaatt   2880
atctaggagt gcaagtcatg tatttgctaa gcgcatgtta aaatctgcaa attacaaaga   2940
aatgacattt aatctctgtg gtatgcttat atcagttgaa aaatcacttg agaataaagt   3000
agaagaaaat agaacattac ttaaacaaat tcaagaggaa ataaattcat ccagggatct   3060
tcacaaacgg ttctcggaat accaaaaaga acagaactca ctcatgatgg ccaatctatc   3120
cacactccat ataattacag atagaggcgg gaaaacggga aatcccagtg atactacaag   3180
gtcaccatca gtcttcacaa aagggaaaga caataaggtc aaaaagacaa ggtttgaccc   3240
ctctatggaa gctctaggag gtcaagagtt caagcctgac ttgataagag aggatgaact   3300
gagagatgac atcaaaaatc cggtactaga agaaaacaac aatgagcctc aagcatccaa   3360
tgcatcacgc ctgattccgt ccactgaaaa acacactctg cactcactca aactagttat   3420
cgaaaacagt cctctaagca gagtagagaa gaaggcttac atcaaatccc tttataagtg   3480
tcggacaaac caagaggtta aaaatgtaat ggagctattc gaggaagaca tagattcact   3540
aactaactaa acatgaatct acaatttcaa ccagcaatca aaatcaatat ccagagccaa   3600
ctcaaaaagc tccctcaaaa caattaagaa aaacttaggg tcaaagaaat tttgcccgga   3660
gaaaggaaat ggctgaaaca tacaggttcc ccagattctc acacgaagaa aatgggacag   3720
tagaacctct ccctctcaaa acaggtcctg acaaaaaagc aatccctcac atcagaatag   3780
tcaaggtagg agatcctcca aaacatggag tcaggtatct tgatgtgcta ctattgggat   3840
tctttgaaac acctaagcaa ggacctctat ctggcagcat atctgatctc acagaatcaa   3900
ccagttattc aatctgtgga tccggatcct taccaattgg catagccaag tattacggca   3960
```

-continued

```
cagatcaaga attattaaaa gcctgcattg acctcaaaat aactgtacga agaacagtta   4020

gatctggaga aatgatagta tacatggtag attcgatcca tgctcctcta ctaccatggt   4080

ccagccgact gagacaaggg atgatatata atgccaataa agtagctcta gcacctcaat   4140

gtctcccagt cgacaaagac atcagattca gggttgtatt tgtcaatgga acatcactag   4200

gtacaattac aattgctaag gtcccagaaa ctcttgcaga tcttgcatta ccgaactcaa   4260

tatcagtgaa tctgctggtt acacttaggg caggagtatc graaacggaa caaaaaggaa   4320

tcctccccgt tctagacgat gatggagaaa agaagctcaa cttcatggta cacctaggaa   4380

tcataagaag aaaagttggg aagatatatt cagttgaata ctgcaaaaat aaaattgaga   4440

agatgaagct aatattctct ctcgggcttg taggtggaat aagtttccat gtacatgcaa   4500

caggcacatt atccaaaact ctaatgaccc aacttgcatg gaaaaaagca gtttgctatc   4560

ctttaatgga tgtaaatcca catatgaatc tagtcatctg ggcagcttca gtagaaatca   4620

caagtgtaga tgctgtgttc caacctgcaa ttccgaaaga atttcgctat tacccaaatg   4680

ttgttgcaaa aagcatcggg aaaatcagga ggatataagt ctacactcct caataatgac   4740

acccattagc tctaaatcgt accattaatc aaatacagat caattcgata caatcagttc   4800

aaataagaaa aacgtaggga caaagtcctc taccaacatc aaggaagaca agagtctcaa   4860

aaagctcagc ctaagcagag agaaaaacaa caacacaaag aaagaaaagg acaagatcac   4920

aaacaagaac aaaagcaaaa acaaaaacaa gaacaaaaaa gggaagaaaa acaaaagtat   4980

acacaaaaac caaaaaagaa aaaaggccag agacaaaaac ggaggcaaga acaaaaattt   5040

aaacaaaaac agaatttaaa ttcataataa acaccaagat agagacaaaa atgcaaaaat   5100

cagagatcct cttcttagta tactcaagct tgctattatc ttcatcatta tgtcaaattc   5160

cggtagaaaa actttcaaat gtaggggtta taatcaatga gggcaaatta cttaaaatag   5220

caggatctta tgaatctaga tacatagtgt taagcttggt accttcaatt gacctacaag   5280

atggatgtgg aacaactcaa attattcaat acaagaattt attaaataga cttctaattc   5340

ctctgaagga tgccttggat cttcaggaat ccctgataac aataactaat gacaccactg   5400

tgacaaatga taatccacaa actagattct ttggtgctgt cattggtacc atagcactag   5460

gagtagccac agctgctcaa ataactgcgg gcattgcatt agctgaagca cgagaagcca   5520

ggaaggacat agcactaata aaagattcca tagtcaagac acacaattct gtagaactca   5580

ttcaaagagg tataggagaa cagataattg cattaaagac attacaagat tttgtaaatg   5640

acgagataag acctgcaata ggagaactaa ggtgtgagac tacggcattg aaactaggga   5700

tcaagctcac ccaacactac tctgaattag caacagcatt cagctccaat cttgggacta   5760

taggagaaaa aagtcttacc ttgcaggcat tatcatctct ctactctgct aatataacag   5820

aaattctaag tacaactaaa aaggataaat cagatatata tgacatcatt tacactgaac   5880

aggttaaggg aactgtgata gatgttgatt tggaaaaata catggttacc ctcttagtta   5940

aaataccaat tttatcagaa ataccaggcg tgttgatata cagagcttca tctatatctt   6000

ataatattga aggagaagaa tggcatgtcg caatcccaaa ttacataatc aataaggcat   6060

catccttagg aggtgcagat gtcacaaact gtatagaatc aaaattggca tatatatgtc   6120

ctagagatcc tacacaatta atacctgata accaacagaa gtgtatactc ggggatgtat   6180

caaagtgccc tgtgactaaa gtaataaaca atctagtacc aaagttcgca ttcatcaatg   6240

gtggtgtagt ggctaattgc attgcatcca catgtacatg cgggacaaac agaataccag   6300

tgaatcaaga tcgctcaaga ggagttacat tcttgaccta taccaattgc ggtttaatag   6360
```

-continued

```
gtataaatgg aatagaacta tatgccaata aaaggggacg agacactact tgggggaatc   6420
aaatcatcaa agtgggtcca gcagtctcca ttagacctgt agacatttct ttaaatcttg   6480
catctgccac aaatttccta gaggaatcca agacagagct catgaaggca agggcaatca   6540
tatcagcagt tggaggatgg cacaacacag agagtactca gataatcatg ataataattg   6600
tgtgcatact tataataatc atatgtggta tattatacta tctatacagg gttagaagac   6660
tattagtaat gattaattca actcataatt cacctgttaa tgcttatact ctggagtcaa   6720
gaatgagaaa tccctacatg ggtaacaact ccaattaaaa aatcagatca agtacattgt   6780
agcatacata caacaatcaa atctatccac aacttcacca atcaggtgta caacaagtaa   6840
gaaaaactta gggttaaaga caatccagtc aacctataag gcaacagcat ccgattatac   6900
aaacgatggc tgaaaaaggg aaaacaaata gttcatattg gtctacaacc cgaaatgaca   6960
attccacggt aaacacacac attaatacac cagcaggaag gacacacatc tggctactga   7020
ttgcaacaac aatgcataca gtattgtcct tcattatcat gatcctatgc attgacctaa   7080
ttataaaaca agacacttgt atgaagacaa acatcatgac agtatcctcc atgaacgaaa   7140
gtgccaaaat aatcaaagag acaatcacag aattaatcag acaagaagta atatcaagga   7200
ccataaacat acaaagttca gtacaaagcg ggatcccaat attgttaaac aagcaaagca   7260
gagatctcac acaattaata gagaagtcat gcaacagaca ggaattggct cagatatgcg   7320
aaaacaccat tgctattcac catgcagacg gcatatctcc tctggaccca cacgatttct   7380
ggagatgtcc cgtaggggaa cccctactga gcaacaaccc caatatctca ttattacctg   7440
gaccaagtct actttctgga tccaccacaa tttcaggatg tgttagacta ccttcattat   7500
caattggtga tgcaatatat gcgtattcat caaacttaat cactcaagga tgtgcagata   7560
tagggaagtc atatcaggtt ttacaattag gttacatatc cttaaattca gatatgtatc   7620
ctgatttaaa cccggtaatt tctcatacct atgacatcaa cgacaacagg aaatcatgtt   7680
ctgtaatagc tgcaggaaca aggggttatc agttatgctc cttgcccact gtgaatgaga   7740
ctacagacta ctcgagtgaa ggtatagaag atttagtatt tgacatatta gatctcaagg   7800
gaaagaccaa atctcatcga tacaaaaatg aagatataac ttttgaccat ccttttttctg   7860
caatgtatcc gagtgtagga agtgggataa aaattgaaaa tacactcatt ttcctagggt   7920
acggtggctt aacaactccg ctccaaggcg acactaagtg tgtgataaac agatgtacca   7980
atgttaatca gagtgtttgc aatgatgctc ttaagataac ttggctaaag aaaagacaag   8040
ttgtcaatgt cttaattcgt atcaataatt atttatctga taggccaaag attgttgtcg   8100
agacaattcc aataactcaa aattacttag gtgccgaagg taggctactt aaactaggta   8160
aaaagatcta catatatact agatcttcag gttggcactc caacctgcaa ataggatcat   8220
tagatatcaa caaccccatg accattaaat gggcgcctca tgaagtcctg tctcgaccag   8280
gaaaccaaga ctgcaactgg tacaacagat gtccgagaga atgcatatca ggtgtatata   8340
ctgatgcata tccactatct cctgatgcag tcaatgttgc tacaaccaca ctgtacgcaa   8400
acacatcacg tgttaatccc accataatgt actcaaatac ctcagaaatt atcaacatgc   8460
taagactcaa gaatgtacaa ctagaggcag catacactac tacatcatgt atcactcatt   8520
tcgggaaggg ctactgcttc cacattgttg aaatcaacca agccagcctt aataccttac   8580
aacctatgtt gttcaagaca agtatcccta aaatatgtaa aatcacatct tgagcagatc   8640
aagacccaac actatatcaa ttatgtgaaa accagatatg atgtataaaa atttaaaaac   8700
```

-continued

```
aaagcatgaa tagacattta tatgacaaat agaataagaa aaacttaggg ttaatgcctg   8760
cctatttgtc aaatatggat aaacaggagt caactcagaa ttcctcagac atcttatatc   8820
cagaatgtca cttgaactct ccgattgtaa aaagcaagat tgctcaactt cacgttttgc   8880
tagatatcaa tcaaccctat gatttaaaag ataacagtat aataaatatc accaaataca   8940
aaatcagaaa tggaggttta tcgccccggc agatcaaaat cagatcgcta ggcaaaatcc   9000
ttaaacaaga aattaaggat attgatcgtt acacttttga accttatccg attttctcat   9060
tagagttact cagactggat atcccagaaa tatgtgacaa aataagatcc attttttcag   9120
tctctgatag attaataaga gaactatcat ctggatttca agaattgtgg ttaaatattc   9180
ttagacaatt aggctgtgtt gaagggaaag agggatttga ctcattaaag gatgtagata   9240
tcatcccaga tataactgat aaatataata aaaacacatg gtatcgccca ttcttaacat   9300
ggtgrbttag catcaaatat gatatgagat ggatgcaaaa gaataagtcg ggaaccatt   9360
tagatgtctc aaattctcac aattttcttg actgtaaatc atatattttg attatatata   9420
gagatttagt gataataata aataaattaa aattaaccgg ttatgtcctt acacctgaat   9480
tagtattaat gtattgtgat gttgtcgaag gaagatggaa tatgtcttca gctggacgac   9540
tcgataaaag gtcatcaaaa ataacatgta agggggaaga attatgggag cttatcgact   9600
ctttatttcc caatcttggt gaggatgtat ataatattat atcactacta gaacctttat   9660
cacttgcttt aatacagttg gatgaccctg taactaattt aaaaggagct ttcatgagac   9720
atgttttgac tgagctacat acaattttaa taaaagataa tatatacaca gattcagaag   9780
cagacagcat aatggaatca ttgataaaga ttttcagaga gacatcaatt gatgaaaaag   9840
cagaaatttt ctcctttttt agaacgtttg gacatcctag cttagaagca ataactgctg   9900
ccgataaagt aaggacacat atgtattcct ccaaaaaaat catactaaag acactatatg   9960
agtgtcatgc aatcttctgt gcaattataa taaacggata tagagaaaga cacggtggtc  10020
aatggccgcc atgcgaattc cccaatcatg tatgtcttga actcaagaat gcacaaggat  10080
ccaactctgc aatttcgtat gaatgtgccg tagacaatta tagtagtttt ataggattta  10140
aatttttaaa atttattgag cctcaattag atgaagattt gacaatttat atgaaggata  10200
aggctctatc acctaggaaa gcagcatggg attcagtata tcccgacagt aatttatatt  10260
acaaagtccc tgaatcagaa gagactcgta ggttaatcga ggtttttata aatgataata  10320
attttaaccc tgcggatatt attaattatg tagagtcagg agaatggtta aatgacgata  10380
gcttcaacat atcttacagt ctcaaagaaa aagaaattaa acaagagggt cgactctttg  10440
ccaagatgac atataagatg agagcagtcc aggtattagc agaaacacta ctagcaaaag  10500
gagtaggtga gttattcagt gaaaatggga tggtaaaggg agaaattgac ctactaaaga  10560
gactgactac attatctgtc tcaggtgttc caagatccaa ctcagtttac aataatccca  10620
tattacatga gaaattgatc aaaaatatga ataagtgcaa ttcaaatggg tattgggatg  10680
aaagaaagaa atctaaaaat gaattcaaag ctgcagactc atcaaccgag gggtatgaga  10740
ctctgagctg ttttttaacc accgatttga aaaaatactg tctcaactgg agatttgaaa  10800
gtacagcgtt gttcggtcaa agatgtaatg agatattcgg gtttaaaact ttctttaact  10860
ggatgcaccc tattctagaa aaaagtacaa tttatgtagg agatccttac tgtccagtac  10920
ctgatagaat gcacaaagaa ctccaagatc atgatgatac cggaatcttt atccataatc  10980
caagaggggg aatagagggt tattgccaga aattatggac actaatctct attagtgcaa  11040
tccatcttgc agctgttaaa gttggtgtca gagtgtcagc aatggtacaa ggagacaatc  11100
```

-continued

```
aagctatagc agtgacatcc agagttcctg tcacacaaac ctataagcaa aaaaagactc  11160
acgtctatga agaaatcaca agatatttcg gtgccttgag agaagttatg tttgatattg  11220
gacatgaatt aaaattaaat gagaccatta taagtagcaa aatgtttgta tacagcaaac  11280
ggatatatta tgatgggaaa atcctcccac agtgcctcaa agctttaaca agatgtgtat  11340
tttggtcaga gactcttgta gatgaaaaca ggtcagcatg ctcaaacatt gcaacatcta  11400
tagccaaagc tattgagaat ggatattcac ctatcttagg ctattgtatt gctcttttta  11460
aaacttgcca acaggtatgt atatcattag gaatgaccat taatcctact attacgtcaa  11520
ctatcaaaga tcaatatttt aaagggaaaa attggttaag atgtgcaata ttgatcccag  11580
ctaacatagg agggttcaac tatatgtcta cagctagatg ttttgtcaga aatataggtg  11640
atccagcagt tgcagctcta gcagacttaa agagattcat caaagcaggt ctgttagata  11700
aacaggtatt atatcgtgtg atgaatcaag aaccaggaga ctcaagcttc ttagattggg  11760
catcagaccc ttattcatgc aatctcccac actcacaaag tataacaact ataatcaaaa  11820
atgtaacagc tagatcagta ttgcaggaat cacctaatcc tctcctatca ggtctctttt  11880
cagaatcaag tagtgaagaa gatctcaact tagcatcatt tttgatggat aggaaagcca  11940
tattgcccag agtagctcac gagatcttag ataactcact tacaggtgta agagaagcta  12000
tagccgggat gcttgataca acgaaatctc tagtaagagc tagtgtcagg agaggaggat  12060
tatcatatag tatcttaaga agacttataa attatgatct attacaatat gagaccttaa  12120
caaggacact cagaaaaccg gttaaggata atatagaata tgagtatatg tgttcagtag  12180
aattggcaat aggattgagg caaaaaatgt ggtttcatct aacttatgga agaccaatcc  12240
acggtttaga aactccagac ccgttagaat tattaagagg atcatttatt gaaggctcag  12300
aaatatgtaa attttgtaga tcagaaggga ataaccctat gtatacttgg ttctatcttc  12360
ctgacaacat cgacttagat acacttagca atggaagtcc tgccatacgt atcccttatt  12420
ttggttctgc tactgatgaa agatcagagg ctcaactagg ttatgttaag aacttaagca  12480
agccggcaaa agcagcaata agaatcgcaa tggtttacac ttgggcttat ggaactgatg  12540
aaatatcatg gatggaagca gcacttatag ctcaaaccag ggctaactta agtttagaga  12600
atttgaagtt actcacccct gtatcgactt ctacaaattt gtcccacaga ttgagagata  12660
ctgctacaca gatgaaattt tcaagtgcta ctttagttcg agcgagtcga tttattacca  12720
tatctaatga taatatggca ttaaaagagg caggagagtc taaagatact aatttagttt  12780
atcaacaaat tatgttaacc ggattgagct tatttgaatt caatatgagg tataaacaag  12840
gatcattatc taaacctatg atattacact tacatttgaa taataaatgc tgtatcatag  12900
aatctcctca agaattgaat attcctccta gatctacatt ggacttagag atcactcagg  12960
aaaataacaa gttaatctat gatcctgatc ctctcaagga catagatcta gagttattta  13020
gtaaggttag ggatgtagta cacacaattg atatgaatta ttggtctgat gatgaaataa  13080
ttagagcaac tagtatatgt acagctatga ctattgcaga cacaatgtct caattagata  13140
gagacaatct taaagaaatg atagcactga taaatgatga tgatataaat agtttaatca  13200
ccgaatttat ggttattgat atacccttat tttgttccac tttcgggggt attctaatca  13260
atcaatttgc atattcactt tacgggttaa acgtcagagg gagggatgaa atatggggat  13320
atgtgatacg cataattaaa gacacatcac atgcagtcct aaaagtactg tccaatgcat  13380
tatcacatcc taaaatattc aaacgattct gggatgcagg agttgtagag cctgtttatg  13440
```

-continued

```
gacctaactt gtccaatcaa gacaagatac tgttagccat ttcagtatgt gaatactctg  13500

ttgacctctt catgcgtgat tggcaagagg gcataccgct tgaaatattt atttgtgata  13560

acgacccaaa tatagcagaa atgagaaaac tttcattttt agctagacat ctagcatact  13620

tgtgtagttt ggcagagata gctaaagagg gaccaaaatt ggaatctatg acatctctcg  13680

aacgactcga atcattgaaa gagtatctag aacttacttt tttagacgat cctatattaa  13740

gatatagtca attgacaggc ttagttatta agatattccc ttcaacgtta acttacatca  13800

ggaaatcttc aattaaggtg ttgagagtaa gaggtatagg gataccagaa gtcttagagg  13860

actgggatcc tgatgccgat agtatgctac tagataatat aactgctgag gttcaacaca  13920

atataccttt aaagaagaac gaaagaactc ccttctgggg gttaagggta tcaaaatcac  13980

aagttctgcg acttagaggt tatgaagaga taaaaaggga agaaagagga agatcaggtg  14040

taggattaac tctacctttt gatgggcgat atttatcaca ccaattgaga cttttcggga  14100

ttaatagcac cagttgtttg aaagcattgg aacttaccta tttactgaat cctctagtca  14160

ataaggataa agatagatta tatctcggag aaggtgcagg tgcaatgctg tcttgttatg  14220

atgctacatt aggaccctgc atgaactatt ataattcagg tgttaattct tgtgatctca  14280

acggacaaag agaattaaat atttatgrcc cttcagaagt ggcactggta gggaagaaat  14340

tgaataatgt cacgagttta tgtcaaagag ttaaggtttt attcaatggg aatcctggat  14400

caacttggat agggaatgat gaatgtgaaa cactaatctg gaatgaatta cagaataatt  14460

caatagggtt tattcattgt gacatggaag gtggagaaca caaatgtgat caggtggtct  14520

tacatgaaca ttatagtgtg atcaggattg catacettgt tggggataag gacgttatct  14580

tagtaagcaa aattgcacca agattaggta cagactggac aaaacaatta agtttgtatt  14640

taagatactg gagagatgtc agcttaatag tgttgaaaac atctaaccca gcctctacag  14700

aaatgtatct gatatcaaaa gatcctaaat ctgatattat agaggatagt aatacagtat  14760

tggcaaacct tcttccatta tctaaagagg atagtattaa gatagaaaaa tggattctag  14820

ttgagaaagc caaagttcat gattggatag ttagagaatt aaaggaaggg agtgcatcgt  14880

caggtatgct aagaccttac catcaagcat tacaaatctt cggatttgag cctaatttaa  14940

acaaattatg tagagatttc ttatctacac taaatatagt agacacaaaa aattgtatta  15000

tcacatttga tagagtatta agagatacaa tctttgagtg gactcggata aaagacgcag  15060

ataagaagct aagacttaca ggtaaatatg atctatatcc tcttagagat tcaggtaagt  15120

taaaagttat ttctagaagg cttgtaatat cttggatagc attgtctatg tctacaagac  15180

tagtaacagg gtcatttcca gacattaaat ttgaatcaag actccaatta ggtatagtat  15240

caatatcctc tcgtgaaatc aaaaatctta gggttatatc aaagattgtc attgacaaat  15300

ttgaagatat tatacatagt gtgacctata ggttcttgac taaagaaata aaaatattga  15360

tgaaaatttt gggagcagtc aaattatttg gggcaagaca gagcacatct gctgatatca  15420

ctaatatcga tacatcggac tccatacaat gatcttatat cttctcatct ttattatcta  15480

atttgtttaa agagatgagt taacaagata agaaatccct ttaactgact cataaaaaca  15540

tagtaagaaa aacttacaac agacaagagt attaataata tatcgatatt tcttaaactc  15600

ttgtctggt                                                          15609
```

<210> SEQ ID NO 132
<211> LENGTH: 6
<212> TYPE: PRT
<213> ORGANISM: Artificial Sequence

```
<220> FEATURE:
<223> OTHER INFORMATION: Description of Artificial Sequence: Synthetic
      amino acid sequence

<400> SEQUENCE: 132

Lys Pro Lys Glu Lys His
  1               5


<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 133

Glu Ala Glu Gly Glu Ala Pro
  1               5


<210> SEQ ID NO 134
<211> LENGTH: 33
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 134

gaagaccaag ttgagggatt tccagaagag gta                                  33


<210> SEQ ID NO 135
<211> LENGTH: 27
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 135

gaagaccaag ttgagccaga agaggta                                         27


<210> SEQ ID NO 136
<211> LENGTH: 33
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 136

gaagaccaag ttgagggatt tccagaagag gta                                  33


<210> SEQ ID NO 137
<211> LENGTH: 27
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 137

gaagaccaag ttgagccaga agaggta                                         27
```

RECOVERY OF RECOMBINANT HUMAN PARAINFLUENZA VIRUS TYPE 1 (HPIV1) FROM CDNA AND USE OF RECOMBINANT HPIV1 IN IMMUNOGENIC COMPOSITIONS AND AS VECTORS TO ELICIT IMMUNE RESPONSES AGAINST PIV AND OTHER HUMAN PATHOGENS

BACKGROUND OF THE INVENTION

Human parainfluenza viruses (HPIVs) are important pathogens in human populations, causing severe lower respiratory tract infections in infants and young children. HPIV1 and HPIV2 are the principal etiologic agents of laryngotracheobronchitis (croup), and can also cause pneumonia and bronchiolitis (Collins et al., 3rd ed. *In "Fields Virology,"* B. N. Fields, D. M. Knipe, P. M. Howley, R. M. Chanock, J. L. Melnick, T. P. Monath, B. Roizman, and S. E. Straus, Eds., Vol. 1, pp. 1205-1243. Lippincott-Raven Publishers, Philadelphia, 1996). HPIV3 ranks second after respiratory syncytial virus (RSV) as a leading cause of hospitalization for viral lower respiratory tract disease in infants and young children (Collins et al., 3rd ed. *In "Fields Virology,"* B. N. Fields, D. M. Knipe, P. M. Howley, R. M. Chanock, J. L. Melnick, T. P. Monath, B. Roizman, and S. E. Straus, Eds., Vol. 1, pp. 1205-1243. Lippincott-Raven Publishers, Philadelphia, 1996; Crowe et al., *Vaccine* 13:415-421, 1995; Marx et al., *J. Infect. Dis.* 176:1423-1427, 1997).

PIVs are also important causes of respiratory tract disease in adults. Collectively, HPIV1, HPIV2, and HPIV3 have been identified through a 20 year study as responsible etiologic agents for approximately 18% of hospitalizations for pediatric respiratory tract disease (Murphy et al., *Virus Res.* 11:1-15, 1988). HPIVs have also been implicated in a significant proportion of cases of virally-induced middle ear effusions in children with otitis media (Heikkinen et al., *N. Engl. J. Med.* 340:260-4, 1999).

Despite considerable efforts to develop effective immunogenic compositions against HPIVs, no vaccines have yet been approved for any HPIV serotype, nor for ameliorating HPIV related illnesses. The most promising prospects to date are live attenuated vaccine viruses since these have been shown to be efficacious in non-human primates even in the presence of passively transferred antibodies, an experimental situation that simulates that present in the very young infant who possesses maternally acquired antibodies (Crowe et al., *Vaccine* 13:847-855, 1995; Durbin et al., *J. Infect. Dis.* 179:1345-1351, 1999). Two live attenuated PIV3 vaccine candidates, a temperature-sensitive (ts) derivative of the wild-type PIV3 JS strain (designated PIV3 cp45) and a bovine PIV3 (BPIV3) strain, are undergoing clinical evaluation (Karron et al., *Pediatr. Infect. Dis. J.* 15:650-654, 1996; Karron et al., *J. Infect. Dis.* 171:1107-1114, 1995a; Karron et al., *J. Infect. Dis.* 172, 1445-1450, 1995b). The live attenuated PIV3 cp45 vaccine candidate was derived from the JS strain of HPIV3 via serial passage in cell culture at low temperature and has been found to be protective against HPIV3 challenge in experimental animals and to be satisfactorily attenuated, genetically stable, and immunogenic in seronegative human infants and children (Belshe et al, *J. Med. Virol.* 10:235-242, 1982; Belshe et al., *Infect. Immun.* 37:160-5, 1982; Clements et al., *J. Clin. Microbiol.* 29:1175-82, 1991; Crookshanks et al., *J. Med. Virol.* 13:243-9, 1984; Hall et al., *Virus Res.* 22:173-184, 1992; Karron et al., *J. Infect. Dis.* 172:1445-1450, 1995b). Because these PIV3 candidate viruses for use in vaccines are biologically derived, there are no proven methods for adjusting the level of attenuation should this be found necessary from ongoing clinical trials.

To facilitate development of PIV vaccines, recombinant DNA technology has recently made it possible to recover infectious negative-stranded RNA viruses from cDNA (for reviews, see Conzelmann, *J. Gen. Virol.* 77:381-89, 1996; Palese et al., *Proc. Natl. Acad. Sci. U.S.A.* 93:11354-58, 1996). In this context, recombinant rescue of infectious virus has been reported for respiratory syncytial virus (RSV), rabies virus (RaV), canine distemper virus, mumps virus, infectious hematopoietic necrosis virus, simian virus 5 (SV5), rinderpest virus, Newcastle disease virus (NDV), vesicular stomatitis virus (VSV), measles virus (MeV), and Sendai virus (murine parainfluenza virus type 1 (MPIV1)) from cDNA-encoded genomic or antigenomic RNA in the presence of essential viral proteins (see, e.g., Garcin et al., *EMBO J.* 14:6087-6094, 1995; Lawson et al., *Proc. Natl. Acad. Sci. U.S.A.* 92:4477-81, 1995; Radecke et al., *EMBO J.* 14:5773-5784, 1995; Schnell et al., *EMBO J.* 13:4195-203, 1994; Whelan et al., *Proc. Natl. Acad. Sci. U.S.A.* 92:8388-92, 1995; Hoffman et al., *J. Virol.* 71:4272-4277, 1997; Kato et al., *Genes to Cells* 1:569-579, 1996, Roberts et al., *Virology* 247:1-6, 1998; Baron et al., *J. Virol.* 71:1265-1271, 1997; International Publication No. WO 97/06270; Collins et al., *Proc. Natl. Acad. Sci. U.S.A.* 92:11563-11567, 1995; Clarke et al., *J. Virol.* 74:4831-4838, 2000; Biacchesi et al., *J. Virol.* 74:11247-11253, 2000; Gassen et al., *J. Virol.* 74:10737-10744, 2000; U.S. patent application Ser. No. 08/892,403, filed Jul. 15, 1997 (corresponding to published International Application No. WO 98/02530 and priority U.S. Provisional Application No. 60/047,634, filed May 23, 1997, 60/046,141, filed May 9, 1997, and 60/021,773, filed Jul. 15, 1996); U.S. patent application Ser. No. 09/291,894, filed on Apr. 13, 1999; International Application No. PCT/US00/09695, filed Apr. 12, 2000 (which claims priority to U.S. Provisional Patent Application Ser. No. 60/129,006, filed Apr. 13, 1999); International Application No. PCT/US00/17755, filed Jun. 23, 2000 (which claims priority to U.S. Provisional Patent Application Ser. No. 60/143,132, filed by Bucholz et al. on Jul. 9, 1999); Juhasz et al., *J. Virol.* 71:5814-5819, 1997; He et al. *Virology* 237:249-260, 1997; Peters et al. *J. Virol.* 73:5001-5009, 1999; Baron et al. *J. Virol.* 71:1265-1271, 1997; Whitehead et al., *Virology* 247:232-9, 1998a; Whitehead et al., *J. Virol.* 72:4467-4471, 1998b; Jin et al. *Virology* 251:206-214, 1998; Bucholz et al. *J. Virol.* 73:251-259, 1999; and Whitehead et al., *J. Virol.* 73:3438-3442, 1999, each incorporated herein by reference in its entirety for all purposes).

Additional publications in the field of the invention report successful recovery of recombinant parainflunza viruses (PIVs), specifically HPIV2, HPIV3, and BPIV3 (see, e.g., Durbin et al., *Virology* 235:323-332, 1997; Schmidt et al., *J. Virol.* 74:8922-8929, 2000; Kawano et al., *Virology* 284:99-112, 2001; U.S. patent application Ser. No. 09/083,793, filed May 22, 1998 (corresponding to U.S. Provisional Application No. 60/059,385, filed Sep. 19, 1997); U.S. Provisional Application No. 60/412,053, filed Sep. 18, 2002; and U.S. Provisional Application No. 60/047,575, filed May 23, 1997 (corresponding to International Publication No. WO 98/53078), each incorporated herein by reference). These reports further address genetic manipulation of viral cDNA clones to determine the genetic basis of phenotypic changes in biological mutants, for example, which mutations in a biological mutant HPIV3 (JS cp45) virus specify its ts, ca and att phenotypes, and which gene(s) or genome segment(s) of BPIV specify its attenuation phenotype. Additionally, these and related publications discuss construction of novel PIV vaccine candidates having a wide range of different mutations, as well as methods for evaluating the level of attenuation, immunogenicity and phenotypic stability exhibited by such recombinant vaccine candidates (see also, U.S. application Ser. No. 09/586,479, filed Jun. 1, 2000 (corresponding to U.S. Provisional Patent Application Ser. No. 60/143,134, filed on Jul. 9, 1999); and U.S. patent application Ser. No. 09/350,821, filed by Durbin et al. on Jul. 9, 1999, each incorporated herein by reference).

Thus, infectious wild-type recombinant PIV3, (r)PIV3, as well as a number of ts and other modified derivatives, have now been recovered from cDNA. Reverse genetics systems have been used to generate infectious virus bearing defined mutations that specify attenuation and other desirable phenotypes, and to study the genetic basis of attenuation and other phenotypic changes in existing vaccine candidate viruses. For example, the three amino acid substitutions found in the L gene of cp45, singularly or in combination, have been found to specify the ts and attenuation phenotypes. Additional ts and other attenuating mutations can be introduced in other regions of the PIV3cp45 genome.

In addition, a chimeric PIV1 vaccine candidate has been generated using the PIV3 cDNA rescue system by replacing the PIV3 HN and F open reading frames (ORFs) with those of PIV1 in a PIV3 full-length cDNA, that optionally contains selected attenuating mutations. Exemplary recombinant chimeric viruses derived from these cDNA-based methods include a HPIV3-1 recombinant bearing all three identified mutations in the L gene, rPIV3-1.cp45L (Skiadopoulos et al., *J. Virol.* 72:1762-8, 1998; Tao et al., *J. Virol.* 72:2955-2961, 1998; Tao et al., *Vaccine* 17:1100-1108, 1999, incorporated herein by reference). rPIV3-1.cp45L was attenuated in hamsters and induced a high level of resistance to challenge with PIV. Yet another recombinant chimeric virus, designated rPIV3-1.cp45, has been produced that contains 12 of the 15 cp45 mutations, i.e., excluding the mutations that occur in HN and F. This recombinant vaccine candidate is highly attenuated in the upper and lower respiratory tract of hamsters and induces a high level of protection against HPIV1 infection (Skiadopoulos et al., *Vaccine* 18:503-510, 1999). However, for use against HPIV1, the immunogenicity of chimeric HPIV3-1 vaccine candidates against HPIV1 challenge is dampened in hosts that exhibit immune recognition of HPIV3.

Recently, a number of studies have focused on the possible use of viral vectors to express foreign antigens toward the goal of developing vaccines against a pathogen for which other vaccine alternatives are not proved successful. In this context, a number of reports suggest that foreign genes may be successfully inserted into a recombinant negative strand RNA virus genome or antigenome with varying effects (Bukreyev et al., *J. Virol.* 70:6634-41, 1996; Bukreyev et al., *Proc. Natl. Acad. Sci. U.S.A.* 96:2367-72, 1999; Finke et al. *J. Virol.* 71:7281-8, 1997; Hasan et al., *J. Gen. Virol.* 78:2813-20, 1997; He et al., *Virology* 237:249-60, 1997; Jin et al., *Virology* 251:206-14, 1998; Johnson et al., J. Virol. 71:5060-8, 1997; Kahn et al., *Virology* 254:81-91, 1999; Kretzschmar et al., *J. Virol.* 71:5982-9, 1997; Mebatsion et al., *Proc. Natl. Acad. Sci. U.S.A.* 93:7310-4, 1996; Moriya et al., *FEBS Lett.* 425:105-11, 1998; Roberts et al., *J. Virol.* 73:3723-32, 1999; Roberts et al., *J. Virol.* 72:4704-11, 1998; Roberts et al., *Virology* 247:1-6, 1998; Sakai et al., *FEBS Lett.* 456:221-226, 1999; Schnell et al., *Proc. Natl. Acad. Sci. U.S.A.* 93:11359-65, 1996a; Schnell et al., *J. Virol.* 70:2318-23, 1996b; Schnell et al., *Cell* 90:849-57, 1997; Singh et al., *J. Gen. Virol.* 80:101-6, 1999; Singh et al., *J. Virol.* 73:4823-8, 1999; Spielhofer et al., *J. Virol.* 72:2150-9, 1998; Yu et al., Genes to Cells 2:457-66 et al., 1999; Duprex et al., *J. Virol.* 74:7972-7979, 2000; Subash et al., *J. Virol.* 74:9039-9047, 2000; Krishnamurthy et al., *Virology* 278:168-182, 2000; Rose et al., *J. Virol.* 74:10903-10910, 2000; Tao et al., *J. Virol.* 74:6448-6458, 2000; McGettigan et al., *J. Virol.* 75:8724-8732, 2001; McGettigan et al., *J. Virol.* 75:4430-4434, 2001; Kahn et al., *J. Virol.* 75:11079-11087, 2001; Stope et al., *J. Virol.* 75:9367-9377, 2001; Huang et al., *J. Gen. Virol.* 82:1729-1736, 2001; Skiadopoulos et al., *J. Virol.* 75:10498-10504, 2001; Bukreyev et al., *J. Virol.* 75:12128-12140, 2001; U.S. patent application Ser. No. 09/614,285, filed Jul. 12, 2000 (corresponding to U.S. Provisional Patent Application Serial No. 60/143,425, filed on Jul. 13, 1999), each incorporated herein by reference). When inserted into the viral genome under the control of viral transcription gene-start and gene-end signals, the foreign gene may be transcribed as a separate mRNA and yield significant protein expression. Surprisingly, in some cases foreign sequence has been reported to be stable and capable of expressing functional protein during numerous passages in vitro.

In order to successfully develop vectors for vaccine use, however, it is insufficient to simply demonstrate a high, stable level of protein expression. For example, this has been possible since the early-to-mid 1980s with recombinant vaccinia viruses and adenoviruses, and yet these vectors have proven to be disappointing tools for developing vaccines for human use. Similarly, most nonsegmented negative strand viruses that have been developed as vectors have not been shown to be amenable for human vaccine use. Examples in this context include vesicular stomatitis virus, an ungulate pathogen with no history of administration to humans except for a few laboratory accidents; Sendai virus, a mouse pathogen with no history of administration to humans; simian virus 5, a canine pathogen with no history of administration to humans; and an attenuated strain of measles virus which must be administered systemically and would be neutralized by measles-specific antibodies present in nearly all humans due to maternal antibodies and widespread use of a licensed measles vaccine. Furthermore, some of these prior vector candidates have adverse effects, such as immunosupression, which are directly inconsistent with their use as vectors. Thus, one must identify vectors whose growth characteristics, tropisms, and other biological properties make them appropriate as vectors for human use. It is further necessary to develop a viable immunization strategy, including efficacious timing and route of administration.

Proposed mononegaviruses for use as vaccine vectors include measles, mumps, VSV, and rabies viruses. Each of these virues have serious limitations relating to their potential use as vaccine vectors. For example, measles virus has been considered for use a vector for the protective antigen of hepatitis B virus (Singh et al., *J. Virol.* 73:4823-8, 1999). However, this combined measles virus-hepatitis B virus vaccine candidate could only be administered after nine months of age, on a schedule comparable to the indicated schedule for the licensed measles virus vaccine, whereas the current hepatitis B virus vaccine is recommended for use in early infancy. This is because the currently licensed measles vaccine is administered parenterally and is sensitive to neutralization and immunosuppression by maternal antibodies, and therefore is not effective if administered before 9-15 months of age. Thus, measles virus is a poor vector for antigens of pathogenic agents that cause disease in early infancy, such as RSV and the HPIVs.

The attenuated measles virus vaccine has been associated with altered immune responses and excess mortality when administered at increased dosages, which may be due at least in part to virus-induced immunosuppression and indicates that even an attenuated measles virus may not be suitable for vaccine vector use. Furthermore, the use of measles virus as a vector would be inconsistent with the global effort to eradicate this pathogen. Indeed, for these reasons it would be desirable to end the use of live measles virus and replace the present measles virus vaccine with a suitable non-measles vector that expresses measles virus protective antigens.

Rabies virus, a rare cause of infection of humans, has been considered for use as a vector (Mebatsion et al., *Proc. Natl. Acad. Sci. USA* 93:7310-4, 1996), but it is unlikely that a virus that is so highly fatal as rabies for humans could be developed for use as a live attenuated virus vector. Moreover, immunity to the rabies virus, which is not a ubiquitous human pathogen, is not needed for the general population, whereas more desirable vectors should be capable of eliciting a multi specific immune response against both the vector virus and the pathogen for which the vector is used as a carrier of antigenic determinants. While mumps and measles viruses are less pathogenic than the rabies virus, infection by either of these other vector candidates can yield undesirable results. Mumps virus infects the parotid gland and can spread to the testes, sometimes resulting in sterility. Measles virus establishes a viremia with widespread infection and associated rash. Mild encephalitis during mumps and measles infection is not uncommon. Measles virus is also associated with a rare progressive fatal neurological disease called subacute sclerosing encephalitis.

In contrast to such vector candidates as rabies, measles and mumps, PIV infection and disease is typically more limited, in part by confinement of infection to the respiratory tract. Viremia and spread to secondary sites can occur in severely immunocompromised subjects, but this is not a typical effect of PIV infection. Acute respiratory tract disease is the only disease associated with PIVs. Thus, the use of PIVs as vectors will, on the basis of their biological characteristics, avoid complications such as interaction of virus with peripheral lymphocytes, leading to immunosuppression, or infection of secondary organs such as the testes or central nervous system, leading to other complications. These characteristics also render PIV a better vector candidate for successful immunization, which can be achieved more easily and effectively via alternate routes, such as direct administration to the respiratory tract, compared to immunization with vectors that require parental administration.

Among a host of human pathogens for which a vector-based vaccine approach may be desirable is the measles virus. A live attenuated vaccine has been available for more than three decades and has been largely successful in eradicating measles disease in the United States. However, the World Health Organization estimates that more than 45 million cases of measles still occur annually, particularly in developing countries, and the virus contributes to approximately one million deaths per year.

Measles virus is a member of the *Morbillivirus* genus of the Paramyxoviridae family (Griffin et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). It is one of the most contagious infectious agents known to man and is transmitted from person to person via the respiratory route (Griffin et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). The measles virus has a complex pathogenesis, involving replication in both the respiratory tract and various systemic sites (Griffin et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). Measles virus is discussed here as an exemplary pathogen for which a live attenuated vector vaccine is particularly desired. For reasons discussed in further detail herein below, a measles vaccine based on a recombinant HPIV1 vector system would satisfy a long-felt need in the art and fulfill an urgent need for additional effective vector systems to generate vaccines against other pathogens as well.

Although both mucosal IgA and serum IgG measles virus-specific antibodies can participate in the control of measles virus, the absence of measles virus disease in very young infants possessing maternally-acquired measles virus-specific antibodies identifies serum antibodies as a major mediator of resistance to disease (Griffin et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). The two measles virus glycoproteins, the hemagglutinin (HA) and fusion (F) proteins, are the major neutralization and protective antigens (Griffin et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996).

The currently available live attenuated measles vaccine is administered by a parenteral route (Griffin et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). Both the wild-type measles virus and the vaccine virus are very readily neutralized by antibodies, and the measles virus vaccine is rendered non-infectious by even very low levels of maternally-acquired measles virus-specific neutralizing antibodies (Halsey et al., *N. Engl. J. Med.* 313:544-9, 1985; Osterhaus et al., *Vaccine* 16:1479-81, 1998). Thus, the vaccine virus is not given until the passively-acquired maternal antibodies have decreased to undetectable levels. In the United States, measles virus vaccine is not given until 12 to 15 months of age, a time when almost all children are readily infected with the measles virus vaccine.

As noted above, measles virus continues to exact a heavy toll of mortality in developing countries, especially in children within the latter half of the first year of life (Gellin et al., *J. Infect. Dis.* 170:S3-14, 1994; Taylor et al., *Am. J. Epidemiol.* 127:788-94, 1988). This occurs because the measles virus, which is highly prevalent in these regions, is able to infect that subset of infants in whom maternally-acquired measles virus-specific antibody levels have decreased to a non-protective level. Therefore, there is a need for a measles virus vaccine that is able to induce a protective immune response even in the presence of measles virus neutralizing antibodies—with the goal of eliminating measles virus disease occurring within the first year of life as well as that which occurs thereafter. Given this need, there have been numerous attempts to develop an immunization strategy to protect infants in the latter half of the first year of life against measles virus, but none of these strategies has been effective to date.

The first strategy for developing an early measles vaccine involved administration of the licensed live attenuated measles virus vaccine to infants about six months of age by one of the following two methods (Cutts et al., *Biologicals* 25:323-38, 1997). In one general protocol, the live attenuated measles virus was administered intranasally by drops (Black et al., *New Eng. J. Med.* 263:165-169; 1960; Kok et al., *Trans. R. Soc. Trop. Med. Hvg.* 77:171-6, 1983; Simasathien et al., *Vaccine* 15:329-34, 1997) or into the lower respiratory tract by aerosol (Sabin et al., *J. Infect. Dis.* 152:1231-7, 1985), to initiate an infection of the respiratory tract. In a second protocol, the measles virus was given parenterally but at a higher dose than that employed for the current vaccine. The administration of vaccines that can replicate on mucosal surfaces has been successfully achieved in early infancy for both live attenuated poliovirus and rotavirus vaccines (Melnick et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 655-712. 2 vols. Lippencott-Raven Publishers, Philadelphia, 1996; Perez-Schael et al., *N. Engl. J. Med.* 337:1181-7, 1997), presumably because passively-acquired IgG antibodies have less access to mucosal surfaces than they do to systemic sites of viral replication. In this situation, the live attenuated poliovirus vaccine viruses are able to infect the mucosal surface of the gastrointestinal tract or the respiratory tract of young infants, including those with maternal antibodies, resulting in the induction of a protective immune response.

Therefore, a plausible method for measles immunization is to administer a live attenuated measles virus vaccine to the respiratory tract of the young infant, since this is the natural route of infection for the measles virus. However, the live attenuated measles virus that is infectious by the parenteral route was inconsistently infectious by the intranasal route (Black et al., *New Eng. J. Med.* 263:165-169, 1960; Cutts et al., *Biologicals* 25:323-38, 1997; Kok et al., *Trans. R. Soc. Trop. Med. Hyg.* 77:171-6, 1983; Simasathien et al., *Vaccine* 15:329-34, 1997), and this decreased infectivity was especially apparent for the Schwartz stain of measles virus vaccine which is the current vaccine strain. Presumably, during the attenuation of this virus by passage in tissue culture cells of avian origin, the virus lost a significant amount of infectivity for the upper respiratory tract of humans. Indeed, a hallmark of measles virus biology is that the virus undergoes rapid changes in biological properties when grown in vitro. Since this relatively simple route of immunization was not successful, a second approach was tried involving administration of the live virus vaccine by aerosol into the lower respiratory tract (Cutts et al., *Biologicals* 25:323-38, 1997; Sabin et al., *J. Infect. Dis.* 152:1231-7, 1985).

Infection of young infants by aerosol administration of measles virus vaccine was accomplished in highly controlled experimental studies, but it has not been possible to reproducibly deliver a live attenuated measles virus vaccine in field settings by aerosol to the young infant (Cutts et al., *Biologicals* 25:323-38, 1997). In another attempt to immunize six-month old infants, the measles vaccine virus was administered parenterally at a 10- to 100-fold increased dose (Markowitz et al., *N. Engl. J. Med.* 322:580-7, 1990). Although high-titer live measles vaccination improved seroconversion in infants 4-6 months of age, there was an associated increase in mortality in the high-titer vaccine recipients later in infancy (Gellin et al., *J. Infect. Dis.* 170:S3-14, 1994; Holt et al., *J. Infect. Dis.* 168:1087-96, 1993; Markowitz et al., *N. Engl. J. Med.* 322:580-7, 1990) and this approach to immunization has been abandoned.

A second strategy previously explored for a measles virus vaccine was the use of a formalin inactivated whole measles virus or a subunit virus vaccine prepared from measles virus (Griffin et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). However, the clinical use of these vaccines in the 1960's revealed a very serious complication, namely, that the inactivated virus vaccines potentiated disease rather than prevented it (Fulginiti et al., *JAMA* 202:1075-80, 1967). This was first observed with formalin-inactivated measles virus vaccine (Fulginiti et al., *JAMA* 202:1075-80, 1967). Initially, this vaccine prevented measles, but after several years vaccinees lost their resistance to infection. When subsequently infected with naturally circulating measles virus, the vaccinees developed an a typical illness with accentuated systemic symptoms and pneumonia (Fulginiti et al., *JAMA* 202:1075-80, 1967; Nader et al., *J. Pediatr.* 72:22-8, 1968; Rauh et al., *Am. J. Dis. Child* 109: 232-7, 1965). Retrospective analysis showed that formalin inactivation destroyed the ability of the measles fusion (F) protein to induce hemolysis-inhibiting antibodies, but it did not destroy the ability of the HA (hemagglutinin or attachment) protein to induce neutralizing antibodies (Norrby et al., *J. Infect. Dis.* 132:262-9, 1975; Norrby et al., *Infect. Immun.* 11:231-9, 1975). When the immunity induced by the HA protein had waned sufficiently to permit extensive infection with wild-type measles virus, an altered and sometimes more severe disease was seen at the sites of measles virus replication (Bellanti, *Pediatrics* 48:715-29, 1971; Buser, *N. Engl. J. Med.* 277:250-1, 1967). This a typical disease is believed to be mediated in part by an altered cell-mediated immune response in which Th-2 cells were preferentially induced leading to heightened disease manifestations at the sites of viral replication (Polack et al., *Nat. Med.* 5:629-34, 1999). Because of this experience with nonliving measles virus vaccines and also because the immunogenicity of such parenterally-administered vaccines can be decreased by passively-transferred antibodies, there has been considerable reluctance to evaluate such vaccines in human infants. It should be noted that disease potentiation appears to be associated only with killed vaccines.

An alternative approach to development of a vaccine vector for measles employed a replication-competent vesicular stomatitis virus (VSV), a rhabdovirus which naturally infects cattle but not humans, expressing the measles virus HA protein. This vector candidate virus was shown to replicate in the respiratory tract of animal hosts (Roberts et al., *J. Virol.* 73:3723-32, 1999; Schnell et al., *Proc. Natl. Acad. Sci. U.S.A.* 93:11359-65, 1996a). However, since VSV is an animal virus that can cause disease in humans, development of this recombinant vector for use in humans will first require that a VSV backbone that is satisfactorily attenuated in human infants be first identified (Roberts et al., *J. Virol.* 73:3723-32, 1999).

Yet another strategy that has been explored for developing a vaccine against measles for use in young infants has been the use of viral vectors to express a protective antigen of the measles virus (Drillien et al., *Proc. Natl. Acad. Sci. U.S.A.* 85:1252-6, 1988; Fooks et al., *J. Gen. Virol.* 79:1027-31, 1998; Schnell et al., *Proc. Natl. Acad. Sci. U.S.A.* 93:11359-65, 1996a; Taylor et al., *Virology* 187:321-8, 1992; Wild et al., *Vaccine* 8:441-2, 1990; Wild et al., *J. Gen. Virol.* 73:359-67, 1992). A variety of vectors have been explored including pox viruses, such as the replication-competent vaccinia virus or the replication-defective modified vaccinia virus Ankara (MVA) stain. Replication-competent vaccinia recombinants expressing the F or HA glycoprotein of measles virus were efficacious in immunologically naive vaccinees. However, when they were administered parenterally in the presence of passive antibody against measles virus, their immunogenicity and protective efficacy was largely abrogated (Galletti et al., *Vaccine* 13:197-201, 1995; Osterhaus et al., *Vaccine* 16:1479-81, 1998; Siegrist et al., *Vaccine* 16:1409-14, 1998; Siegrist et al., *Dev. Biol. Stand.* 95:133-9, 1998).

Replication-competent vaccinia recombinants expressing the protective antigens of RSV have also been shown to be ineffective in inducing a protective immune response when they are administered parenterally in the presence of passive antibody (Murphy et al., *J. Virol.* 62:3907-10, 1988a), but they readily protected such hosts when administered intranasally. Unfortunately, replication-competent vaccinia virus recombinants are not sufficiently attenuated for use in immunocompromised hosts such as persons with human immunodeficiency virus (HIV) infection (Fenner et al., World Health Organization, Geneva, 1988; Redfield et al., *N. Engl. J. Med.* 316:673-676, 1987), and their administration by the intranasal route even to immunocompetent individuals would be problematic. Therefore they are not being pursued as vectors for use in human infants, some of whom could be infected with HIV.

The MVA vector, which was derived by more than 500 passages in chick embryo cells (Mayr et al., *Infection* 3:6-14, 1975; Meyer et al., *J. Gen. Virol.* 72:1031-1038, 1991), has also been evaluated as a potential vaccine vector for the protective antigens of several paramyxoviruses (Durbin et al., *J. Infect. Dis.* 179:1345-51, 1999a; Wyatt et al., *Vaccine* 14:1451-1458, 1996). MVA is a highly attenuated host range mutant that replicates well in avian cells but not in most mammalian cells, including those obtained from monkeys and humans (Blanchard et al., *J. Gen. Virol.* 79:1159-1167, 1998; Carroll et al., *Virology* 238:198-211, 1997; Drexler et al., *J. Gen. Virol.* 79:347-352, 1998; Sutter et al., *Proc. Natl. Acad. Sci. U.S.A.* 89:10847-10851, 1992). Avipox vaccine vectors, which have a host range restriction similar to that of MVA, also have been constructed that express measles virus protective antigens (Taylor et al., *Virology* 187:321-8, 1992). MVA is non-pathogenic in immunocompromised hosts and has been administered to large numbers of humans without incident (Mayr et al., *Zentralbl. Bakteriol.* [B] 167:375-90, 1978; Stickle et al., *Dtsch. Med. Wochenschr.* 99:2386-92, 1974; Werner et al., *Archives of Virology* 64:247-256, 1980). Unfortunately, both the immunogenicity and efficacy of MVA expressing a paramyxovirus protective antigen were abrogated in passively-immunized rhesus monkeys whether delivered by a parenteral or a topical route (Durbin et al., *Virology* 235:323-332, 1999). The immunogenicity of DNA vaccines expressing measles virus protective antigens delivered parenterally was also decreased in passively-immunized hosts (Siegrist et al., *Dev. Biol. Stand.* 95:133-9, 1998). Replication-defective vectors expressing measles virus protective antigens are presently being evaluated, including adenovirus-measles virus HA recombinants (Fooks et al., *J. Gen. Virol.* 79:1027-31, 1998). In this context, MVA recombinants expressing parainfluenza virus antigens, unlike replication-competent vaccinia virus recombinants, lacked protective efficacy when given by a mucosal route to animals with passively-acquired antibodies, and it is unlikely that they, or the similar avipox vectors, can be used in infants with maternally-acquired measles virus antibodies. Based on these reports, it is not expected that poxvirus vectors or DNA vaccines expressing a measles virus protective antigens will be satisfactorily immunogenic or efficacious in infants that possess passively-acquired maternal measles virus-specific antibodies.

More recent developments in the field of negative stranded RNA viral vaccines have involved the use of HPIV3-based vaccine vectors to deliver antigenic determinants of heterologous pathogens, including heterologous PIVs. In particular, recombinant HPIV3 vaccine candidates have been disclosed that use a HPIV3 "vector" genome or antigenome combined with one or more heterologous genes of a different PIV, or of a non-PIV pathogen to form a chimeric, bivalent or multivalent, HPIV3 vaccine candidate (see, e.g., Durbin et al., *Virology* 235:323-332, 1997; Skiadopoulos et al., *J. Virol.* 72:1762-1768, 1998; Skiadopoulos et al., *J. Virol.* 73:1374-1381, 1999; Tao et al., *Vaccine* 19:3620-3631, 2001; Durbin et al., *J. Virol.* 74:6821-6831, 2000; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), U.S. Provisional Application No. 60/059,385, filed Sep. 19, 1997; U.S. Provisional Application No. 60/170,195 filed Dec. 10, 1999; and U.S. patent application Ser. No. 09/733,692, filed Dec. 8, 2000 (corresponding to International Publication No. WO 01/42445A2), each incorporated herein by reference. The recombinant HPIV3 viruses are engineered to incorporate one or more heterologous donor sequences encoding one or more antigenic determinants of a different PIV or heterologous pathogen to produce an infectious, chimeric, bivalent or multivalent virus or subviral particle. In this manner, candidate HPIV3-based chimeric vaccine viruses can be made to elicit an immune response against one or more PIVs or a polyspecific response against a selected PIV and a non-PIV pathogen in a mammalian host susceptible to infection therefrom. Various modifications to chimeric HPIV3 vaccine candidates are reported to yield desired phenotypic effects, such as attenuation.

Although there have been numerous advances toward development of effective vaccine agents against PIV and other pathogens, including measles, there remains a clear need in the art for additional tools and methods to engineer safe and effective immunogenic compositions to alleviate the serious health problems attributable to these pathogens, particularly among young infants. Among the remaining challenges in this context is the need for additional tools to generate suitably attenuated, immunogenic and genetically HPIV1 candidates for use in diverse clinical settings against one or more pathogens. Additional challenges arise from the fact that HPIV1, HPIV2, and HPIV3 represent distinct viral serotypes, that do not elicit significant cross-protective immunity. Accordingly, there is an urgent need in the art for new immunogenic compositions and methods directed against multiple HPIV serotypes to treat, prevent, or alleviate the frequency or severity of the serious lower respiratory tract disease and the otitis media that accompanies different HPIV infections. To facilitate these goals, existing methods for identifying and incorporating attenuating mutations into recombinant viral strains and for developing vector-based immunogenic compositions and immunization methods must be expanded. In this context, it is particularly desirable to develop a method for recovery and genetic manipulation of HPIV1, to generate immunogenic compositions to elicit immune responses against this important human PIV, and to provide additional tools to generate novel vectors and immunization methods. Surprisingly, the present invention satisfies these needs and fulfills additional objects and advantages as described herein below.

SUMMARY OF THE INVENTION

The instant invention provides methods and compositions for recovering infectious, recombinant human parainfluenza virus type 1 (HPIV1). The invention also provides novel tools and methods for introducing defined, predetermined structural and phenotypic changes into an infectious HPIV1 recombinant virus or viral particle for use within immunogenic compositions and methods for stimulating immune responses in hosts succeptible to infection by an HPIV or other human pathogen.

In one embodiment of the invention, methods are provided for producing an infectious, self-replicating, recombinant human parainfluenza virus type 1 (HPIV1) from one or more isolated polynucleotide molecules encoding the virus. The methods generally involve coexpressing in a cell or cell-free system one or more expression vector(s) comprising a polynucleotide molecule that encodes a partial or complete, recombinant HPIV1 genome or antigenome and one or more polynucleotide molecules encoding PIV N, P and L proteins, so as to produce an infectious HPIV1 virus or viral particle.

Typically, the polynucleotide molecule that encodes the recombinant HPIV1 genome or antigenome is a cDNA. Thus, the invention is directed in more detailed aspects to such novel polynucleotides and their equivalents that encode a recombinant HPIV1, as disclosed herein. Likewise, the invention embraces expression vectors and constructs that incorporate a polynucleotide molecule encoding a recombinant HPIV1 genome or antigenome.

The HPIV1 genome or antigenome, and the N, P, and L proteins may all be produced from a single expression vector. More typically, the genome or antigenome is produced by a separate expression vector, and the N, P, and L proteins are produced by one, two, or three additional expression vector(s). In certain embodiments, one or more of the N, P and L proteins is supplied by expression of a recombinant HPIV genome or antigenome of the invention, or by coinfection with the same or different PIV. In alternate embodiments, one or more of the N, P and L proteins are from a heterologous PIV (e.g., HPIV1 or HPIV3).

The invention further embraces infectious, recombinant, self-replicating viral particles produced according to the foregoing methods, which particles include complete viruses as well as viruses that lack one or more non-essential protein(s) or non-essential portion(s) (e.g., a cytoplasmic, transmembrane or extracellular domain) of a viral protein. Viruses of the invention that lack one or more such non-essential component(s) (e.g., a gene or genome segment from one or more of the PIV C, C', Y1, and/or Y2 open reading frames (ORFs) or other auxiliary gene) are referred to herein as incomplete viruses or "subviral particles." Exemplary subviral particles may lack a selected structural element, e.g., a gene segment, gene, protein, or protein functional domain, which is present in a complete virus (eg., an assembled virion including a complete genome or antigenome, nucleocapsid and envelope). For example, a subviral particle of the invention may comprise an infectious nucleocapsid containing a genome or antigenome, and the products of N, P, and L genes. Other subviral particles are produced by partial or complete deletions or substitutions of non-essential genes and/or their products (eg., C, C', Y1 or Y2), among other non-essential structural elements.

Complete viruses and subviral particles produced according to the methods of the invention are infectious and self-replicative through multiple rounds of replication in a mammalian host amenable to infection by PIV, including various in vitro mammalian cell populations, in vivo animal models widely known and accepted in the art as reasonably predictive of PIV activity, infection and/or immunogenicity in humans (including, mice, hamsters, cotton rats, non-human primates including African green monkeys and chimpanzees), including seronegative and seropositive infants, children, juveniles, immunocompromized individuals, and/or adults.

In certain detailed aspects of the invention, the polynucleotide molecule enconding the recombinant HPIV1 genome or antigenome encodes a sequence of a wild-type HPIV1. Alternatively, the genome or antigenome may bear one or more mutations from a biologically derived mutant HPIV1, or any combination of recombinantly-introduced mutation(s); including one or more polynucleotide insertions, deletions, substitutions, or rearrangements that is/are selected to yield desired phenotypic effect(s) in the recombinant virus.

Thus, the recombinant HPIV1 genome or antigenome may be engineered according to the methods of the invention to incorporate a recombinantly-introduced restriction site marker, or a translationally silent point mutation for handling or marking purposes. In other embodiments, the polynucleotide molecule encoding the recombinant HPIV1 genome or antigenome may incorporate one or more recombinantly-introduced attenuating mutations. In exemplary embodiments, the recombinant HPIV1 genome or antigenome incorporates one or more recombinantly-introduced, temperature sensitive (ts) or host range (hr) attenuating (att) mutations.

Often, the recombinant HPIV1 genome or antigenome will incorporate one or more attenuating mutation(s) identified in a biologically derived mutant PIV strain, or in another mutant nonsegmented negative stranded RNA virus, for example RSV or murine PIV (MPIV). For example, the recombinant HPIV1 genome or antigenome can be modified or constructed to incorporate one or more mutation(s) corresponding to mutation(s) identified in a HPIV1, or a heterologous PIV such as the well known immunogenic composition candidate HPIV3 JS cp45. Useful mutations of HPIV3 JS cp45 or another mutant virus can specify a change in a HPIV1 protein selected from L, M, N, C, F, or HN or in a HPIV1 extragenic sequence selected from a 3' leader or N gene start sequence. Where the mutation relates to a particular amino acid residue, the recombinant HPIV1 genome or antigenome will often incorporate multiple nucleotide changes in a codon specifying the mutation to stabilize the modification against reversion.

In additional aspects of the invention, the recombinant HPIV1 genome or antigenome comprises an additional nucleotide modification specifying a phenotypic change selected from a change in growth characteristics, attenuation, temperature-sensitivity, cold-adaptation, plaque size, host-range restriction, or a change in immunogenicity. These additional modifications can alter one or more of the HPIV1 N, P, C, C', Y1, Y2, M, F, HN and/or L genes and/or a 3' leader, 5' trailer, a cis-acting sequence such as a gene start (GS) or gene end (GE) sequence, and/or intergenic region within the HPIV1 genome or antigenome. For example, one or more HPIV1 gene(s) can be deleted in whole or in part, or expression of the gene(s) can be reduced or ablated by a mutation in an RNA editing site, by a frameshift mutation, by a mutation that alters a translation start site, by introduction of one or more stop codons in an open reading frame (ORF) of the gene, or by a mutation in a transcription signal. In specific embodiments, the recombinant HPIV1 genome or antigenome is modified by a partial or complete deletion of one or more C, C', Y1, and/or Y2 ORF(s) or other auxiliary gene, or one or more nucleotide change(s) that reduces or ablates expression of one or more of the C, C', Y1, and/or Y2 ORF(s) or other auxiliary gene. In other embodiments, the recombinant HPIV1 genome or antigenome is modified to encode a non-PIV molecule selected from a cytokine, a T-helper epitope, a restriction site marker, or a protein of a microbial pathogen capable of eliciting an immune response in a mammalian host.

In yet additional aspects of the invention, the recombinant HPIV1 genome or antigenome comprises a partial or complete HPIV1 "vector" genome or antigenome that is combined with one or more heterologous gene(s) or genome segment(s) encoding one or more antigenic determinant(s) of one or more heterologous pathogen(s) to form a chimeric HPIV1 genome or antigenome. The heterologous gene(s) or genome segment(s) encoding the antigenic determinant(s) can be added as supernumerary gene(s) or genome segment(s) adjacent to or within a noncoding region of the partial or complete HPIV1 vector genome or antigenome, or can be substituted for one or more counterpart gene(s) or genome segment(s) in a partial HPIV1 vector genome or antigenome. The heterologous gene(s) or genome segment(s) can include one or more heterologous coding sequences and/or one or more heterologous regulatory element(s) comprising an extragenic 3' leader or 5' trailer region, a gene-start signal, gene-end signal, editing region, intergenic region, or a 3' or 5' non-coding region.

In more detailed embodiments, the heterologous pathogen is one or more heterologous PIV(s) (e.g., HPIV2 and/or HPIV3) and the heterologous gene(s) or genome segment(s) encode(s) one or more PIV N, P, C, C', Y1, M, F, HN and/or L protein(s) or fragment(s) thereof. Thus, the antigenic determinant(s) may be selected from HPIV2 and HPIV3 HN and F glycoproteins, and antigenic domains, fragments and epitopes thereof, is/are added to or substituted within the partial or complete HPIV1 genome or antigenome. In certain exemplary embodiments, genes encoding HN and F glycoproteins of HPIV3 or HPIV2 are substituted for counterpart HPIV1 HN and F genes in a partial HPIV1 vector genome or antigenome. In more detailed embodiments, the partial or complete HPIV1 genome or antigenome is modified to incorporate one or more gene(s) or genome segment(s) encoding one or more antigenic determinant(s) of HPIV2, and one or more gene(s) or genome segment(s) encoding one or more antigenic determinant(s) of HPIV3, to yield a chimeric HPIV1 capable of eliciting an immune response against HPIV2 and HPIV3 in a mammalian host. In this manner, a plurality of heterologous genes or genome segments encoding antigenic determinants of multiple heterologous PIVs can be added to or incorporated within the partial or complete HPIV vector genome or antigenome.

In related embodiments of the invention, chimeric HPIV1 viruses are provided wherein the vector genome is combined with one or more heterologous antigenic determinant(s) of a heterologous pathogen selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumoviruses, and influenza viruses. In exemplary aspects, the heterologous antigenic determinant(s) is/are selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein, filovirus G protein, bunyavirus G protein, flavivirus pre M, E, and NS1 proteins, human metapneuomovirus G and F protein, and alphavirus E protein, and antigenic domains, fragments and epitopes thereof. In certain specific embodiments, the heterologous pathogen is measles virus and the heterologous antigenic determinant(s) is/are selected from the measles virus HA and F proteins and antigenic domains, fragments and epitopes thereof. For example, a transcription unit comprising an open reading frame (ORF) of a measles virus HA gene can be added to or incorporated within a HPIV1 vector genome or antigenome to yield a chimeric viral candidate useful in immunogenic compositions to elicit an immune response against measles and/or HPIV1 or another HPIV.

In additional embodiments, the partial or complete HPIV1 vector genome or antigenome is modified to incorporate one or more supernumerary heterologous gene(s) or genome segment(s) to form the chimeric HPIV1 genome or antigenome. Typically, the supernumerary gene(s) or genome segments(s) encode(s) one or more heterologous antigenic determinant(s), although non-coding inserts are also useful within recombinant, chimeric HPIV1 of the invention. In exemplary embodiments, one or more supernumerary heterologous gene(s) or genome segment(s) may be selected from HPIV2 HN, HPIV2 F, HPIV3 HN, HPIV3 F, measles HA and F, and/or RSV subgroup A or B G and F proteins. These and other supernumerary heterologous gene(s) or genome segment(s) can be inserted at various sites within the recombinant genome or antigenome, for example at a position 3' to N, between the N/P, P/M, and/or HN/L genes, or at another intergenic junction or non-coding region of the HPIV1 vector genome or antigenome.

In more detailed embodiments, the chimeric HPIV1 genome or antigenome is engineered to encode protective antigens from one, two, three or four pathogens. For example, the genome or antigenome may encode protective antigens from up to four different pathogens selected from a HPIV1, HPIV2, HPIV3, measles virus, respiratory syncytial virus, mumps virus, human papilloma virus, type 1 or type 2 human immunodeficiency virus, herpes simplex virus, cytomegalovirus, rabies virus, Epstein Barr Virus, filovirus, bunyavirus, flavivirus, alphavirus, human metapneumovirus, or influenza virus.

Where a gene or genome segment is added or substituted to or within a recombinant HPIV1 genome or antigenome of the invention, it may be added or substituted at a position corresponding to a wild-type gene order position of a counterpart gene or genome segment within the partial or complete HPIV1 genome or antigenome, which is often the case when chimeric HPIV1 are generated by addition or substitution of a heterologous gene or genome segment into a partial or complete HPIV1 vector genome or antigenome. Alternatively, the added or substituted (e.g., heterologous) gene or genome segment can be located at a position that is more promoter-proximal or promoter-distal compared to a wild-type gene order position of a counterpart gene or genome segment within the partial or complete HPIV1 background genome or antigenome.

In additional aspects of the invention, chimeric HPIV1 viral candidates for use in immunogenic compositions are provided wherein the HPIV1 vector genome or antigenome is modified to encode a chimeric glycoprotein incorporating one or more heterologous antigenic domains, fragments, or epitopes of a heterologous PIV, or of a non-PIV pathogen to form a chimeric genome or antigenome. In certain embodiments, the HPIV1 vector genome or antigenome is modified to encode a chimeric glycoprotein incorporating one or more antigenic domains, fragments, or epitopes from a second, antigenically distinct PIV to form the chimeric genome or antigenome. Additional embodiments include a chimeric HPIV1 wherein the genome or antigenome encodes a chimeric glycoprotein having antigenic domains, fragments, or epitopes from two or more HPIVs. In one example, the heterologous genome segment encodes a glycoprotein cytoplasmic, transmembrane or ectodomain which is substituted for a corresponding glycoprotein domain in the HPIV1 vector genome or antigenome. In more specific embodiments, one or more heterologous genome segment(s) of a second, antigenically distinct HPIV encoding one or more antigenic domains, fragments, or epitopes is/are substituted within a HPIV1 vector genome or antigenome to encode said chimeric glycoprotein. For example, the one or more heterologous genome segment(s) can be selected from ectodomains of HPIV2 and/or HPIV3 HN and/or F glycoproteins.

The chimeric HPIV1 candidates of the invention will typically be modified as described above for non-chimeric HPIV1 recombinants, e.g., by introduction of one or more attenuating mutations identified in a biologically derived mutant PIV or other mutant nonsegmented negative stranded RNA virus. Thus, the HPIV1 genome or antigenome, or the chimeric HPIV1 genome or antigenome, can be modified to incorporate one or more point mutation(s), for example point mutations in one or more non-coding nucleotides or point mutations specifying an amino acid substitution, deletion or insertion, such as are identified in HPIV3 JS cp45.

In other embodiments, the chimeric HPIV1 genome or antigenome is modified to incorporate an attenuating mutation at an amino acid position corresponding to an amino acid position of an attenuating mutation identified in a heterologous, mutant nonsegmented negative stranded RNA virus, for example, respiratory syncitial virus (RSV) or murine parainfluenza virus type 1 (MPIV1).

In yet additional detailed embodiments, the chimeric HPIV1 genome or antigenome is further modified to incorporate an additional nucleotide modification specifying a phenotypic change selected from a change in growth characteristics, attenuation, temperature-sensitivity, cold-adaptation, plaque size, host-range restriction, or a change in immunogenicity. Such additional nucleotide modifications can alter one or more ORFs, including but not limited to the HPIV1 N, P, C, C', Y1, Y2, M, F, HN and/or L ORFs and/or a 3' leader, 5' trailer, and/or intergenic region within the HPIV1 genome or antigenome. In exemplary embodiments, the chimeric HPIV1 genome or antigenome is further modified such that one or more HPIV1 gene(s) is/are deleted in whole or in part or expression of the gene(s) is reduced or ablated by a mutation in an RNA editing site, by a frameshift mutation, by a mutation that alters a translation start site, by introduction of one or more stop codons in an open reading frame (ORF) of the gene, or by a mutation in a transcription signal. Often, the chimeric HPIV1 genome or antigenome will be engineered to incorporate a a partial or complete deletion of one or more C, C', Y1, and/or Y2 ORF(s) or other auxiliary gene, or one or more nucleotide change(s) that reduces or ablates expression of said one or more of the C, C', Y1, and/or Y2 ORF(s) or other auxillary gene. In other aspects, the chimeric HPIV1 genome or antigenome is modified to encode a non-PIV molecule selected from a cytokine, a T-helper epitope, a restriction site marker, or a protein of a microbial pathogen capable of eliciting a detectable immune response in a mammalian host.

In still other aspects of the invention, the recombinant HPIV1 genome or antigenome is recombinantly modified to form a human-bovine chimeric HPIV1 genome or antigenome, to yield a human-bovine chimeric candidate for use in immunogenic compositions having novel phenotypic properties, e.g., increased genetic stability, or altered attenuation, reactogenicity or growth in culture. Such recombinants may be produced by constructing a partial or complete HPIV1 vector genome or antigenome combined with one or more heterologous genes or genome segments from a bovine parainfluenza virus (BPIV). For example, the partial or complete HPIV1 vector genome or antigenome can be combined with one or more heterologous gene(s) or genome segment(s) of a N, P, L, or M gene of a BPIV3 to form a human-bovine chimeric genome or antigenome and produce novel recombinant viruses having a host-range (hr) attenuation phenotype. In more detailed embodiments, a bovine PIV type 3 (BPIV3) N, M, L, or P open reading frame (ORF) or a genome segment thereof is substituted for a counterpart HPIV1 N, M, L, or P ORF or genome segment to form the chimeric HPIV1-BPIV genome or antigenome. Alternateively, the PIV from which the heterologous gene(s) or genome segment(s) are donated to form the chimeric virus can be murine parainfluenza virus (MPIV).

In further aspects of the invention, the recombinant HPIV1 genome or antigenome incorporates a polynucleotide insertion of between 150 nucleotides (nts) and 4,000 nucleotides in length in a non-coding region (NCR) of the genome or antigenome or as a separate gene unit (GU). The recombinant HPIV1 candidates comprising NCR and GU inserts replicate efficiently in vitro and typically exhibit an attenuated phenotype in vivo. The polynucleotide insertion will typically lack a complete open reading frame (ORF) and will often specify an attenuated phenotype in the recombinant HPIV1. The polynucleotide insert can be introduced into the HPIV1 genome or antigenome in a reverse, non-sense orientation whereby the insert does not encode protein. In more specific embodiments, the polynucleotide insert is approximately 2,000 nts, 3,000 nts, or greater in length. In other embodiments, the polynucleotide insertion adds a total length of foreign sequence to the recombinant HPIV1 genome or antigenome of 30% to 50% or greater compared to the wild-type HPIV1 genome length of 15,600 nt. In more detailed aspects, the polynucleotide insertion specifies an attenuation phenotype of the recombinant HPIV1 which exhibits at least a 10-to 100-fold decrease in replication in the upper and/or lower respiratory tract.

In other embodiments of the invention polynucleotide molecules that encode, or correspond, to a recombinant HPIV1 or chimeric HPIV1 genome or antigenome as described above are provided. In additional embodiments, polynucleotide expression vectors or constructs comprising a polynucleotide encoding a recombinant HPIV1 or chimeric HPIV1 genome or antigenome as described above and operably connected to expression regulatory sequences (e.g., promotor and terminator sequences) to direct expression of the vector in suitable host cell or cell-free expression system. In yet additional embodiments, a cell or cell-free expression system (e.g., a cell-free lysate) is provided which incorporates an expression vector comprising an isolated polynucleotide molecule encoding a recombinant HPIV1 genome or antigenome, as described above, and optionally including an expression vector comprising one or more isolated polynucleotide molecules encoding N, P, and L proteins of a PIV. One or more of the N, P, and L proteins may be expressed from HPIV1 or from a heterologous PIV. Upon expression, the genome or antigenome and N, P, and L proteins combine to produce an infectious HPIV particle, such as a viral or subviral particle. The isolated polynucleotide molecules encoding the HPIV1 genome or antigenome and the one or more isolated polynucleotide molecules encoding N, P, and L proteins of PIV can be expressed by a single vector. Alternatively, the genome and one or more of the N, P, and L proteins can be incorporated into two or more separate vectors.

The recombinant HPIV1 viruses of the invention are useful in various compositions to generate a desired immune response against one or more PIVs, or against PIV and a non-PIV pathogen, in a host susceptible to infection therefrom. Recombinant HPIV1 as disclosed herein are capable of eliciting a mono- or poly-specific immune response in an infected mammalian host, yet are sufficiently attenuated so as to not cause unacceptable symptoms of disease in the immunized host. The attenuated viruses, including subviral particles, may be present in a cell culture supernatant, isolated from the culture, or partially or completely purified. The virus may also be lyophilized, and can be combined with a variety of other components for storage or delivery to a host, as desired.

The invention further provides novel immunogenic compositions comprising a physiologically acceptable carrier and/or adjuvant and an isolated attenuated recombinant HPIV1 virus as described above. In preferred embodiments, the immunogenic composition is comprised of a recombinant HPIV1 having at least one, and preferably two or more attenuating mutations or other nucleotide modifications that specify a suitable balance of attenuation and immunogenicity, and optionally additional phenotypic characteristics. The composition can be formulated in a dose of $10^3$ to $10^7$ PFU of attenuated virus. The composition may comprise attenuated recombinant HPIV1 that elicits an immune response against a single PIV strain or against multiple PIV strains or groups. In this regard, recombinant HPIV1 can be combined in immunogenic compositions with other PIV strains, or with other viruses such as a live attenuated RSV.

In related aspects, the invention provides a method for stimulating the immune system of an individual to elicit an immune response against one or more PIVs, or against PIV and a non-PIV pathogen, in a mammalian subject. The method comprises administering a formulation of an immunologically sufficient amount of a recombinant HPIV1 in a physiologically acceptable carrier and/or adjuvant. In one embodiment, the immunogenic composition is comprised of a recombinant HPIV1 having at least one, and preferably two or more attenuating mutations or other nucleotide modifications specifying a desired phenotype and/or level of attenuation as described above. The composition can be formulated in a dose of $10^3$ to $10^7$ PFU of attenuated virus. The composition may comprise a recombinant HPIV1 that elicits an immune response against a single PIV, against multiple PIVs, e.g., HPIV1 and HPIV3, or against one or more PIV(s) and a non-PIV pathogen such as measles or RSV.

In this context, recombinant HPIV1 viruses of the invention can elicit a monospecific immune response or a polyspecific immune response against multiple PIVs, or against one or more PIV(s) and a non-PIV pathogen. Alternatively, recombinant HPIV1 having different immunogenic characteristics can be combined in an immunogenic composition or administered separately in a coordinated treatment protocol to elicit more effective immune responses against one PIV, against multiple PIVs, or against one or more PIV(s) and a non-PIV pathogen such as measles or RSV. Typically, the immunogenic compositions of the invention are administered to the upper respiratory tract, e.g., by spray, droplet or aerosol.

BRIEF DESCRIPTION OF THE DRAWINGS

FIG. 1 provides a diagram of the assembled cDNA clone, pFLCHPIV1, that yields the antigenomic RNA of HPIV1 WASH/64 when transcribed by T7 RNA polymerase. Restriction sites along with their nucleotide positions that were used to assemble the clone are shown above the boxed diagram of the viral genome. The T7 polymerase promoter (T7) (light shaded box) and two non-viral G residues that enhance transcription (Durbin et al., *Virology* 234:74-83, 1997, incorporated herein by reference) flank the upstream end of the antigenome, and the hepatitis delta virus ribozyme sequence (Aribo)(darkly shaded box) flanks the downstream end.

FIG. 2 provides nucleotide sequences (negative-sense, 3' to 5') covering the first 96 nucleotides (nts) at the 3' end (Panel A) (SEQ ID NOS 1-4, respectively in order of appearance) and last 96 nt at the 5' end (Panel B) of the genomic RNA of the following strains of PIV: HPIV1 WASH/64, MPIV1 Z, HPIV3 JS, and BPIV3 KA. The sequences are shown as hexamers, consistent with the rule of six (Vulliemoz et al., *J. Virol.* 75:4506-45 18, 2001, incorporated herein by reference) and are numbered according to the distance from the 3' (Panel A) or the 5' end (Panel B) (SEQ ID NOS 5-8, respectively in order of appearance) of the genomic vRNA. Bold-faced nucleotide positions represent residues that are conserved among the four viruses. Regions of MPIV1 that are important for viral replication and transcription are underlined in both panels (Calain et al., *Virology* 212:163-173, 1995; Vulliemoz et al., *J. Virol.* 75:4506-4518, 2001, each incorporated herein by reference). The 3'-leader (Panel A), 5'-trailer (Panel B), the N gene untranslated (N-UTR) (Panel A), and the L gene untranslated (L-UTR) (Panel B) regions are identified. The N gene-start (Panel A) and the L gene-end (Panel B) signals are boxed, and the intergenic-like triplet that preceeds the N gene-start and follows the L gene-end signal is identified ("IG") and italicized. The black-shaded C residues in panel A are part of a CNNNNN motif that is important for MPIV1 replication (Tapparel et al., *J. Virol.* 72:3117-3128, 1998, incorporated herein by reference). In panel B, this motif occurs as NNNNNG, since the sequence shown is the complement of the 3'-end of the antigenome.

FIG. 3 provides nucleotide sequences (negative-sense, 3' to 5') of the gene-start, gene-end, and intergenic transcriptional signals of HPIV1 WASH/64 (SEQ ID NOS 9-10, 17-18, 25-26, 33-34, 41-42, and 49-50, respectively in order of appearance), MPIV1 Z (SEQ ID NOS 11-12, 19-20, 27-28, 35-36, 43-44, and 51-52, respectively in order of appearance), HPIV3 JS (SEQ ID NOS 13-14, 21-22, 29-30, 37-38, 45-46, and 53-54, respectively in order of appearance), and BPIV3 KA (SEQ ID NOS 15-16, 23-24, 31-32, 39-40, 47-48, and 55-56, respectively in order of appearance). Non-conserved residues are in bold-faced type. For the consensus sequence, Y=C or T, N=A, C, G or T, R=A or G, H=A, C or T, B=C, G or T, and W=A or T. In determining the consensus gene-end signal, the eight-nucleotide nonhomologous segment in the HPLV3 M gene-end sequence was not considered.

FIG. 4 illustrates organization of the P, C and auxiliary ORFs in edited and unedited MPIV1 (Panel A) and HPIV1 (Panel B) P mRNA. For MPIV1 (Panel A), the first two rectangles illustrate the P and C ORFs in unedited P mRNA. The nucleotide sequence (SEQ ID NO: 59) (negative-sense, 3' to 5') of the P gene editing motif (underlined) and its adjacent 3' sequence is shown above the P ORF. The translation start site of X also is indicated. The translational start sites of the C', C, Y1, and Y2 proteins in the C ORF are shown together with the amino acid length of each protein, and the nonstandard ACG start site is indicated. The next two rectangles indicate the two alternative edited forms of the P ORF: a single-nucleotide insert (+1G) fuses the N-terminal 317 amino acids of P to the 68-amino acid V segment, and a two-nucleotide insert (+2G) fuses the same P segment to an additional amino acid to create W (Curran et al., *Embo J.* 10:3079-3085, 1991, incorporated herein by reference). Asterisks identify the positions of nine cysteine residues in the MPIV1 V ORF. Panel B shows a schematic representation of the P, C, and relict V ORFs of HPIV1. HPIV1 lacks a homologous V gene editing motif compared to MPIV1 as illustrated by the sequence (SEQ ID NO: 60) above the P ORF. The nonstandard GUG translational start site for C' is shown, as is the start site for C and the amino acid length for each protein. The putative start site for Y1 is enclosed by brackets; its expression has been demonstrated in an in vitro translation reaction (Power et al., *Virology* 189, 340-343, 1992, incorporated herein by reference). A putative start site for Y2 that would use a nonstandard ACG codon is also shown. Below the C ORF, a relict of the V ORF is shown; cysteine residues that are homologous to those in MPIV1 are indicated by asterisks above the relict V ORF while the nine stop codons are indicated with bullets below the ORF. Panel C shows an alignment of the amino acid sequences (SEQ ID NOS 61-63, respectively in order of appearance) encoded by the V ORF of MPIV1 Z and the relict V ORFs from HPIV1 strains WASH/64 and C39 (Matsuoka et al., *J. Virol.* 65:3406-3410, 1991). Conserved residues among the three viruses are shown in bold-faced type and similarities in a Clustal W alignment are underlined (Thompson et al., *Nucleic Acids Res.* 22:4673-4680, 1994, incorporated herein by reference). The dash inserted in the two HPIV1 sequences is a gap introduced by the Clustal W alignment. Conserved cysteine residues are marked with an asterisk above the sequence, and stop codons are identified with bullets.

FIG. 5 provides partial nucleotide sequences (positive-sense) that show two translationally silent markers in the rHPIV1 L gene at positions 10706 (Panel A) (the nucleotide and encoded amino acid sequences are SEQ ID NOS 64 and 65 and SEQ ID NOS 66 and 67, respectively in order of appearance) and 14267 (Panel B) (the nucleotide and encoded amino acid sequences are SEQ ID NOS 68 and 69 and SEQ ID NOS 70 and 71, respectively in order appearance) aligned against the corresponding partial wild-type HPIV1 sequence. The predicted amino acid sequence is shown below each mRNA sequence.

FIG. 6 illustrates alignment of the L polymerase-binding domain of the P protein of MPIV1 Z (SEQ ID NO: 72) compared to the corresponding region in the P proteins of HPIV1 WASH/64 (SEQ ID NO: 73), and HPIV3 JS (SEQ ID NO: 74), based on a Clustal W alignment of the three P proteins (Thompson et al., *Nucleic Acids Res.* 22:4673-4680, 1994, incorporated herein by reference). Amino acid identities are indicated by an asterisk and similarities are indicated by a period. The amino acid residues shown in bold are residues that are identical or similar among the three viruses that have been shown to be important for mRNA synthesis and leader RNA synthesis (Bowman et al., *J. Virol.* 73:6474-6483, 1999, incorporated herein by reference).

FIGS. 7A and 7B (comprising Panels A-C) exemplify introduction of mutations identified in a heterologous negative stranded RNA virus into a recombinant HPIV1. The sets of mutations, indicated by the capital the numbers 1 through 11, are indicated in the HPIV 1 genome in Panel A. In Panel B, sequence alignments are provided between HPIV1 wild-type (wt), HPIV3 wt, and HPIV3 cp45(SEQ ID NOS 75-94, respectively in order of appearance in the left column and SEQ ID NOS 95-118, respectively in order of appearance in the right column). For mutations in the 3' leader region, sequence is presented as cDNA, and nucleotide numbering is shown at the top relative to the 3' end of the genome. For the other mutations, alignment of the appropriate protein sequences is shown. The number in parenthesis indicates the amino acid at the beginning and end of the sequences compared, respectively. At the top of each alignment, the proposed changes that will be made to HPIV1 are indicated. Each residue in bold faced type is altered to match the corresponding residue in HPIV3 cp45 as identified through conventional alignment and sequence comparison methods as described further herein below. In Panel C, HPIV1 wt sequence (SEQ ID NO: 120) is aligned to murine parainfluenza virus type 1 (MPIV1) (SEQ ID NO: 121) and an MPIV1 mutant (SEQ-ID NO: 122) containing an attenuating mutation in the C protein, indicated by the bullet under the number five in the HPIV1 genome (Panel A). At the top of the alignment is the mutational change that is made to the corresponding residue of HPIV1 (HPIV1 F170S (SEQ ID NO: 119); corresponding to a phenylalanine to seine substitution). Below this sequence alignment is a comparison for mutation number nine (in Panel A) among HPIV1 wt (SEQ ID NO: 124), HPIV3 wt (SEQ ID NO: 125), and HPIV3 L F456L (SEQ ID NO: 126), a recombinant HPIV3 in which a mutation in a heterologous (RSV) virus (the mutation comprising a phenylalanine to leucine change at position 521 in the RSV L protein) has been adopted and incorporated into the recombinant HPIV3 genome or antigenome. The corresponding change that is made to HPIV1 is shown at the top of the alignment (HPIV1 L F456L (SEQ ID NO: 123)). All amino acid sequences were globally aligned using either the GAP program of the Wisconsin Package version 10.2 or by Clustal W alignment (incorporated herein by reference).

FIGS. 10A-10D provide a complete consensus sequence (SEQ ID NO: 131) for the genomic RNA of a multiply-passaged human parainfluenza virus type 1 (HPIV1) strain (designated HPIV1$_{LLC4}$, see Example XI below) derived from a wild-type clinical isolate Washington/20993/1964 shown to be virulent in human adults. The sequence of HPIV1$_{LLC4}$ differs from the wild-type parental sequence by five nucleotide changes indicated below in Table 12.

FIG. 11 illustrates codon substitution mutations introduced at amino acid position 942 of the HPIV1 L polymerase. The two possible codons encoding the wt assignment of tyrosine at codon 942 are shown at the top of each column for ease of reference. The codon substitution mutations encoding each of the indicated amino acids that were incorporated into antigenomic cDNA are shown and are organized into three groups: A. Mutant codons generated by a 1-nt substitution relative to either of the two possible tyrosine codons; B. Mutant codons generated by a 2-nt substitution; and C. Mutant codons generated by a 3-nt substitution. rHPIV1 mutants were recovered for each of the codon substitution mutations in groups A, B, and C, except as indicated.

FIG. 12 illustrates codon substitution mutations introduced at amino acid position 992 of the HPIV1 L polymerase. The six possible codons encoding the wt assignment of leucine are shown at the top of each column for ease of reference. The codon substitution mutations encoding each of the indicated amino acids that were incorporated into antigenomic cDNA are shown and are organized into two groups: A. Mutant codons generated by a 1-nt substitution relative to any of the six leucine codons; and B. Mutant codons generated by a 2-nt substitution. rHPIV1 mutants were recovered for each of the codon substitution mutations in groups A and B, except as indicated.

FIG. 13 provides a schematic representation of deletion mutations introduced in the P/C gene of HPIV1. A diagram of the overlapping P and C open reading frames (ORFs) is illustrated for each mutant, and the relative translation start position for the C', P, and C proteins are indicated by the arrows. The C and C' are translated in the same frame from alternative start codons. P is translated from another reading frame. Panel A: Deletion mutations within amino acids 10-15 (SEQ ID NO: 132) of the C protein and amino acids 13-19 (SEQ ID NO: 133) of the P protein. Panel B: Deletion mutation within amino acids 168-170 of the C protein and amino acids 172-173 of the P protein, with the sequence of the relevant region of each ORF shown below (SEQ ID NOS 134-137, respectively in order of appearance). In both panels, the amino acids deleted for both the C protein and the P protein are indicated. Each of the mutated P genes functioned to support recovery of wt HPIV1 in vitro (indicated by +). Two mutant HPIV1 viruses containing P/C gene deletions have been recovered from cDNA (indicated by +).

DESCRIPTION OF THE SPECIFIC EMBODIMENTS

Figure 8:
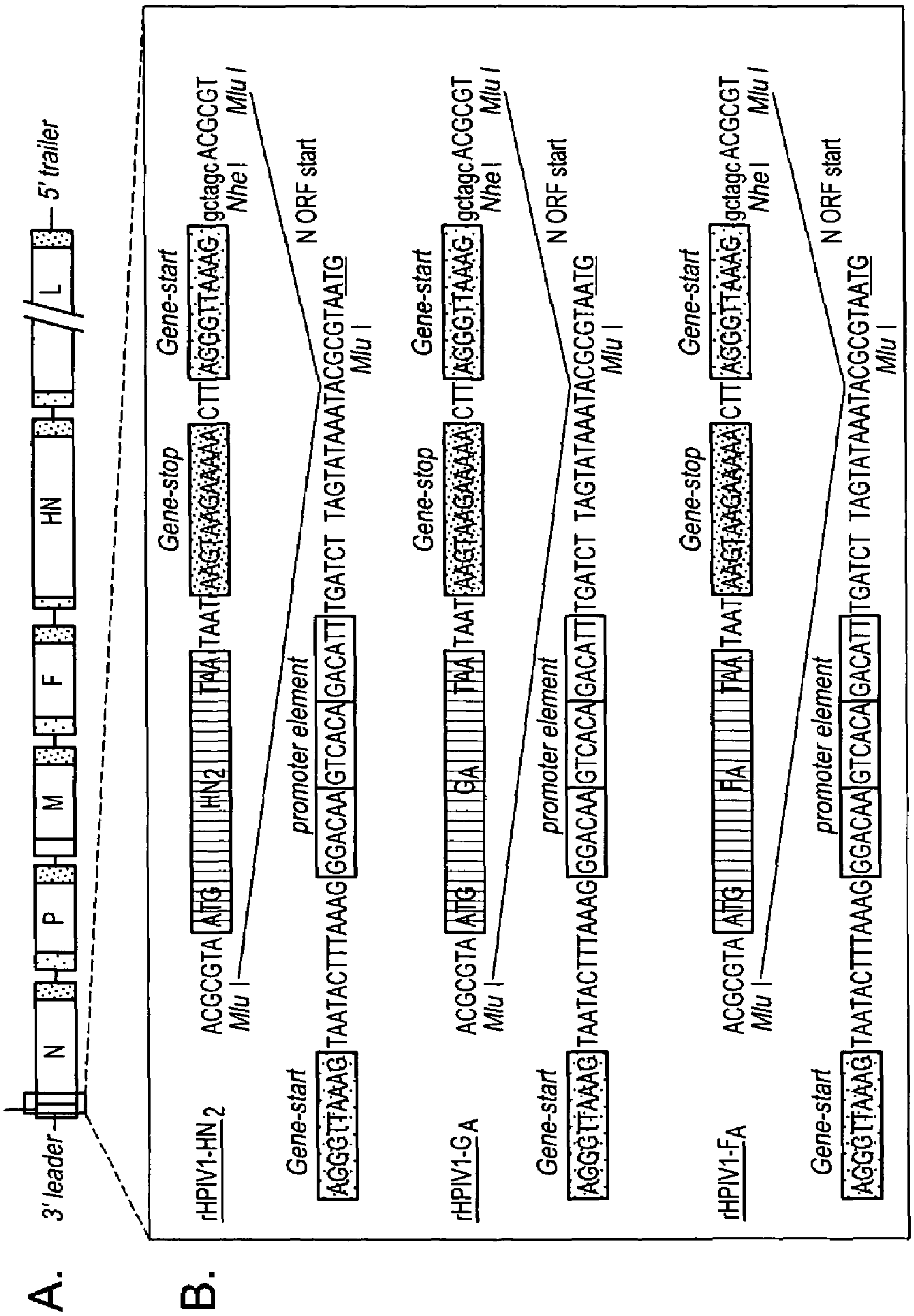
FIG. 8 illustrates modification of recombinant HPIV1 of the invention for use as a vector for heterologous protective antigens of different PIV and non-PIV pathogens according to the invention. Panel A provides a diagram of the HPIV1 genome that has been modified from wild-type to contain an Mlu I restriction site one nucleotide prior to the translational start of the N protein. Gene-start and gene-stop signals for each gene are shaded in gray and black, respectively. The area enclosed by the rectangle is expanded in Panel B, and illustrates the insertion of the HN ORF from HPIV2 or the G or F ORFs from RSV subgroup A into the HPIV1 genome. For each recombinant virus that is constructed, which is indicated on the left hand side of panel B (e.g. rHPIV1-$HN_2$), the top shows the insert that is generated using PCR with a sense oligo (SEQ ID NO: 127) that includes an Mlu I restriction site and an antisense oligo that contains gene-stop and gene-start sequences (SEQ ID NOS 128 and 130) that are used to terminate transcription for the inserted gene and promote transcription for the N gene, respectively. A unique Nhe I site is included which allows for the subsequent insertion of a second ORF (Latorre et al., *Mol. Cell. Biol.* 18:5021-5031, 1998, incorporated herein by reference). The bottom section for each virus details the sequence of the HPIV1 backbone where the ORFs are inserted (SEQ ID NO: 129). The naturally occurring gene-start sequence is boxed and shaded in gray. The promoter element is a sequence that has been demonstrated to be important for viral replication and transcription. This strategy can be used to engineer other unique restriction sites at any one of the gene junctions or 3' or 5' portions of the genome or antigenome to allow for the insertion of foreign genes, as desired.

The instant invention provides methods and compositions for the production and use of novel human parainfluenza virus type 1 (HPIV1) candidates for use in immunogenic compositions. The recombinant HPIV1 viruses of the invention are infectious and immunogenic in humans and other mammals and are useful for generating immune responses against one or more PIVs, for example against one or more human PIVs (HPIVs). In additional embodiments, chimeric HPIV1 viruses are provided that elicit an immune response against a selected PIV and one or more additional pathogens, for example against multiple HPIVs or against a HPIV and a non-PIV virus such as respiratory syncytial virus (RSV), human metapneumovirus, or measles virus. The immune response elicited can involve either or both humoral and/or cell mediated responses. Preferably, recombinant HPIV1 viruses of the invention are attenuated to yield a desired balance of attenuation and immunogenicity for use in immunogenic compositions. The invention thus provides novel methods for designing and producing attenuated, HPIV1 viruses that are useful as immunological agents to elicit immune responses against HPIV1 and other pathogens.

Exemplary recombinant HPIV1 viruses of the invention incorporate a recombinant HPIV1 genome or antigenome, as well as a PUV major nucleocapsid (N) protein, a nucleocapsid phosphoprotein (P), and a large polymerase protein (L). The N, P, and L proteins may be HPIV1 proteins, or one or more of the N, P, and L proteins may be of a different HPIV, for example HPIV3. Additional PIV proteins may be included in various combinations to provide a range of infectious viruses, defined herein to include subviral particles lacking one or more non-essential viral components and complete viruses having all native viral components, as well as viruses containing supernumerary proteins, antigenic determinants or other additional components.

As set forth in the examples below, a complete consensus sequence (FIGS. 10A-10D; GenBank Accession No. AF457102, incorporated herein by reference) was determined herein for the genomic RNA of a multiply-passaged human parainfluenza virus type 1 (HPIV1) strain (designated HPIV1$_{LLC4}$, see Example XI below) derived from a wild-type (wt) clinical isolate Washington/20993/1964 that has been shown to be virulent in adults (Murphy et al., *Infect. Immun.* 12:62-68, 1975, incorporated herein by reference). The sequence thus identified exhibits a high degree of relatedness to both Sendai virus (a PIV1 virus isolated from mice that is referred to here as MPIV1), and human PIV3 (HPIV3) with regard to cis-acting regulatory regions and protein-coding sequences. This consensus sequence was used to generate a full-length antigenomic cDNA and to recover a recombinant wild-type HPIV1 (rHPIV1). Surprisingly, the rHPIV1 could be rescued from full-length antigenomic rHPIV1 cDNA using HPIV3 support plasmids, HPIV1 support plasmids, or a mixture thereof.

The replication of rHPIV1 in vitro and in the respiratory tract of hamsters was similar to that of its biologically derived parent virus. The similar biological properties of rHPIV1 and HPIV1 WASH/64 in vitro and in vivo, together with the previous demonstration of the virulence of this specific isolate in humans, authenticates the rHPIV1 sequence as that of a wild-type virus. This is a critical finding since the high mutation rate characteristic of these viruses often results in errors that reduce viability. This rHPIV1 therefore serves as a novel and proven substrate for recombinant introduction of attenuating mutations for the generation of live-attenuated HPIV1 recombinants.

The Paramyxovirinae subfamily of the Paramyxoviridae family of viruses includes human parainfluenza virus types 1, 2, 3, 4A and 4B (HPIV1, HPIV2, HPIV3, HPIV4A, and HPIV4B, respectively). HPIV1, HPIV3, MPIV1, and bovine PIV3 (BPIV3) are classified together in the genus Respirovirus, whereas HPIV2 and HPIV4 are more distantly related and are classified in the genus Rubulavirus. MPIV1, simian virus 5 (SV5), and BPIV3 are animal counterparts of HPIV1, HPIV2, and HPIV3, respectively (Chanock et al., in *Parainfluenza Viruses*, Knipe et al. (Eds.), pp. 1341-1379, Lippincott Williams & Wilkins, Philadelphia, 2001, incorporated herein by reference).

The human PIVs have a similar genomic organization, although significant differences occur in the P gene (Chanock et al., in *Parainfluenza Viruses*, Knipe et al. (eds.), pp. 1341-1379, Lippincott Williams & Wilkins, Philadelphia, 2001; Lamb et al., in Paramyxoviridae: The viruses and their replication, Knipe et al. (eds.), pp. 1305-1340, Lippincott Williams & Wilkins, Philadelphia, 2001, each incorporated herein by reference). The 3' end of genomic RNA and its full-length, positive-sense replicative intermediate antigenomic RNA contain promoter elements that direct transcription and replication. The nucleocapsid-associated proteins are composed of the nucleocapsid protein (N), the phosphoprotein (P), and the large polymerase (L). The internal matrix protein (M) and the major antigenic determinants, the fusion glycoprotein (F) and hemagglutinin-neuraminidase glycoprotein (HN) are the envelope-associated proteins. The gene order is N, P, M, F, HN, and L.

With the exception of the P gene, each HPIV gene contains a single ORF and encodes a single viral protein. The P gene of the Paramyxovirinae subfamily encodes a number of proteins that are generated from alternative open reading frames (ORFs), by the use of alternative translational start sites within the same ORF, by an RNA polymerase editing mechanism, by ribosomal shunting, or through ribosomal frame shifting (Lamb et al., in Paramyxoviridae: The viruses and their replication, Knipe et al. (Eds.), pp. 1305-1340, Lippincott Williams & Wilkins, Philadelphia, 2001; Liston et al., *J Virol* 69:6742-6750, 1995; Latorre et al., *Mol. Cell. Biol.* 18:5021-5031, 1998, incorporated herein by reference). For example, the MPIV1 P gene expresses eight proteins. Four of these, C, C', Y1, and Y2, are expressed by translational initiation at four different codons within the C ORF that is present in a +1 reading frame relative to the P ORF (Curran et al., *Embo J.* 7:245-251, 1988, Dillon et al., *J. Virol.* 63:974-977, 1989; Curran et al., *Virology* 189:647-656, 1989, each, incorporated herein by reference).

The translation start sites for the C', C, Y1, and Y2 proteins are, respectively, a nonstandard ACG codon at nucleotides (nt) 81-83 (numbered according to the P mRNA) and AUG codons at nt 114-117, 183-185, and 202-204 (for comparison, the translation start site for the P ORF is at nt 104-106) (Curran et al., *Embo J.* 7:245-251, 1988, incorporated herein by reference). Expression of the Y1 and Y2 proteins involves a ribosomal shunt mechanism (Latorre et al., *Mol Cell Biol* 18:5021-5031, 1998, incorporated herein by reference). Collectively, these four proteins act to down regulate viral replication, contribute to virion assembly, and interfere with interferon action (Curran et al., Virology 189:647-656, 1992; Tapparel et al., *J. Virol.* 71:9588-9599, 1997; Garcin et al., *J. Virol.* 74:8823-8830, 2000; Hasan et al., *J. Virol.* 74:5619-5628, 2000; Garcin et al., *J. Virol.* 75:6800-6807, 2001; Kato et al., *J. Virol.* 75:3802-3810, 2001, each incorporated herein by reference).

The MPIV1 P ORF gives rise to the P protein and to two additional proteins, V and W, which share the N-terminal half of the P protein but which each have a unique carboxy-terminus due an RNA polymerase-dependent editing mechanism that inserts one or two G residues, respectively (Curran et al., *Embo J.* 10:3079-3085, 1991, incorporated herein by reference). In W, the carboxy-terminal extension that results from the frame shift consists of a single added amino acid, while that of V contains a cysteine-rich domain that is highly conserved among members of Paramyxovirinae (Lamb et al., in *Paramyxoviridae: The viruses and their replication*, Knipe et al. (Eds.), pp. 1305-1340, Lippincott Williams & Wilkins, Philadelphia, 2001, incorporated herein by reference). The V protein does not appear to be necessary for MPIV1 replication in cell culture, but mutants that lack this protein are attenuated in mice (Kato et al., *EMBO J.* 16:578-587, 1997, incorporated herein by reference).

One additional protein, X, is expressed from the downstream end of the P ORF by a mode of translational initiation that appears to be dependent on the 5' cap but is independent of ribosomal scanning (Curran et al., *Embo J.* 7:2869-2874, 1988, incorporated herein by reference). As another example, measles virus encodes a P protein, a V protein, a single C protein, and a novel R protein (Liston et al., *J. Virol.* 69:6742-6750, 1995; Bellini et al., *J. Virol.* 53:908-919, 1985; Cattaneo et al., *Cell* 56, 759-764, 1989, each incorporated herein by reference). R is a truncated version of P attached to the downstream end of V, and likely results from a ribosomal frame shift during translation of the downstream half of the P ORF (Liston et al., *J Virol* 69:6742-6750, 1995, incorporated herein by reference). For HPIV1, in vitro translation experiments suggest the expression of C', C, and Y1 proteins (Power et al., *Virology* 189:340-343, 1992, incorporated herein by reference). HPIV1 encodes a P protein but does not appear to encode a V protein, based on the lack of a homologous RNA editing site and the presence of a relict V coding sequence that is interrupted by 9-11 stop codons (Matsuoka et al., *J. Virol.* 65:3406-3410, 1991; Rochat et al., *Virus Res.* 24:137-144, 1992, incorporated herein by reference).

Infectious recombinant HPIV1 viruses according to the invention are produced by a recombinant coexpression system that permits introduction of defined changes into the recombinant HPIV1. These modifications are useful in a wide variety of applications, including the development of live attenuated HPIV1 strains bearing predetermined, defined attenuating mutations. Infectious PIV of the invention are typically produced by intracellular or cell-free coexpression of one or more isolated polynucleotide molecules that encode the HPIV1 genome or antigenome RNA, together with one or more polynucleotides encoding the viral proteins desired, or at least necessary, to generate a transcribing, replicating nucleocapsid.

cDNAs encoding a HPIV1 genome or antigenome are constructed for intracellular or in vitro coexpression with the selected viral proteins to form infectious PIV. By "HPIV1 antigenome" is meant an isolated positive-sense polynucleotide molecule which serves as a template for synthesis of progeny HPIV1 genome. Preferably a cDNA is constructed which is a positive-sense version of the HPIV1 genome corresponding to the replicative intermediate RNA, or antigenome, so as to minimize the possibility of hybridizing with positive-sense transcripts of complementing sequences encoding proteins necessary to generate a transcribing, replicating nucleocapsid.

In some embodiments of the invention the genome or antigenome of a recombinant HPIV1 (rHPIV1) need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule. In other embodiments, the PIV genome or antigenome encodes all functions necessary for viral growth, replication, and infection without the participation of a helper virus or viral function provided by a plasmid or helper cell line.

By "recombinant HPIV1" is meant a HPIV1 or HPIV1-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious HPIV1 from a cDNA-expressed HPIV1 genome or antigenome, the genome or antigenome is coexpressed with those PIV (HPIV1 or heterologous PIV) proteins necessary to produce a nucleocapsid capable of RNA replication, and render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Synthesis of PIV antigenome or genome together with the above-mentioned viral proteins can also be achieved in vitro (cell-free), e.g., using a combined transcription-translation reaction, followed by transfection into cells. Alternatively, antigenome or genome RNA can be synthesized in vitro and transfected into cells expressing PIV proteins. In certain embodiments of the invention, complementing sequences encoding proteins necessary to generate a transcribing, replicating HPIV1 nucleocapsid are provided by one or more helper viruses. Such helper viruses can be wild-type or mutant. Preferably, the helper virus can be distinguished phenotypically from the virus encoded by the HPIV1 cDNA. For example, it may be desirable to provide monoclonal antibodies which react immunologically with the helper virus but not the virus encoded by the HPIV1 cDNA. Such antibodies can be neutralizing antibodies. In some embodiments, the antibodies can be used in affinity chromatography to separate the helper virus from the recombinant virus. To aid the procurement of such antibodies, mutations can be introduced into the HPIV1 cDNA to provide antigenic diversity from the helper virus, such as in the HN or F glycoprotein genes.

Expression of the HPIV1 genome or antigenome and proteins from transfected plasmids can be achieved, for example, by each cDNA being under the control of a selected promoter (e.g., for T7 RNA polymerase), which in turn is supplied by infection, transfection or transduction with a suitable expression system (e.g., for the T7 RNA polymerase, such as a vaccinia virus MVA strain recombinant which expresses the T7 RNA polymerase, as described by Wyatt et al., *Virology* 210:202-205, 1995, incorporated herein by reference). The viral proteins, and/or T7 RNA polymerase, can also be provided by transformed mammalian cells or by transfection of preformed mRNA or protein.

A HPIV1 genome or antigenome may be constructed for use in the present invention by, e.g., assembling cloned cDNA segments, representing in aggregate the complete genome or antigenome, by polymerase chain reaction or the like (PCR; described in, e.g., U.S. Pat. Nos. 4,683,195 and 4,683,202, and PCR Protocols: A Guide to Methods and Applications, Innis et al., eds., Academic Press, San Diego, 1990, each incorporated herein by reference) of reverse-transcribed copies of HPIV1 mRNA or genome RNA. For example, a first construct may be generated which comprises cDNAs containing the left hand end of the antigenome, spanning from an appropriate promoter (e.g., T7 RNA polymerase promoter) and assembled in an appropriate expression vector, such as a plasmid, cosmid, phage, or DNA virus vector. The vector may be modified by mutagenesis and/or insertion of synthetic polylinker containing unique restriction sites designed to facilitate assembly. For ease of preparation the N, P, L and other desired PIV proteins can be assembled in one or more separate vectors. The right hand end of the antigenome plasmid may contain additional sequences as desired, such as a flanking ribozyme and tandem T7 transcriptional terminators. The ribozyme can be hammerhead type, which would yield a 3' end containing a single nonviral nucleotide, or can be any of the other suitable ribozymes such as that of hepatitis delta virus (Perrotta et al., *Nature* 350:434-436, 1991, incorporated herein by reference) which would yield a 3' end free of non-PIV nucleotides. The left- and righthand ends are then joined via a common restriction site.

Alternative means to construct cDNA encoding the HPIV1 genome or antigenome include reverse transcription-PCR using improved PCR conditions (e.g., as described in Cheng et al., *Proc. Natl. Acad. Sci. USA* 91:5695-5699, 1994, incorporated herein by reference) to reduce the number of subunit cDNA components to as few as one or two pieces. In other embodiments different promoters can be used (e.g., T3, SPQ or different ribozymes (e.g., that of hepatitis delta virus. Different DNA vectors (e.g., cosmids) can be used for propagation to better accommodate the larger size genome or antigenome.

By "infectious clone" of HPIV1 is meant cDNA or its product, synthetic or otherwise, as well as RNA capable of being directly incorporated into infectious virions which can be transcribed into genomic or antigenomic HPIV1 RNA capable of serving as a template to produce the genome of infectious HPIV1 viral or subviral particles. As noted above, defined mutations can be introduced into an infectious HPIV1 clone by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA constructs provide for better ease of manipulation than large cDNA constructs, and then readily assembled into a complete cDNA.

Isolated polynucleotides (e.g., cDNA) encoding the HPIV1 genome or antigenome may be inserted into appropriate host cells by transfection, electroporation, mechanical insertion, transduction or the like, into cells which are capable of supporting a productive HPIV1 infection, e.g., HEp-2, FRhL-DBS2, LLC-MK2, MRC-5, and Vero cells. Transfection of isolated polynucleotide sequences may be introduced into cultured cells by, for example, calcium phosphate-mediated transfection (Wigler et al., *Cell* 14:725, 1978; Corsaro et al., *Somatic Cell Genetics* 7:603, 1981; Graham et al., *Virology* 52:456, 1973, electroporation (Neumann et al., *EMBO J.* 1:841-845, 1982), DEAE-dextran mediated transfection (Ausubel et al., (ed.) Current Protocols in Molecular Biology, John Wiley and Sons, Inc., NY, 1987, cationic lipid-mediated transfection (Hawley-Nelson et al., Focus 15:73-79, 1993) or a commercially available transfection regent, e.g., Lipofectamine-2000 (Invitrogen, Carlsbad, Calif.) or the like (each of the foregoing references are incorporated herein by reference in its entirety).

By providing infectious clones of HPIV1, the invention permits a wide range of alterations to be recombinantly produced within the HPIV1 genome (or antigenome), yielding defined mutations that specify desired phenotypic changes. The compositions and methods of the invention for producing recombinant HPIV1 permit ready detailed analysis and manipulation of HPIV1 molecular biology and pathogenic mechanisms using, e.g., defined mutations to alter the function or expression of selected HPIV1 proteins. Using these methods and compositions, one can readily distinguish mutations responsible for desired phenotypic changes from silent incidental mutations, and select phenotype-specific mutations for incorporation into a recombinant HPIV1 genome or antigenome for production of immunogenic compositions. In this context, a variety of nucleotide insertions, deletions, substitutions, and rearrangements can be made in the HPIV1 genome or antigenome during or after construction of the cDNA. For example, specific desired nucleotide sequences can be synthesized and inserted at appropriate regions in the cDNA using convenient restriction enzyme sites. Alternatively, such techniques as site-specific mutagenesis, alanine scanning, PCR mutagenesis, or other such techniques well known in the art can be used to introduce mutations into the cDNA.

Recombinant modifications of HPIV1 provided within the invention are directed toward the production of improved viruses for use in immunogenic compositions, e.g., to enhance viral attenuation and immunogenicity, to ablate epitopes associated with undesirable immunopathology, to accommodate antigenic drift, etc. To achieve these and other objectives, the compositions and methods of the invention allow for a wide variety of modifications to be introduced into a HPIV1 genome or antigenome for incorporation into infectious, recombinant HPIV1. For example, foreign genes or gene segments encoding protective antigens or epitopes may be added within a HPIV1 clone to generate recombinant HPIV1 viruses capable of inducing immunity to both HPIV1 and another virus or pathogenic agent from which the protective antigen was derived. Alternatively, foreign genes may be inserted, in whole or in part, encoding modulators of the immune system, such as cytokines, to enhance immunogenicity of a candidate virus for use in immunogenic compositions. Other mutations which may be included within HPIV1 clones of the invention include, for example, substitution of heterologous genes or gene segments (e.g., a gene segment encoding a cytoplasmic tail of a glycoprotein gene) with a counterpart gene or gene segment in a PIV clone. Alternatively, the relative order of genes within a HPIV1 clone can be changed, a HPIV1 genome promoter or other regulatory element can be replaced with its antigenome counterpart, or selected HPIV1 gene(s) rendered non-functional (e.g., by functional ablation involving introduction of a stop codon to prevent expression of the gene). Other modifications in a HPIV1 clone can be made to facilitate manipulations, such as the insertion of unique restriction sites in various non-coding or coding regions of the HPIV1 genome or antigenome. In addition, nontranslated gene sequences can be removed to increase capacity for inserting foreign sequences.

As noted above, it is often desirable to adjust the phenotype of recombinant HPIV1 viruses for use in immunogenic compositions by introducing additional mutations that increase or decrease attenuation or otherwise alter the phenotype of the recombinant virus. Detailed descriptions of the materials and methods for producing recombinant PIV from cDNA, and for making and testing various mutations and nucleotide modifications set forth herein as supplemental aspects of the present invention are provided in, e.g., Durbin et al., *Virology* 235:323-332, 1997; U.S. patent application Ser. No. 09/083, 793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference.

In particular, these incorporated references describe methods and procedures for mutagenizing, isolating and characterizing PIV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing incorporated references detail procedures for determining replication, immunogenicity, genetic stability and immunogenic efficacy of biologically derived and recombinantly produced attenuated HPIVs in accepted model systems reasonably correlative of human activity, including hamster or rodent and non-human primate model systems. In addition, these references describe general methods for developing and testing immunogenic compositions, including monovalent and bivalent compositions, for eliciting an immune response against HPIV and other pathogens. Methods for producing infectious recombinant PIV by construction and expression of cDNA encoding a PIV genome or antigenome coexpressed with essential PUV proteins are also described in the above-incorporated references, which include description of the following exemplary plasmids that may be employed to produce infectious HPIV3 clones:p3/7 (131) (ATCC 97990); p3/7(131)2G (ATCC 97889); and p218 (131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers (deposits incorporated herein by reference).

Also disclosed in the above-incorporated references are methods for constructing and evaluating infectious recombinant HPIV that are modified to incorporate phenotype-specific mutations identified in biologically derived PIV mutants, e.g., cold passaged (cp), cold adapted (ca), host range restricted (hr), small plaque (sp), and/or temperature sensitive (ts) mutants, for example the JS HPIV3 cp 45 mutant strain. The HPIV3 JS cp45 strain has been deposited under the terms of the Budapest Treaty with the American Type Culture Collection (ATCC) of 10801 University Boulevard, Manassas, Va. 20110-2209, U.S.A. under Patent Deposit Designation PTA-2419 (deposit incorporated herein by reference). Mutations identified in this and other heterologous mutants viruses can be readily incorporated into recombinant HPIV1 of the instant invention, as described herein below.

As exemplified by FIGS. 7A and 7B (Panels A-C) various mutations identified in a heterologous negative stranded RNA virus can be incorporated into recombinant HPIV1 candidates of the invention to yield attenuation or other desired phenotypic changes. In Panel B, sequence alignments are provided between HPIV1 wild-type (wt), HPIV3 wt, and HPIV3 cp45. Based on these and similar comparisons, mutations are identified in a heterologous PIV or non-PIV virus for transfer into recombinant HPIV1 of the invention.

In certain detailed embodiments, the polynucleotide molecule encoding the recombinant HPIV1 genome or antigenome incorporates one or any combination of mutation(s) selected from the following exemplary list: a) mutations specifying amino acid substitution(s) in the L protein at a position corresponding to Tyr942, Leu992, and/or Leu1558 of wild-type (wt) HPIV1 L; b) amino acid substitution in the N protein at a position corresponding to residue Val99 of wt HPIV1 N; c) amino acid substitution(s) in the F protein at a position corresponding to residue Ile423 and/or Ser453 of wt HPIV1 F; d) amino acid substitution in the HN protein at a position corresponding to residue Arg386 of wt HPIV1 RN; e) amino acid substitution in the C protein at a position corresponding to Ser102 of wt HPIV1 C; f) amino acid substitution in the M protein at a position corresponding to residue Pro195 of wt HPIV1 M; g) nucleotide substitution(s) in a 3' leader sequence of the genome or antigenome at a position corresponding to nucleotide 23 and/or nucleotide 28 of wild-type (wt) HPIV1; and/or f) nucleotide substitution in a N gene start sequence at a position corresponding to nucleotide 62 of wild-type (wt) HPIV1. In more specific embodiments, the HPIV1 genome or antigenome incorporates one or any combination of mutation(s) selected from mutations specifying amino acid substitution(s) in the L protein of Tyr942His, Leu992Phe, and/or Leu1558Ile of HPIV1 L, amino acid substitution in the N protein of Val99Ala of HPIV1 N, amino acid substitution(s) in the F protein of Ile423Val and/or Ser453Thr of HPIV1 F, amino acid substitution in the HN protein at a position of Arg386Ala of HPIV1 HN, amino acid substitution in the C protein of Ser102Thr of HPIV1 C, amino acid substitution in the M protein Pro195Thr of HPIV1 M, nucleotide substitution(s) in a 3' leader sequence of the genome or antigenome of HPIV1 of T to C at nucleotide 23, and/or A to T at nucleotide 28, and/or nucleotide subsitution in a N gene start sequence of HPIV1 of A to T at nucleotide 62. (See, FIGS. 7A and 7B, Panels A-C). Mutations that are identical or conservative to these exemplary mutations in a heterologous PIV or other heterologous nonsegmented negative stranded RNA virus are preferred to achieve desired attenuation in recombinant HPIV1 candidates. These and additional representative mutations are exemplified herein below, e.g., as exemplified by mutations specifying conservative or non-conservative amino acid substitutions C: $S102T_{cp45}$, M: $P195T_{cp45}$, F: $I423V_{cp45}$, F: $S453T_{cp45}$, HN: $R386A_{cp45}$, L: $Y942H_{cp45}$, Y942F, Y942N, Y942D, Y942C, L: $L992F_{cp45}$, L: L9921, L: L992M, L: L992H, L: L992W, and L: $L1558I_{cp45}$.

In other detailed embodiments, the recombinant HPIV1 genome or antigenome incorporates multiple mutations for example a combination of mutations selected from (i) mutations specifying amino acid substitutions in the L protein at positions corresponding to Tyr942 and Leu992 of wild-type (wt) HPIV1 L, (ii) mutations specifying amino acid substitutions in the L protein at positions corresponding to Leu992 and Leu1558 of wild-type wt HPIV1 L, (iii) mutations specifying amino acid substitutions in the L protein at positions corresponding to Tyr942, Leu992 and Leu1558 of wt HPIV1 L, (iv) mutations specifying amino acid substitutions in the F protein at positions corresponding to Ile423 and Ser453 of wt HPIV1 F, and (v) mutations specifying an amino acid substitution in the N protein at a position corresponding to residue Val99 of wt HPIV1 N, mutations in a 3' leader sequence of the genome or antigenome at positions corresponding to nucleotide 23 and nucleotide 28 of wt HPIV1, and a nucleotide substitution in a N gene start sequence at a position corresponding to nucleotide 62 of wt HPIV1. In exemplary embodiments, the recombinant HPIV1 genome or antigenome incorporates multiple mutations selected from (i) 3'-N $V99A_{cp45}$, (ii) F: I423V/S453Tcp45, Y942H/L992Fcp45, (iii) L992F/L1558Icp45, and (iv) Y942H/L992F/$L1558I_{cp45}$.

The foregoing exemplary mutations which can be engineered in a recombinant HPIV1 candidate of the invention have been successfully engineered and recovered in recombinant HPIV3 based candidates (Durbin et al., *Virology* 235: 323-332, 1997; Skiadopoulos et al., *J. Virol.* 72:1762-1768, 1998; Skiadopoulos et al., *J. Virol.* 73:1374-1381, 1999; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In addition, the above-incorporated references describe construction of chimeric PIV recombinants, e.g., having the HN and F genes of HPIV1 substituted into a partial HPIV3 background genome or antigenome, which is further modified to bear one or more of the attenuating mutations identified in HPIV3 JS cp45. One such chimeric recombinant incorporates all of the attenuating mutations identified in the L gene of cp45. It has since been shown that all of the cp45 mutations outside of the heterologous (HPIV1) HN and F genes can be incorporated in a HPIV3-1 recombinant to yield an attenuated, chimeric HPIV.

Yet additional mutations that may be incorporated in recombinant HPIV1 of the invention are mutations, e.g., attenuating mutations, identified in non-PIV pathogens, particularly other nonsegmented negative stranded RNA viruses besides PIV. In this context, attenuating and other desired mutations identified in one negative stranded RNA virus may be "transferred", e.g., copied, to a corresponding position within the genome or antigenome of a recombinant HPIV1 of the invention. Briefly, desired mutations in one heterologous negative stranded RNA virus are transferred to the recombinant HPIV1 recipient (either in a "vector" HPIV1 genome or antigenome or in the heterologous "donor" gene or genome segment). This involves mapping the mutation in the heterologous mutant virus, identifying by routine sequence alignment the corresponding site in the recipient, recombinant HPIV1, and mutating the native sequence in the recombinant HPIV1 to the mutant genotype (either by an identical or conservative mutation), as described in International Application No. PCT/US00/09695, filed Apr. 12, 2000, corresponding to U.S. Provisional Patent Application Ser. No. 60/129,006, filed on Apr. 13, 1999, each incorporated herein by reference. It is preferable to modify the recipient recombinant HPIV1 genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution can be engineered at the corresponding residue(s) in the recombinant HPIV1. Preferably the substitution will specify an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a recombinant HPIV1 of the invention include other PIVs (e.g., HPIV1, HPIV2, HPIV3, BPIV3 and MPIV), RSV, Newcastle disease virus (NDV), simian virus 5 (SV5), measles virus (MeV), rinderpest virus, canine distemper virus (CDV), rabies virus (RaV) and vesicular stomatitis virus (VSV), among others.

Thus, in certain detailed embodiments of the invention, the recombinant HPIV1 genome or antigenome incorporates a recombinant modification that specifies an attenuating mutation at an amino acid position corresponding to an amino acid position of an attenuating mutation identified in a heterologous, mutant nonsegmented negative stranded RNA virus. In exemplary embodiments, the heterologous, mutant nonsegmented negative stranded RNA virus is respiratory syncitial virus (RSV). In one specific embodiment, the attenuating mutation comprises an amino acid substitution of phenylalanine at position 456 of the HPIV1 L protein, for example wherein phenylalanine at position 456 of the HPIV1 L protein is substituted by leucine. In other exemplary embodiments, the heterologous, mutant nonsegmented negative stranded RNA virus is murine parainfluenza virus type 1 (MPIV1). In a specific embodiment, the attenuating mutation comprises an amino acid substitution of phenylalanine at position 170 of the HPIV1 C protein, for example wherein phenylalanine at position 170 of the HPIV1 C protein is substituted by serine. In yet additional embodiments, the heterologous, mutant nonsegmented negative stranded RNA virus is a bovine parainfluenza virus type 3 (BPIV3). In one exemplary embodiment, the attenuating mutation identified in BPIV3 comprises an amino acid substitution at a corresponding target position Glu1711 in the HPIV1 L protein.

In related aspects of the invention, the recombinant HPIV1 genome or antigenome incorporates one or more attenuating mutation(s) identified in a biologically derived mutant PIV strain, and one or more attenuating mutation(s) at an amino acid position corresponding to an amino acid position of an attenuating mutation identified in a heterologous, mutant nonsegmented negative stranded RNA virus. In exemplary embodiments, the recombinant HPIV1 genome or antigenome incorporates a combination of mutations selected from (i) F170SMPIV1/Y942H/L992Fcp45, and (ii) F170SMPIV1/L992F/L1558Icp45.

In yet additional embodiments of the invention, he recombinant HPIV1 genome or antigenome incorporates at least one attenuating mutation stabilized by multiple nucleotide changes in a codon specifying the mutation. In exemplary embodiments, the recombinant HPIV1 genome or antigenome incorporates one or any combination of mutation(s) selected from Y942W, Y942S, Y942Q, Y942T, Y942G, Y942A, Y942V, Y942M, Y942T, Y942L, L992K, L992A, L992Y, and L992C.

In still other embodiments of the invention, the recombinant HPIV1 genome or antigenome incorporates one or more attenuating host range mutation(s). For example, the recombinant HPIV1 genome or antigenome may incorporate one or more attenuating host range mutation(s) identified in a biologically derived mutant strain of HPIV1 designated herein below as $HPIV1_{LLC4}$. As described below, this host-range attenuated strain has five nucleotide mutations in comparison to its wild-type parental strain. One or more of these mutations will therefore be useful to attenuate recombinant PIV candidates for use in immunogenic compositions of the invention. In exemplary embodiments, the recombinant HPIV1 genome or antigenome will incorporate one or more attenuating host range mutation(s) selected from (i) a mutation at codon 119 of the HPIV1 P open reading frame (ORF) and corresponding mutation at codon 84 of the HPIV1 C ORF and (ii) a mutation at codon 553 of the HPIV1 HN ORF. In more detailed embodiments, the recombinant genome or antigenome incorporates one or more attenuating host range mutation(s) that specify one or more amino acid change(s) selected from (i) Ell9G in HPIV1 P, (ii) R84G in HPIV1, and (iii) T553A in HPIV1 HN.

Attenuating mutations in biologically derived PIV and other nonsegmented negative stranded RNA viruses for incorporation within recombinant HPIV1 of the invention may occur naturally or may be introduced into wild-type PIV strains and thereafter identified and characterized by well known mutagenesis and analytic procedures. For example, incompletely attenuated parental PIV or other heterologous viral mutant strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as described in the above incorporated references. By "biologically derived" is meant any virus not produced by recombinant means. Thus, biologically derived PIV include all naturally occurring PIV, including, e.g., naturally occurring PIV having a wild-type genomic sequence and PIV having allelic or mutant genomic variations from a reference wild-type PIV sequence, e.g., PIV having a mutation specifying an attenuated phenotype. Likewise, biologically derived PIV include PIV mutants derived from a parental PIV by, inter alia, artificial mutagenesis and selection procedures.

As noted above, production of a sufficiently attenuated biologically derived PIV mutant can be accomplished by several known methods. One such procedure involves subjecting a partially attenuated virus to passage in cell culture at progressively lower, attenuating temperatures. For example, partially attenuated mutants are produced by passage in cell cultures at suboptimal temperatures. Thus, a cp mutant or other partially attenuated PIV strain is adapted to efficient growth at a lower temperature by passage in culture. This selection of mutant PIV during cold-passage substantially reduces any residual virulence in the derivative strains as compared to the partially attenuated parent. Alternatively, specific mutations can be introduced into biologically derived PIV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into PIV include replication of the virus in the presence of a mutagen such as 5-fluorouridine according to generally known procedures. Other chemical mutagens can also be used. Attenuation can result from a ts mutation in almost any PIV gene, although a particularly amenable target for this purpose has been found to be the polymerase (L) gene. The level of temperature sensitivity of replication in exemplary attenuated PIV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of PIV correlate with the mutant's shutoff temperature.

The JS cp45 HPIV3 mutant has been found to be relatively stable genetically, highly immunogenic, and satisfactorily attenuated. Nucleotide sequence analysis of this biologically derived virus, and of recombinant viruses incorporating various individual and combined mutations found therein, indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious PIV clones. This process coupled with evaluation of phenotype characteristics of parental and derivative viruses identifies mutations responsible for such desired characteristics as attenuation, temperature sensitivity, cold-adaptation, small plaque size, host range restriction, etc.

From JS cp45 and other biologically derived PIV mutants, a large "menu" of attenuating mutations is provided, each of which can be combined with any other mutation(s) for adjusting the level of attenuation, immunogenicity and genetic stability in recombinant HPIV1 of the invention. In this context, many recombinant HPIV1 canidates will include one or more, and preferably two or more, mutations from biologically derived PIV or other heterologous viral mutants, e.g., any one or combination of mutations identified in JS cp45. Preferred recombinant HPIV1 viruses within the invention will incorporate a plurality and up to a full complement of the mutations present in JS cp45 or other biologically derived mutant PIV or non-PIV viruses identified herein. Preferably, these mutations are stabilized against reversion in recombinant HPIV1 by multiple nucleotide substitutions in a codon specifying each mutation.

Mutations thus identified are compiled into a "menu" and are then introduced as desired, singly or in combination, to adjust recombinant HPIV1 of the invention to an appropriate level of attenuation, immunogenicity, genetic resistance to reversion from an attenuated phenotype, etc., as desired. In accordance with the foregoing description, the ability to produce infectious recombinant HPIV1 from cDNA permits introduction of specific engineered changes within the recombinant HPIV1. In particular, infectious, recombinant HPIV1 viruses can be employed for further identification of specific mutation(s) in biologically derived, attenuated HPIV1 strains, for example mutations which specify ts, ca, att and other phenotypes. Desired mutations identified by this and other methods are introduced into the recombinant HPIV1 strains. The capability of producing virus from cDNA allows for routine incorporation of these mutations, individually or in various selected combinations, into a full-length cDNA clone, whereafter the phenotypes of rescued recombinant viruses containing the introduced mutations to be readily determined.

By identifying and incorporating specific mutations associated with desired phenotypes, e.g., a cp or ts phenotype, into infectious recombinant HPIV1, the invention provides for other, site-specific modifications at, or within close proximity to, the identified mutation. Whereas most attenuating mutations produced in biologically derived PIVs are single nucleotide changes, other "site specific" mutations can also be incorporated by recombinant techniques into a recombinant HPIV1. As used herein, site-specific mutations include insertions, substitutions, deletions or rearrangements of from 1 to 3, up to about 5-15 or more altered nucleotides (e.g., altered from a wild-type PIV sequence, from a sequence of a selected mutant PIV strain, or from a parent recombinant PIV clone subjected to mutagenesis). Such site-specific mutations may be incorporated at, or within the region of, a selected, biologically derived point mutation. Alternatively, the mutations can be introduced in various other contexts within a recombinant HPIV1 clone, for example at or near a cis-acting regulatory sequence or nucleotide sequence encoding a protein active site, binding site, immunogenic epitope, etc.

Site-specific recombinant HPIV1 mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant HPIV1 mutants engineered to incorporate additional, stabilizing nucleotide mutations in a codon specifying an attenuating point mutation. Where possible, two or more nucleotide substitutions are introduced at codons that specify attenuating amino acid changes in a parent mutant or recombinant HPIV1 clone, yielding a recombinant HPIV1 with greater genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to the recombinant HPIV1 disclosed herein include deletions, insertions, substitutions or rearrangements of one or more gene(s) or genome segment(s). Particularly useful are deletions involving one or more gene(s) or genome segment(s), which deletions have been shown to yield additional desired phenotypic effects (see, e.g., U.S. patent application Ser. No. 09/350,821, filed by Durbin et al. on Jul. 9, 1999, incorporated herein by reference). For example, expression of one or more recombinant HPIV1 genes (e.g., one or more of the C, C', Y1, and/or Y2 open reading frame(s) (ORF(s) or other auxillary gene) can be reduced or ablated by modifying the recombinant HPIV1 genome or antigenome, e.g., to incorporate a mutation that alters the coding assignment of an initiation codon or mutation(s) that introduce one or one or more stop codon(s). Alternatively, one or more of the C, C', Y1, and/or Y2 ORF(s) or other auxillary gene can be deleted in whole or in part to render the corresponding protein(s) partially or entirely non-functional or to disrupt protein expression altogether.

In certain embodiments of the invention, a partial gene deletion specifies an attenuation phenotype or other desired phenotypic change in the recombinant PIV of the invention. In exemplary embodiments, the recombinant HPIV1 genome or antigenome is modified by one or more partial gene deletions corresponding to (i) codons 10-11 of the C ORF (ii) codons 12-13 of the C ORF (iii) codons 14-15 of the C ORF, (iv) codons 10-15 of the C ORF, and/or (v) codons 168-170 of the C ORF. These deletions specify attendant changes in the C, C' and P ORFs, e.g., as exemplified in FIG. 13.

Figure 9:
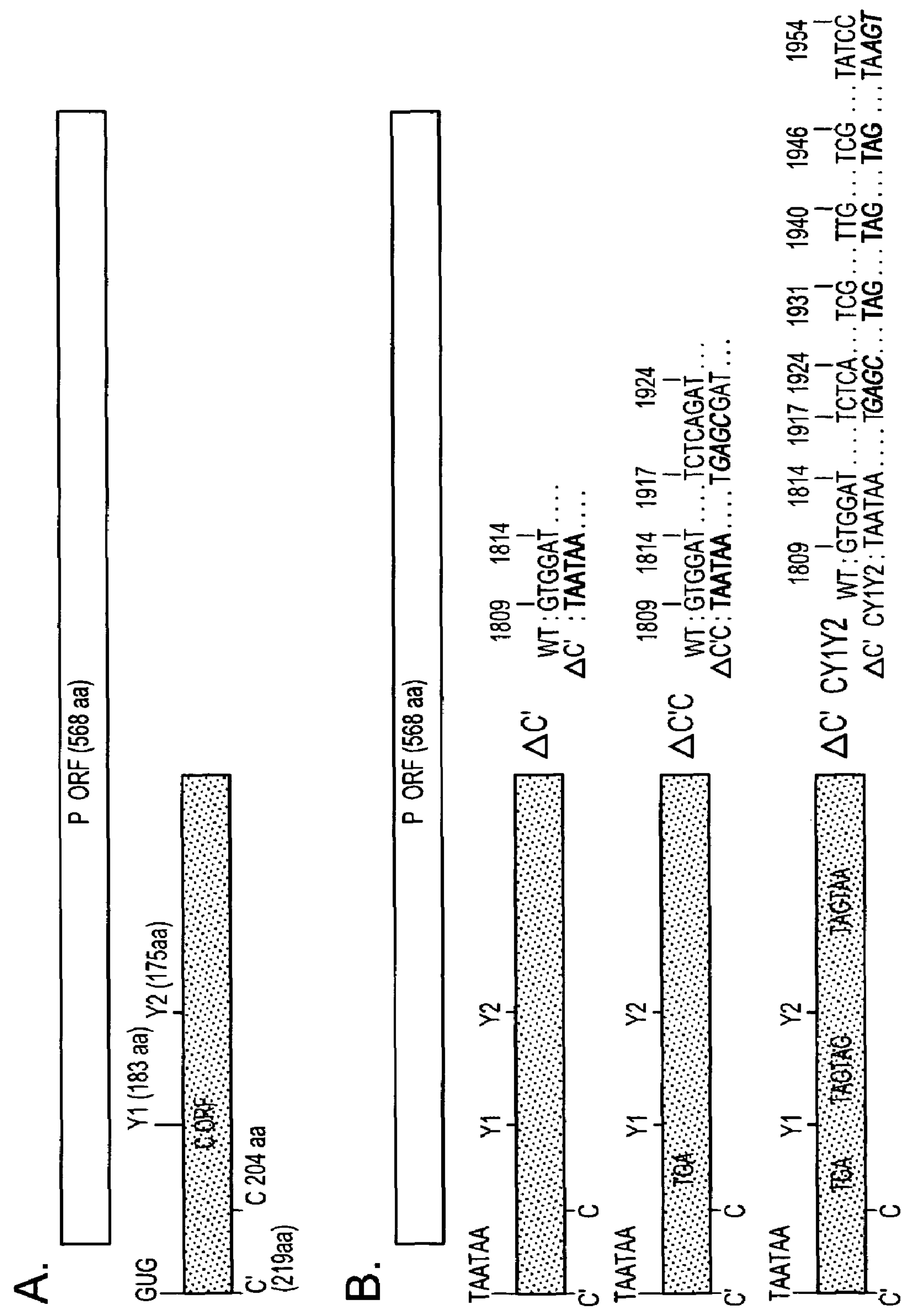
FIG. 9 illustrates modification of recombinant HPIV1 to delete all or part of a non-essential HPIV1 gene or alter or ablate expression of a HPIV1 gene, as exemplified by introduction of stop codons into the C ORF of HPIV1. A schematic diagram of the P ORF and the C ORF of HPIV1 is shown in Panel A. Both ORFs are expressed from the P mRNA, and the C ORF is in a +1 reading frame relative to the P ORF. In the case of the C ORF, four proteins are expressed. The C' protein is expressed from a non-standard GUG codon, while the Y1 and Y2 proteins have been proposed to be expressed using a ribosomal shunting mechanism (Boeck et al., *J. Virol.* 66:1765-1768, 1992, incorporated herein by reference). Panel B illustrates how the introduction of stop codons is implemented to eliminate the expression of C' (ΔC), C' and C (ΔC'C), and all four proteins (ΔC'CY1Y2) in three different viruses that can be readily tested in cell culture and animal models for replicative ability and immunogenicity. The left hand side of Panel B shows a block diagram of the ORFs, while the specific nucleotide sequences that are to be altered are shown on the right hand side. Nucleotide numbering corresponds to the HPIV1 WASH/64 genome, and the sequence is written as cDNA in the antigenomic or positive sense. Changes from the wild-type sequence are shown in bold-faced type; residues in bold-faced italic type allow for the introduction of a stop codon in C while maintaining a serine residue for P.

As illustrated in FIG. 9 various mutations involving partial or complete gene deletions or other alterations that reduce or ablate expression of a targeted gene can be engineered in recombinant HPIV1 candidates of the invention to yield attenuation or other desired phenotypic changes.

Recombinant HPIV1 having such mutations in C, C', Y1, and/or Y2 ORF(s) or other auxiliary gene(s), possess highly desirable phenotypic characteristics for development of immunogenic compositions. For example, these modifications may specify one or more desired phenotypic changes including (i) altered growth properties in cell culture, (ii) attenuation in the upper and/or lower respiratory tract of mammals, (iii) a change in viral plaque size, (iv) a change in cytopathic effect, and (v) a change in immunogenicity.

Thus, in more detailed aspects of the instant invention, a recombinant HPIV1 incorporate one or more deletion or knock out mutations in the C, C', Y1, and/or Y2 ORF(s) or other auxiliary gene which alters or ablates expression of the selected gene(s) or genome segment(s). This can be achieved, e.g., by introducing a frame shift mutation or termination codon within a selected coding sequence, altering translational start sites, changing the position of a gene or introducing an upstream start codon to alter its rate of expression, changing GS and/or GE transcription signals to alter phenotype, or modifying an RNA editing site (e.g., growth, temperature restrictions on transcription, etc.). In more detailed aspects of the invention, recombinant HPIV1 viruses are provided in which expression of one or more gene(s), e.g., a C, C', Y1, and/or Y2 ORF(s), is ablated at the translational or transcriptional level without deletion of the gene or of a segment thereof, by, e.g., introducing multiple translational termination codons into a translational open reading frame, altering an initiation codon, or modifying an editing site. These forms of knock-out virus will often exhibit reduced growth rates and small plaque sizes in tissue culture. Thus, these methods provide yet additional, novel types of attenuating mutations which ablate expression of a viral gene that is not one of the major viral protective antigens. In this context, knock-out virus phenotypes produced without deletion of a gene or genome segment can be alternatively produced by deletion mutagenesis, as described, to effectively preclude correcting mutations that may restore synthesis of a target protein. Several other gene knock-outs for the C, C', Y1, and/or Y2 ORF deletion and knock out mutants can be made using alternate designs and methods that are well known in the art (as described, for example, in (Kretschmer et al., *Virology* 216:309-316, 1996; Radecke et al., *Virology* 217: 418-421, 1996; Kato et al., *EMBO J.* 16:578-587, 1987; and Schneider et al., *Virology* 277:314-322, 1996, each incorporated herein by reference).

Nucleotide modifications that may be introduced into recombinant HPIV1 constructs of the invention may alter small numbers of bases (e.g., from 15-30 bases, up to 35-50 bases or more), large blocks of nucleotides (e.g., 50-100, 100-300, 300-500, 500-1,000 bases), or nearly complete or complete genes (e.g., 1,000-1,500 nucleotides, 1,500-2,500 nucleotides, 2,500-5,000, nucleotides, 5,00-6,5000 nucleotides or more) in the vector genome or antigenome or heterologous, donor gene or genome segment, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In related aspects, the invention provides for supplementation of mutations adopted into a recombinant HPIV1 clone from biologically derived PIV, e.g., cp and ts mutations, with additional types of mutations involving the same or different genes in a further modified recombinant HPIV1. Each of the HPIV1 genes can be selectively altered in terms of expression levels, or can be added, deleted, substituted or rearranged, in whole or in part, alone or in combination with other desired modifications, to yield a recombinant HPIV1 exhibiting novel immunological characteristics. Thus, in addition to or in combination with attenuating mutations adopted from biologically derived PIV and/or non-PIV mutants, the present invention also provides a range of additional methods for attenuating or otherwise modifying the phenotype of a recombinant HPIV1 based on recombinant engineering of infectious PIV clones. A variety of alterations can be produced in an isolated polynucleotide sequence encoding a targeted gene or genome segment, including a donor or recipient gene or genome segment in a recombinant HPIV1 genome or antigenome for incorporation into infectious clones. More specifically, to achieve desired structural and phenotypic changes in recombinant HPIV1, the invention allows for introduction of modifications which delete, substitute, introduce, or rearrange a selected nucleotide or nucleotide sequence from a parent genome or antigenome, as well as mutations which delete, substitute, introduce or rearrange whole gene(s) or genome segment(s), within a recombinant HPIV1.

Thus provided are modifications in recombinant HPIV1 of the invention which simply alter or ablate expression of a selected gene, e.g., by introducing a termination codon within a selected PIV coding sequence or altering its translational start site or RNA editing site, changing the position of a PIV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s). In this context, any PIV gene or genome segment which is not essential for growth can be ablated or otherwise modified in a recombinant PIV to yield desired effects on virulence, pathogenesis, immunogenicity and other phenotypic characters. As for coding sequences, noncoding, leader, trailer and intergenic regions can be similarly deleted, substituted or modified and their phenotypic effects readily analyzed, e.g., by the use of minireplicons and recombinant PIV.

In addition, a variety of other genetic alterations can be produced in a recombinant HPIV1 genome or antigenome, alone or together with one or more attenuating mutations adopted from a biologically derived mutant PIV or other virus, e.g., to adjust growth, attenuation, immunogenicity, genetic stability or provide other advantageous structural and/or phenotypic effects. These additional types of mutations are also disclosed in the foregoing incorporated references and can be readily engineered into recombinant HPIV1 of the invention. For example, restriction site markers are routinely introduced within chimeric PIVs to facilitate cDNA construction and manipulation.

In addition to these changes, the order of genes in a recombinant HPIV1 construct can be changed, a PUV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Other mutations for incorporation into recombinant HPIV1 constructs of the invention include mutations directed toward cis-acting signals, which can be readily identified, e.g., by mutational analysis of PIV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations that affect RNA replication or transcription. Any of these mutations can be inserted into a chimeric PIV antigenome or genome as described herein. Evaluation and manipulation of trans-acting proteins and cis-acting RNA sequences using the complete antigenome cDNA is assisted by the use of PIV minigenomes as described in the above-incorporated references.

Additional mutations within recombinant HPIV1 viruses of the invention may also include replacement of the 3' end of genome with its counterpart from antigenome, which is associated with changes in RNA replication and transcription. In one exemplary embodiment, the level of expression of specific PIV proteins, such as the protective HN and/or F antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315-324, 1996, incorporated herein by reference). Optimization by recombinant methods of the codon usage of the mRNAs encoding the HN and F proteins of recombinant HPIV1 will provide improved expression for these genes.

In another exemplary embodiment, a sequence surrounding a translational start site (preferably including a nucleotide in the −3 position) of a selected HPIV1 gene is modified, alone or in combination with introduction of an upstream start codon, to modulate gene expression by specifying up- or down-regulation of translation. Alternatively, or in combination with other recombinant modifications disclosed herein, gene expression of a recombinant HPIV1 can be modulated by altering a transcriptional GS or GE signal of any selected gene(s) of the virus. In alternative embodiments, levels of gene expression in a recombinant HPIV1 candidate are modified at the level of transcription. In one aspect, the position of a selected gene in the PIV gene map can be changed to a more promoter-proximal or promotor-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. These and other transpositioning changes yield novel recombinant HPIV1 viruses having attenuated phenotypes, for example due to decreased expression of selected viral proteins involved in RNA replication, or having other desirable properties such as increased antigen expression.

In other embodiments, recombinant HPIV1 viruses useful in immunogenic composition s can be conveniently modified to accommodate antigenic drift in circulating virus. Typically the modification will be in the HN and/or F proteins. An entire HN or F gene, or a genome segment encoding a particular immunogenic region thereof, from one PIV (HPIV1 or another HPIV) strain or group is incorporated into a recombinant HPIV1 genome or antigenome cDNA by replacement of a corresponding region in a recipient clone of a different PIV strain or group, or by adding one or more copies of the gene, such that multiple antigenic forms are represented. Progeny virus produced from the modified recombinant HPIV1 can then be used in immunization protocols against emerging PIV strains.

In certain aspects of the invention, replacement of a HPIV1 coding sequence or non-coding sequence (e.g., a promoter, gene-end, gene-start, intergenic or other cis-acting element) with a heterologous (e.g., non-HPIV1) counterpart yields chimeric HPIV1 having a variety of possible attenuating and other phenotypic effects. For example, host range and other desired effects can be engineered by substituting a bovine PIV (BPIV) or murine PIV (MPIV) protein, protein domain, gene or genome segment imported within a recombinant HPIV1 "background" genome or antigenome, wherein the bovine or murine gene does not function efficiently in a human cell, e.g., from incompatibility of the heterologous sequence or protein with a biologically interactive HPIV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In exemplary embodiments, bovine PIV sequences are selected for introduction into HPIV1 based on known aspects of bovine and human PIV structure and function.

In more detailed aspects, the invention provides methods for attenuating recombinant HPIV1 candidates based on the further construction of chimeras between HPIV1 and a non-human PIV, for example MIV1 and BPIV3 (e.g., as disclosed in U.S. patent application Ser. No. 09/586,479, filed Jun. 1, 2000 by Schmidt et al. (corresponding to PCT Publication WO 01/04320); Schmidt et al., *J. Virol.* 74:8922-9, 2000, each incorporated herein by reference). This method of attenuation is based on host range effects due to the introduction of one or more gene(s) or genome segment(s) of the non-human PIV into a human PIV vector-based chimeric virus. For example, there are numerous nucleotide and amino acid sequence differences between BPIV and HPIVs, which are reflected in host range differences. Between HPIV3 and BPIV3 the percent amino acid identity for each of the following proteins is: N (86%), P (65%), M (93%), F (83%), HN (77%), and L (91%). The host range difference is exemplified by the highly permissive growth of HPIV3 in rhesus monkeys, compared to the restricted replication of two different strains of BPIV3 in the same animal (van Wyke Coelingh et al., *J. Infect. Dis.* 157:655-662, 1988, incorporated herein by reference). Although the basis of the host range differences between HPIV3 and BPIV3 remains to be determined, it is likely that they will involve more than one gene and multiple amino acid differences. The involvement of multiple genes and possibly cis-acting regulatory sequences, each involving multiple amino acid or nucleotide differences, gives a very broad basis for attenuation, one which cannot readily be altered by reversion. This is in contrast to the situation with other live attenuated HPIV3 viruses which are attenuated by one or several point mutations. In this case, reversion of any individual mutation may yield a significant reacquisition of virulence or, in a case where only a single residue specified attenuation, complete reacquisition of virulence. In exemplary embodiments of the invention, the recombinant HPIV1 genome or antigenome is combined with a heterologous gene or genome segment, such as an N, P, M, or L, ORF derived from a BPIV3.

This mode of attenuation contrasts sharply to HPIV1 candidates that are attenuated by one or more point mutations, where reversion of an individual mutation may yield a significant or complete reacquisition of virulence. In addition, several known attenuating point mutations in HPIV typically yield a temperature sensitive phenotype. One problem with attenuation associated with temperature sensitivity is that the virus can be overly restricted for replication in the lower respiratory tract while being under attenuated in the upper respiratory tract. This is because there is a temperature gradient within the respiratory tract, with temperature being higher (and more restrictive) in the lower respiratory tract and lower (less restrictive) in the upper respiratory tract. The ability of an attenuated virus to replicate in the upper respiratory tract can result in complications including congestion, rhinitis, fever and otitis media. Thus, attenuation achieved solely by temperature sensitive mutations may not be ideal. In contrast, host range mutations present in chimeric PIV of the invention will not in most cases confer temperature sensitivity. Therefore, the novel method of PIV attenuation provided by these kinds of modifications will be more stable genetically and phenotypically and less likely to be associated with residual virulence in the upper respiratory tract compared to other known PIV strains.

The above-incorporated reference discloses that both Ka and SF HPIV3/BPIV3 chimeric recombinants are viable and replicate as efficiently in cell culture as either HPIV3 or BPIV3 parent—indicating that the chimeric recombinants did not exhibit gene incompatibilities that restricted replication in vitro. This property of efficient replication in vitro is important since it permits efficient manufacture of this biological. Also, the Ka and the SF HPIV3/BPIV3 chimeric recombinants (termed cKa and cSF), bearing only one bovine gene, are nearly equivalent to their BPIV3 parents in the degree of host range restriction in the respiratory tract of the rhesus monkey. In particular, the cKa and cSF viruses exhibit approximately a 60-fold or 30-fold reduction, respectively, in replication in the upper respiratory tract of rhesus monkeys compared to replication of HPIV3. Based on this finding, it is expected that other BPIV3 genes will also confer desired levels of host range restriction within chimeric PIV of the invention. Thus, according to the methods herein, a list of attenuating determinants will be readily identified in heterologous genes and genome segments of BPIV and other non-human PIVs that will confer, in appropriate combination, a desired level of host range restriction and immunogenicity on recombinant HPIV1 viruses selected for use in immunogenic compositions.

Chimeric human-bovine or human-murine recombinant HPIV1 are therefore provided herein that include a partial or complete "background" HPIV1 genome or antigenome derived from or patterned after HPIV1 combined with one or more heterologous gene(s) or genome segment(s) of a non-human PIV to form the chimeric PIV genome or antigenome. In preferred aspects of the invention, chimeric HPIV1 of this type incorporate a partial or complete HPIV1 background genome or antigenome combined with one or more heterologous gene(s) or genome segment(s), e.g., from a bovine PIV. The partial or complete background genome or antigenome typically acts as a recipient backbone into which the heterologous genes or genome segments of the counterpart, non-human PIV are incorporated. Heterologous genes or genome segments from the counterpart PIV represent "donor" genes or polynucleotides that are combined with, or substituted within, the background genome or antigenome to yield a chimeric HPIV1 that exhibits novel phenotypic characteristics compared to one or both of the contributing PIVs. For example, addition or substitution of heterologous genes or genome segments within a selected recipient HPIV1 strain may result in an increase or decrease in attenuation, growth changes, altered immunogenicity, or other desired phenotypic changes as compared with corresponding phenotype(s) of the unmodified recipient and/or donor (U.S. patent application Ser. No. 09/586,479, filed Jun. 1, 2000 by Schmidt et al.; Schmidt et al., *J. Virol.* 74:8922-9, 2000, each incorporated herein by reference).

Genes and genome segments that may be selected for use as heterologous substitutions or additions within chimeric PIV vectors include genes or genome segments encoding a PIV N, P, C, C', Y1, Y2, M, F, SH (where appropriate), HN and/or L protein(s) or portion(s) thereof. In addition, genes and genome segments encoding non-PIV proteins, for example, an SH protein as found in mumps, RSV, and SV5 viruses, may be incorporated within additional chimeric HPIV1 recombinants of the invention. Regulatory regions, such as the extragenic 3' leader or 5' trailer regions, and gene-start, gene-end, intergenic regions, or 3' or 5' non-coding regions, are also useful as heterologous substitutions or additions. In exemplary aspects, chimeric HPIV1 bearing one or more bovine or murine gene(s) or genome segment(s) exhibit a high degree of host range restriction, e.g., in the respiratory tract of mammalian models of human PIV infection such as hamsters and non-human primates. In exemplary embodiments HPIV1 is attenuated by the addition or substitution of one or more bovine gene(s) or genome segment(s) selected from N, M, L and P genes and genome segments to a partial or complete HPIV1 background genome or antigenome.

Preferably, the degree of host range restriction exhibited by human-bovine and other chimeric HPIV1 for use in immunogenic compositions of the invention is comparable to the degree of host range restriction exhibited by the respective non-human PIV "donor" strain. Preferably, the restriction should have a true host range phenotype, i.e., it should be specific to the host in question and should not restrict replication and immunogenic composition preparation in vitro in a suitable cell line. In addition, chimeric HPIV1 bearing one or more bovine or murine gene(s) or genome segment(s) elicit a high level of resistance in hosts susceptible to HPIV1 infection. Thus, the invention provides a new basis for attenuating a live HPIV1 virus vector for developing immunogenic compositions against HPIV1 and other pathogens based on host range effects.

In combination with the host range phenotypic effects provided in the human-non-human chimeric HPIV1 of the invention, it is often desirable to adjust the attenuation phenotype by introducing additional mutations that increase or decrease attenuation of the chimeric virus. Thus, in additional aspects of the invention, attenuated, human-bovine or human-murine chimeric HPIV1 are produced in which the chimeric genome or antigenome is further modified by introducing one or more attenuating mutations specifying an attenuating phenotype in the resultant virus or subviral particle. These can include mutations in RNA regulatory sequences or in encoded proteins. These attenuating mutations may be generated de novo and tested for attenuating effects according to a rational design mutagenesis strategy. Alternatively, the attenuating mutations may be identified in existing biologically derived mutant PIV and thereafter incorporated into a human-bovine or human-murine chimeric HPIV1 of the invention.

In preferred chimeric HPIV1 candidates of the invention, attenuation marked by replication in the lower and/or upper respiratory tract in an accepted animal model that is reasonably correlated with PIV replication and immunogenic activity in humans, e.g., hamsters, rhesus monkeys or chimpanzees, may be reduced by at least about two-fold, more often about 5-fold, 10-fold, or 20-fold, and preferably 50-100-fold and up to 1,000-fold or greater overall (e.g., as measured between 3-8 days following infection) compared to growth of the corresponding wild-type or mutant parental PIV strain.

Within the methods of the invention, additional genes or genome segments may be inserted into or proximate to a recombinant or chimeric HPIV1 genome or antigenome. For example, various supernumerary heterologous gene(s) or genome segment(s) can be inserted at any of a variety of sites within the recombinant genome or antigenome, for example at a position 3' to N, between the N/P, P/M, and/or HN/L genes, or at another intergenic junction or non-coding region of the HPIV1 vector genome or antigenome. Exemplary gene insertion details are provided in FIG. 8. The inserted genes may be under common control with recipient genes, or may be under the control of an independent set of transcription signals. Genes of interest in this context include genes encoding cytokines, for example, an interleukin (e.g., interleukin 2 (IL-2), interleukin 4 (IL-4), interleukin 5 (IL-5), interleukin 6 (IL6), interleukin 18 (IL-18)), tumor necrosis factor alpha (TNFα), interferon gamma (IFNγ), or granulocyte-macrophage colony stimulating factor (GM-CSF), as well as IL-2 through IL-18, especially IL-2, IL-6 and IL-12, and IL-18, gamma-interferon (see, e.g., U.S. application Ser. No. 09/614,285, filed Jul. 12, 2000, corresponding to U.S. Provisional Application Serial No. 60/143,425 filed July 13, 1999, incorporated herein by reference). Coexpression of these additional proteins provides the ability to modify and improve immune responses against recombinant HPIV1 of the invention both quantitatively and qualitatively.

In other aspects of the invention, insertion of heterologous nucleotide sequences into recombinant HPIV1 candidates are employed separately to modulate the level of attenuation of candidate recombinants, e.g., for the upper respiratory tract. Thus, it is possible to insert nucleotide sequences into a rHPIV1 that both direct the expression of a foreign protein and that attenuate the virus in an animal host, or to use nucleotide insertions separately to attenuate candidate viruses. To define some of the rules that govern the effect of gene insertion on attenuation, gene units of varying lengths may be inserted into a wild-type HPIV1 backbone and the effects of gene unit length on attenuation examined. Novel gene unit insertions are contemplated in this regard that do not contain a significant ORF, permitting identification of the effect of gene unit length independently of an effect of the expressed protein of that gene. These heterologous sequences may be inserted as an extra gene unit of various sizes, e.g., from about 150 or more nts in length up to 3,000 nts or more in length. As demonstrated herein, gene insertions or extensions larger than about 3,000 nts in length.

Gene unit (GU) insertions of about 1,000 or 2,000 nts in length will substantially attenuate rHPIV1 candidates for the upper respiratory tract of mammalian subjects. In addition, gene unit insertions can have the dual effect of both attenuating a candidate virus and inducing an immune response against a second virus. Alternately, gene extensions in the 3'-noncoding region (NCR) of a HPIV1 gene, which cannot express additional proteins, can also be attenuating in and of themselves. Within these methods of the invention, gene insertion length is a determinant of attenuation.

GU and NCR insertions within recombinant HPIV1 of the invention produce an attenuation phenotype characterized by efficient replication in vitro and decreased replication in vivo, a phenotype not previously described for other paramyxovirus insertions. The mechanism of attenuation resulting from a GU insertion may result from one or more of the following factors acting predominantly in vivo. The addition of an extra gene unit may decrease the level of transcription of downstream genes since there is a transcriptional gradient in which more promoter-proximal genes are transcribed at a higher rate than the more promoter-distal genes. The decreased expression of the downstream gene products resulting from the decreased abundance of their mRNAs could result in attenuation if their gene product is limiting or if a specific ratio of gene products that is required for efficient replication is altered. It is thought that the transcription gradient is a consequence of the transcriptase complex falling off the template during transcription as well as during the transfer across gene junctions. Alternatively, the increase in the overall length of the genome and the extra mRNAs transcribed may increase the level of viral double stranded RNA made which in turn may induce a higher level of the antiviral activity of the interferon system. Finally, the overall level of genome replication may be reduced due to the increase in length of the genome and the antigenome. This may result from a disengagement of replicase complexes from the template during replication of the genomic RNA or antigenomic RNA. The decreased amount of genome available for packaging into virions may result in a decrease in virus yield which results in attenuation.

The mechanism of attenuation resulting from a NCR insertion may result from one or more of the following factors. The extra length of the 3'-end of HN mRNA resulting from the NCR insertion may contribute to the instability of the mRNA and lead to a decrease in the expression of the HN protein. Alternatively, the increase in the overall length of the genome and the extra length of the HN mRNA may increase the level of viral double stranded RNA made that can induce a higher level of the antiviral activity of the interferon system. Alternatively or additionally, the overall level of genome replication may be reduced due to the increase in length of the genome and the antigenome. This may result from a disengagement of replicase complexes from the template during replication of the genomic RNA or antigenomic RNA. The decreased amount of genome available for packaging into virions could result in a decrease in virus yield which results in attenuation. Finally, the addition of extra nucleotides to the 3' end of the HN gene could decrease the level of transcription of downstream genes since the transcriptase complex could fall off the template during transcription of the extra nucleotides at the 3' end of the HN gene.

Deletions, insertions, substitutions and other mutations involving changes of whole viral genes or genome segments within rHPIV1 of the invention yield highly stable recombinants, which are particularly important in the case of immunosuppressed individuals. Many of these changes will result in attenuation of resultant strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578-87, 1997, incorporated herein by reference). Ablation of such genes in candidate viruses is expected to reduce virulence and pathogenesis and/or improve immunogenicity.

In yet additional embodiments of the invention, chimeric HPIV1 viruses are constructed using a HPIV1 "vector" genome or antigenome that is recombinantly modified to incorporate one or more antigenic determinants of a heterologous pathogen. The vector genome or antigenome is comprised of a partial or complete HPIV1 genome or antigenome, which may itself incorporate nucleotide modifications such as attenuating mutations. The vector genome or antigenome is modified to form a chimeric structure through incorporation of a heterologous gene or genome segment. More specifically, chimeric HPIV1 viruses of the invention are constructed through a cDNA-based virus recovery system that yields recombinant viruses that incorporate a partial or complete vector or "background" HPIV1 genome or antigenome combined with one or more "donor" nucleotide sequences encoding the heterologous antigenic determinant(s). In exemplary embodiments a HPIV1 vector genome or antigenome is modified to incorporate one or more genes or genome segments that encode antigenic determinant(s) of one or more heterologous PIVs (e.g., HPIV2 and/or HPIV3), and/or a non-PIV pathogen (e.g., RSV, human metapneumovirus, or measles virus). Thus constructed, chimeric HPIV1 viruses of the invention may elicit an immune response against a specific PIV, e.g., HPIV1, HPIV2, and/or HPIV3, or against a non-PIV pathogen. Alternatively, compositions and methods are provided emplying a HPIV1-based chimeric virus to elicit a polyspecific immune response against multiple PIVs, e.g., HPIV1 and HPIV3, or against one or more HPIVs and a non-PIV pathogen such as measles virus. Exemplary construction of a chimeric, vector HPIV1 candidate virus is illustrated in FIG. 8.

In preferred aspects of the invention, chimeric HPIV1 incorporate a partial or complete human HPIV1 incorporating one or more heterologous polynucleotide(s) encoding one or more antigenic determinants of the heterologous pathogen, which polynucleotides may be added to or substituted within the HPIV1 vector genome or antigenome to yield the chimeric HPIV1 recombinant. The chimeric HPIV1 virus thus acquires the ability to elicit an immune response in a selected host against the heterologous pathogen. In addition, the chimeric virus may exhibit other novel phenotypic characteristics compared to one or both of the vector PIV and heterologous pathogens.

The partial or complete vector genome or antigenome generally acts as a backbone into which heterologous genes or genome segments of a different pathogen are incorporated. Often, the heterologous pathogen is a different PIV from which one or more gene(s) or genome segment(s) is/are combined with, or substituted within, the vector genome or antigenome. In addition to providing novel immunogenic characteristics, the addition or substitution of heterologous genes or genome segments within the vector HPIV1 strain may confer an increase or decrease in attenuation, growth changes, or other desired phenotypic changes as compared with the corresponding phenotype(s) of the unmodified vector and donor viruses. Heterologous genes and genome segments from other PIVs that may be selected as inserts or additions within chimeric PUV of the invention include genes or genome segments encoding the PIV N, P, C, C', Y1, Y2, M, F, HN and/or L protein(s) or one or more antigenic determinant(s) thereof.

Heterologous genes or genome segments of one PIV maybe added as a supernumerary genomic element to a partial or complete genome or antigenome of HPIV1. Alternatively, one or more heterologous gene(s) or genome segment(s) of one PIV may be substituted at a position corresponding to a wild-type gene order position of a counterpart gene(s) or genome segment(s) that is deleted within the HPIV1 vector genome or antigenome. In yet additional embodiments, the heterologous gene or genome segment is added or substituted at a position that is more promoter-proximal or promotor-distal compared to a wild-type gene order position of the counterpart gene or genome segment within the vector genome or antigenome to enhance or reduce, respectively, expression of the heterologous gene or genome segment.

The introduction of heterologous immunogenic proteins, protein domains and immunogenic epitopes to produce chimeric HPIV1 is particularly useful to generate novel immune responses in an immunized host. Addition or substitution of an immunogenic gene or genome segment from one, donor pathogen within a recipient HPIV1 vector genome or antigenome can generate an immune response directed against the donor pathogen, the HPIV1 vector, or against both the donor pathogen and vector.

General methods and compositions useful within the invention for engineering chimeric PIV and PIV "vector" viruses apre provided by Durbin et al., *Virology* 235:323-332, 1997; Skiadopoulos et al., *J. Virol.* 72:1762-1768, 1998; Tao et al., *J Virol* 72:2955-2961, 1998; Skiadopoulos et al., *J. Virol.* 73:1374-1381, 1999; Skiadopoulos et al., *Vaccine* 18:503-510, 1999; Tao et al., *Vaccine* 17:1100-1108, 1999; Tao et al., *Vaccine* 18:1359-1366, 2000; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078); and U.S. Provisional Application No. 60/059,385, filed Sep. 19, 1997; U.S. Provisional Application No. 60/170,195; and PCT publication WO 01/42445A2 published Jun. 14, 2001, each incorporated herein by reference.

In particular, the above-incorporated references describe construction of chimeric PIV recombinants, e.g., having the HN and F genes of HPIV1 substituted into a partial HPIV3 background genome or antigenome, which is further modified to bear one or more of the attenuating mutations identified in HPIV3 JS cp45. One such chimeric recombinant incorporates all of the attenuating mutations identified in the L gene of cp45 outside of the heterologous (HPIV1) HN and F genes, yielding an attenuated, chimeric HPIV.

However, it has been reported that prior infection with HPIV3 partially restricts both the immunogenicity of HPIV3-1 recombinant viruses and the efficacy of such viruses against subsequent HPIV1 challenge. This restriction appears to be due to an immune response against the HPIV3 internal proteins that are shared by the two viruses (Tao et al., *Vaccine* 17:1100-1108, 1999; Tao et al., *Vaccine* 18:1359-1366, 2000, each incorporated herein by reference). The immune response against the internal HPIV3 proteins was short lived and did not appear to contribute to long-term immunogenic composition efficacy, but it might be sufficient to interfere with sequential immunizations spaced at relatively short intervals such as two months, as is envisioned for the live-attenuated RSV and PIV immunogenic compositions (see Introduction). Therefore, successful immunization against HPIV1 and HPIV2 using this model might require the development of viruses that do not share any proteins with the RSV and PIV3 viruses. The HPIV1 reverse genetics system described here resolves this problem by providing live-attenuated HPIV1 that will be infectious and immunogenic in infants that have been previously exposed to HPIV3, as well as other viruses such as RSV.

Chimeric HPIV1 of the invention may also be constructed that express a chimeric protein, for example an immunogenic glycoprotein having a cytoplasmic tail and/or transmembrane domain specific to a HPIV1 vector fused to a heterologous ectodomain of a different PIV or non-PIV pathogen to provide a fusion protein that elicits an immune response against the heterologous pathogen. For example, a heterologous genome segment encoding a glycoprotein ectodomain from a HPIV2 or HPIV3 HN or F glycoprotein may be joined with a genome segment encoding the corresponding HPIV1 HN or F glycoprotein cytoplasmic and transmembrane domains to form a HPIV1-2 or HPIV1-3 chimeric glycoprotein that elicits an immune response against HPIV2 or HPIV3.

Briefly, HPIV1 of the invention expressing a chimeric glycoprotein comprise a major nucleocapsid (N) protein, a nucleocapsid phosphoprotein (P), a large polymerase protein (L), and a HPIV1 vector genome or antigenome that is modified to encode a chimeric glycoprotein. The chimeric glycoprotein incorporates one or more heterologous antigenic domains, fragments, or epitopes of a second, antigenically distinct HPIV. Preferably, this is achieved by substitution within the HPIV1 vector genome or antigenome of one or more heterologous genome segments of the second HPIV that encode one or more antigenic domains, fragments, or epitopes, whereby the genome or antigenome encodes the chimeric glycoprotein that is antigenically distinct from the parent, vector virus.

In more detailed aspects, the heterologous genome segment or segments preferably encode a glycoprotein ectodomain or immunogenic portion or epitope thereof, and optionally include other portions of the heterologous or "donor" glycoprotein, for example both an ectodomain and transmembrane region that are substituted for counterpart glycoprotein ecto- and transmembrane domains in the vector genome or antigenome. Preferred chimeric glycoproteins in this context may be selected from HPIV HN and/or F glycoproteins, and the vector genome or antigenome may be modified to encode multiple chimeric glycoproteins. In preferred embodiments, the HPIV1 vector genome or antigenome is a partial genome or antigenome and the second, antigenically distinct HPIV is either HPIV2 or HPIV3. In one exemplary embodiment, both glycoprotein ectodomain(s) of HPIV2 or HPIV3 HN and F glycoproteins are substituted for corresponding HN and F glycoprotein ectodomains in the HPIV1 vector genome or antigenome. In another exemplary embodiment, HPIV2 or HPIV3 ectodomain and transmembrane regions of one or both HN and/or F glycoproteins are fused to one or more corresponding PIV1 cytoplasmic tail region(s) to form the chimeric glycoprotein. Further details concerning these aspects of the invention are provided in U.S. patent application entitled CONSTRUCTION AND USE OF RECOMBINANT PARAINFLUENZA VIRUSES EXPRESSING A CHIMERIC GLYCOPROTEIN, filed on Dec. 10, 1999 by Tao et al. and identified by Ser. No. 09/456,062 incorporated herein by reference.

To construct chimeric HPIV1 viruses of the invention carrying a heterologous antigenic determinant of a non-PIV pathogen, a heterologous gene or genome segment of the donor pathogen may be added or substituted at any operable position in the vector genome or antigenome. In one embodiment, heterologous genes or genome segments from a non-PIV pathogen can be added (i.e., without substitution) within a HPIV1 vector genome or antigenome to create novel immunogenic properties within the resultant clone (see, e.g., FIG. 8). In these cases, the heterologous gene or genome segment may be added as a supernumerary gene or genome segment, optionally for the additional purpose of attenuating the resultant chimeric virus, in combination with a complete HPIV1 vector genome or antigenome. Alternatively, the heterologous gene or genome segment may be added in conjunction with deletion of a selected gene or genome segment in the vector genome or antigenome.

In preferred embodiments of the invention, the heterologous gene or genome segment is added at an intergenic position within the partial or complete HPIV1 vector genome or antigenome. Alternatively, the gene or genome segment can be inserted within other noncoding regions of the genome, for example, within 5' or 3' noncoding regions or in other positions where noncoding nucleotides occur within the vector genome or antigenome. In one aspect, the heterologous gene or genome segment is inserted at a non-coding site overlapping a cis-acting regulatory sequence within the vector genome or antigenome, e.g., within a sequence required for efficient replication, transcription, and/or translation. These regions of the vector genome or antigenome represent target sites for disruption or modification of regulatory functions associated with introduction of the heterologous gene or genome segment.

As used herein, the term "gene" generally refers to a portion of a subject genome, e.g., a HPIV1 genome, encoding an mRNA and typically begins at the upstream end with a gene-start (GS) signal and ends at the downstream end with the gene-end (GE) signal. The term gene is also interchangeable with the term "translational open reading frame", or ORF, particularly in the case where a protein, such as the C protein, is expressed from an additional ORF rather than from a unique mRNA. The viral genome of all PIVs also contains extragenic leader and trailer regions, possessing part of the promoters required for viral replication and transcription, as well as non-coding and intergenic regions. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination. Exemplary genome sequences have been described for the human PIV3 strains JS (GenBank accession number Z11575, incorporated herein by reference) and Washington (Galinski M. S. In Kingsbury, D. W. (Ed.), *The Paramyxoviruses*, pp. 537-568, Plenum Press, New York, 1991, incorporated herein by reference), and for the bovine PIV3 strain 910N (GenBank accession number D80487, incorporated herein by reference).

To construct chimeric HPIV1 viruses of the invention, one or more PIV gene(s) or genome segment(s) may be deleted, inserted or substituted in whole or in part. This means that partial or complete deletions, insertions and substitutions may include open reading frames and/or cis-acting regulatory sequences of any one or more of the PIV genes or genome segments. By "genome segment" is meant any length of continuous nucleotides from the PIV genome, which might be part of an ORF, a gene, or an extragenic region, or a combination thereof. When a subject genome segment encodes an antigenic determinant, the genome segment encodes at least one immunogenic epitope capable of eliciting a humoral or cell mediated immune response in a mammalian host. The genome segment may also encode an immunogenic fragment or protein domain. In other aspects, the donor genome segment may encode multiple immunogenic domains or epitopes, including recombinantly synthesized sequences that comprise multiple, repeating or different, immunogenic domains or epitopes.

In preferred embodiments of the invention, the chimeric HPIV1 bear one or more major antigenic determinants of a human PIV, or multiple human PIVs, including HPIV1, HPIV2 or HPIV3. These preferred candidates elicit an effective immune response in humans against one or more selected HPIVs. As noted above, the antigenic determinant(s) that elicit(s) an immune response against HPIV may be encoded by the HPIV1 vector genome or antigenome, or may be inserted within or joined to the PIV vector genome or antigenome as a heterologous gene or gene segment. The major protective antigens of human PIVs are their HN and F glycoproteins. However, all PIV genes are candidates for encoding antigenic determinants of interest, including internal protein genes which may encode such determinants as, for example, CTL epitopes.

Preferred chimeric HPIV1 viruses of the invention bear one or more major antigenic determinants from each of a plurality of HPIVs or from a HPIV and a non-PIV pathogen. Chimeric HPIV1 viruses thus constructed include one or more heterologous gene(s) or genome segment(s) encoding antigenic determinant(s) of the same or a heterologous (for example HPIV2 or HPIV3) PIV. These and other constructs yield chimeric PIVs that elicit either a mono- or poly-specific immune response in humans to one or more HPIVs. Further detailed aspects of the invention are provided in U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), U.S. Provisional Application No. 60/059, 385, filed Sep. 19, 1997; U.S. Provisional Application No. 60/170,195 filed Dec. 10, 1999; and U.S. patent application Ser. No. 09/733,692, filed Dec. 8, 2000 (corresponding to International Publication No. WO 01/42445A2), each incorporated herein by reference.

In other exemplary aspects of the invention, chimeric HPIV1 incorporate a HPIV1 vector genome or antigenome modified to express one or more major antigenic determinants of non-PIV pathogen, for example measles virus. The methods of the invention are generally adaptable for incorporation of antigenic determinants from a wide range of additional pathogens within chimeric HPIV1 candidates. In this regard the invention also provides for development of candidates for eliciting immune responses against subgroup A and subgroup B respiratory syncytial viruses (RSV), mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses, among other pathogens. Pathogens that may be targeted according to the methods of the invention include viral and bacterial pathogens, as well as protozoans and multicellular pathogens. Useful antigenic determinants from many important human pathogens in this context are known or readily identified for incorporation within chimeric HPIV1 of the invention. Thus, major antigens have been identified for the foregoing exemplary pathogens, including the measles virus HA and F proteins; the F, G, SH and M2 proteins of RSV, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, flavivirus E and NS 1 proteins, metapneumovirus G and F proteins, and alphavirus E protein. These major antigens, as well as other antigens known in the art for the enumerated pathogens and others, are well characterized to the extent that many of their antigenic determinants, including the full length proteins and their constituent antigenic domains, fragments and epitopes, are identified, mapped and characterized for their respective immunogenic activities.

Among the numerous, exemplary mapping studies that identify and characterize major antigens of diverse pathogens for use within the invention are epitope mapping studies directed to the hemagglutinin-neuraminidase (HN) gene of HPIV (van Wyke Coelingh et al., *J. Virol.* 61:1473-1477, 1987, incorporated herein by reference). This report provides detailed antigenic structural analyses for 16 antigenic variants of HPIV3 variants selected by using monoclonal antibodies (MAbs) to the HN protein which inhibit neuraminidase, hemagglutination, or both activities. Each variant possessed a single-point mutation in the HN gene, coding for a single amino acid substitution in the HN protein. Operational and topographic maps of the HN protein correlated well with the relative positions of the substitutions. Computer-assisted analysis of the HN protein predicted a secondary structure composed primarily of hydrophobic β sheets interconnected by random hydrophilic coil structures. The HN epitopes were located in predicted coil regions. Epitopes recognized by MAbs which inhibit neuraminidase activity of the virus were located in a region which appears to be structurally conserved among several paramyxovirus HN proteins and which may represent the sialic acid-binding site of the HN molecule.

This exemplary work, employing conventional antigenic mapping methods, identified single amino acids which are important for the integrity of HN epitopes. Most of these epitopes are located in the C-terminal half of the molecule, as expected for a protein anchored at its N terminus (Elango et al., *J. Virol.* 57:481-489, 1986). Previously published operational and topographic maps of the PIV3 HN indicated that the MAbs employed recognized six distinct groups of epitopes (I to VI) organized into two topographically separate sites (A and B), which are partially bridged by a third site (C). These groups of epitopes represent useful candidates for antigenic determinants that may be incorporated, alone or in various combinations, within chimeric HPIV1 viruses of the invention. (See, also, Coelingh et al., *Virology* 143:569-582, 1985; Coelingh et al., *Virology* 162:137-143, 1988; Ray et al., *Virology* 148:232-236, 1986; Rydbeck et al., *J. Gen. Virol.* 67:1531-1542, 1986, each incorporated herein by reference), Additional studies by van Wyke Coelingh et al. (*J. Virol.* 63:375-382, 1989) provide further information relating to selection of PIV antigenic determinants for use within the invention. In this study, twenty-six monoclonal antibodies (MAbs) (14 neutralizing and 12 nonneutralizing) were used to exanine the antigenic structure, biological properties, and natural variation of the fusion (F) glycoprotein of HPIV3. Analysis of laboratory-selected antigenic variants and of PIV3 clinical isolates indicated that the panel of MAbs recognizes at least 20 epitopes, 14 of which participate in neutralization. Competitive binding assays confirmed that the 14 neutralization epitopes are organized into three nonoverlapping principal antigenic regions (A, B, and C) and one bridge site (AB), and that the 6 nonneutralization epitopes form four sites (D, E, F, and G). Most of the neutralizing MAbs were involved in nonreciprocal competitive binding reactions, suggesting that they induce conformational changes in other neutralization epitopes.

Other antigenic determinants for use within the invention have been identified and characterized for respiratory syncytial virus (RSV). For example, Beeler et al., *J. Virol.* 63:2941-2950, 1989, incorporated herein by reference, employed eighteen neutralizing monoclonal antibodies (MAbs) specific for the fusion glycoprotein of the A2 strain of RSV to construct a detailed topological and operational map of epitopes involved in RSV neutralization and fusion. Competitive binding assays identified three nonoverlapping antigenic regions (A, B, and C) and one bridge site (AB). Thirteen MAb-resistant mutants (MARMs) were selected, and the neutralization patterns of the MAbs with either MARMs or RSV clinical strains identified a minimum of 16 epitopes. MARMs selected with antibodies to six of the site A and AB epitopes displayed a small-plaque phenotype, which is consistent with an alteration in a biologically active region of the F molecule. Analysis of MARMs also indicated that these neutralization epitopes occupy topographically distinct but conformationally interdependent regions with unique biological and immunological properties. Antigenic variation in F epitopes was then examined by using 23 clinical isolates (18 subgroup A and 5 subgroup B) in cross-neutralization assays with the 18 anti-F MAbs. This analysis identified constant, variable, and hypervariable regions on the molecule and indicated that antigenic variation in the neutralization epitopes of the RSV F glycoprotein is the result of a noncumulative genetic heterogeneity. Of the 16 epitopes, 8 were conserved on all or all but 1 of 23 subgroup A or subgroup B clinical isolates. These antigenic determinants, including the full length proteins and their constituent antigenic domains, fragments and epitopes, all represent useful candidates for integration within chimeric PIV of the invention to elicit novel immune responses as described above. (See also, Anderson et al., *J. Infect. Dis.* 151:626-633, 1985; Coelingh et al., *J. Virol.* 63:375-382, 1989; Fenner et al., *Scand. J. Immunol.* 24:335-340, 1986; Fernie et al., *Proc. Soc. Exp. Biol. Med.* 171:266-271, 1982; Sato et al., *J. Gen. Virol.* 66:1397-1409, 1985; Walsh et al., *J. Gen. Virol.* 67:505-513, 1986, and Olmsted et al., *J. Virol.* 63:411-420, 1989, each incorporated herein by reference).

To express antigenic determinants of heterologous PIVs and non-PIV pathogens, the invention provides numerous methods and contstructs. In certain detailed embodiments, a transcription unit comprising an open reading frame (ORF) of a gene encoding an antigenic protein (e.g., the measles virus HA gene) is added to a HPIV1 vector genome or antigenome at various positions, yielding exemplary chimeric PIV1/measles candidates. In exemplary embodiments, chimeric HPIV1 viruses are engineered that incorporate heterologous nucleotide sequences encoding protective antigens from respiratory syncytial virus (RSV) to produce infectious, attenuated viruses. The cloning of RSV cDNA and other disclosure is provided in U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892,403, filed Jul. 15, 1997 (corresponding to International Publication No. WO 98/02530); U.S. patent application Ser. No. 09/291,894, filed on Apr. 13, 1999; International Application No. PCT/US00/09696, filed Apr. 12, 2000, corresponding to U.S. Provisional Patent Application Serial No. 60/129,006, filed on Apr. 13, 1999; Collins et al., *Proc Nat. Acad. Sci. U.S.A.* 92:11563-11567, 1995; Bukreyev et al., *J. Virol.* 70:6634-41, 1996, Juhasz et al., *J. Virol.* 71:5814-5819, 1997; Durbin et al., *Virology* 235:323-332, 1997; He et al. *Virology* 237:249-260, 1997; Baron et al. *J. Virol.* 71:1265-1271, 1997; Whitehead et al., *Virology* 247:232-9, 1998a; Whitehead et al., *J. Virol.* 72:4467-4471, 1998b; Jin et al. *Virology* 251:206-214, 1998; and Whitehead et al., *J. Virol.* 73:3438-3442, 1999, and Bukreyev et al., *Proc. Nat. Acad. Sci. U.S.A.* 96:2367-72, 1999, each incorporated herein by reference in its entirety for all purposes). Other reports and discussion incorporated or set forth herein identify and characterize RSV antigenic determinants that are useful within the invention.

PIV chimeras incorporating one or more RSV antigenic determinants, preferably comprise a HPIV1 vector genome or antigenome combined with a heterologous gene or genome segment encoding an antigenic RSV glycoprotein, protein domain (e.g., a glycoprotein ectodomain) or one or more immunogenic epitopes. In one embodiment, one or more genes or genome segments from RSV F and/or G genes is/are combined with the vector genome or antigenome to form the chimeric HPIV1. Certain of these constructs will express chimeric proteins, for example fusion proteins having a cytoplasmic tail and/or transmembrane domain of HPIV1 fused to an ectodomain of RSV to yield a novel attenuated virus that optionally elicits a multivalent immune response against both PIV1 and RSV.

Considering the epidemiology of RSV and HPIV1, HPIV2, and HPIV3, it will be optimal to administer immunogenic compositions of the invention in a predetermined, sequential schedule. RSV and HPIV3 cause significant illness within the first four months of life whereas most of the illness caused by HPIV1 and HPIV2 occur after six months of age (Chanock et al., in *Parainfluenza Viruses*, Knipe et al. (Eds.), pp. 1341-1379, Lippincott Williams & Wilkins, Philadelphia, 2001; Collins et al., In *Fields Virology*, Vol. 1, pp. 1205-1243, Lippincott-Raven Publishers, Philadelphia, 1996; Reed et al., *J. Infect. Dis.* 175:807-13, 1997, each incorporated herein by reference). Accordingly, certain sequential immunization protocols of the invention will involve administration of immunogenic compositions to elicit a response against HPIV3 and/or RSV (e.g., as a combined formulation) two or more times early in life, with the first dose administered at or before one month of age, followed by an immunogenic composition directed against HPIV1 and/or HPIV2 at about four and six months of age.

The invention therefore provides novel combinatorial immunogenic compositions and coordinate immunization protocols for multiple pathogenic agents, including multiple PIV's and/or PIV and a non-PIV pathogen. These methods and formulations effectively target early immunization against RSV and PIV3. One preferred immunization sequence employs one or more live attenuated viruses that elicit a response against RSV and PIV3 as early as one month of age (e.g., at one and two months of age) followed by a bivalent PIV1 and PIV2 immunogenic composition at four and six months of age. It is thus desirable to employ the methods of the invention to administer multiple PIV immunogenic compositions, including one or more chimeric PIV compositions, coordinately, e.g., simultaneously in a mixture or separately in a defined temporal sequence (e.g., in a daily or weekly sequence), wherein each virus preferably expresses a different heterologous protective antigen. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

Other sequential immunizations according to the invention permits the induction of the high titer of antibody targeted to a heterologous pathogen, such as measles. In one embodiment, young infants (e.g. 2-4 month old infants) are immunized with an attenuated HPIV3 or a chimeric HPIV1 and/or HPIV3 virus that elicits an immune response against HPIV3 and/or measles (for example a chimeric HPIV1 or HPIV3 virus expressing the measles virus HA protein and also adapted to elicit an immune response against HPIV3). Subsequently, e.g., at four months of age the infant is again immunized but with a different, secondary vector construct, such as a rHPIV1 virus expressing the measles virus HA gene and the HPIV1 antigenic determinants as functional, obligate glycoproteins of the vector. Following the first immunization, the subject will demonstrate a primary antibody response to both the PIV3 HN and F proteins and to the measles virus HA protein, but not to the PIV1 HN and F protein. Upon secondary immunization with the rHPIV1 expressing the measles virus HA, the subject will be readily infected with the immunizing virus because of the absence of antibody to the PIV1 HN and F proteins and will develop both a primary antibody response to the PIV1 HN and F protective antigens and a high titered secondary antibody response to the heterologous measles virus HA protein. A similar sequential immunization schedule can be developed where immunity is sequentially elicited against HPIV3 and then HPIV2 by one or more of the chimeric viruses disclosed herein, simultaneous with stimulation of an initial and then secondary, high titer protective response against measles or another non-PIV pathogen. This sequential immunization strategy, preferably employing different serotypes of PIV as primary and secondary vectors, effectively circumvents immunity that is induced to the primary vector, a factor ultimately limiting the usefulness of vectors with only one serotype. The success of sequential immunization with rHPIV3 and rHPIV3-1 virus candidates as described above has been reported (Tao et al., *Vaccine* 17:1100-8, 1999, incorporated herein by reference), but with the limitation of decreased immunogenicity of rHPIV3-1 against HPIV1 challenge. The present invention, in which the backbone of the booster virus is antigenically unrelated to the primary virus or vector, overcomes this important limitation.

Further in accordance with these aspect of the invention, exemplary coordinate immunization protocols may incorporate two, three, four and up to six or more separate HPIV viruses administered simultaneously (e.g., in a polyspecific mixture) in a primary immunization step, e.g., at one, two or four months of age. For example, two or more HPIV1-based viruses for use in immunogenic compositions can be administered that separately express one or more antigenic determinants (i.e., whole antigens, immunogenic domains, or epitopes) selected from the G protein of RSV subgroup A, the F protein of RSV subgroup A, the G protein of RSV subgroup B, the F protein of RSV subgroup B, the HA protein of measles virus, and/or the F protein of measles virus. Coordinate booster administration of these same PIV1-based constructs can be repeated at two months of age. Subsequently, e.g., at four months of age, a separate panel of 2-6 or more antigenically distinct (referring to vector antigenic specificity) live attenuated HPIV1-based recombinant viruses can be administered in a secondary immunization step. For example, secondary immunization may involve concurrent administration of a mixture or multiple formulations that contain(s) multiple HPIV1 constructs that collectively express RSV G from subgroup A, RSV F from subgroup A, RSV F from subgroup B, RSV G from subgroup B, measles virus HA, and/or measles virus F, or antigenic determinants from any combination of these proteins. This secondary immunization provides a boost in immunity to each of the heterologous RSV and measles virus proteins or antigenic determinant(s) thereof. At six months of age, a tertiary immunization step involving administration of one to six or more separate live attenuated HPIV1-2 or HPIV1-3 vector-based recombinants can be coordinately administered that separately or collectively express RSV G from subgroup A, RSV F from subgroup A, RSV G from subgroup B, RSV F from subgroup B, measles virus HA, and/or measles virus F, or antigenic determinant(s) thereof. Optionally at this step in the immunization protocol, rPIV3 and rPIV1 may be administered in booster formulations. In this way, the strong immunity characteristic of secondary antibody to PIV1, PIV2, PIV3, RSV A, RSV B, and measles viruses are all induced within the first six months of infancy. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

The present invention thus overcomes the difficulties inherent in prior approaches to development of vector based immunogenic compositions and provides unique opportunities for immunization of infants during the first year of life against a variety of human pathogens. Previous studies in developing live-attenuated PIV indicate that, unexpectedly, rPIVs and their attenuated and chimeric derivatives have properties which make them uniquely suited among the nonsegmented negative strand RNA viruses as vectors to express foreign proteins to provide immunogenic compositions against a variety of human pathogens. The skilled artisan would not have predicted that the human PIVs, which tend to grow substantially less well than the model nonsegmented negative strand viruses and which typically have been underrepresented with regard to molecular studies, would prove to have characteristics which are highly favorable as vectors. It is also surprising that the intranasal route of administration of these immunogenic compositions has proven a very efficient means to stimulate a robust local and systemic immune response against both the vector and the expressed heterologous antigen. Furthermore, this route provides additional advantages for immunization against heterologous pathogens which infect the respiratory tract or elsewhere.

The present invention provides major advantages over previous attempts to immunize young infants against measles virus and other microbial pathogens. First, the HPIV1 recombinant vector into which the protective antigen or antigens of heterologous pathogens such as measles virus are inserted can be attenuated in a finely adjusted manner by incorporation of one or more attenuating mutations or other modifications to attenuate the virus for the respiratory tract of the very young, seronegative or seropositive human infant. An extensive history of prior clinical evaluation and practice (see, e.g., Karron et al., *Pediatr. Infect. Dis. J.* 15:650-654, 1996; Karron et al., *J. Infect. Dis.* 171:1107-1114, 1995a; Karron et al., *J. Infect. Dis.* 172:1445-1450, 1995, each incorporated herein by reference) greatly facilitates evaluation of derivatives of these recombinants bearing foreign protective antigens in the very young human infant.

Yet another advantage of the invention is that chimeric HPIV1 bearing heterologous sequences will replicate efficiently in vitro to enable large scale production of virus for use in immunogenic compositions. This is in contrast to the replication of some single-stranded, negative-sense RNA viruses which can be inhibited in vitro by the insertion of a foreign gene (Bukreyev et al., *J. Virol.* 70:6634-41, 1996). Also, the presence of three antigenic serotypes of HPIV, each of which causes significant disease in humans and hence can serve simultaneously as vector and immunogen, presents a unique opportunity to sequentially immunize the infant with antigenically distinct variants of HPIV each bearing the same foreign protein. In this manner the sequential immunization permits the development of a primary immune response to the foreign protein which can be boosted during subsequent infections with the antigenically distinct HPIV also bearing the same or a different foreign protein or proteins, i.e., the protective antigen of measles virus or of another microbial pathogen. It is also likely that readministration of homologous HPIV vectors will also boost the response to both HPIV and the foreign antigen since the ability to cause multiple reinfections in humans is an unusual but characteristic attribute of the HPIVs (Collins et al., *In "Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1205-1243. Lippincott-Raven Publishers, Philadelphia, 1996).

Yet another advantage of the invention is that the introduction of a gene unit into a HPIV1 vector has several highly desirable effects for the production of attenuated viruses. First, the insertion of gene units expressing, for example, the HA of measles virus or the HN of PIV2 can specify a host range phenotype on the HPIV1 vector, i.e., where the resulting HPIV1 vector replicates efficiently in vitro but is restricted in replication in vivo in both the upper and lower respiratory tracts. Thus, the insertion of a gene unit expressing a viral protective antigen as an attenuating factor for the HPIV1 vector is a desirable property in live attenuated viruses of the invention.

The HPIV1 vector system has unique advantages over other members of the single-stranded, negative-sense viruses of the Order Mononegavirales. First, most other mononegaviruses that have been used as vectors are not derived from human pathogens (e.g., murine HPIV1 (Sendai virus) (Sakai et al., *FEBS Lett.* 456:221-6, 1999), vesicular stomatitis virus (VSV) which is a bovine pathogen (Roberts et al., *J. Virol.* 72:4704-11, 1998), and canine PIV2 (SV5) He et al., *Virology* 237:249-60, 1997)). For these nonhuman viruses, little or only weak immunity would be conferred against any human virus by antigens present in the vector backbone. Thus, a nonhuman virus vector expressing a supernumerary gene for a human pathogen would induce resistance only against that single human pathogen. In addition, use of viruses such as VSV, SV5, rabies, or Sendai virus as vector would expose subjects to viruses that they likely would not otherwise encounter during life. Infection with, and immune responses against, such nonhuman viruses would be of marginal benefit and would pose safety concerns, because there is little experience of infection with these viruses in humans.

An important and specific advantage of the HPIV1 vector system is that its preferred, intranasal route of administration, mimicking natural infection, will induce both mucosal and systemic immunity and reduces the neutralizing and immunosuppressive effects of maternally-derived serum IgG that is present in infants. While these same advantages theoretically are possible for using RSV as a vector, for example, we have found that RSV replication is strongly inhibited by inserts of greater than approximately 500 bp (Bukreyev et al., *Proc. Natl. Acad. Sci. USA* 96:2367-72, 1999). In contrast, as described herein, HPIV1 can readily accommodate several large gene inserts. The finding that recombinant RSV is unsuitable for bearing large inserts, whereas recombinant PIVs are highly suitable, represents unexpected results.

It might be proposed that some other viral vector could be given intranasally to obtain similar benefits as shown for PIV vectors, but this has not been successful to date. For example, the MVA strain of vaccinia virus expressing the protective antigens of HPIV3 was evaluated as a live attenuated intranasal vaccine against HPIV3. Although this vector appeared to be a very efficient expression system in cell culture, it was inexplicably inefficient in inducing resistance in the upper respiratory tract of primates (Durbin et al., *Vaccine* 16:1324-30, 1998) and was inexplicably inefficient in inducing a protective response in the presence of passive serum antibodies (Durbin et al., *J. Infect. Dis.* 179:1345-51, 1999). In contrast, PIV3 and RSV vaccine candidates have been found to be protective in the upper and lower respiratory tract of non-human primates, even in the presence of passive serum antibodies (Crowe et al., *Vaccine* 13:847-855, 1995; Durbin et al., *J. Infect. Dis.* 179:1345-51, 1999).

As noted above, the invention permits a wide range of alterations to be recombinantly produced within the HPIV1 genome or antigenome, yielding defined mutations that specify desired phenotypic changes. As also noted above, defined mutations can be introduced by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA constructs provide for better ease of manipulation than large cDNA constructs, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-gen® kit of Bio-Rad Laboratories (Richmond, Calif.), or a method using the double-stranded plasmid directly as a template such as the Chameleon® mutagenesis kit of Strategene (La Jolla, Calif.), or by the polymerase chain reaction employing either an oligonucleotide primer or a template which contains the mutation(s) of interest. A mutated subfragment can then be assembled into the complete antigenome or genome cDNA. A variety of other mutagenesis techniques are known and can be routinely adapted for use in producing the mutations of interest in a PIV antigenome or genome cDNA of the invention.

Thus, in one illustrative embodiment mutations are introduced by using the MUTA-gene® phagemid in vitro mutagenesis kit available from Bio-Rad Laboratories. In brief, cDNA encoding a PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15-35 nucleotides in the case of genome segments encoding small functional domains of proteins, e.g., epitopic sites, to about 50, 75, 100, 200-500, and 500-1,500 or more nucleotides.

The ability to introduce defined mutations into infectious recombinant HPIV1 has many applications, including the manipulation of PIV pathogenic and immunogenic mechanisms. For example, the functions of HPIV1 proteins, including the N, P, M, F, HN, and L proteins and products of the C, C', Y1, and Y2 ORFs, can be manipulated by introducing mutations which ablate or reduce the level of protein expression, or which yield mutant protein. Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock et al., *J. Virol.* 67:2772-8, 1993, incorporated herein by reference in its entirety), whose rescue-dependent status is useful in characterizing those mutants that may be too inhibitory to be recovered in replication-independent infectious virus.

Certain substitutions, insertions, deletions or rearrangements of genes or genome segments within recombinant HPIV1 of the invention (e.g., substitutions of a genome segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or genome segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

As used herein, "counterpart" genes, genome segments, proteins or protein regions, are typically from heterologous sources (e.g., from different PIV genes, or representing the same (i.e., homologous or allelic) gene or genome segment in different PIV types or strains). Typical counterparts selected in this context share gross structural features, e.g., each counterpart may encode a comparable protein or protein structural domain, such as a cytoplasmic domain, transmembrane domain, ectodomain, binding site or region, epitopic site or region, etc. Counterpart domains and their encoding genome segments embrace an assemblage of species having a range of size and sequence variations defined by a common biological activity among the domain or genome segment variants.

Counterpart genes and genome segments, as well as other polynucleotides disclosed herein for producing recombinant PIV within the invention, often share substantial sequence identity with a selected polynucleotide "reference sequence," e.g., with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, (*Adv. Appl. Math.* 2:482, 1981), by the homology alignment algorithm of Needleman & Wunsch, (*J. Mol. Biol.* 48:443, 1970), by the search for similarity method of Pearson & Lipman, (*Proc. Natl. Acad. Sci. U.S.A.* 85:2444, 1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant HPIV1 of the invention are also typically selected to have conservative relationships, i.e. to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (*Immunology—A Synthesis,* 2nd ed., E. S. Golub & D. R. Gren, eds., Sinauer Associates, Sunderland, Mass., 1991, incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). Moreover, amino acids may be modified by glycosylation, phosphorylation and the like.

To select candidate viruses according to the invention, the criteria of viability, attenuation and immunogenicity are determined according to well known methods. Viruses that will be most desired in immunogenic compositions of the invention must maintain viability, have a stable attenuation phenotype, exhibit replication in an immunized host (albeit at lower levels), and effectively elicit production of an immune response in a subject sufficient to elicit an immune response against wild-type virus. The recombinant HPIV1 viruses of the invention are not only viable and more appropriately attenuated than previous immunogenic agents, but are more stable genetically in vivo—retaining the ability to stimulate an immune response and in some instances to expand immunity afforded by multiple modifications, e.g., induce an immune response against different viral strains or subgroups, or by a different immunologic basis, e.g., secretory versus serum immunoglobulins, cellular immunity, and the like.

Recombinant HPIV1 viruses of the invention can be tested in various well known and generally accepted in vitro and in vivo models to confirm adequate attenuation, resistance to phenotypic reversion, and immunogenicity for use in immunogenic compositions. In in vitro assays, the modified virus (e.g., a multiply attenuated, biologically derived or recombinant PIV) is tested, e.g., for temperature sensitivity of virus replication, i.e. ts phenotype, and for the small plaque or other desired phenotype. Modified viruses are further tested in animal models of PIV infection. A variety of animal models have been described and are summarized in various references incorporated herein. PIV model systems, including rodents and non-human primates, for evaluating attenuation and immunogenic activity of PIV candidates of the invention are widely accepted in the art, and the data obtained therefrom correlate well with PIV infection, attenuation and immunogenicity in humans.

In accordance with the foregoing description, the invention also provides isolated, infectious recombinant HPIV1 compositions for use in immunogenic compositions. The attenuated virus which is a component of an immunogenic composition is in an isolated and typically purified form. By isolated is meant to refer to PIV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated HPIV1 of the invention may be produced by an infected cell culture, separated from the cell culture and added to a stabilizer.

For use in immunogenic compositions, recombinant HPIV1 produced according to the present invention can be used directly in formulations, or lyophilized, as desired, using lyophilization protocols well known to the artisan. Lyophilized virus will typically be maintained at about 4° C. When ready for use the lyophilized virus is reconstituted in a stabilizing solution, e.g., saline or comprising SPG, $Mg^{++}$ and HEPES, with or without adjuvant, as further described below.

HPIV1-based immunogenic compositions of the invention contain as an active ingredient an immunogenically effective amount of a recombinant HPIV1 produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-o-deacylated monophosphoryl lipid A; RIBI ImmunoChem Research, Inc., Hamilton, Mont.) and IL-12 (Genetics Institute, Cambridge Mass.), among many other suitable adjuvants well known in the art.

Upon immunization with a recombinant HPIV1 composition as described herein, via aerosol, droplet, oral, topical or other route, the immune system of the host responds to the immunogenic composition by producing antibodies specific for PIV proteins, e.g., F and HN glycoproteins. As a result of the immunization with an immunogenically effective amount of a recombinant HPIV1 produced as described herein, the host becomes at least partially or completely immune to infection by the targeted PIV or non-PIV pathogen, or resistant to developing moderate or severe infection therefrom, particularly of the lower respiratory tract.

The host to which the immunogenic compositions are administered can be any mammal which is susceptible to infection by PIV or a selected non-PIV pathogen and which host is capable of generating an immune response to the antigens of the vaccinizing strain. Accordingly, the invention provides methods for creating immunogenic compositions for a variety of human and veterinary uses.

The compositions containing the recombinant HPIV1 of the invention are administered to a host susceptible to or otherwise at risk for PIV infection to enhance the host's own immune response capabilities. Such an amount is defined to be a "immunogenically effective dose." In this use, the precise amount of recombinant HPIV1 to be administered within an effective dose will depend on the host's state of health and weight, the mode of administration, the nature of the formulation, etc., but will generally range from about $10^3$ to about $10^7$ plaque forming units (PFU) or more of virus per host, more commonly from about $10^4$ to $10^6$ PFU virus per host. In any event, the immunogenic composition should provide a quantity of modified PIV of the invention sufficient to effectively elicit a detectable immune response in the subject.

The recombinant HPIV1 produced in accordance with the present invention can be combined with viruses of other PIV serotypes or strains to achieve immunization against multiple PIV serotypes or strains. Alternatively, immunization against multiple PIV serotypes or strains can be achieved by combining protective epitopes of multiple serotypes or strains engineered into one virus, as described herein. Typically when different viruses are administered they will be in admixture and administered simultaneously, but they may also be administered separately. Immunization with one strain may elicit an immune response against different strains of the same or different serotype.

In some instances it may be desirable to combine the recombinant HPIV1 immunogenic compositions of the invention with immunogenic compositions that induce immune responses to other agents, particularly other childhood viruses. In another aspect of the invention the recombinant HPIV1 can be employed as a vector for protective antigens of other pathogens, such as respiratory syncytial virus (RSV) or measles virus, by incorporating the sequences encoding those protective antigens into the recombinant HPIV1 genome or antigenome which is used to produce infectious virus, as described herein.

In all subjects, the precise amount of recombinant HPIV1 immunogenic composition administered, and the timing and repetition of administration, will be determined based on the patient's state of health and weight, the mode of administration, the nature of the formulation, etc. Dosages will generally range from about $10^3$ to about $10^7$ plaque forming units (PFU) or more of virus per patient, more commonly from about $10^4$ to $10^6$ PFU virus per patient. In any event, the immunogenic compositions should provide a quantity of attenuated recombinant HPIV1 sufficient to effectively stimulate or induce an anti-PIV or other anti-pathogenic immune response, e.g., as can be determined by hemagglutination inhibition, complement fixation, plaque neutralization, and/or enzyme-linked immunosorbent assay, among other methods. In this regard, individuals are also monitored for signs and symptoms of upper respiratory illness. As with administration to chimpanzees, the attenuated virus grows in the nasopharynx at levels approximately 10-fold or more lower than wild-type virus, or approximately 10-fold or more lower when compared to levels of incompletely attenuated virus.

In neonates and infants, multiple administration may be required to elicit sufficient levels of immunity. Administration should begin within the first month of life, and at intervals throughout childhood, such as at two months, six months, one year and two years, as necessary to maintain sufficient levels of immunity against native (wild-type) PUV infection. Similarly, adults who are particularly susceptible to repeated or serious PIV infection, such as, for example, health care workers, day care workers, family members of young children, the elderly, individuals with compromised cardiopulmonary function, may require multiple immunizations to establish and/or maintain immune responses. Levels of induced immunity can be monitored by measuring amounts of neutralizing secretory and serum antibodies, and dosages adjusted or immunizations repeated as necessary to maintain desired levels of immunity. Further, different recombinant viruses may be indicated for administration to different recipient groups. For example, an engineered HPIV1 expressing a cytokine or an additional protein rich in T cell epitopes may be particularly advantageous for adults rather than for infants.

HPIV1-based immunogenic compositions produced in accordance with the present invention can be combined with viruses expressing antigens of another subgroup or strain of PIV to achieve an immune response against multiple PIV subgroups or strains. Alternatively, the immunogenic virus may incorporate protective epitopes of multiple PIV strains or subgroups engineered into one PIV clone, as described herein.

The recombinant HPIV1 immunogenic compositions of the invention elicit production of an immune response that alleviates serious lower respiratory tract disease, such as pneumonia and bronchiolitis when the individual is subsequently infected with wild-type PIV. While the naturally circulating virus is still capable of causing infection, particularly in the upper respiratory tract, there is a very greatly reduced possibility of rhinitis as a result of the immunization. Boosting of resistance by subsequent infection by wild-type virus can occur. Following immunization, there are detectable levels of host engendered serum and secretory antibodies which are capable of neutralizing homologous (of the same subgroup) wild-type virus in vitro and in vivo.

Preferred recombinant HPIV1 candidates of the invention exhibit a very substantial diminution of virulence when compared to wild-type virus that naturally infects humans. The virus is sufficiently attenuated so that symptoms of infection will not occur in most immunized individuals. In some instances the attenuated virus may still be capable of dissemination to unimmunized individuals. However, its virulence is sufficiently abrogated such that severe lower respiratory tract infections in the immunized or incidental host do not occur.

The level of attenuation of recombinant HPIV1 candidates may be determined by, for example, quantifying the amount of virus present in the respiratory tract of an immunized host and comparing the amount to that produced by wild-type PUV or other attenuated PIV which have been evaluated as candidate strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal candidate virus should exhibit a restricted level of replication in both the upper and lower respiratory tract. However, the attenuated viruses of the invention must be sufficiently infectious and immunogenic in humans to elicit an immune response in immunized individuals. Methods for determining levels of PIV in the nasopharynx of an infected host are well known in the literature.

Levels of induced immunity provided by the immunogenic compositions of the invention can also be monitored by measuring amounts of neutralizing secretory and serum antibodies. Based on these measurements, dosages can be adjusted or immunizations repeated as necessary to maintain desired levels of immunity. Further, different viruses may be advantageous for different recipient groups. For example, an engineered recombinant HPIV1 strain expressing an additional protein rich in T cell epitopes may be particularly advantageous for adults rather than for infants.

In yet another aspect of the invention the recombinant HPIV1 is employed as a vector for transient gene therapy of the respiratory tract. According to this embodiment the recombinant HPIV1 genome or antigenome incorporates a sequence that is capable of encoding a gene product of interest. The gene product of interest is under control of the same or a different promoter from that which controls PIV expression. The infectious recombinant HPIV1 produced by coexpressing the recombinant HPIV1 genome or antigenome with the N, P, L and other desired PIV proteins, and containing a sequence encoding the gene product of interest, is administered to a patient. Administration is typically by aerosol, nebulizer, or other topical application to the respiratory tract of the patient being treated. Recombinant HPIV1 is administered in an amount sufficient to result in the expression of therapeutic or prophylactic levels of the desired gene product. Representative gene products that may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and viral antigens.

The following examples are provided by way of illustration, not limitation. These examples describe the development of a novel reverse genetics system for the recovery of HPIV1 from cDNA, and the use of this system for construction of novel recombinant HPIV1 immunogenic composition candidates. Briefly, the examples below detail investigations leading to the complete sequence of a clinical isolate of HPIV1. Also described is the construction of a complete antigenomic cDNA, rescue of infectious, recombinant HPIV1 virus, and investigations to characterize the phenotype of recombinant HPIV1 candidates of the invention in vitro and in vivo.

Viruses and Cells

LLC-MK2 cells (ATCC CCL 7.1) and HEp-2 cells (ATCC CCL 23) were maintained in Opti-MEM I (Gibco-Invitrogen Corp. Carlsbad, Calif.) supplemented with 5% FBS and gentamicin sulfate (50 μg/ml), and 2 mM glutamine or in EMEM (Quality Biological, Inc. Gaithersburg, Md.) supplemented with 10% FBS, gentamicin sulfate (50 μg/ml), and 2 mM glutamine. The isolation of biologically derived HPIV1/Washington/20993/1964 (HPIV1 WASH/64) was previously described (Murphy et al., *Infect. Immun.* 12:62-68, 1975, incorporated herein by reference). HPIV1 was grown on LLC-MK2 cells in EMEM or Opti-MEM I that was supplemented with gentamicin sulfate (50 μg/ml), 2 mM glutamine, and porcine derived trypsin (5 μg/ml; BioWhittaker, Walkersville, Md.). The modified vaccinia virus Ankara (MVA T7) was employed for expression of the T7 polymerase (Wyatt et al., *Virology* 210:202-205, 1995, incorporated herein by reference).

HPIV1 Virion RNA Isolation

Confluent monolayers of LLC-MK2 cells were infected with HPIV1 WASH/64 at a multiplicity of infection (MOI) of approximately one $TCID_{50}$ per cell. At 3-4 days post-infection, clarified supernatants were harvested and virus was precipitated by incubation in 7.5% (w/v) PEG-8000 on ice for 2 hr followed by centrifugation at 10,845×g for 1 hr. Virion RNA (vRNA) was isolated by extraction of the pellet with TRIzol reagent (Invitrogen, Inc. Carlsbad, Calif.) and chloroform. The aqueous layer was then extracted with an equal volume of chloroform. vRNA was precipitated with an equal volume of isopropanol. The vRNA pellet was washed in 70% ethanol and resuspended in diethyl pyrocarbonate (DEPC) treated $H_2O$.

Reverse Transcription (RT), Polymerase Chain Reaction (PCR) and Nucleotide Sequencing vRNA was reverse transcribed using the SuperScript II Preamplification System (Invitrogen, Inc.) and random hexamer primers. PCR was carried out on the reverse transcribed cDNA product using the Advantage cDNA PCR Kit (Clontech Laboratories, Palo Alto, Calif.). The antigenomic HPIV1 cDNA was generated from the RT and RACE products in seven overlapping PCR fragments using primers homologous to fragments from previously published strains of HPIV1 (Tao et al., *J. Virol.* 72:2955-2961, 1998; Gorman et al., *Virology* 175:211-221, 1990; Lyn et al., *J. Gen. Virol.* 72:983-987, 1991; Miyahara et al., *Arch. Virol.* 124:255-268, 1992, each incorporated herein by reference), MPIV1 Z (Galinski, in Kingsbury, D. W. (ed.) Annotated nucleotide and protein sequences for selected paramyxoviridae. Plenum Press, New York, 1991, 537-568, incorporated herein by reference), or primers based on HPIV1 WASH/64 sequence obtained during the course of the experiments. The nucleotide sequences of cDNA products were determined by direct sequence analysis of the RT-PCR products using a Perkin-Elmer ABI 310 sequencer with the dRhodamine sequencing kit (Perkin-Elmer Applied Biosystems, Warrington, UK). The sequence was assembled from the seven overlapping RT-PCR fragments and previously published F and HN sequences for HPIV1 WASH/64 (Tao et al., *J. Virol.* 72:2955-2961, 1998, incorporated herein by reference) spanning the HPIV1 genome using the Autoassembler (Perkin-Elmer Applied Biosystems), the AssemblyLIGN (Accelrys, San Diego, Calif.), or the SeqMan II program (DNAstar, Madison, Wis.).

The 3' terminal genomic sequence of HPIV1 was converted to cDNA using the 3' RACE System for Rapid Amplification of cDNA Ends (Invitrogen, Inc.) as specified by the manufacturer. Briefly, vRNA was polyadenylated at its 3' end using poly A polymerase (Invitrogen. Inc.), followed by first-strand cDNA synthesis primed with oligo(dT) and PCR using an HPIV1 specific reverse primer and a forward adapter-primer supplied with the kit. RACE products were sequenced directly as described above. To determine the sequence for the 3' end, two independently derived RACE products were sequenced and were found to be identical.

The 5' genomic terminus of HPIV1 was amplified from vRNA following first-strand cDNA synthesis, terminal transferase tailing, and PCR amplification as specified by the 5' RACE System (Invitrogen, Inc.). The amplified cDNA RACE products were sequenced directly. The sequence for the 5' end was determined with multiple sequencing reactions of two independently derived 5'RACE products, and the sequences were found to be identical.

Sequence Comparison with Heterologous Paramyxoviruses

The assembled HPIV1 genome was compared to the following heterologous paramyxoviruses: MPIV1 Z strain, GenBank accession no. M30202; HPIV2 Toshiba strain, GenBank accession no. X55759; SV5 W3A strain, GenBank accession no. AF052755; HPIV3 JS strain, GenBank accession no. Z11575; and BPIV3 Kansas (KA) strain, GenBank accession no. AF178654 (all GenBank data cited herein is incorporated by reference). Identification of the gene-start and gene-end signals was made by performing a Clustal W alignment (Thompson et al., *Nucleic Acids Res.* 22, 4673-4680, 1994, incorporated herein by reference) of HPIV1 with MPIV1 sequences using the MacVector program (Accelrys) with the original program default settings and by comparison with HPIV3 and BPIV3 sequences (Galinski, supra; Bailly et al., Virus Genes 20:173-182, 2000, each incorporated herein by reference). Clustal W alignment from the MacVector program (Accelrys) was used to align the complete P protein sequences of MPIV1 Z, HPIV1 WASH/64, and HPIV3 JS to identify the L polymerase-binding domain present in the three viruses. Percent identities for the gene products in Table 3 were calculated with the GAP program of the Wisconsin Package Version 10.2 (Accelrys).

Assembly of a Full-Length rHPIV1 cDNA Antigenomic Clone

A full-length cDNA clone encoding the HPIV1 antigenomic RNA was constructed from six overlapping RT-PCR and RACE products using the following restriction sites in the HPIV1 genome: Hind III (nt 800 position in the complete antigenomic sequence), Eag I (nt 2531), Sac I(nt 6517), Sph I(nt 11374), and Ppu M1 (nt 14226) (FIG. 1). Briefly, the first fragment was generated using the 3' RACE system (Invitrogen, Inc.) and the Herculase Enhanced Polymerase Blend (Stratagene, La Jolla, Calif.) with specific HPIV1 primers and a primer containing an Xho I site followed by a T7 promoter, two non-viral G residues, and the antigenomic cDNA corresponding to 3' of the viral genome. The next four fragments (FIG. 1) were reverse transcribed using the Thermoscript RT-PCR System (Invitrogen, Inc.) and PCR amplified with the Herculase Enhanced Polymerase Blend (Stratagene). The final fragment containing the 5' end was reverse transcribed using the 5' RACE System (Invitrogen, Inc.) and amplified with the Herculase Enhanced Polymerase Blend (Stratagene).

The individual PCR products were cloned, sequenced using a Perkin-Elmer ABI 3100 sequencer with the BigDye sequencing kit (Perkin-Elmer Applied Biosystems), and compared to the consensus sequence of HPIV1 WASH/64 prior to assembly. All six PCR products were assembled into a modified pBluescript KS II (Stratagene) vector previously described (Durbin et al., *Virology* 235:323-332, 1997, incorporated herein by reference) further modified to contain Xho I, Sac I, Sph I, Ppu M1, and Rsr II restriction sites. The resulting full-length cDNA clone, designated as pFLCH-PIV1, contains the following elements: a T7 promoter followed by two nonviral guanosine residues, the complete antigenomic sequence of HPIV1 (FIGS. 10A-10D), a hepatitis delta virus ribozyme, and a T7 polymerase transcriptional terminator as previously described for HPIV3 and BPIV3 (Durbin et al., *Virology* 235:323-332, 1997; Schmidt et al., *J. Virol.* 74:8922-8929, 2000, each incorporated herein by reference). The sequence of the full-length cDNA was verified by DNA sequence analysis. Two transcriptionally silent point mutations were identified in the L ORF of the full-length cDNA that occurred during the assembly of the clone at positions 10706 (T-C) and 14267 (T-C). These mutations were employed as markers to distinguish the recombinant HPIV1 from the biologically derived HPIV1 WASH/64 parent.

HPIV1 N, P, and L Support Plasmids for Recovering HPIV1 from cDNA

A support plasmid encoding the N protein of HPIV1 WASH/64 was derived from vRNA using the Thermoscript RT-PCR System (Invitrogen, Inc.) and the Herculase Enhanced Polymerase Blend (Stratagene) using a sense oligo that contained an Nco I site spanning the ATG initiation codon site and an anti-sense oligo containing an Asc I site. The PCR product was digested with Nco I and Ase I and cloned into a pTM1 vector (Elroy-Stein, *Proc. Natl. Acad. Sci. USA* 86:6126-6130, 1989; Durbin et al., *Virology* 234:74-83, 1997, each incorporated herein by reference) that was modified to contain Asc I, Nhe I, Sph I, and Rsr II restriction sites, to generate plasmid pTM($N_1$).

A support plasmid encoding the P gene was derived from PCR amplification from a HPIV1 subclone containing the P ORF. The HPIV1 P protein support plasmid was engineered to contain a point mutation that eliminates the start codon for the C protein but maintains the correct protein sequence for the P protein as described previously for the HPIV3 P support plasmid (Durbin et al., *Virology* 261:319-330, 1999, incorporated herein by reference). In addition, the sense oligo contains a Bsa I site that was engineered to leave an CATG overhang when digested with Bsa I, which contains the ATG initiation codon and is compatible with the Nco I sequence overhang in the pTM1 vector. The antisense primer contained a Not I site, and the resulting PCR product was cloned into a pTM1 vector (Elroy-Stein, *Proc. Natl. Acad. Sci. USA* 86:6126-6130, 1989; Durbin et al., *Virology* 234:74-83, 1997, each incorporated herein by reference) that was modified to contain Not I Sph 1 Mlu I, and Rsr II restriction sites generating plasmid pTM($P_1$).

An HPIV1 L polymerase expression plasmid pTM($L_1$) was made by PCR amplification with a sense oligo containing an Nco I site spanning the ATG initiation codon, and an antisense oligo downstream of a unique Sph I site in the L ORF. The PCR product was digested with Nco I and Sph I and cloned into the same modified pTM1 vector used to clone P. The remainder of the L ORF was derived from a subclone used to construct the full-length clone.

Recovery of a Recombinant Wild-type HPIV1 from cDNA

HEp-2 cells in Swell plates (Costar, Corning, Inc., Corning, N.Y.) were co-transfected with the full-length cDNA plasmid and three previously described HPIV3 support plasmids (Durbin et al., Virology 234:74-83, 1997, incorporated herein by reference) referred to here as (i) pTM($N_3$), pTM ($P_3$), and pTM($L_3$); (ii) a heterologous mixture of pTM($N_1$), pTM($P_1$) and pTM($L_3$); or (iii) a homologous combination of pTM($N_1$), pTM($P_1$) and pTM($L_1$) support plasmids using Lipofectamine-2000 reagent (Invitrogen, Inc.). The HEp-2 cells were simultaneously infected with MVA-T7 as described previously (Durbin et al., *Virology* 235:323-332, 1997, Schmidt et al., *J. Virol.* 74:8922-8929, 2000, each incorporated herein by reference). On day two post-transfection cells and media were supplemented with porcine trypsin to a final concentration of 5 μg/ml (BioWhittaker, Inc). Supernatant and cells were harvested on day three or four post-transfection and were passaged three times in LLC-MK2 monolayers.

To confirm that viruses were derived from the cDNA clone, RT was performed and segments of the viral genome were PCR amplified. Sequence analysis of the PCR products revealed the presence of the two silent point mutations that are present in the L gene of the recombinant virus but that are not present in the wild-type parental virus. rHPIV1 viruses were then biologically cloned by two rounds of serial terminal dilutions on LLC-MK2 monolayers in 96-well plates (Costar, Corning, Inc.) vRNA was then purified, and its sequence was determined in its entirety by RT-PCR, 3' RACE, and 5' RACE as described above.

Replication of rHPIV1 and Wild-Type HPIV1 WASH/64 in Hamsters

Four week-old Golden Syrian hamsters were inoculated intranasally (IN) with 0.1 ml Opti-MEM I containing $10^{6.0}$ $TCID_{50}$ of rHPIV1 or wild-type HPIV1 WASH/64. Lungs and nasal turbinates were harvested on days three, four, and five post-infection. The lungs were homogenized in a 10% w/v L-15 suspension containing 4.9 μg/ml amphotericin B (Quality Biologicals, Gaithersburg, Md.) and 100 μg/ml gentamicin (Gibco-Invitrogen Corp. Carlsbad, Calif.) Similarly, the nasal turbinates were homogenized in a 10%-w/v L-15 suspension. After homogenization, the samples were centrifuged and the supernatants were aliquoted and rapidly frozen on dry ice. Virus present in the samples was titered at 32° C. on LLC-MK2 monolayers. On day six post-infection, guinea pig erythrocytes were added to monolayers and the presence of hemadsorption foci was determined. The mean $\log_{10}$ $TCID_{50}$/g was calculated for each group of six hamsters.

EXAMPLE I

Nucleotide Sequence of the Genomic RNA of HPIV1 WASH/64 and Sequence Comparison with Heterologous Paramyxoviruses The complete genomic sequence of HPIV1 WASH/64 was determined from RT-PCR products amplified from vRNA. The sequence analysis was performed directly on RT-PCR products without a cloning step, and thus yields a consensus sequence. The HPIV1 genome was found to be 15,600 nt in length and conformed to the rule of six (Kolakofsky et al., *J. Virol.* 72:891-898, 1998, incorporated herein by reference). For comparison, the viral genomic length of other parainfluenza viruses sequenced to date are as follows: (i) among respiroviruses, MPIV1, 15,384 nt; HPIV3, 15,462 nt; and BPIV3, 15,480 nt; (ii) among rubulaviruses, HPIV2, 15,646 nt or 15,665 nt (50), SV5, 15,246 nt, SV41, 15,450 nt (GenBank accession no. X64275), and Newcastle disease virus, 15,186 nt (GenBank accession nos. AF309418 and AF375823).

The first 96 nt of the 3' terminus of HPIV1 genomic RNA (FIG. 2A) and the last 96 nt at the 5' end (FIG. 2B), organized in hexamer spacing, are compared to the corresponding sequences of MPIV1 Z, HPIV3 JS, and BPIV3 KA. The 3'-leader sequence of HPIV1 is identical in length (55 nt) and shares sequence identity and similarity to that of MPIV1 and to that of the more distantly related HPIV3 JS and BPIV3 KA (FIG. 2A). Overall, there is 56% identity in the 55 nt leader region for all 4 viruses and 81% identity between HPIV1 and MPIV1. The first 12 nt among all four viruses are identical. The 5'-trailer sequences differ in length among the four viruses, but 11 of the 12 terminal nucleotides are conserved. The length of the trailer is conserved between HPIV1 and MPIV1 (54 nt), while both PIV3 trailer sequences are 13 nucleotides shorter. Over the 41 nt region shared by all four viruses, there is 44% identity.

The 3' ends of genomic and antigenomic RNA (the latter is the complement of the trailer sequence shown in FIG. 2B) contain, respectively, the genomic and antigenomic promoters. The genomic promoter initiates sequential transcription and the first step in RNA replication, namely the synthesis of the antigenome, and the antigenomic promoter initiates the second step of RNA replication, namely the synthesis of progeny genomes (Calain et al., *Virology* 212:163-173, 1995; Tapparel et al., *Virology* 225:163-171, 1996, Vulliemoz et al., *J. Virol.* 75:4506-4518, 2001, each incorporated herein by reference). These previous studies with MPIV1 identified two promoter elements contained within the first 96 nt of each end: one element is located within the 3' terminal 30 nt (underlined in FIG. 2), although the exact boundaries and positions involved remain to be mapped precisely. The second element consists of three hexamers from positions 79 to 96. The C residues (genome-sense) at positions 79, 85, and 91 (highlighted in black in FIG. 2A) constitute the first nucleotide in each hexamer.

For MPIV1, conservation of the position of these triple CNNNNN motifs relative to the 3' end is required for MPIV1 replication (Tapparel et al., *J Virol* 72, 3117-3128, 1998, incorporated herein by reference). This triple CNNNNN motif is also present in the antigenomic promoter (shown as NNNNNG in the genome sense sequence in FIG. 2B), and, as with the genomic promoter, replication depends on their exact position relative to the 3' end of the antigenomic promoter (id.) As illustrated in FIG. 2, these promoter elements have a high degree of sequence identity between HPIV1 and MPIV1.

The ORF and nontranslated regions of each gene of HPIV1 and MPIV1 were compared (Table 1). The lengths of the corresponding protein-coding and noncoding regions for the N, P, and M genes are identical between the two viruses. The 3' (untranslated region) UTR for the F gene is substantially longer for HPIV1 (275 nt vs. 52 nt), and there are small differences in the lengths of the F ORF, the 5° F. UTR, the 5' HN UTR, the L ORF, and the 5' L UTR. The percent nucleotide identity between HPIV1 and MPIV1 for each of these various genes ranges from 63% for the P gene to 74% for the L gene. For the HPIV1 F gene, the GAP program did not include most of the extra 223 nt in the 3' UTR in its analysis to align the F genes of the two viruses.

TABLE 1

Comparison of the nucleotide sequences of the genes of HPIV1 WASH/64 and MPIV1 Z.

| Gene | Virus | 3' UTR (nt)[a] | ORF length (nt) | 5' UTR (nt)[b] | % nt sequence identity of complete gene[c] |
|---|---|---|---|---|---|
| N | HPIV1 | 64 | 1575 | 43 | |
| | MPIV1 | 64 | 1575 | 43 | 71 |
| P | HPIV1 | 103 | 1707 | 83 | |
| | MPIV1 | 103 | 1707 | 83 | 63 |
| M | HPIV1 | 32 | 1047 | 94 | |
| | MPIV1 | 32 | 1047 | 94 | 72 |
| F | HPIV1 | 275 | 1668 | 88 | |
| | MPIV1 | 53 | 1698 | 70 | 64 |
| HN | HPIV1 | 56 | 1728 | 110 | |
| | MPIV1 | 56 | 1728 | 104 | 65 |
| L | HPIV1 | 28 | 6672 | 100 | |
| | MPIV1 | 28 | 6687 | 85 | 74 |

[a]The 3' untranslated regions (UTR) includes the 10 nucleotide gene-start motif (See FIG. 3). (Note, that 3' and 5' here refers to genome sense).
[b]The 5' UTR includes the gene-end motif.
[c]Percent identity calculation includes the 3' UTR, the ORF, and the 5' UTR.

The genes of all four viruses possess highly conserved 10 nt gene-start and 12 nt gene-end sequences (FIG. 3). The nucleotide assignments at positions one, two, three, seven, eight, and ten of the gene-start signals are identical for each of the four viruses. In addition, position four of the gene-start sequence is identical between HPIV1 and MPIV1. The sixth position shows the most variability among the four viruses. For the gene-end sequences, there is conservation at positions two, five, and eight through twelve. The most variable positions are one, three, and six. The intergenic sequence for all four viruses is GAA except for the N-leader intergenic-like sequence (AAA for HPIV1 and MPIV1, FIG. 2), M-F intergenic for HPIV1, the HN-L intergenic for MPIV1, and the L-trailer intergenic-like sequence for HPIV3 JS and BPIV3 KA.

As with other members of the Paramyxovirinae subfamily, HPIV1 shows a specific pattern for the positioning of the gene-start signals within the subunit hexamer phasing (Kolakofsky et al., *J. Virol.* 72:891-898, 1998, incorporated herein by reference). As shown in Table 2, the first nucleotide of the gene-start signals is in a 6n+x phase where 6n is a multiple of six and x is equal to 1 or 2. MPIV1 and HPIV1 show an identical pattern of 2, 1, 1, 1, 1, and 2 for the N, P, M, F, HN, and L genes, respectively, despite the minor differences in gene lengths indicated in Table 1. This pattern has also been observed for BPIV3, HPIV3, and SV5 (id.)

TABLE 2

Hexamer phasing of gene-start signals between MPIV1 and HPIV1

| VIRUS | Gene | mRNA start position[a] | 6n + x (phase)[b] |
|---|---|---|---|
| HPIV1 WASH/64 | N | 56 | x = 2 |
| | P | 1741 | 1 |
| | M | 3637 | 1 |
| | F | 4813 | 1 |
| | HN | 6847 | 1 |
| | L | 8744 | 2 |
| MPIV1 Z | N | 56 | 2 |
| | P | 1741 | 1 |
| | M | 3637 | 1 |
| | F | 4813 | 1 |

TABLE 2-continued

| Hexamer phasing of gene-start signals between MPIV1 and HPIV1 | | | |
|---|---|---|---|
| VIRUS | Gene | mRNA start position[a] | 6n + x (phase)[b] |
| | HN | 6637 | 1 |
| | L | 8528 | 2 |

[a]mRNA start position is defined as the first residue of the gene-start sequence for each gene. The gene-start sequences are shown in FIG. 3.
[b]Position of the mRNA start site with regard to hexamer (6n) phasing (i.e., "1" is the first nucleotide of a hexamer, and "2" is the second).

The percent amino acid sequence identities between HPIV1 versus MPIV1, HPIV3 and HPIV2 for the N, P, C, M, F, HN and L proteins are shown in Table 3. Since HPIV1 lacks an intact V coding sequence, this sequence was not compared among the viruses. For each of the proteins that were compared, HPIV1 was most closely related to MPIV1, its serotype 1 animal virus counterpart, and had an intermediate level of relatedness with HPIV3; all three viruses are members of the Respirovirus genus (Lamb et al., in Paramyxoviridae: The viruses and their replication, Knipe et al. (Eds.), pp. 1305-1340, Lippincott Williams & Wilkins, Philadelphia, 2001, incorporated herein by reference). Each of the HPIV1 proteins exhibited the least relatedness with its counterpart of HPIV2, a member of the heterologous Rubulavirus genus (Lamb et al., in Paramyxoviridae: The viruses and their replication, Knipe et al. (Eds.), pp. 1305-1340, Lippincott Williams & Wilkins, Philadelphia, 2001).

For a comparison of HPIV1 versus MPIV1 and HPIV3, the N, M and L proteins exhibited the greatest percent identity. Between HPIV1 and HPIV2, the N, HN, and L proteins were the most related. The P protein exhibited the lowest level of amino acid sequence identity in each comparison, and the P proteins of HPIV1 and HPIV2 had insufficient sequence identity to be aligned. Since HPIV1 and MPIV1 are human and animal PIV1 counterparts, respectively, it was of interest to compare the percent identity between other PIV human and animal virus counterparts. This is indicated in the footnotes to Table 3 for HPIV3 and BPIV3, which are human and animal PIV3 counterparts, and for HPIV2 and SV5, which are human and animal PIV2 counterparts. The values given in the footnote were derived from a GAP alignment of each of the proteins obtained from the appropriate GenBank accession file (see above). This showed that HPIV3 and BPIV3 is the most closely-related pair, followed in order by HPIV1/MPIV1 and HPIV2/SV5.

TABLE 3

| Amino acid sequence identity of the proteins of HPIV1 WASH/64 and their counterparts in MPIV1 Z, HPIV2, and HPIV3 JS | | | |
|---|---|---|---|
| HPIV1 Protein | % Identity MPIV1[a] | % Identity HPIV3 | % Identity HPIV2 |
| N (524)[b] | 84 (524) | 62 (515) | 25 (542) |
| P (568) | 58 (568) | 29 (603) | NA[c] (395) |
| C (204) | 70 (204) | 39 (199) | NA[d] |
| M (348) | 86 (348) | 63 (353) | 20 (377) |
| F (555) | 68 (565) | 45 (539) | 24 (551) |
| HN (575) | 73 (575) | 49 (572) | 28 (571) |
| L (2223) | 86 (2228) | 61 (2233) | 31 (2262) |

[a]As a reference for comparing HPIV1 and its animal counterpart, MPIV1, the % identity for the proteins of HPIV3 JS versus its bovine counter part, BPIV3 Ka, are as follows: N (86%), P (65%), C (79%), M (93%), F (82%), HN (77%), and L (91%). For HPIV2 versus its animal SV5 counterpart, the % identity for each of the proteins is as follows: N (58%), P (44%), M (49%), F (47%), HN (47%), and L (62%).
[b]Number in parenthesis is the amino acid length of the predicted protein.
[c]NA, Not applicable: The HPIV1 P and HPIV2 P proteins do not align due to insufficient amino acid sequence relatedness.
[d]NA, Not applicable: Like all rubulaviruses, HPIV2 does not encode a C protein.

The organization and coding assignments of the HPIV1 and MPIV1 P genes are compared in FIG. 4. The unedited version of the MPIV1 P mRNA encodes the P, X, C', C, Y1, and Y2 proteins from the P and C ORFs by the use of alternative translational start sites (Lamb et al., in Paramyxoviridae: The viruses and their replication, Knipe et al. (Eds.), pp. 1305-1340, Lippincott Williams & Wilkins, Philadelphia, 2001, incorporated herein by reference). Editing of the MPIV1 P mRNA by the insertion of 1 or 2 G residues (mRNA-sense) shifts the reading frame and gives rise to the V and W proteins, respectively (Curran et al., *Embo J.* 10:3079-3085, 1991, incorporated herein by reference).

In comparison, as described previously for other strains of HPIV1 (Matsuoka et al., *J. Virol.* 65:3406-3410, 1991; Rochat et al., *Virus Res.* 24:137-144, 1992, each incorporated herein by reference), the HPIV1 WASH/64 P gene lacks an editing signal and does not contain an intact V ORF due to the presence of nine stop codons. The HPIV1 WASH/64 C ORF putatively initiates synthesis of the C' and C proteins from a nonstandard GUG codon and an AUG codon, respectively; expression of C from the GUG codon has been demonstrated with another strain of HPIV1 (Boeck et al., *J. Virol.* 66:1765-1768, 1992, incorporated herein by reference).

In contrast to the MPIV1 C ORF, the nonstandard GUG codon used to initiate HPIV1 C' protein is 12 nt upstream of the ACG codon used to initiate MPIV1 C'. The C ORF also has an AUG codon that corresponds exactly with the Y1 translational start site of MPIV1, and there is evidence from in vitro translation that a HPIV1 Y1 protein is made (Power et al., *Virology* 189:340-343, 1992). The Y2 translational start site of MPIV1 corresponds to an ACG codon in HPIV1. Since the ribosomal shunt that is responsible for translational initiation of the Y1 and Y2 proteins of MPIV1 was shown to be operational with an ACG codon in place of the native AUG (Latorre et al., *Mol Cell Biol* 18:5021-5031, 1998), an HPIV1 Y2 protein might also be made.

EXAMPLE II

Construction and Rescue of a Full-Length Recombinant HPIV1 Antigenomic cDNA Clone Using Homologous Heterologous, or a Mixed Set of Support Plasmids A complete HPIV1 antigenomic cDNA, designated pFLCHPIV1, was constructed which contained two desirable translationally-silent nucleotide changes in the L gene as markers (FIG. 5). The antigenomic cDNA was transfected into HEp-2 cells and virus was recovered using three different sets of N, P, and L support plasmids: N, P, and L of HPIV3 (pTM($N_3$), pTM($P_3$), and pTM($L_3$)), N and P of HPIV1 and L of HPIV3 (pTM($N_1$), pTM($P_1$) and pTM($L_3$)), or N, P, and L of HPIV1 (pTM($N_1$), pTM($P_1$) and pTM($L_1$)). In each case, virus was readily recovered, and the presence of the nucleotide markers was confirmed by RT-PCR and sequence analysis. Amplification was dependent on the addition of RT, indicating that the template was RNA and not contaminating DNA.

The growth properties in cell culture of rHPIV1 recovered using various sets of support plasmids was indistinguishable from that of biologically derived HPIV1; all three viruses replicated to approximately $10^8$ $TCID_{50}$/ml in LLC-MK2 cells. The virus recovered with pTM($N_1$), pTM($P_1$) and pTM ($L_3$), or with pTM($N_3$), pTM($P_3$), and pTM($L_3$), was given the lot designation $r_A$HPIV1 or $r_B$HPIV1, respectively, and compared with biologically derived HPIV1 WASH/64 with regard to replication in vivo (below).

In addition, the complete sequence of $r_A$HPIV1 was determined by RT-PCR of vRNA isolated from recovered virus that had been biologically cloned by sequential terminal dilutions. Specifically, the isolated genomic sequence of the recombinant virus was identical to that of a biologically derived HPIV1 WASH/64 parent designated below as $HPIV1_{LLC4}$ (See Example XI; FIGS. 10A-10D) from nucleotide positions 1 to 15,600 except for the two introduced, transcriptionally silent, single-nt markers.

EXAMPLE III

Replication of rHPIV1 and Biologically Derived HPIV1 WASH/64 in Hamsters

Wild-type HPIV1 WASH/64 has been shown to be virulent in human adults, confirming its status as a wild-type virus (Murphy et al., *Infect. Immun.* 12:62-68, 1975, incorporated herein by reference). The replication of rHPIV1 in the respiratory tract of hamsters was compared to that of the biologically derived HPIV1 WASH/64 parental strain $HPIV1_{LLC4}$ to determine whether the recovered rHPIV1 retained the replicative properties of its biological parent in vivo. In this regard, hamsters are accepted in the art as a useful animal model of HPIV infection in humans that provides reasonably correlative findings for such activities as attenuation and immunogenicity between the model and humans, wherein the model is understood to be a less permissive host than humans.

Two pools of biologically derived HPIV1 WASH/64 ($HPIV1_{LLC4}$ a multiply-passaged strain derived from a wild-type parental strain and having five mutations that are associated with a host range attenuated phenotype in primate subjects) were studied in parallel to assess the variability in replication between two separate preparations of the same virus as the trypsin requirement can damage the cell monolayers and affect the titer values. These were compared with two separate preparations of rHPIV1, designated $r_A$HPIV1 and $r_B$HPIV1 as noted above. Groups of 6 to 18 hamsters were separately inoculated intranasally (IN) with $10^{6.0}$ $TCID_{50}$ of each HPIV1. On days three, four, or five, the lungs and nasal turbinates were harvested from six hamsters, and the level of replication of each virus was determined (Table 4). The level of replication of the two preparations of rHPIV1 was similar to that of the two preparations of the biologically derived HPIV1 viruses on all of the days tested. One or both of the biologically derived HPIV1 WASH/64 viruses replicated to slightly higher titers than the rHPIV1 viruses on several of the days tested (Table 4).

TABLE 4

Comparison of the replication of rHPIV1 and its biologically derived HPIV1 parent in the respiratory tract of hamsters[a]

| Virus | Mean virus titer ($log_{10}$ $TCID_{50}$/g ± S.E.) in: Nasal Turbinates | | | Lungs | | |
|---|---|---|---|---|---|---|
| | Day 3 | Day 4 | Day 5 | Day 3 | Day 4 | Day 5 |
| $r_A$HPIV1[b] | 5.7 ± 0.2 | 6.0 ± 0.3 | 4.8 ± 0.3 | 4.5 ± 0.2 | 5.5 ± 0.2 | 6.7 ± 0.2 |
| $r_B$HPIV1[b] | 5.4 ± 0.2 | 6.4 ± 0.4 | 4.9 ± 0.3 | 5.9 ± 0.3 | 5.6 ± 0.3 | 7.0 ± 0.3 |
| HPIV1 Wash/64[c] | 6.1 ± 0.1 | 7.1 ± 0.2 | 6.2 ± 0.4 | 5.7 ± 0.3 | 6.9 ± 0.3 | 7.5 ± 0.3 |
| HPIV1 Wash/64[c] | ND[d] | 6.3 ± 0.5 | ND[d] | ND[d] | 6.4 ± 0.3 | ND[d] |

[a]Hamsters were inoculated IN with $10^6$ $TCID_{55}$ of the indicated virus. Nasal turbinates and lung tissues from six animals from each group where harvested on days three, four, and five post-infection or on day four only. Virus present in tissues was quantified by serial dilution on LLC-MK2 monolayers at 32° C.

[b]$r_A$HPIV1 and $r_B$HPIV1 are independent preparations of rHPIV1 that were recovered with pTM($N_1$), pTM($P_1$) and pTM($L_3$ support plasmids or) pTM($N_3$), pTM($P_3$), and pTM($L_3$) support plasmids, respectively (see text).

[c]These are two preparations of wild-type virus HPIV1, designated herein as $HPIV_{LLC1}$ viruses studied to estimate variability that can occur in this hamster model with identical viruses.

[d]ND, Not determined.

Briefly summarizing the foregoing examples, the complete consensus nucleotide sequence for HPIV1 genomic RNA was determined using the WASH/64 wild-type HPIV1 strain previously shown to be virulent in human adults. A reverse genetics system was developed for recovery of novel, recombinant HPIV1 candidates from cDNA. Using this system, recombinant, infectious HPIV1 was recovered successfully. Recombinant HPIV1 viruses made from cDNA according to the invention replicate independently and can be propagated in the same manner as if they were biologically derived viruses. These recombinant viruses were shown to replicate in vitro and in an accepted animal model (hamsters) for in vivo activity in humans, to levels that were essentially equivalent to that of its biologically derived parent virus. These findings validate the fidelity of sequence data determined for the rHPIV1 WASH/64 virus. With this wild-type HPIV1 recombinant rescue system, novel recombinant derivatives of HPIV1 are available for development as candidates for use in immunogenic compositions to elicit immune responses against HPIV1 and other pathogens.

Comparison of the complete genomes of HPIV1 WASH/64 and MPIV1 Z demonstrated a high degree of relatedness between these viruses, in agreement with previous observations. For example, there is greater than 80% amino acid sequence identity of the N, M, and L proteins of HPIV1 and MPIV1, and this level of amino acid sequence identity is also observed when HPIV3 is compared to its bovine counterpart BPIV3 (Bailly et al., *Virus Genes* 20:173-182, 2000, incorporated herein by reference). For comparison, between HPIV1 and HPIV3 the percent amino acid sequence identity of the most closely-related proteins, N, M and L, was greater than 60%, while between HPIV1 and HPIV2, the percent amino acid identity was 31% or less, consistent with HPIV2 being classified separately in the Rubulavirus genus. Among HPIV1, MPIV1, HPIV3, and BPIV3, there was extensive nucleotide sequence identity in the gene-start, gene-end, intergenic, and promoter sequences. In addition, the hexameric phasing of the gene-start signals was identical between the two viruses, as well as in HPIV3 and BPIV3.

In contrast to the many shared features between HPIV1 and MPIV1 Z the P protein exhibited the lowest percent amino acid sequence identity (58%), and the numbers of proteins that are expressed from the P gene differ for the two viruses. The HPIV1 WASH/64 P gene lacks the RNA editing site to generate an mRNA for a V protein, a finding that is consistent with other HPIV1 strains (Matsuoka et al., *J Virol* 65:3406-3410, 1991; Rochat et al., *Virus Res.* 24:137-144, 1992, each incorporated herein by reference). While there is a remnant of the V ORF in HPIV1 WASH/64, it is interrupted by multiple stop codons—an observation that has been made with other strains of HPIV1 (Power et al., *Virology* 189:340-343, 1992; Matsuoka et al., *J. Virol.* 65:3406-3410, 1991; Rochat et al., *Virus Res.* 24:137-144, 1992, each incorporated herein by reference).

The number of proteins expressed from the HPIV1 C ORF has not been completely determined. A six-way Clustal W alignment (Thompson et al., *Nucleic Acids Res.* 22:4673-4680, 1994, incorporated herein by reference) of the P gene of MPIV1, HPIV1 WASH/64, HPIV1 C39 (GenBank accession no. M37792), HPIV1 CI-5/73 (GenBank accession no. M74082), HPIV1 CI-14/83 (GenBank accession no. M74080), and HPIV1 C35 (GenBank accession no. M74081) shows that all of these HPIV1 isolates contain a homologous AUG codon for the expression of Y1, a protein whose expression has only been demonstrated by the use of an in vitro translation reaction (Power et al., *Virology* 189:340-343, 1992, incorporated herein by reference). For Y2, the same alignment demonstrates that these same HPIV1 P gene sequences have an ACG codon in place of the AUG codon used for Y2 expression in MPIV1.

While all of these HPIV1 strains lack the GAU sequence shown to be necessary for expression from a nonstandard ACG codon (Boeck et al., *Embo J.* 13:3608-3617, 1994, incorporated herein by reference), it has been recently demonstrated that Y1 and Y2 expression from MPIV1 occurs via a ribosomal shunting mechanism, even when the AUG codons are changed to ACG codons, albeit with a reduced expression of Y2 (Latorre et al., *Mol. Cell. Biol.* 18:5021-5031, 1998, incorporated herein by reference). Thus, it is possible that HPIV1 WASH/64 and other HPIV1 isolates do express a Y2 protein through a similar mechanism, although the expression of either Y1 or Y2 from the P gene mRNA has not been demonstrated in vivo for HPIV1. This can now be readily determined using the methods and materials provided herein.

The foregoing examples also demonstrate that recombinant HPIV1 cDNA clones and viruses can be recovered using N, P and L support plasmids of HPIV1, or N, P and L of the heterologous HPIV3, or a mixture of N and P from HPIV1 and L from HPIV3. This demonstrates a surprising commonality in regard to the cis-acting recognition sequences of HPIV3 and HPIV1, as well as the ability of non-homologous proteins of the nucleocapsid and polymerase complex to interact with sufficient efficiency to generate a biologically-active nucleocapsid capable of producing infectious virus. In particular, HPIV3 N, P, and L proteins, or a mixture of HPIV1 N and P and HPIV3 L proteins, are able to encapsidate a plasmid-encoded HPIV1 antigenome to form an active antigenomic nucleocapsid. This heterogeneous complex can be used as a template to produce an active genomic nucleocapsid, which in turn is able to execute sequential transcription and thus launch a productive infection. In a situation where all of the support plasmids are HPIV3-specific, the HPIV3 N and P proteins are capable of encapsidating the heterologous HPIV1 genomic and antigenomic RNAs into functional nucleocapsids. In a situation where the proteins are HPIV1 N, HPIV1 P, and HPIV3 L, the heterologous HPIV3 L protein is capable of utilizing a template coated with HPIV1 N and P proteins. It is also possible that the HPIV1 N and P proteins could have been expressed from mRNA generated by the MVA-T7 RNA polymerase using pFLCHPIV1 as a template (Hoffman et al., *J. Virol.* 71:4272-4277, 1997, incorporated herein by reference).

Earlier studies have reported that a cDNA-encoded MPIV1 defective interfering antigenome may be replicated intracellularly with plasmid-supplied PIV3 proteins, specifically with N and P from HPIV3 and L from BPIV3 (Pelet et al., *J. Gen. Virol.* 77:2465-2469, 1996, incorporated herein by reference). The present examples demonstrate that cis-acting template signals are recognized between HPIV1 and HPIV3, and also provides direct evidence that the heterologous proteins execute all steps of RNA synthesis and produce infectious nucleocapsids. Previously, in an in vitro transcription assay using standard MPIV1 or HPIV3 nucleocapsids purified from infected cells, activity was observed only when the complementing P and L proteins were homologous with the purified template (id.) This suggested that P and L of one serotype virus would not function with the N-RNA complex of another. In the present examples, a different heterologous combination, namely N and P from HPIV1 and L from HPIV3, led to successful rescue. This indicates that having a homologous pairing between N and P is critical, whereas L can be of the heterologous virus. It is particularly noteworthy that the heterologous HPIV3 proteins, or the mixture of HPIV1 and HPIV3 proteins, were able to produce fully-infectious nucleocapsids containing the HPIV1 genome—providing direct evidence of functional activity across these two PIV serotypes.

To illustrate one aspect of the interactions involved in the heterologous mix of support proteins, the region of the P protein that was previously suggested to be involved in interaction between P and L, specifically amino acids 411-445 of MPIV1 (Lamb et al., in Paramyxoviridae: The viruses and their replication, Knipe et al. (Eds.), pp. 1305-1340, Lippincott Williams & Wilkins, Philadelphia, 2001; Smallwood et al., *Virology* 202:154-163, 1994; Curran et al., *Virology* 202, 875-884, 1994, each incorporated herein by reference) was evaluated herein. The P-L interaction is of interest because it presumably must occur across serotypes in the mixture where N and P were derived from HPIV1 and L from HPIV3. A three-way alignment of the P proteins of MPIV1, HPIV1, and HPIV3 shows that this region is fairly well conserved (FIG. 6). Several amino acid residues within this region have been shown to affect mRNA and leader synthesis (Bowman et al., *J. Virol.* 73:6474-6483, 1999, incorporated herein by reference); those residues that are identical or similar among the three viruses are shown in bold-faced type in FIG. 6. Additional combinations of support plasmids are therefore contemplated within the invention that will be biologically active with full-length synthetic antigenomes and genomes.

EXAMPLE IV

Importation of Attenuating Mutations Identified in Heterologous Paramyxoviruses into a Recombinant HPIV1 to Generate ts and Non-ts Live-Attenuated HPIV1 Recombinant Virus for Use in Immunogenic Compositions The instant disclosure demonstrates that it is possible to rapidly generate a series of candidate HPIV1 viruses capable of eliciting immune responses against wild-type HPIV1 by the introduction of previously identified temperature sensitive (ts) and non-ts attenuating mutations into HPIV1 using the techniques of reverse genetics. It has previously been reported that combining ts and non-ts attenuating mutations into a single recombinant virus is highly desirable since it greatly enhances the stability of the attenuation phenotype (Murphy et al., *Vaccine,* 15:1372-1378, 1997, incorporated herein by reference). The present example demonstrates this strategy for HPIV1. It has also previously been reported that ts and non-ts attenuating mutations can be "imported" into HPIV3 from heterologous members of the Paramyxovriidae, and that the imported mutation can confer the ts or non-ts attenuation phenotype upon HPIV3 (Durbin et al., *Virology,* 261:319-330, 1999; Skiadopoulos et al., *Virology,* 260:125-135, 1999b, incorporated herein by reference). A substantial set of attenuating mutations has now been generated and characterized for HPIV3 (Durbin et al., *Virology,* 261:319-330, 1999; Skiadopoulos et al., *J. Virol.,* 73:1374-1381, 1999a; Skiadopoulos et al., *Virology,* 260:125-135, 1999b, each incorporated herein by reference). In the instant disclosure, the importation of these ts and non-ts attenuating mutations into the homologous region of the heterologous HPIV1 virus via cDNA intermediates readily yields a series of satisfactorily attenuated live HPIV1 candidates containing one or more attenuating mutations, for use in immunogenic compositions of the invention. As indicated above, the presence of multiple attenuating mutations, including both ts and non-ts attenuating mutations, should greatly augment the stability of the attenuation phenotype of the recombinant viruses following their replication in vivo. An attenuated HPIV1 candidate was rapidly generated in this manner obviating the need to employ the alternative, time consuming, and uncertain strategy of developing such attenuating mutations by trial and error. These successes were achieved despite a significant degree of sequence divergence between HPIV3 and HPIV1 at the nucleotide and protein sequence level (Newman et al., *Virus Genes,* 24:1, 77-92, 2002, incorporated herein by reference). Several of the previously identified attenuating mutations in HPIV3 occurred at amino acid residues that were not identical in HPIV1 (but they were located in a region with a high level of sequence identity). The instant disclosure demonstrates that importation of these non-conserved mutations allows for the recovery of viable viruses, and in fact yields recombinants with a desirable level of attenuation for use in immunogenic compositions and methods of the invention.

The attenuating mutations identified in several HPIV3 and RSV candidate viruses, including HPIV3 cp45, RSV cpts530, and murine PIV1 (MPIV1) (Sendai virus) (Skiadopoulos et al., *J. Virol.,* 73:1374-1381, 1999a; Juhasz et al., *J. Virol.,* 73:5176-5180, 1999; Garcin et al., *Virology,* 238: 424-431, 1997, each incorporated herein by reference), were introduced into recombinant HPIV1 (rHPIV1), and rHPIV1 viruses bearing these mutations were recovered as indicated in Table 5.

TABLE 5

| The recoverability of rHPIV1s bearing mutations imported from heterologous paramyxoviruses. |
|---|
| A. Single point mutations imported from HPIV3 cp45 recovered in rHPIV1 |
| rHPIV1 C: S102T$_{cp45}$ |
| rHPIV1 M: P195T$_{cp45}$ |
| rHPIV1 F: I423V$_{cp45}$ |
| rHPIV1 F: S453T$_{cp45}$ |
| rHPIV1 HN: R386A$_{cp45}$ |
| rHPIV1 L: Y942H$_{cp45}$[a] |
| rHPIV1 L: L992F$_{cp45}$ |
| rHPIV1 L: L1558I$_{cp45}$[b] |
| B. Mutations imported from other heterologous viruses recovered in rHPIV1 |
| rHPIV1 L: F456L$_{RSV}$ |
| rHPIV1 C: F170S$_{MPIV1}$ |
| C. Combination of mutations recovered in rHPIV1 |
| rHPIV1 3'-N V99A$_{cp45}$[c] |
| rHPIV1 F: I423V/S453T$_{cp45}$ |
| rHPIV1 Y942H/L992F$_{cp45}$ |
| rHPIV1 L992F/L1558I$_{cp45}$ |
| rHPIV1 Y942H/L992F/L1558I$_{cp45}$[d] |
| rHPIV1 F170S$_{MPIV1}$/Y942H/L992F$_{cp45}$ |
| rHPIV1 F170S$_{MPIV1}$/L992F/L1558I$_{cp45}$ |
| D. Combinations of mutations that could not be recovered in rHPIV1 |
| rHPIV1 Y942H/L1558I$_{cp45}$ |
| rHPIV1 3'N-C-M-F-HN$_{cp45}$[e] |
| rHPIV1$_{cp45}$[f] |
| rHPIV1 F170S$_{MPIV1}$/Y942H/L1558I$_{cp45}$ |
| rHPIV1 F456L$_{RSV}$/Y942H/L992F$_{cp45}$ |
| rHPIV1 F456L$_{RSV}$/Y942H/L1558I$_{cp45}$ |
| rHPIV1 F456L$_{RSV}$/L992F/L1558I$_{cp45}$ |
| rHPIV1 F456L$_{RSV}$/Y942H/L992F/L1558I$_{cp45}$ |

Mutations are designated according to the protein involved, followed by the wild-type aa assignment, the aa position, in the HPIV1 protein, the mutant aa assignment and the heterologous virus the mutation was imported from.

[a]Found to contain an additional T->A mutation at nt position 13,727 of the antigenomic cDNA sequence that is translationally silent.

[b]Found to contain an additional T->C mutation at position 12,326 that is silent.

[c]Contains three 3' leader and GS mutations and the V99A mutation in the N protein imported from HPIV3 cp45. The remaining 3 mutations identified in the 3' leader and N protein of HPIV3 cp45 at nt 24 and 25, and N protein aa 389 were not imported into HPIV1, because the analogous positions in HPIV1 have the same nt or aa assignment as HPIV3 cp45; HPIV1 nt 24 and 45 are both thymidine residues (antigenomic sense), and the HPIV1 N protein aa at position 390 is an alanine.

[d]Contains two additional adventitious point mutations: 1- T->A at 14,046 causes a Leu->Gln and 2- G->A at 14,266 causes a Cys-Tyr change.

[e]Contains the mutations derived from HPIV3cp45 in the 3'-leader, N, C, M, F, and HN proteins but has a wt HPIV1 L sequence.

[f]Contains all of the 12 mutations imported from HPIV3cp45 in one virus.

The HPIV3 cp45 candidate was chosen as a donor of attenuating mutations since it is a promising candidate vaccine (Karron et al., *J. Infect. Dis.,* 172:1445-1450, 1995b, incorporated herein by reference) that is restricted in replication in the upper and lower respiratory tract of hamsters and primates and has 15 significant point mutations compared to its wt JS strain parent. These include three well-defined ts attenuating mutations in L, one non-ts attenuating mutation in C, and two non-ts attenuating mutations in F (Skiadopoulos et al., *J. Virol.,* 73:1374-1381, 1999a, incorporated herein by reference). The remaining mutations include 4 leader mutations, a nt substitution in the N gene-start transcription signal, and amino acid point mutations in the N, M and HN proteins: these remaining mutations are not major independent attenuating mutations, although some of them are included among the HPIV3 cp45 mutations introduced into HPIV1 in Table 5. Three HPIV3 cp45 substitution mutations in the 3' leader and N protein (see Table 5 legend) did not have to be imported into HPIV1, because the corresponding position in HPIV1 is the same as found in HPIV3 cp45. In addition, the attenuating mutations in the L polymerase (amino acid Phe-521 to Leu) of the RSV cpts530 candidate vaccine or a non-ts attenuating amino acid substitution mutation (Phe-170 to Ser) in the accessory C protein of Sendai virus (murine PIV1; MPIV1) were chosen for importation into rHPIV1 since each mutation specifies the attenuation phenotype for both rodents and primates (Durbin et al., 1999; Skiadopoulos et al., 1999b, incorporated herein by reference). A series of point mutations were designed by comparing the sequence of regions of the HPIV3, RSV, or MPIV1 viruses that bear the attenuating mutations with the analogous regions of HPIV1 (FIG. 7). These mutations were introduced into the HPIV1 antigenomic cDNA by site-directed PCR mutagenesis. Recombinant HPIV1 s bearing each of the listed substitution mutations as single point mutations were successfully recovered by transfection of the full-length HPIV1 cDNA into tissue culture cells, as described herein (see also, Newman et al., *Virus Genes,* 24:1, 77-92, 2002, incorporated herein by reference), and the presence of the introduced mutation in recovered virus was confirmed by direct sequencing of a vRNA RT-PCR product spanning the introduced point mutation (Table 5A and 5B). Recovery of each of the recombinant HPIV1s bearing mutations imported from a heterologous paramyxovirus demonstrates that these substitution mutations are not lethal for replication of HPIV1 in vitro. While various combinations of mutations could be recovered from cDNA (Table 5C), there were several combinations that did not yield the expected recombinant virus, suggesting that these combinations of mutations may not be compatible for viability (Table 5D). This was not unexpected, since previous studies showed that certain combinations of attenuating mutations identified in various separate attenuated RSV mutants were not compatible when introduced together into a single RSV by reverse genetics (Whitehead et al., *J. Virol.* 73:871-877, 1999, incorporated herein by reference). Nonetheless, most combinations of mutations selected for use within the invention will be viable, and the disclosure herein provides for production of a wide range of useful candidate viruses by this strategy through readily practicable methods.

The present results demonstrate that mutations identified in three diverse viruses, namely RSV, MPIV1, and HPIV3, can be readily transferred to HPIV1 to yield recombinant mutant HPIV1 viruses that efficiently replicate in tissue culture. Each single mutation was viable in rHPIV1, and various combinations of mutations were also shown to be viable.

EXAMPLE V

Characterization of the Level of Replication and Temperature Sensitivity of Mutant Recombinant HPIV Is in Cell Culture The in vitro growth characteristics of the mutant of HPIV1s bearing single mutations were first examined. Each of the mutants grew to high titer (approximately $10^7$ $TCID_{50}$/ml or higher) when incubated at 32° C. in LLC-MK2 monolayer cultures. This demonstrated that importation of the attenuating mutations from RSV, MPIV1, or HPIV3 permitted the efficient replication of HPIV1 in vitro, a property that is essential for the manufacture of recombinant virus for use in immunogenic compositions.

To measure the temperature sensitivity of replication of specific rHPIV1 mutant viruses in vitro, the virus titer ($TCID_{50}$/ml) at 32° C. and at graded temperatures from 36° C. to 40° C. was determined by titration on LLC-MK2 monolayer cultures as described previously (Skiadopoulos et al., *Vaccine,* 18:503-510, 1999c, incorporated herein by reference). The amino acid substitution mutations at positions 456, 942, and 1558 in the L protein that specified a ts phenotype in their respective RSV or HPIV3 wild-type virus also specified a moderate or highly ts phenotype in rHPIV1 (Table 6).

TABLE 6

Replication of recombinant mutant HPIV1 at permissive and restricted temperatures

| Virus | Mean titer at 32° C. | Mean $log_{10}$ reduction in virus titer at the indicated temperature (° C.)[a] 36 | 37 | 38 | 39 | 40 | ts phenotype of indicated mutation in: rHPIV3 | rHPIV1 |
|---|---|---|---|---|---|---|---|---|
| rHPIV1 | 7.8 | −0.4 | 0.5 | 0.8 | 1.3 | 2.3 | **NA**[b] | **NA** |
| rHPIV1 3'-N V99A$_{cp45}$ | 7.5 | | | | **5.8** | **≧6.3** | + | + |
| rHPIV1 C: S102T$_{cp45}$ | 8.0 | | | | 1.5 | 2.8 | − | − |
| rHPIV1 M: P195T$_{cp45}$ | 7.5 | | | | 0.3 | 2.0 | − | − |
| rHPTV1 F: 1423V$_{cp45}$ | 7.2 | | | | 0.7 | 3.5 | − | − |
| rHPIV1 F: S453T$_{cp45}$ | 7.2 | | | | **4.0** | **≧6.0** | − | + |
| rHPIV1 F: I423V/S453T$_{cp45}$ | 6.5 | | | | **4.3** | **5.5** | − | + |
| rHPIV1 HN: R386A$_{cp45}$ | 7.0 | | | | **5.3** | **5.5** | − | + |
| rHPIV1 L: Y942H$_{cp45}$ | 7.6 | 0.8 | **2.6** | **4.8** | **5.8** | **6.5** | + | + |
| rHPIV1 L: L992F$_{cp45}$ | 8.1 | 0.2 | 0.3 | 1.3 | 1.4 | 2.5 | + | − |
| rHPIV1 L: L1558I$_{p45}$ | 7.8 | 0.4 | 0.2 | 2.5 | 2.4 | **4.7** | + | + |
| rHPIV1 L: F456L$_{RSV}$ | 7.1 | 0.7 | **2.6** | **4.9** | **5.6** | **≧5.9** | + | + |
| rHPIV1 C: F170S$_{MPIV1}$ | 7.3 | 0.2 | 0.6 | 1.2 | 2.0 | 2.3 | − | − |

TABLE 6-continued

Replication of recombinant mutant HPIV1 at permissive and restricted temperatures

| Virus | Mean titer at 32° C. | Mean $\log_{10}$ reduction in virus titer at the indicated temperature (° C.)[a] | | | | | ts phenotype of indicated mutation in: | |
|---|---|---|---|---|---|---|---|---|
| | | 36 | 37 | 38 | 39 | 40 | rHPIV3 | rHPIV1 |
| rHPIV3 wt | 8.3 | −0.1 | 0.1 | −0.1 | 0.0 | −0.2 | **NA** | **NA** |
| rHPIV3 cp45 | 8.1 | 0.9 | **3.4** | **5.6** | **6.5** | **≧6.7** | **+** | **NR**[C] |

[a]Values in bold type are at or below the shut-off temperature. These values are considered strongly attenuated, which is defined as a 100-fold or more reduction in titer compared to the titer at 32° C. This 100-fold reduction was in addition to the reduction in titer of rHPIV1 at the indicated temperature. Other recombinants were moderately attenuated, which designation is marked by a 10-fold or greater reduction in titer in this or a comparable assay.
[b]NA = Not applicable.
[c]NR = Not recoverable.

The four point mutations in HPIV3 cp45 that were transferred to rHPIV1 3'-N V99A$_{cp45}$ specified a ts phenotype in both PIVs. These observations support the concept that ts mutations identified in heterologous paramyxoviruses can indeed transfer the ts phenotype to HPIV1. However, the HPIV3 cp45 Leu-992 to Phe mutation in the L protein did not confer a ts phenotype, as it had in HPIV3. This indicates that ts mutations identified in heterologous paramyxoviruses do not always transfer the ts phenotype to HPIV1.

Additionally, several mutations (present in rHPIV1 F: 1423V$_{cp45}$; rHPIV1 F: 1423V/S453T$_{cp45}$; and rHPIV1 HN: R386A$_{cp45}$) that were not ts in HPIV3 cp45, conferred a ts phenotype when transferred to HPIV1. Interestingly, the amino acids at these positions were not conserved between HPIV1 and HPIV3 (FIG. 7). This indicates mutations that do not specify the ts phenotype in one virus can specify a ts phenotype when imported into the corresponding position in a heterologous virus.

rHPIV1 C: F170S$_{MPIV1}$ bearing the non-ts attenuating mutation in the C protein of MPIV1 was non-ts, and therefore this virus possessed the non-ts phenotype of the HPIV3 recombinant bearing the same mutation.

EXAMPLE VI

Characterization of the Level of Replication and Immunogenicity of Mutant Recombinant HPIV Is in Hamsters The in vivo growth characteristics of selected mutant HPIV1s containing either a single imported mutation or a combination of imported mutations were next examined in an animal model generally accepted as predictive of HPIV replicative potential and immunogenic activity in humans. The level of replication of the rHPIV1 mutants in the upper and lower respiratory tract of infected hamsters was compared to that of rHPIV1, rHPIV3 wt or HPIV3 cp45 control viruses (Table 7).

TABLE 7

Replication of rHPIV1 and mutant viruses in hamsters and their efficacy against challenge with HPIV1 WT

| Virus | No. of animals[c] | Mean virus titer ($\log_{10}$ $TCID_{50}$/g ± S.E.[d]) Nasal Turbinates | Lungs |
|---|---|---|---|
| rHPIV1 | 18 | 4.7 ± 0.1 | 5.2 ± 0.2 |
| rHPIV1 C: F170S$_{MPIV1}$ | 12 | **2.5 ± 0.1**[d] | **2.5 ± 0.1**[d] |
| rHPIV1 L: F456L$_{RSV}$ | 12 | **2.0 ± 0.2**[d] | **1.7 ± 0.1**[d] |
| rHPIV1 L: L992F$_{cp45}$ | 12 | 4.5 ± 0.1 | 3.6 ± 0.2 |
| rHPIV1 M: P195T$_{cp45}$ | 6 | 4.0 ± 0.2 | 4.2 ± 0.2 |
| rHPIV1 C: S102T$_{cp45}$ | 6 | 3.9 ± 0.1 | 4.2 ± 0.1 |
| rHPIV1 F: I423V$_{cp45}$ | 6 | 3.9 ± 0.2 | 4.5 ± 0.3 |
| rHPIV1 HN: R386A$_{cp45}$ | 6 | 3.7 ± 0.0 | 4.3 ± 0.2 |
| rHPIV1 3'-N V99A$_{cp45}$ | 6 | 3.7 ± 0.1 | 4.0 ± 0.2 |
| rHPIV1 L: L1558I$_{cp45}$ | 12 | 3.3 ± 0.2 | **2.9 ± 0.1**[e] |
| rHPIV1 F: S453T$_{cp45}$ | 6 | 3.2 ± 0.1 | 3.7 ± 0.1 |
| rHPIV1 L: Y942H$_{cp45}$ | 12 | **2.4 ± 0.2**[e] | **2.2 ± 0.2**[e] |
| rHPIV1 F: I423V/S453T$_{cp45}$ | 6 | **≦1.5 ± 0.0**[e] | **≦1.5 ± 0.0**[e] |
| rHPIV1 L992F/L1558I$_{cp45}$ | 6 | **2.5 ± 0.0**[e] | **2.0 ± 0.4**[e] |
| rHPIV1 Y942H/L992F$_{cp45}$ | 6 | **2.0 ± 0.3**[e] | **1.6 ± 0.1**[e] |
| rHPIV1 Y942H/L992F/L1558I$_{cp45}$ | 6 | **1.5 ± 0.1**[e] | **1.9 ± 0.2**[e] |
| rHPIV3 WT | 6 | 6.2 ± 0.2 | 5.7 ± 0.4 |
| rHPIV3 cp45 | 6 | 2.8 ± 0.1 | 1.6 ± 0.1 |

[a]Hamsters were inoculated IN with $10^6$ $TCID_{50}$ of the indicated virus. Nasal turbinates and lung tissues from 6, 12, or 18 animals for each group were harvested on day 4. Virus present in the tissues was quantified by serial dilution on LLC-MK2 monolayers at 32° C.
[b]After rHPIV1, viruses are divided into four groups. The single point mutations imported from MPIV1 and RSV are listed first. The single point mutations imported from HPIV3cp45 are listed second, and combinations of the L mutations imported from rHPIV3cp45 are listed third. Finally, the two control viruses, rHPIV3 and rHPIV3cp45 that were described previously are listed last ( ). Within each group, viruses are listed from the least to most attenuated in the upper respiratory tract.
[b]Indicates the number of animals used to calculate the titer from either one (6), two (12), or three (18) independent experiments, respectively.
[c]S.E. Standard error
[d]Values in bold show a 100-fold or more reduction in titer compared to the titer of rHPIV1. These values are considered strongly attenuated, which is defined as a 100-fold or more reduction in titer. Other recombinants were moderately attenuated, which designation is marked by a 10-fold or greater reduction in titer in this or a comparable assay.

Of those mutant recombinants tested, all of the recombinants shown in Table 7 exhibited some level of attenuateion. Some of the recombinants were moderately attenuated (e.g., approximately 10-fold or greater reduction in titer), while others were strongly attenuated (e.g., approximately 100-fold or greater reduction in titer). The C protein F170S mutation, the L protein F456L, and the Y942H mutations each specified at least a 100-fold reduction in replication in both the upper and lower respiratory tract of hamsters indicating that the transferred mutation confers either a ts (rHPIV1 L: F456L$_{RSV}$ and rHPIV1 L: Y942H$_{cp45}$) or non-ts (rHPIV1 C: F170S$_{MPIV1}$) attenuation phenotype on rHPIV1. The L1558I mutation in the L polymerase resulted in a 100-fold restriction of replication in the lower respiratory tract. Thus, the introduction of a single attenuating mutation present in a heterologous virus into HPIV1 can confer on HPIV1 the desired attenuation phenotype. Several combinations of HPIV3 cp45 L mutations also resulted in viruses that were attenuated for replication in hamsters, namely rHPIV1 Y942H/L992F$_{cp45}$, rHPIV1 L992F/L1558I$_{cp45}$, and rHPIV1 Y942H/L992F/L1558I$_{cp45}$.

For certain of the recombinants described herein, immunized hamsters were challenged with wild-type HPIV1 at 35 or 36 days after immunization and the level of replication of the challenge virus in the upper and the lower respiratory tract was determined (Table 7). Some of the viruses examined were attenuated for replication in the respiratory tract of hamsters yet protected hamsters from subsequent challenge with wt HPIV1. These included rHPIV1 C: F170SMPIV1 and rHPIV1 L992F/L1558I$_{cp45}$. A recombinant bearing all three of these mutations (rHPIV1 F170S$_{MPIV1}$/L992F/L1558I$_{cp45}$) was also highly protective against challenge with wt HPIV1. This recombinant contains both ts and non-ts attenuating mutations and is thus an important HPIV1 candidate virus for use in immunogenic compositions and methods of the invention that can be used either alone or in combination with additional attenuating mutations to protect against HPIV1 disease. Such an attenuated virus can also be used as a vector of foreign viral proteins to induce immunity to HPIV1 as well as to additional human viral pathogens.

EXAMPLE VIII

Modification of Codons Specifying Amino Acid Substitutions to Generate Attenuated rHPIV1 Mutants With Increased Genetic Stability The importation of attenuating mutations identified in heterologous paramyxoviruses into HPIV1 is a useful method for generating live-attenuated HPIV1 candidates for use in immunogenic compositions. However, in most cases, the attenuating mutation is conferred by a single amino acid substitution, and only a single nucleotide substitution would be necessary for reversion back to a codon that encodes the wild-type amino acid assignment. Using recombinant cDNA technology, in some cases mutant codons can be designed such that two or three nucleotides would have to be substituted in order to revert to encode the amino acid assignment in the wild-type virus. The mutation frequency at any nt position of a negative strand virus has been found to be between $10^{-4}$ and $10^{-5}$, a value that therefore would approximate the frequency of reversion of an amino acid substitution involving a single nt point mutation (the actual frequency would be up to three-fold less, depending on the codon, since not all nt alternatives would restore the wt coding assignment). Because of the degeneracy of the genetic code, in many instances it is possible to choose a mutant codon such that it differs from all possible codons encoding the wt assignment by two or even three nt. A difference of 2 nt relative to wt would alter the frequency of reversion to approximately $10^{-8}$ to $10^{-10}$, and three changes would alter the frequency to $10^{-12}$ to $10^{-15}$, based on the principle that the frequency of two events occurring together is the product of the frequency of each occurring individually.

Each of the mutations that conferred a ts or attenuation phenotype in Table 5 of Example 1V was stable following the passages in cell culture that were required to generate the recombinant virus and to prepare the biologically-cloned virus suspension. This indicated that for these mutants there is only weak, if any, selective pressure in vitro to select viruses in which the coding assignment has reverted to the wt coding sequence. However, such revertants can possibly emerge following replication in vivo where there is strong selective pressure for the emergence of revertant viruses with increased ability to replicate. The stability and, therefore, the safety of the virus for use in immunogenic compositions would be improved if each mutant codon could be stabilized such that it would require 2 or 3 nucleotide substitutions, rather than just one, to revert the mutant codon to that of a codon that specifies the wild-type amino acid.

The present example demonstrates that this strategy to enhance the genetic stability of the virus is readily practicable to achieve desired codon stabilization and to generate a variety of viable rHPIV1 mutants that incorporate stabilizing mutations.

To examine the feasibility of using alternative amino acid substitutions at a single residue, the codon that encodes amino acid residue 942 in the L polymerase protein, which specifies a tyrosine in wild-type virus, was mutated to encode each of the other 19 amino acids, including the original mutation (a histidine substitution) imported from HPIV3 cp45. As shown in FIG. 11, the codon substitution mutations can be grouped into three categories: A) mutations requiring 1 nucleotide substitution in the codon to yield the wt amino acid, B) mutations requiring 2 nucleotide substitutions to yield the wt amino acid, and C) mutations requiring 3 nucleotide substitutions to yield the wt amino acid. Each of the mutations was introduced into the antigenomic HPIV1 cDNA by PCR mutagenesis, as described previously (Moeller et al., *J. Virol.,* 75:7612-7620, 2001, incorporated herein by reference). In several instances the corresponding mutation was also introduced into the L ORF of the pTM($L_1$) support plasmid in order to eliminate the possibility of generating a wt rHPIV1 by homologous recombination between a mutant antigenomic cDNA and a wt L polymerase support plasmid during recovery of the virus in vitro.

Certain of the mutant viruses could not be recovered from cDNA, including viruses containing a codon specifying an Arg, Glu, Ile, Lys, or Pro at position 942 of the L gene (FIG. 11). This identified amino acid assignments at this position that were highly inhibitory to HPIV1 replication. In all cases, the recovered mutant viruses were sequenced to confirm the presence of the desired mutations.

The growth properties of the recovered mutant rHPIV1 viruses were characterized. Each of the mutant HPIV1 recombinants grew to high titer in LLC-MK2 cells at 32° C., indicating that these mutations are not attenuating in vitro. Growth of mutant viruses at 35° C. to 39° C. was compared to growth at the permissive temperature (32° C.), to determine if the viruses had a temperature sensitivity phenotype, as described above. Surprisingly, each of the substitutions at amino acid 942 of the L polymerase conferred a ts phenotype (Table 8).

TABLE 8

Each of the viable rHPIV1s with a codon substitution mutation at amino acid 942 of the HPIV1 L polymerase is ts.

| VIRUS | Titer[a] at indicated temperature (° C.) ($log_{10}$ $TCID_{50}$/ml) 32 | 35 | 36 | 37 | 38 | 39[b] | # NTs to revert to wt |
|---|---|---|---|---|---|---|---|
| rHPIV1 wt | 8.0 | 8.0 | 7.2 | 7.2 | 6.7 | 6.5 | 0 |
| rHPIV1 Y942H | 7.5 | | **4.5** | **≦1.2** | **≦1.2** | **≦1.2** | 1 |
| rHPIV1 Y942F | 8.2 | 8.5 | 7.2 | **5.2** | **4.2** | **≦1.2** | 1 |
| rHPIV1 Y942C | 8.7 | 6.7 | 6.2 | **5.5** | **5.2** | **2.0** | 1 |
| rHPIV1 Y942N | 9.2 | 8.5 | 7.5 | **3.5** | **3.7** | **2.2** | 1 |
| rHPIV1 Y942D | 8.7 | **6.5** | **1.5** | **≦1.2** | **<1.2** | **≦1.2** | 1 |
| rHPIV1 Y942W | 9.2 | 8.5 | 7.2 | **4.2** | **4.5** | **2.2** | 2 |
| rHPIV1 Y942S | 9.0 | 8.5 | 7.0 | **3.0** | **1.5** | **≦1.2** | 2 |
| rHPIV1 Y942Q | 7.2 | 5.7 | **3.0** | **≦1.2** | **≦1.2** | **≦1.2** | 2 |
| rHPIV1 Y942G | 9.0 | 8.0 | **4.5** | **≦1.2** | **≦1.2** | **≦1.2** | 3 |
| rHPIV1 Y942T | 8.7 | **6.5** | **4.7** | **≦1.2** | **≦1.2** | **≦1.2** | 3 |
| rHPIV1 Y942V | 8.0 | **4.7** | **1.7** | **≦1.2** | **≦1.2** | **≦1.2** | 3 |
| rHPIV1 Y942M | 7.5 | **5.2** | **1.5** | **≦1.2** | **≦1.2** | **≦1.2** | 3 |
| rHPIV1 Y942A | 8.7 | **6.5** | **4.2** | **≦1.2** | **≦1.2** | **≦1.2** | 3 |

[a]Values in bold type are at or below the shut-off temperature, which is defined as a 100-fold or more reduction in titer compared to the titer at 32° C. while correcting for the loss of wild-type titer. A 10-fold reduction in titer is considered moderately attenuated.
[b]The values at 39° C. were determined in a separate experiment.

The ts viruses included several mutants that would require 3 nt substitutions to occur in codon-942 to revert to a wt virus. These mutations would, therefore be expected to be stably maintained following prolonged replication in vitro and in vivo. To determine if attenuation was also conferred, the level of replication of the mutant rHPIV1 encoding an alanine at amino acid position 942 (rHPIV1 L: Y942A), was compared to that of rHPIV1 and the mutant rHPIV1 L: $Y942H_{cp45}$ in hamsters. As shown in Table 9, the 942-alanine codon substitution mutation conferred a similar level of attenuation as the 942-histidine mutation that was imported from HPIV3cp45. Thus, by judicious choice of codon usage, the attenuation phenotype that was conferred by a codon change involving single-nt substitution relative to wt can now be achieved with a codon change involving three nt substitutions relative to wt. This changes the expected rate of reversion from $10^{-4}$-$10^{-5}$ to $10^{-12}$-$10^{-15}$.

TABLE 9

The rHPIV1 virus bearing the Tyr942 to Ala mutation is highly attenuated in the respiratory tract of hamsters.

| Virus[b] | Replication in hamsters: No. of animals[c] | Mean virus titer ($log_{10}$ $TCID_{50}$/g ± S.E.[a]) in: Nasal Turbinates | Lungs |
|---|---|---|---|
| rHPIV1 | 12 | 4.6 ± 0.2 | 5.2 ± 0.2 |
| rHPIV1 L: $Y942H_{cp45}$ | 12 | **2.4 ± 0.2**[d] | **2.2 ± 0.2**[d] |
| rHPIV1 L: Y942A | 6 | **2.4 ± 0.3** | **1.8 ± 0.2** |

[a]S.E. Standard error
[b]Hamsters were inoculated IN with $10^6$ $TCID_{50}$ of the indicated virus. Nasal turbinates and lung tissues from six or twelve animals for each group were harvested on day 4. Virus present in the tissues was quantified by serial dilution on LLC-MK2 monolayers at 32° C.
[c]Indicates the number of animals used to calculate the titer from either one (six) or two (twelve) independent experiments, respectively.
[d]Values in bold show a 100-fold or more reduction in titer compared to the titer of rHPIV1
[e]NA = not applicable Thus, introduction of the 942-alanine mutation has achieved the goals of conferring the ts and attenuation phenotypes, as well as diminishing the possibility of reversion to wt. Importantly, since each of the 19 amino acids other than the tyrosine present in the wt virus at position 942 were either lethal or specified a mutant phenotype (ts or att), it is clear that only the assignment of 942-Tyr can yield a wt phenotype. Thus, any mutant 942 codon, such as the alanine codon, would have to undergo all three changes to generate a rHPIV1 recombinant with a wt phenotype. This indicates that at this position, this codon substitution should be highly stable. The level of attenuation, immunogenicity and efficacy of each of the other viable rHPIV1 codon substitution mutants produced as described in this Example can be readily determined by the methods exemplified in Table 9. rHPIV1 codon substitution mutations that require three nt substitutions to revert to the wt amino acid sequence and that specify a satisfactory level of attenuation and immunogenicity in hamster or primates will be selected for inclusion in an immunogenic composition comprising a live attenuated rHPIV1.

Additional substitution mutations can be generated and characterized as described in this example. For instance, the HPIV3cp45 L protein Leu-992 to Phe mutation was imported into rHPIV1 by substitution of a single nt in codon-992, but did not confer a ts or att phenotype. Codon-992 in HPIV1 L was mutagenized to encode each of the other 18 amino acids. Many of these required 2-nt substitutions and, thus, would be expected to be more stable than mutations generated by a single NT substitution. The 992 codon substitution mutations were introduced into the full-length antigenomic HPIV1 cDNA and were used to recover mutant viruses as described above and in FIG. 12.

The growth properties of the recovered mutant rHPIV1 viruses were characterized each of the mutant HPIV1 recombinants grew to high titer in LLC-MK2 cells at 32° C., indicating that these mutations are not attenuating in vitro. Growth of mutant viruses at 35° C. to 39° C. was compared to growth at the permissive temperature (32° C.), to determine if the viruses had a temperature sensitivity phenotype, as described above. Surprisingly, several of the substitutions at amino acid 992 of the L polymerase conferred a ts phenotype (Table 10), including amino acid substitutions encoded by mutant codons that would require 2 nt to revert to wt.

The level of attenuation, immunogenicity and efficacy of each of the variable rHPIV1 codon substitution mutants can now be readily determined by the methods exemplified in Table 9, and the rHPIV1 codon substitution mutations that require two nucleotide substitutions to revert to the wt amino acid sequence and that specify a satisfactory level of attenuation and immunogenicity in hamster or primates will be selected for inclusion in immunogenic compositions comprising a live attentuated rHPIV1.

TABLE 10

Several of the viable rHPIV1s with a codon substitution mutation at amino acid 992 of the HPIV1 L polymerase are ts.

| Virus | Titer[a] at indicated temperature (° C.) ($log_{10}$ $TCID_{50}$/ml) 32 | 35 | 36 | 37 | 38 | 39[b] | # NTs to revert to wt |
|---|---|---|---|---|---|---|---|
| rHPIV1 wt | 8.0 | 8.0 | 7.2 | 7.2 | 6.7 | 6.5 | 0 |
| rHPIV1 $L992F_{cp45}$ | 8.1 | 7.9 | 7.8 | 6.8 | 6.7 | 5.6 | 1 |
| rHPIV1 L992H | 8.5 | 8.2 | 6.7 | 6.7 | 5.5 | **3.0** | 1 |
| rHPIV1 L992I | 8.2 | 8.5 | 8.7 | 7.7 | 6.2 | **2.7** | 1 |
| rHPIV1 L992M | 8.9 | 8.7 | 8.7 | 8.5 | 9.0 | 5.6 | 1 |

TABLE 10-continued

Several of the viable rHPIV1s with a codon substitution mutation at amino acid 992 of the HPIV1 L polymerase are ts.

| Virus | Titer[a] at indicated temperature (° C.) (log$_{10}$ TCID$_{50}$/ml) | | | | | | # NTs to revert to wt |
|---|---|---|---|---|---|---|---|
| | 32 | 35 | 36 | 37 | 38 | 39[b] | |
| rHPIV1 L992W | 9.0 | 9.0 | 8.5 | 8.2 | 6.7 | **5.0** | 1 |
| rHPIV1 L992A | 7.7 | 7.2 | 8.0 | 6.5 | 7.0 | **2.2** | 2 |
| rHPIV1 L992C | 7.5 | 6.5 | **2.2** | **≦1.2** | **1.5** | **≦1.2** | 2 |
| rHPIV1 L992K | 8.7 | 8.7 | 7.5 | 8.5 | 8.0 | — | 2 |
| rHPIV1 L992Y | 8.7 | 8.7 | 8.5 | 8.2 | 7.7 | 6.5 | 2 |

[a]Values in bold type are at or below the shut-off temperature, which is defined as a 100-fold or more reduction in titer compared to the titer at 32° C. compared to the difference in the titer of wt virus between the respective temperature and 32 C.
[b]The values at 39° C. were determined in a separate experiment

EXAMPLE IX

Production and Characterization of Recombinant HPIV1 P/C Gene Deletion Mutants Interferons, which are host cell proteins elaborated in response to infection with viruses, induce an antiviral state in cells that restricts replication of virus in the interferon treated cells. Since this is a powerful component of the host's innate immunity, it is not surprising that many viruses have developed elaborate strategies to counteract the antiviral activity of the interferons (Garcia-Sastre, *Virology,* 279:375-384, 2001; Goodbourn et al., *J. Gen. Virol.,* 81:2341-2364, 2000; Samuel, *Clin. Microbio;. Rev.,* 14:778-809, 2001, incorporated herein by reference). The C and V proteins of many paramyxoviruses, which are encoded by alternative translational open reading frames (ORFs) in the P gene of the paramyxoviruses (Chanock et al., *In "Fields Virology",* 1:1341—1379, 2001), are involved in inhibition of the host-cell response to both Type 1 and Type 2 interferons. Mutations that affect the C or V ORFs of PIV1 or PIV2 viruses often result in ablation of this anti-interferon activity (Didcock et al., *J. Virol.,* 1999; Garcin et al., *J. Virol.,* 75:6800-6807, 2001; Garcin et al., *Virology,* 295:256-265, 2002; Parisien et al., *Virology,* 283: 230-239, 2001, incorporated herein by reference), and viruses with such mutations become sensitive to antiviral actions of interferon and exhibit reduced replication in vitro in interferon competent cells and in vivo in interferon competent animals (Garcia-Sastre, *Virology,* 279:375-384, 2001). Viruses with such mutations have been considered for use as live attenuated virus vaccines (Garcia-Sastre, *Virology,* 279: 375-384, 2001), since they can readily be prepared in vitro in known interferon-negative cells. The V and C proteins have functions other than just putative interferon function (Chanock et al., *In "Fields Virology",* 1:1341—1379, 2001); Lamb et al., *In "Fields Virology",* 1:1305-1340, 2001), therefore, introduced mutations could affect one or more of the functions of the accessory proteins. Since the complete set of the functions of the accessory proteins have not been defined, mutations in the accessory proteins that attenuate the virus might do so by a mechanism that is not related to its anti-interferon properties. Thus, a goal in developing immunogenic compositions of the invention includes production of live attenuated HPIV1 whose attenuation is based solely, or in part, on the presence of mutations that render the virus fully susceptible to the host's interferon response.

Since HPIV1 lacks a V ORF (Newman et al., *Virus Genes,* 24:1, 77-92, 2002), the anti-interferon protein of this virus may be one or more of the C proteins (including the set of C, C', Y1, and Y2 proteins). Mutations in the C protein of Sendai virus, a murine PIV1 highly related to HPIV1, that interfere with the antiviral activity of interferon and that attenuate the replication of this virus for mice have been described (Garcin et al., *J. Virol.,* 75:6800-6807, 2001; Garcin et al., *Virology,* 295:256-265, 2002, incorporated herein by reference). Single-nucleotide substitution mutations that affect the C protein, but not the P protein, in recombinant HPIV3 have been reported (Durbin et al., *Virology,* 261:319-330, 1999; Skiadopoulos et al., *J. Virol.,* 73:1374-1381, 1999a, incorporated herein by reference) and HPIV1 (see Example IV). HPIV3 recombinants bearing the HPIV3 cp45 C mutation (196T) or the F170S mutation were restricted for replication in vivo but not in vitro and, similarly, rHPIV1 bearing the F170$_{SMPIV1}$ mutation in C was attenuated in hamsters (Table 7). These mutants were not ts and replicated efficiently in vitro. These types of non-ts attenuating mutations are an important element in the production of phenotypically stable live-attenuated viruses of the invention, as outlined in Example IV. However, only a single-nucleotide substitution specifies the HPIV3cp45 C mutation (I96T) or the F170S mutation, and such mutations would therefore require only a single nt substitution to revert to wt. The findings summarized in the present example present a method to produce live attenuated rHPIV1 subviral particles that contain functional deletions in the C proteins, which should exhibit greater stability of the attenuation phenotype in vivo. Also described is the recovery of rHPIV1 viruses bearing these deletion mutations.

To generate live-attenuated HPIV1 recombinants whose likelihood to revert to wt is highly diminished, deletion mutations were introduced within the P/C gene of HPIV1 in the region of the overlap of the P and C ORFs. A region located in the 5' end of the HPIV1 C protein that may interact with and abrogate the cell's interferon response (Garcin et al., *J. Virol.,* 75:6800-6807, 2001) pathway was mutagenized. Mutations were introduced in this area by PCR mutagenesis that deleted codons 10-15 of the C ORF. This mutation also deleted codons 13-19 of the P ORF. A subset of mutations deleting C ORF codons 10-11, 12-13, and 14-15 were also generated by PCR mutagenesis (FIG. 13A). Preferable mutants would be ones in which C function was altered without affecting P function, since the latter is an essential protein required for viable HPIV1. Therefore, we first evaluated the ability of a P gene containing these mutations to support the recovery of rHPIV1 from a full-length rHPIV1 antigenomic cDNA in transfected cells. This is an appropriate assay for P function, since a functional P support plasmid is an essential component of the set of three support plasmids used in the recovery of infectious viruses from transfected infectious parainfluenza virus cDNAs. Each of the five deletion mutations indicated in FIG. 13 were introduced into pTM-(P$_1$). HEp-2 cells were transfected with pTM (N$_1$), pTM (L$_1$), wt full-length HPIV1 antigenomic cDNA, and each of the pTM (P$_1$) containing the deletions indicated in FIG. 13 and were coinfected with MVA-T7, as described above. Surprisingly, each of the P deletion mutants supported the recovery of rHPIV1 from cDNA. Importantly, infectious rHPIV1 was not recovered from control transfection reactions lacking a P support plasmid.

Four of the P/C gene deletion mutations specifying mutations in the N-terminal end of the encoded proteins were introduced into the full-length antigenomic HPIV1 cDNA, and these cDNAs were used to recover mutant recombinant HPIV1 containing P/C gene deletions. Two viruses have been recovered to date (FIG. 13) and they grew to high titer in cell culture indicating that the introduced mutations were not attenuating in vitro. rHPIV1 dl 10-15 grew to 8.5 $\log_{10}$ $TCID_{50}$/ml, and rHPIV1 dl 14-15 grew to 9.0 $\log_{10}$ TCID50. This is high for HPIV1 and may be due to the ablation of another, as yet undefined, function of a protein(s) encoded by the P gene (Garcin et al. *Virology* 295:256-265, 2002, incorporated herein by reference). These mutants can be readily evaluated for their immunogenicity and replicative capacity in hamsters and non-human primates such as African green monkeys using methods described herein. If appropriately attenuated and immunogenic, these mutations can be introduced into HPIV1 alone or along with other ts and non-ts attenuating mutations to generate phenotypically stable live-attenuated HPIV1s.

Additional deletion mutations in the P/C gene can now be generated in an analogous manner and can be evaluated for their ability to attenuate the virus in vivo. To generate additional P/C gene deletion mutations, a 2-codon deletion mutation was introduced in the middle of the P gene (FIG. 13B). This mutation spans amino acid F170, whose substitution at amino acid residue 170 of the rHPIV1 C protein has been shown (Table 6) to confer a non-ts attenuation phenotype. The mutation was introduced into pTM ($P_1$) and this support plasmid was functional in the rescue assay described above (FIG. 13B), indicating that the function of the P protein is not adversely affected. This mutation and other similar deletion mutations can now be introduced throughout the P/C gene, as well as the N, M or L genes, and evaluated for their level of replication in vitro and in vivo. Satisfactorily attenuated mutations can be combined to develop highly stable live-attenuated viruses for use in immunogenic compositions and methods of the invention.

EXAMPLE X

Use of HPIV1 as a Vector for the Expression of Heterologous Antigenic Determinants HPIV1, like HPIV2, infects and produces disease predominantly in infants and children over the age of six months, whereas HPIV3 and RSV infect early within the first six months of life (Chanock et al., *In "Fields Virology"*, 1:1341—1379, 2001); Collins et al., *In "Fields Virology"*, 1:1443-14486, 2001). Therefore, immunization with HPIV3 and RSV will need to be initiated within the first month of life to elicit an immune response against this early disease, and immunization with HPIV1 will need to be initiated by approximately six months of age. Since RSV and HPIV3 continue to cause serious disease throughout the first two to three years of life, there will be a need to provide continued immunological coverage against these viruses throughout the first three years of life. The differing epidemiology of these viruses dictates that HPIV1 and HPIV2 immunogenic compositions will be given after RSV and PIV3, and this sequential administration of the paramyxovirus compositions provides an opportunity to use HPIV1 as a vector to express the protective antigens of RSV and HPIV3. For example, an HPIV1 virus expressing the RSV F protective antigen that is administered at six months of age should effectively boost the immunity to RSV following RSV immunization at one month of age. Thus, such a HPIV1 vector given at six months of age will induce immunity to HPIV1 and, at the same time, will boost the immunity to RSV induced by an immunogenic composition given at one month of age. The need to boost the immunity to RSV reflects its greater role as a pathogen in infants (it causes four times the number of hospitalizations as HPIV1) (Chanock et al., *In "Fields Virology"*, 1:1341-1379, 2001; Collins et al., *In "Fields Virology"*, 1:1443-1486, 2001) and the need to augment immune responses that are induced within the first six months of life since such immune responses are often weaker than in infants greater than six months of age (Clements et al., *J. Infect. Dis.*, 173:44-51, 1996; Karron et al., *Pediatr. Infect. Dis. J.*, 14:10-16, 1995a; Wright et al., *J. Infect. Dis.*, 182:1331-1342, 2000).

Modification of a single recombinant virus to induce immunity against multiple pathogens has several advantages. In certain circumstances it is more feasible and expeditious to develop a single attenuated backbone expressing antigens against multiple pathogens than it is to develop a separate attenuated recombinant virus for use against each pathogen. Each pathogen offers different challenges for manipulation, attenuation and demonstration of safety and efficacy. There are additional reasons for developing a live attenuated RSV immunogenic composition that is not based solely on infectious RSV. RSV is a pathogen that grows less well in vitro than HPIV1 and may be less stable with regard to infectivity. The development of a live-attenuated RSV vaccine has been underway for more than 35 years, indicating the difficulty of achieving an appropriate balance between immunogenicity and attenuation for this human pathogen. Thus, a second aspect of the invention is to use the superior characteristics of HPIV1 as an immunogenic agent and as a vector to use as the primary immunogen against RSV. In this case, it could be administered early in infancy to elicit an immune response against the RSV disease that occurs within the first six months of life.

One aspect of the invention outlined below is the method of using various versions of rHPIV1 as vectors to express one or multiple protective antigens of a heterologous pathogen as supernumerary genes. In the present example, rHPIV1 was engineered as a vector to express the F protective antigen of RSV. Thus, a single rHPIV1 vector expressing the protective antigen of RSV can induce an immune response against two human pathogens, namely, HPIV1 via an immune response to the glycoproteins present in the vector backbone, and RSV via the F protective antigen expressed from the extra gene inserted into rHPIV1.

There have been numerous obstacles to engineering HPIV1 to express a protective antigen of RSV or any other pathogen. For example, the molecular genetics of HPIV1 were not previously well-characterized, and knowledge of the cis-acting signals involved in HPIV1 replication and gene expression was based on uncertain and untested extrapolation from other parainfluenza viruses. However, this knowledge is critical to inserting and expressing a foreign gene, since such an insertion must avoid disturbing essential cis-acting signals in the vector backbone. Also, an insert must contain appropriate cis-acting signals that will permit it to be recognized and expressed as part of the transcriptional program of the HPIV1 vector. In addition, it was possible that particular insertion sites might not be compatible with efficient virus growth for reasons that do not involve direct disruption of cis-acting signals, such as the recent finding that insertion of a foreign gene into the N/P junction of vesicular stomatitis virus inhibited virus growth, apparently because it reduced the efficiency of expression of the downstream P gene compared to the upstream N gene (Wertz et al., *J. Virol.*, 76:7642-7650, 2002). Furthermore, not all combinations of viruses and foreign antigens are compatible. For example, the expression of measles virus F glycoprotein from recombinant vesicular stomatitis virus was toxic to the virus (Quinones-Kochs et al., *Virology*, 287:427-435, 2001), and expression of HPIV1 HN from rHPIV3 also reduced the efficiency of virus replication in vitro by 10- to 100-fold (Skiadopoulos et al., *Virology,* 297:136-152, 2002).

To generate an antigenomic HPIV1 cDNA that could be used as a vector, a unique Mlu I restriction site was introduced immediately upstream of the HPIV1 N gene translation initiation codon in the full-length antigenomic HPIV1 cDNA (FIG. 8) by PCR mutagenesis, as described previously. The supernumerary gene insertion site in the vector was designed so that it did not disrupt any of the postulated, presumptive HPIV1 replication and transcription cis-acting elements predicted by analogy to heterologous paramyxoviruses. The present example describes insertion into an MluI site preceding the N protein ORF (FIG. 8). However, based on the successful results described herein, alternative unique restriction sites can also be used, and these can also be introduced at other gene junctions, such as the N-P or P-M junction.

To generate the HPIV1 expression vector, the previously described RSV subgroup A ($RSV_A$) F glycoprotein ORF ($F_{RSV-A}$) (GenBank accession no. M74568, incorporated herein by reference) was modified for insertion into the promoter-proximal Mlu I site of rHPIV1 (FIG. 8). The strategy was to express the heterologous ORF as an additional, separate mRNA, and hence it was important that it be introduced into the rHPIV1 genome so that it was preceded by a functional HPIV1 gene start signal and followed by a functional HPIV1 gene end signal. The Mlu I insertion site followed the putative gene start signal of the N gene (FIG. 8). Hence, for insertion at this site, the RSV ORF needed to be modified by insertion of an Mlu I site at its upstream end and addition of a putative HPIV1 gene end signal, intergenic region, gene start signal, and Mlu I site at its downstream end. The inserted sequence was 1764 nucleotides in length and thus the length of the modified HPIV1 antigenomic cDNA conformed to the rule of six, which holds for other members of Genus Respirovirus (Chanock et al., *In "Fields Virology",* 1:1341—379, 2001) and also appears to apply to HPIV1.

Recombinant virus (rHPIV1-$F_{RSV-A}$) was readily recovered from transfected HEp-2 cells using the HPIV1 N, P and L protein expression plasmids and MVA-T7 infection, as described above. The virus supernatant was then passaged several times on LLC-MK2 cells grown at 32° C. vRNA isolated from LLC-MK2 cells infected with rHPIV1-$F_{RSV-A}$ was used to generate an RT-PCR product flanking the supernumerary gene, and sequence analysis confirmed that the sequence of the supernumerary gene present in rHPIV1-$F_{RSV-A}$ was as designed. Thus, an additional gene encoding a foreign antigen can be readily inserted into recombinant HPIV1 using the putative transcription signals and insertion strategy identified in the present example, and this inserted sequence is stably maintained following prolonged replication in tissue culture cells.

It was important to demonstrate functionality of the expressed protein, since a functional protein would be in the native conformation and thus would be capable of inducing antibodies to appropriately presented F protein epitopes. Unexpectedly, LLC-MK2 cells infected with rHPIV1-$F_{RSV-A}$ formed very large multinucleated syncytia that rapidly covered the entire cell culture monolayer, indicating that the RSV F protein was well expressed and was functional in membrane fusion. This extensive syncytia formation is in contrast to HPIV1 infection of tissue culture cells, which typically results in little or no cytopathic effect (c.p.e.), and no syncytia formation. It is not known why rHPIV1-$F_{RSV-A}$ is substantially more active in syncytia formation than wt RSV or other PIV based RSV F protein expression vectors (Schmidt et al., *J. Virol.,* 75:4594-4603, 2001). Expression of the paramyxovirus glycoproteins was also confirmed by indirect immunofluorescence of LLC-MK2 cells infected with either wt HPIV1, wt $RSV_A$, or rHPIV1-$F_{RSV-A}$. LLC-MK2 cells grown on glass slides were infected with virus, and approximately 44 hours post-infection the cells were fixed and permeabilized as described previously. Mouse monoclonal anti-HPIV1 HN (8.2.2.A and 4.5) and mouse monoclonal anti-RSV F antibodies (1129, 1243, 1269) were used to detect the HPIV1 HN and RSV F proteins in LLC-MK2 cells infected with wt RSV, wt HPIV1 and rHPIV-1-$F_{RSV}$. Fluorescein isothiocyanate (FITC) conjugated goat anti-mouse IgG antibody (Jackson Immunochemicals, PA) was used for indirect immunofluorescence of RSV or HPIV1 glycoproteins. Bright-field and corresponding fluorescent images were captured simultaneously and were evaluated separately or merged. These studies demonstrated that rHPIV1-$F_{RSV}$ expresses the glycoprotein of both HPIV1 and RSV, since it is the only virus tested that reacted with both anti-RSV and anti-PIV1 antibodies.

Since the glycoproteins of HPIV1 and RSV are expressed efficiently in tissue cultures infected with rHPIV1-$F_{RSV}$, it is expected that they will be immunogenic and efficacious in vivo since similar PIV3-based recombinants induced protective immune responses directed against both the protective antigens in vector backbone and against the heterologous antigen expressed by the vector (Durbin et al., *J. Virol.,* 74:6821-6831, 2000; Schmidt et al., *J. Virol.,* 75:4594-4603, 2001; Skiadopoulos et al., *Virology,* 297:136-152, 2002). These observations demonstrate that recombinant HPIV1 can be used to express the protective glycoproteins of a heterologous virus for use either as a primary immunogen against the heterologous virus, eg., RSV, or to boost immunity to the heterologous virus that was induced by prior immunization or natural infection. In both cases, immunity is induced against HPIV1 itself as well as against the heterologous virus. Additional rHPIV1-based expression vectors encoding the $RSV_A$ G protein as well as the RSV subtype B ($RSV_B$) G and F glycoproteins can similarly be generated following the example of rHPIV1-$F_{RSV-A}$ to provide immunogenic compositions to induce broad immune responses against RSV disease caused by both subtypes. In addition, recombinant HPIV1 based expression vectors can be used to elicit immune responses against a broader range of viral pathogens, for example, one or more pathogens selected from measles virus, respiratory syncytial virus, mumps virus, human papilloma virus, human metapneumovirus (HMPV), type 1 or type 2 human immunodeficiency virus, herpes simplex virus, cytomegalovirus, rabies virus, Epstein Barr Virus, filovirus, bunyavirus, flavivirus, alphavirus, human metapneumoviruses, and influenza virus.

The level of attenuation of rHPIV1-$F_{RSV-A}$ or of a rHPIV1 expressing another viral protective antigen can be modified by the introduction of one or more of the defined attenuating mutations described herein. Similarly the invention provides for combination of more than one foreign heterologous viral protective antigen into one rHPIV1 vector by inserting distinct foreign proteins as additional gene units into two or more insertion sites, such as those indicated above. In this way multivalent immunogenic compositions can be formulated. Alternatively, one can immunize with two or more HPIV1 vectors each expressing a single distinct foreign antigen (eg. one expressing the RSV F and another the HMPV G protective antigen) to achieve a multivalent immunogenic composition capable of inducing immunity to multiple viral pathogens (Skiadopoulos et al., *Virology,* 297:136-152, 2002). In addition, various sequential immunization methods are provided by the invention. In exemplary embodiments, initial immunization is conducted using a rHPIV3 vector expressing a heterologous antigen, and immunity to the heterologous virus is later boosted by administering a rHPIV1 vector expressing the same heterologous antigen. The availability of multiple PIV vectors, eg HPIV3 and HPIV1, provides a flexible vector system that is able to induce needed immunity to both the vector and the expressed heterologous antigen.

EXAMPLE XI

Identification of Spontaneous Mutations that Attenuate HPIV1 for Primate Hosts The present example identifies host range mutations that arose spontaneously in an HPIV1 virus and that are useful for generating live attenuated HPIV1 viruses for use in immunogenic compositions and methods of the invention. The mutations permit efficient replication of rHPIV1 in tissue culture and in hamsters yet restrict replication in the upper and lower respiratory tract of an accepted model for HPIV and other viral activity in humans, African green monkeys. The data herein further show that viruses possessing these mutations replicate sufficiently well in African green monkeys to induce an immune response against challenge with HPIV1 wt virus. In addition, the host range mutations are compatible with each of three of the single-gene attenuating mutations both for efficient replication in vitro and for immunogenicity in African green monkeys.

The rHPIV1 virus recovered from cDNA replicated like biologically derived wild-type HPIV1/Washington/20993/1964 in the lungs and nasal turbinates of hamsters (Table 4), but it was unexpectedly partially restricted in replication in the upper and lower respiratory tract of African green monkeys (Table 11).

TABLE 11

Comparison of the level of replication of rHPIV1 and biologically derived HPIV1 in the upper and lower respiratory tract of African Green Monkeys (AGM).

| | | Replication of virus in AGM: | |
|---|---|---|---|
| | Number | Mean peak virus titer ($log_{10}$ $TCID_{50}$/ml ± S.E.)[b] | |
| Virus[a] | of animals | NP swab fluid[c] | Tracheal lavage fluid[d] |
| rHPIV1[f] | 6 | 2.1 ± 0.2 | 4.5 ± 0.3 |
| $HPIV1_{LLC1}$[g] | 4 | 4.7 ± 0.3 | 5.8 ± 0.5 |

[a]Monkeys were inoculated intranasally and intratracheally with $10^6$ $TCID_{50}$ of the indicated virus.
[b]Mean of the peak virus titers for the animals in each group irrespective of sampling day. SE = standard error. Virus titrations were performed on LLC-MK2 cells at 32° C. The limit of detection was 1.0 $log_{10}$ $TCID_{50}$/ml.
[c]Nasopharyngeal samples were collected on days 0 to 10 post-infection for rHPIV1 and days 0, 2, 4, 6, 8 for HPIV1 $_{LLC1}$. The titers on day 0 were ≦0.5 $log_{10}$ $TCID_5$/ml.
[d]Tracheal lavage samples were collected on days 2, 4, 6, 8, and 10 post-infection for rHPIV1 and days 2, 4, 6, and 8 for HPIV1 $_{LLC1}$.
[f]rHPLV1 is the recombinant (referred to as rHPIV1 in all previous Examples) derived from cDNA using the HPIV1/Washington/20993/1964 wild-type virus, which had a history of three passages in African green monkey cells and four passages in LLC-MK2 cells, and is designated $HPIV1_{LLC4}$, which is the source of the consensus sequence provided in FIGS. 10A-10D (this sequence differs from the corresponding wild-type parental sequence by the five nucleotide changes identified in FIG. 12).
[g]$HPIV1_{LLC1}$ = HPIV1/Washington/20993/1964 with three passages in African green monkey cells but only one passage in LLC-MK2 cells. This passage level of the parent virus is herein designated $HPIV1_{LLC1}$, and represents an earlier step in the passage history of $HPIV1_{LLC4}$.
HPIV1 LLC1 is the biologically derived wt virus referred to as HPIV1 or HPIV1/Wash 64 in previous examples.

The HPIV1 biologically derived virus used in this study had been isolated in 1964 from a child experiencing respiratory tract disease. The nomenclature for the two HPIV1 viruses compared in this example is indicated in the footnotes in Table 10. A HPIV1 virus suspension prepared by three passages in primary African green monkey cells had previously been shown to be virulent in humans (Murphy et al., *Infect. Immun.,* 12:62-68, 1975). This virus was next subjected to a single additional passage in LLC-MK2 cells, a continuous line of Rhesus monkey kidney cells, resulting in the $HPIV1_{LLC1}$ virus used in Table 10. The $HPIV1_{LLC1}$ virus is the preparation that was used in the foregoing examples as the biologically-derived wt control virus, and indeed is virulent in both hamsters (Newman et al., *Virus Genes,* 24:1, 77-92, 2002) and in African green monkeys. However, for the purposes of determining a complete consensus sequence and constructing an antigenomic cDNA, it was necessary to amplify this virus by three additional passages in LLC-MK2 cells, resulting in the pool herein designated $HPIV1_{LLC4}$. The recombinant virus, that was subsequently recovered, was a faithful copy of this $HPIV1_{LLC4}$ virus.

Since the $HPIV1_{LLC4}$ virus and its recombinant copy rHPIV1 differed from the $HPIV1_{LLC1}$ wt virus by three additional passages in LLC-MK2 cells, it was possible that it had sustained spontaneous mutations stemming from the additional three passages. Such spontaneous mutations could account for its restricted replication in African green monkeys (Table 11). Therefore, the complete nucleotide sequence of the virulent $HPIV1_{LLC1}$ parent virus was compared to that of rHPIV1. A comparison of the full-length nucleotide sequence and the deduced amino acid sequence of the $HPIV1_{LLC1}$ and that of rHPIV1 revealed the presence of coding mutations in the P/C genes and in the HN gene that presumably occurred during the three additional passages in LLC-MK2 cells (Table 12). Additional mutations that are translationally silent were also identified. This set of mutations likely reflects initial adaptation to growth of $HPIV1_{LLC1}$ in the LLC-MK2 cells. It is noteworthy that the recombinant virus (rHPIV1) appears to be genetically stable in LLC-MK2 cells during further propagation in these cells, as confirmed by sequence analysis following additional passages involved in terminal dilution and amplification.

TABLE 12

Sequence differences between biologically derived $HPIV1_{LLC1}$ and rHPIV1 representing HPIV1 LLC4

| Gene sequenced | ORF | NT[a] | Codon change[b] | Amino acid change[c] |
|---|---|---|---|---|
| N | N | 1097 | CCC to CCT | Silent |
| | P | 2103 | GAG to GGG | E119<u>G</u>[d,e] |
| P/C gene | P | 2815 | TCA to TCG | Silent |
| | C | 2103 | AGA to GGA | R84<u>G</u>[d,e] |
| M | M | 4625 | GTA to GTC | Silent |
| HN gene | HN | 8559 | ACC to GCC | T553<u>A</u>[d,e] |

[a]Nucleotide numbering starting from the 3' end of the HPIV1 viral genome. The number given is the position of the base pair change between the two viruses. Codons are in positive sense.
[b]The codon of $HPIV1_{LLC1}$ is listed first, and the codon for rHPIV1 is listed second.
[c]The amino acid of $HPIV1_{LLC1}$ is indicated first, the position of the amino acid follows next, and the amino acid of rHPIV1 is listed last.
[d]Amino acid numbering is in reference to the C ORF; this amino acid change is also present in the C', Y1, and Y2 ORFs.
[e]Underlined Amino acid are the amino acids substitutions that occurred during the passage of $HPIV1_{LLC1}$ to $HPIV1_{LLC4}$.

Any or all of these mutations could contribute to the host range attenuation phenotype of the rHPIV1. Importantly, rHPIV1 replicated sufficiently well in African green monkeys to induce an immune response (Table 13) effective against challenge with HPIV1$_{LLC1}$ wt, indicating that rHPIV1 has achieved a satisfactory balance between attenuation and immunogenicity and that it, therefore, has many properties of a satisfactory live attenuated HPIV1 candidate for use in immunogenic compositions and methods of the invention.

TABLE 13

Immunization of African green monkeys (AGM) with rHPIV1 induces resistance to challenge with biologically derived HPIV1$_{LLC1}$

| | | Replication of challenge virus in AGM: | |
|---|---|---|---|
| | | Mean peak virus titer ($log_{10}$ $TCID_{50}$/ml ± S.E.)[b,c] | |
| Immunizing virus[a] | Number of animals | NP swab fluid[d] | Tracheal lavage fluid[e] |
| rHPIV1 | 6 | 0.5 ± 0.0 | 0.5 ± 0.0 |
| None | 4 | 4.7 ± 0.3 | 5.8 ± 0.5 |

[a]Monkeys were inoculated intranasally and intratracheally with $10^6$ $TCID_{50}$ of rHPIV1 in a 1-ml volume at each site, or with an equivalent volume of cell culture medium.
[b]Mean of the peak virus titers for the animals in each group irrespective of sampling day. SE = standard error.
[c]Virus titrations were performed on LLC-MK2 cells at 32° C. The limit of detection was 1.0 $log_{10}$ $TCID_{50}$/ml.
[d]Nasopharyngeal samples were collected on days 0, 2 4, 6, and 8. The titers on day 0 were ≦0.5 $log_{10}$ $TCID_{50}$/ml.
[e]Tracheal lavage samples were collected on days 2, 4, 6, and 8 post-infection.

The specific mutation(s) in rHPIV1$_{LLC4}$ identified in P/C and/or HN that determine the attenuation phenotype seen in African green monkeys will be readily identified by inserting the sequence of the HPIV1$_{LLC1}$ virus at either or both of sites of the mutations in the rHPIV1$_{LLC4}$ cDNA indicated in Table 11 and evaluating the rHPIV1 derivatives for their level of replication in African green monkeys. It is possible that the substitution mutation in C is the sole attenuating host range mutation in rHPIV1$_{LLC4}$ since this is the ORF that bears the F170S attenuating mutation in the C of Sendai virus (analogous to the F170S site in HPIV1 and F164S in HPIV3) (Garcin et al., *Virology,* 238:424-431, 1997). The F170S mutation in the C of Sendai virus (MPIV1) was also a spontaneous attenuating mutation that also similarly arose during its passage in LLC-MK2 cells (Garcin et al., *Virology,* 238:424-431, 1997). Importantly, the site of the two mutations in C of HPIV1 are different indicating that it should be possible to combine the two C mutations (i.e., the F170S and R84G mutations) into one rHPIV1 virus and thereby increase the genetic stability or level of attenuation of the rHPIV1 for African green monkeys, and a virus with this combination has been produced.

Since the cDNA backbone used to generate the rHPIV1 mutant viruses indicated in Table 5 of Example IV contained the P/C and HN mutations indicated in Table 13, all of the viruses listed in Table 5 of Example IV bear both the indicated mutation from HPIV3 cp45, RSV, or Sendai virus and the C/P and HN mutations present in the cDNA backbone used to generate the rHPIV1 mutant viruses. This indicates that each mutation in a successfully recovered rHPIV1 indicated in Table 5 of Example IV is compatible for viability with the mutations in P/C and HN (Table 13). Furthermore, rHPIV1 viruses bearing the potentially attenuating mutations in P/C and/or HN and the attenuating F456L in L, the F170S in C, or Y942H in L mutation were also satisfactorily attenuated and protective in African green monkeys (Table 14). This indicates that these sets of mutations are compatible for efficient replication in vitro and for a sufficient level of replication in vivo to induce an effective immune response.

TABLE 14

The mutations in rHPIV1$_{LLC4}$ are compatible with an imported mutation in the C protein (F170S) and imported mutations in the L protein (F456L or Y942H) for replication in African green monkeys (AGM) and protection against subsequent challenge with HPIV1$_{LLC1}$ wt.

| | | Replication of immunizing virus in AGM: | | Response to challenge with biological HPIV1$_{LLC1}$ wt[f]: | |
|---|---|---|---|---|---|
| | | Mean virus titer ($log_{10}$ $TCID_{50}$/g ± S.E.)[a,b] in: | | Mean virus titer ($log_{10}$ $TCID_{50}$/g ± S.E.) | |
| Immunizing virus[c] | No. of animals | NP swab fluid[d] | Tracheal lavage fluid[e] | NP swab fluid[g] | Tracheal lavage fluid[h] |
| rHPIV1$_{LLC4}$ | 6 | 2.1 ± 0.2 | 4.5 ± 0.3 | 0.5 ± 0.0 | 0.5 ± 0.0 |
| rHPIV1 C: F170S$_{MPIV1}$ | 4 | 2.0 ± 0.1 | 3.5 ± 0.6 | 1.1 ± 0.4 | 0.5 ± 0.0 |
| rHPIV1 L: F456L$_{RSV}$ | 4 | 1.0 ± 0.2 | 2.0 ± 0.3 | 0.5 ± 0.0 | 1.0 ± 0.3 |
| rHPIV1 L: Y942H$_{cp45}$ | 4 | 1.7 ± 0.2 | 3.5 ± 0.1 | 0.5 ± 0.0 | 1.0 ± 0.3 |
| none | 4 | NA[i] | NA | 4.7 ± 0.5 | 6.2 ± 0.7 |

[a]Mean of the peak virus titers for the animals in each group irrespective of sampling day. SE = standard error.
[b]Virus titrations were performed on LLC-MK2 cells at 32° C. The limit of detection was 1.0 $log_{10}$ $TCID_{50}$/ml.
[c]Monkeys were inoculated intranasally and intratracheally with $10^6$ $TCID_{50}$ of the indicated virus at each site.
[d]Nasopharyngeal samples were collected on days 0 to 10 post-infection. The titers on day 0 were ≦0.5 $log_{10}$ $TCID_{50}$/ml.
[e]Tracheal lavage samples were collected on days 2, 4, 6, 8, and 10 post-infection.
[f]Monkeys were challenged intranasally and intratracheally with $10^6$ $TCID_{50}$ of HPIV1$_{LLC1}$.
[g]Nasopharyngeal samples were collected on days 0, 2, 4, 6, and 8. The titers on day 0 were ≦0.5 $log_{10}$ $TCID_{50}$/ml.
[h]Tracheal lavage samples were collected on days 2, 4, 6, 8, and 10 post-infection for rHPIV1 and days 2, 4, 6, and 8 for HPIV1$_{LLC1}$.
[i]NA = not applicable These unexpected findings have identified one or more host range and ts mutations that are useful for attenuation of HPIV1 wild-type virus in primate hosts, in both the upper and lower respiratory tracts. The host range mutation(s) that is/are attenuating include one or more of the P/C mutations and single HN mutation. This can be readily determined according to the methods set forth herein. It is unlikely that the translationally-silent nt changes are important in the attenuation phenotype, although this also can be readily determined. The level of replication of rHPIV1$_{LLC4}$, which bears the P/C and HN mutations, in the African green monkeys was sufficient to induce a protective immune response against wild-type HPIV1$_{LLC1}$ challenge suggesting that it could be useful within immunogenic compositions of the invention, alone or in combination with other attenuating mutations to yield a satisfactorily attenuated, phenotypically stable, highly immunogenic virus. Importantly, the P/C and HN mutations were compatible for viability with a large set of other mutations located in many loci of the HPIV1 genome and for immunogenicity in African green monkeys. It thus could serve as a primary attenuating mutation or a member of a set of attenuating mutations that contribute to attenuation and to phenotypic stability of a recombinant HPIV1 for use in immunogenic compositions and methods of the invention. Thus, the P/C and/or the HN host range attenuating mutations are useful additions to the menu of individual or combined mutations for incorporation into recombinant HPIV1 to yield attenuated viral candidates for eliciting immune responses in mammalian hosts.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited within the foregoing disclosure for economy of description. Each of these references is incorporated herein by reference in its entirety for all purposes.

DEPOSIT OF BIOLOGICAL MATERIAL

The following materials have been deposited with the American Type Culture Collection, 10801 University Boulevard, Manassas, Va. 20110-2209, under the terms of the Budapest Treaty.

| Virus | Accession No. | Deposit Date |
|---|---|---|
| p3/7(131)2G | (ATCC 97989) | Apr. 18, 1997 |
| p3/7(131) | (ATCC 97990) | Apr. 18, 1997 |
| p218(131) | (ATCC 97991) | Apr. 18, 1997 |
| HPIV3 JS cp45 | (ATCC PTA-2419) | Aug. 24, 2000 |

What is claimed is:

1. A method for producing an infectious, self-replicating, recombinant human parainfluenza virus type 1 (HPIV 1) from one or more isolated polynucleotide molecules encoding said HPIV1, comprising: coexpressing in a cell or cell-free system one or more expression vector(s) comprising a polynucleotide molecule that encodes a partial or complete, recombinant HPIV 1 genome or antigenome and one or more polynucleotide molecules encoding PIV N, P and L proteins, thereby producing an infectious HPIV 1, said recombinant HPIV1 genome or antigenome including at least one mutation selected from the group consisting of:

a mutation in the L protein Y942 to an amino acid selected from the group consisting of F, C, N, D, W, S, Q, G, T, V, M, L and A;

a mutation in the L protein L992 to an amino acid selected from the group consisting of H, I, M, W, A, C, K, N, V and Y;

a mutation in the L protein of E1711 to another amino acid;

a mutation in the HN protein T553 to another amino acid;

a mutation in the C protein R84 to another amino acid;

a mutation in the C protein R84 to another amino acid and mutation of the P protein E119 to another amino acid;

a mutation in the P protein E119 to another amino acid;

a deletion of codons 10-15 of the C protein and codons 13-19 of the P protein;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein;

a deletion of codons 168-170 of the C protein and codons 172-173 of the P protein.

2. The method of claim 1, wherein the HPIV1 genome or antigenome and the N, P, and L proteins are expressed by multiple expression vectors.

3. The method of claim 1, wherein at least one of the N, P and L proteins is supplied by coinfection with PIV.

4. The method of claim 1, wherein the polynucleotide molecule that encodes the recombinant HPIV 1 genome or antigenome is cDNA.

5. The method of claim 1, wherein the infectious HPIV 1 particle is a complete virus.

6. The method of claim 1, wherein one or more of said N, P and L proteins is/are of a heterologous PIV.

7. The method of claim 1, wherein the recombinant HPIV 1 genome or antigenome further incorporates a recombinantly-introduced restriction site marker or transcriptionally silent point mutation.

8. The method of claim 1, wherein the recombinant HPIV 1 genome or antigenome further incorporates one or more recombinantly-introduced attenuating mutations.

9. The method of claim 1, wherein the recombinant HPIV1 genome or antigenome further incorporates one or more recombinantly-introduced, temperature sensitive (ts) attenuating mutations.

10. The method of claim 1, wherein the recombinant HPIV1 genome or antigenome further incorporates one or more attenuating mutations identified in a mutant PIV strain or other mutant nonsegmented negative stranded RNA virus.

11. The method of claim 10, wherein one or more attenuating mutations is one or any combination of mutations selected from mutations specifying amino acid substitutions in the L protein at a position corresponding to Tyr942, Leu992, and/or Leu1558 of wild-type (wt) HPIV1 L, amino acid substitution in the N protein at a position corresponding to residue Val99 of wt HPIV1 N, amino acid substitutions in the F protein at a position corresponding to residue Ile423 and/or Ser453 of wt HPIV1 F, amino acid substitution in the HN protein at a position corresponding to residue Arg386 of wt HPIV 1 HN, amino acid substitution in the C protein at a position corresponding to Ser102 of wt HPIV1 C, amino acid substitution in the M protein at a position corresponding to residue Pro 195 of wt HPIV 1 M, nucleotide substitutions) in a 3' leader sequence of the genome or antigenome at a position corresponding to nucleotide 23 and/or nucleotide 28 of wt HPIV 1, and/or nucleotide substitution in a N gene start sequence at a position corresponding to nucleotide 62 of wt HPIV 1.

12. The method of claim 11, wherein the one or any combination of mutations is selected from C:S102$T_{cp45}$, M: P195$T_{cp45}$, F: I423$V_{cp45}$, F: S453$T_{cp45}$, HN: R386$A_{cp45}$, L: Y942$H_{cp45}$, L: Y942F, L: Y942N, L: Y942D, L: Y942C, L:Y942W, L: Y942S, L: Y942Q, L: Y942G, L: Y942T, L: Y942T, L: Y942M, L: Y942L, L: Y942A, L: L992$F_{cp45}$, L: L992I, L: L992M, L: L992H, L: L992W, L: L992A, L: L992C, L: L992K, L: L992N, L: L992V, L: L992Y and L: L1558$T_{cp45}$.

13. The method of claim 11, wherein the recombinant HPIV 1 genome or antigenome incorporates multiple mutations selected from (i) mutations specifying amino acid substitutions in the L protein at positions corresponding to Tyr942 and Leu992 of wild-type (wt) HPIV 1 L, (ii) mutations specifying amino acid substitutions in the L protein at positions corresponding to Leu992 and Leu1558 of wild-type wt HPIV1 L, (iii) mutations specifying amino acid substitutions in the L protein at positions corresponding to Tyr942, Leu992 and Leu1558 of wt HPIV1 L, (iv) mutations specifying amino acid substitutions in the F protein at positions corresponding to Ile423 and Ser453 of wt HPIV1 F, and (v) mutations specifying an amino acid substitution in the N protein at a position corresponding to residue Val99 of wt HPIV 1 N, mutations in a 3' leader sequence of the genome or antigenome at positions corresponding to nucleotide 23 and nucleotide 28 of wt HPIV 1, and a nucleotide substitution in a N gene start sequence at a position corresponding to nucleotide 62 of wt HPIV 1.

14. The method of claim 13, wherein the multiple mutations are selected from (i) 3'-NV99$A_{cp45}$, (ii) F: I423V/S453$T_{cp45}$, Y942H/L992$F_{cp45}$, (iii) L992F/L1558$I_{cp45}$, and (iv) Y942H/L992F/L1558$I_{cp45}$.

15. The method of claim 9, wherein one or more attenuating mutations is from a different PIV or a non-PIV nonsegmented negative stranded RNA virus.

16. The method of claim 15, wherein one or more attenuating mutation is an attenuating mutation at an amino acid position corresponding to an amino acid position of an attenuating mutation identified in a heterologous, mutant nonsegmented negative stranded RNA virus.

17. The method of claim 16, wherein an attenuating mutation comprises an amino acid substitution of phenylalanine at position 456 of the HPIV 1 L protein.

18. The method of claim 16, wherein an attenuating mutation comprises an amino acid substitution of phenylalanine at position 170 of the HPIV 1 C protein.

19. The method of claim 16, wherein a heterologous, mutant nonsegmented negative stranded RNA virus is a bovine parainfluenza virus type 3 (BPIV3), and wherein an attenuating mutation comprises an amino acid substitution at a corresponding target position Glu1711 in the HPIV1 L protein.

20. The method of claim 9, wherein one or more attenuating mutation(s) is identified in a mutant PIV strain, and one or more attenuating mutation(s) is at an amino acid position corresponding to an amino acid position of an attenuating mutation identified in a heterologous, mutant nonsegmented negative stranded RNA virus.

21. The method of claim 20, wherein the attenuating mutations are a combination of mutations selected from (i) $F170S_{MPIV\ 1}$/Y942H/$L992F_{cp45}$, and (ii) F170SMPIV1/L992F/$L1558I_{cp45}$.

22. The method of claim 1, wherein at least one attenuating mutation is stabilized by multiple nucleotide changes in a codon specifying the mutation.

23. The method of claim 22, whereinat least one stabilized mutation is one or any combination of mutation(s) in the L protein selected from Y942W, Y942S, Y942Q, Y942T, Y942G, Y942A, Y942V, Y942M, Y942T, Y942L, L992K, L992A, L992Y, and L992C.

24. The method of claim 9, wherein the recombinant HPIV 1 genome or antigenome further incorporates one or more attenuating host range mutation(s).

25. The method of claim 24, wherein the one or more attenuating host range mutations comprises one or both of the attenuating host range mutation(s): (i) E119G in HPIV 1 P and R84G in HPIV 1 C, or (ii) T553A in HPIV 1 HN.

26. The method of claim 1, wherein the recombinant HPIV 1 genome or antigenome further comprises a nucleotide modification that alters one or more HPIV 1 N, P, C, C', Y1, Y2, M, F, HN and/or L genes and/or a 3' leader, 5' trailer, and/or intergenic region within the HPIV1 genome or antigenome and specifies a phenotypic change selected from a change in growth characteristics, attenuation, temperature-sensitivity, cold-adaptation, plaque size, host-range restriction, or a change in immunogenicity.

27. The method of claim 1, wherein one or more HPIV 1 gene(s) is deleted in whole or in part or expression of the gene(s) is reduced or ablated by a mutation in an RNA editing site, by a frameshift mutation, by a mutation that alters a translation start site, by introduction of one or more stop codons in an open reading frame (ORF) of the gene, or by a mutation in a transcription signal.

28. The method of claim 1, wherein the recombinant HPIV1 genome or antigenome is modified by a partial or complete deletion of one or more C, C', Y1, and/or Y2 ORF(s), or one or more nucleotide change(s) that reduces or ablates expression of said one or more C, C', Y1, and/or Y2 ORF(s).

29. The method of claim 1, wherein at least one mutation is one or more partial deletions corresponding to (i) codons 10-11 of the C ORF (ii) codons 12-13 of the C ORF (iii) codons 14-15 of the C ORF, (iv) codons 10-15 of the C ORF, and/or (v) codons 168-170 of the C ORF.

30. The method of claim 1, wherein the recombinant HPIV1 genome or antigenome is further modified to encode a non-PIV molecule selected from a cytokine, a T-helper epitope, a restriction site marker, or a protein of a microbial pathogen capable of eliciting an immune response in a mammalian host.

31. The method of claim 30, wherein the recombinant HPIV 1 genome or antigenome is modified to encode a cytokine.

32. The method of claim 1, wherein the recombinant HPIV1 genome or antigenome comprises a partial or complete HPIV 1 genome or antigenome, wherein said genome or antigenome is combined with one or more heterologous gene(s) or genome segment(s) encoding one or more antigenic determinant(s) of one or more heterologous pathogen(s) to form a chimeric HPIV 1 genome or antigenome.

33. The method of claim 32, wherein said one or more heterologous gene(s) or genome segment(s) encoding the antigenic determinants is/are added as supernumerary gene(s) or genome segment(s) adjacent to or within a noncoding region of the partial or complete HPIV 1 genome or antigenome, or wherein said one or more heterologous gene(s) or genome segment(s) encoding the antigenic determinant(s) is/are substituted for one or more counterpart gene(s) or genome segment(s) in a partial HPIV 1 genome or antigenome.

34. The method of claim 32, wherein said one or more heterologous gene(s) or genome segment(s) includes a heterologous regulatory element comprising an extragenic 3' leader or 5' trailer region, a gene-start signal, gene-end signal, editing region, intergenic region, or a 3' or 5' non-coding region.

35. The method of claim 32, wherein said one or more heterologous pathogens is one or more heterologous PIV(s) and said heterologous gene(s) or genome segment(s) encode(s) one or more PIV N, P, C, D, V, M, F, HN and/or L protein(s) or fragment(s) thereof.

36. The method of claim 32, wherein the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumoviruses, and influenza viruses.

37. The method of claim 32, wherein the partial or complete HPIV 1 genome or antigenome is combined with one or more supernumerary heterologous gene(s) or genome segment(s) to form the chimeric HPIV 1 genome or antigenome.

38. The method of claim 32, wherein said one or more heterologous gene(s) or genome segment(s) is selected from HPIV2 HN, HPIV2 F, HPIV3 HN, HPIV3 F, respiratory syncytial virus (RSV) G, RSV F, human metapneumovirus (HMPV) F, HMPV G and measles HA proteins, and antigenic domains, fragments and epitopes thereof.

39. The method of claim 32, wherein the heterologous gene or genome segment is added or substituted at a position corresponding to a wild-type gene order position of a counterpart gene or genome segment within the partial or complete HPIV 1 genome or antigenome.

40. The method of claim 32, wherein the heterologous gene or genome segment is added or substituted at a position that is more promoter-proximal or promoter-distal compared to a wild-type gene order position of a counterpart gene or genome segment within the partial or complete HPIV 1 genome or antigenome.

41. The method of claim 32, wherein the chimeric HPIV 1 genome or antigenome encodes a chimeric glycoprotein incorporating one or more heterologous antigenic domains, fragments, or epitopes of a heterologous PIV or non-PIV pathogen to form the chimeric genome or antigenome.

42. The method of claim 41, wherein the chimeric HPIV1 genome or antigenome encodes a chimeric glycoprotein incorporating one or more antigenic domains, fragments, or epitopes from a heterologous PIV to form the chimeric genome or antigenome.

43. The method of claim 41, wherein the chimeric genome or antigenome encodes a chimeric virus or chimeric glycoprotein having antigenic domains, fragments, or epitopes from two or more HPIVs.

44. The method of claim 41, wherein the heterologous genome segment encodes a glycoprotein cytoplasmic, transmembrane or ectodomain which is substituted for a corresponding glycoprotein domain in the HPIV 1 genome or antigenome.

45. The method of claim 41, wherein said one or more heterologous genome segment(s) is selected from ectodomains of HPIV2 and/or HPIV3 HN and/or F glycoproteins.

46. The method of claim 32, wherein the chimeric HPIV 1 genome or antigenome is further modified by introduction of one or more attenuating mutations identified in a mutant PIV or other mutant nonsegmented negative stranded RNA virus.

47. The method of claim 46, wherein the further modification is one or any combination of mutation(s) selected from mutations specifying amino acid substitution(s) in the L protein at a position corresponding to Tyr942, Leu992, and/or Leu1558 of wild-type (wt) HPIV 1 L, amino acid substitution in the N protein at a position corresponding to residue Val99 of wt HPIV 1 N, amino acid substitution(s) in the F protein at a position corresponding to residue Ile423 and/or Ser453 of wt HPIV 1 F, amino acid substitution in the HN protein at a position corresponding to residue Arg386 of wt HPIV 1 HN, amino acid substitution in the C protein at a position corresponding to Ser102 of wt HPIV 1 C, amino acid substitution in the M protein at a position corresponding to residue Pro 195 of wt HPIV 1 M, nucleotide substitution(s) in a 3' leader sequence of the genome or antigenome at a position corresponding to nucleotide 23 and/or nucleotide 28 of wt HPIV 1, and/or nucleotide substitution in a N gene start sequence at a position corresponding to nucleotide 62 of wt HPIV 1.

48. The method of claim 32, wherein the one or any combination of mutation(s) is selected from C:S102$T_{cp45}$, M: P195$T_{cp45}$, F: I423$V_{cp45}$, F: S453$T_{cp45}$, HN: R386$A_{cp45}$, L:Y942$H_{cp45}$, Y942F, Y942N, Y942D, Y942C, L:Y942W, L: Y942S, L: Y942Q, L: Y942G, L: Y942T, L: Y942T, L: Y942M, L: Y942L, L: Y942A, L: L992$F_{cp45}$, L: L992I, L: L992M, L: L992H, L: L992W, L: L992A, L: L992C, L: L992K, L: L992N, L: L992V, L: L992Y and L: L1558$T_{cp45}$.

49. The method of claim 46, wherein t the chimeric HPIV 1 genome or antigenome further incorporates multiple mutations selected from (i) mutations specifying amino acid substitutions in the L protein at positions corresponding to Tyr942 and Leu992 of wild-type (wt) HPIV 1 L, (ii) mutations specifying amino acid substitutions in the L protein at positions corresponding to Leu992 and Leu1558 of wild-type wt HPIV 1 L, (iii) mutations specifying amino acid substitutions in the L protein at positions corresponding to Tyr942, Leu992 and Leu1558 of wt HPIV1 L, (iv) mutations specifying amino acid substitutions in the F protein at positions corresponding to Ile423 and Ser453 of wt HPIV 1 F, and (v) mutations specifying an amino acid substitution in the N protein at a position corresponding to residue Val99 of wt HPIV 1 N, mutations in a 3' leader sequence of the genome or antigenome at positions corresponding to nucleotide 23 and nucleotide 28 of wt HPIV 1, and a nucleotide substitution in a N gene staff sequence at a position corresponding to nucleotide 62 of wt HPIV 1.

50. The method of claim 49, wherein the multiple mutations are selected from (i) 3'-N V99$A_{cp45}$, (ii) F: I423V/S453$T_{cp45}$, Y942H/L992$F_{cp45}$, (iii) L992F/L1558$I_{cp45}$, and (iv) Y942H/L992F/L 1558$I_{cp45}$.

51. The method of claim 46, wherein the chimeric HPIV 1 genome or antigenome further incorporates an attenuating mutation at an amino acid position corresponding to an amino acid position of an attenuating mutation identified in a heterologous, mutant nonsegmented negative stranded RNA virus.

52. The method of claim 51, wherein said attenuating mutation comprises an amino acid substitution of phenylalanine at position 456 of the HPIV 1 L protein.

53. The method of claim 51, wherein said attenuating mutation comprises an amino acid substitution of phenylalanine at position 170 of the HPIV 1 C protein.

54. The method of claim 51, wherein the heterologous, mutant nonsegmented negative stranded RNA virus is a bovine parainfluenza virus type 3 (BPIV3), and wherein said attenuating mutation comprises an amino acid substitution at a corresponding target position Glu1711 in the HPIV1 L protein.

55. The method of claim 46, wherein one or more attenuating mutations is one or more attenuating mutation(s) identified in mutant PIV strain, and one or more attenuating mutation(s) at an amino acid position corresponding to an amino acid position of an attenuating mutation identified in a heterologous, mutant nonsegmented negative stranded RNA virus.

56. The method of claim 55, wherein the one or more attenuating mutations is a combination of mutations selected from (i) F170$S_{MPIV\ 1}$/Y942H/L992$F_{cp45}$, or (ii) F170$S_{MPIV\ 1}$/L992F/L1558$I_{cp45}$.

57. The method of claim 32, wherein at least one attenuating mutation is stabilized by multiple nucleotide changes in a codon specifying the mutation.

58. The method of claim 57, wherein at least one stabilized mutation is one or any combination of mutation(s) in the L protein selected from Y942W, Y942S, Y942Q, Y942T, Y942G, Y942A, Y942V, Y942M, Y942T, Y942L, L992K, L992A, L992Y, and L992C.

59. The method of claim 32, wherein the chimeric HPIV 1 genome or antigenome further incorporates one or more attenuating host range mutation(s).

60. The method of claim 59, wherein the one or more attenuating host range mutations comprises one or both of the attenuating host range mutation(s): (i) E119G in HPIV 1 P and R84G in HPIV 1 C, or (ii) T553A in HPIV 1 HN.

61. The method of claim 32, wherein the chimeric HPIV 1 genome or antigenome further comprises a nucleotide modification specifying a phenotypic change selected from a change in growth characteristics, attenuation, temperature-sensitivity, cold-adaptation, plaque size, host-range restriction, or a change in immunogenicity.

62. The method of claim 61, wherein one or more HPIV 1 gene(s) is deleted in whole or in part or expression of the gene(s) is reduced or ablated by a mutation in an RNA editing site, by a frameshift mutation, by a mutation that alters a translation start site, by introduction of one or more stop codons in an open reading frame (ORF) of the gene, or by a mutation in a transcription signal.

63. The method of claim 62, wherein the chimeric HPIV 1 genome or antigenome is modified by a partial or complete deletion of one or more C, C', Y1, and/or Y2 ORF(s), or one or more nucleotide changes that reduces or ablates expression of said one or more C, C', Y1, and/or Y2 ORF(s).

64. The method of claim 63, wherein the chimeric HPIV 1 genome or antigenome is modified by one or more partial deletions corresponding to (i) codons 10-11 of the C ORF (ii) codons 12-13 of the C ORF (iii) codons 14-15 of the C ORF, (iv) codons 10-15 of the C ORF, and/or (v) codons 168-170 of the C ORF.

65. The method of claim 32, wherein the chimeric HPIV 1 genome or antigenome is further modified to encode a non-PIV molecule selected from a cytokine, a T helper epitope, a restriction site marker, or a protein of a microbial pathogen capable of eliciting an immune response in a mammalian host.

66. The method of claim 1, wherein the recombinant HPIV1 genome or antigenome further incorporates a polynucleotide insertion of between 150 nucleotides (nts) and 4,000 nucleotides in length in a non-coding region (NCR) of the genome or antigenome or as a separate gene unit (GU), said polynucleotide insertion lacking a complete open reading frame (ORF) and specifying an attenuated phenotype in said recombinant HPIV 1.

67. The method of claim 66, wherein said polynucleotide insert is introduced into the HPIV 1 genome or antigenome in a reverse, non-sense orientation whereby the insert does not encode protein.

68. The method of claim 66, wherein said polynucleotide insert is 2,000 nts or greater in length.

69. The method of claim 66, wherein said polynucleotide insert is 3,000 nts or greater in length.

70. The method of claim 66, wherein said recombinant HPIV 1 replicates efficiently in vitro and exhibits an attenuated phenotype in vivo.

71. The method of claim 66, wherein said polynucleotide insertion adds a total length of foreign sequence to the recombinant HPIV 1 genome or antigenome of 30% to 50% or greater compared to the wild-type HPIV 1 genome length of 15,600 nt.

72. The method of claim 66, wherein said polynucleotide insertion specifies an attenuation phenotype of the recombinant HPIV 1 which exhibits at least a 10-to 100-fold decrease in replication in the upper and/or lower respiratory tract.

73. An infectious, self-replicating, recombinant human parainfluenza virus type 1 (HPIV1) that is a complete virus or a sub-viral particle comprising a PIV major nucleocapsid (N) protein, a PIV nucleocapsid phosphoprotein (P), a PIV large polymerase protein (L), and a partial or complete, recombinant HPIV 1 genome or antigenome, said recombinant HPIV1 genome or antigenome including at least one mutation selected from the group consisting of:

- a mutation in the L protein Y942 to an amino acid selected from the group consisting of F, C, N, D, W, S, Q, G, T, V, M, L and A;
- a mutation in the L protein L992 to an amino acid selected from the group consisting of H, I, M, W, A, C, K, N, V and Y;
- a mutation in the L protein of E1711 to another amino acid; a mutation in the HN protein T553 to another amino acid;
- a mutation in the C protein R84 to another amino acid;
- a mutation in the C protein R84 to another amino acid and mutation of the P protein E119 to another amino acid;
- a mutation in the P protein E119 to another amino acid;
- a deletion of codons 10-15 of the C protein and codons 13-19 of the P protein;
- a deletion of codons 10-11 of the C protein and codons 13-15 of the P protein;
- a deletion of codons 12-13 of the C protein and codon 15-17 of the P protein;
- a deletion of codons 14-15 of the C protein and codons 17-19 of the P protein; and
- a deletion of codons 168-170 of the C protein and codons 172-173 of the P protein.

74. The recombinant HPIV 1 of claim 73, wherein one or more of the PIV N, P and/or L proteins are of a heterologous PIV.

75. The recombinant HPIV 1 of claim 73, wherein at least one of the N, P and L proteins is of a different HPIV or a bovine PIV (BPIV).

76. The recombinant HPIV 1 of claim 73, wherein one or more of said N, P and L proteins is/are of HPIV3.

77. The recombinant HPIV 1 of claim 73, wherein the infectious HPIV 1 particle is a complete virus.

78. The recombinant HPIV 1 of claim 73, wherein the recombinant HPIV 1 genome or antigenome further incorporates a recombinantly-introduced restriction site marker or transcriptionally silent point mutation.

79. The recombinant HPIV 1 of claim 73, wherein the recombinant HPIV 1 genome or antigenome further incorporates one or more recombinantly-introduced attenuating mutations.

80. The recombinant HPIV 1 of claim 73, wherein the recombinant HPIV 1 genome or antigenome further incorporates one or more recombinantly introduced, temperature sensitive (ts) attenuating mutations.

81. The recombinant HPIV 1 of claim 73, wherein the recombinant HPIV 1 genome or antigenome further incorporates one or more attenuating mutation(s) identified in a mutant PIV strain or other mutant nonsegmented negative stranded RNA virus.

82. The recombinant HPIV 1 of claim 73, wherein the recombinant HPIV 1 genome or antigenome further incorporates two or more recombinantly-introduced, temperature sensitive (ts) attenuating mutations.

83. The recombinant HPIV 1 of claim 73, wherein the recombinant HPIV 1 genome or antigenome further incorporates two or more attenuating mutation(s) identified in a mutant PIV strain or other mutant nonsegmented negative stranded RNA virus.

84. The recombinant HPIV 1 of claim 73, wherein the recombinant HPIV 1 genome or antigenome further incorporates one or any combination of mutation(s) selected from mutations specifying amino acid substitution(s) in the L protein at a position corresponding to Tyr942, Leu992, and/or Leu1558 of wild-type (wt) HPIV1 L, amino acid substitution in the N protein at a position corresponding to residue Val199 of wt HPIV 1 N, amino acid substitution(s) in the F protein at a position corresponding to residue Ile423 and/or Ser453 of wt HPIV 1 F, amino acid substitution in the HN protein at a position corresponding to residue Arg386 of wt HPIV 1 HN, amino acid substitution in the C protein at a position corresponding to Ser102 of wt HPIV 1 C, amino acid substitution in the M protein at a position corresponding to residue Pro195 of wt HPIV 1 M, nucleotide substitution(s) in a 3' leader sequence of the genome or antigenome at a position corresponding to nucleotide 23 and/or nucleotide 28 of wt HPIV1, and/or nucleotide substitution in a N gene start sequence at a position corresponding to nucleotide 62 of wt HPIV 1.

85. The recombinant HPIV 1 of claim 84, wherein the one or any combination of mutation(s) is selected from C:S102$T_{cp45}$, M: P195$T_{cp45}$, F: I423$V_{cp45}$, F: S453$T_{cp45}$, HN: R386$A_{cp45}$, L: Y942$H_{cp45}$, L: Y942F, L: Y942N, L: Y942D, L: Y942C, L:Y942W, L: Y942S, L: Y942Q, L: Y942G, L: Y942T, L: Y942T, L: Y942M, L: Y942L, L: Y942A, L: L992$F_{cp45}$, L: L992I, L: L992M, L: L992H, L: L992W, L: L992A, L: L992C, L: L992K, L: L992N, L: L992V, L: L992Y and L: L1558$I_{cp45}$.

86. The recombinant HPIV 1 of claim 73, wherein the recombinant HPIV 1 genome or antigenome further incorporates multiple mutations selected from (i) mutations specifying amino acid substitutions in the L protein at positions corresponding to Tyr942 and Leu992 of wild-type (wt) HPIV 1 L, (ii) mutations specifying amino acid substitutions in the L protein at positions corresponding to Leu992 and Leu1558 of wild-type wt HPIV 1 L, (iii) mutations specifying amino acid substitutions in the L protein at positions corresponding to Tyr942, Leu992 and Leu 1558 of wt HPIV 1 L, (iv) mutations specifying amino acid substitutions in the F protein at positions corresponding to Ile423 and Ser453 of wt HPIV 1 F, and (v) mutations specifying an amino acid substitution in the N protein at a position corresponding to residue Val99 of wt HPIV 1 N, mutations in a 3' leader sequence of the genome or antigenome at positions corresponding to nucleotide 23 and nucleotide 28 of wt HPIV1, and a nucleotide substitution in a N gene start sequence at a position corresponding to nucleotide 62 of wt HPIV 1.

87. The recombinant HPIV 1 of claim 73, wherein the recombinant HPIV 1 genome or antigenome multiple mutations are selected from (i) 3'-N $V99A_{cp45}$, (ii) F: I423 $V/S453T_{cp45}$, $Y942H/L992F_{cp45}$, (iii) L992F/L $1558I_{cp45}$, and (iv) $Y942H/L992F/L1558I_{cp45}$.

88. The recombinant HPIV 1 of claim 73, wherein the recombinant HPIV 1 genome or antigenome further incorporates one or more attenuating mutations from a different PIV or a non-PIV nonsegmented negative stranded RNA virus.

89. The recombinant HPIV 1 of claim 73, wherein the recombinant HPIV 1 genome or antigenome further incorporates an attenuating mutation at an amino acid position corresponding to an amino acid position of an attenuating mutation identified in a heterologous, mutant nonsegmented negative stranded RNA virus.

90. The recombinant HPIV 1 of claim 89, wherein said attenuating mutation comprises an amino acid substitution of phenylalanine at position 456 of the HPIV 1 L protein.

91. The recombinant HPIV 1 of claim 89, wherein said attenuating mutation comprises an amino acid substitution of phenylalanine at position 170 of the HPIV 1 C protein.

92. The recombinant HPIV 1 of claim 89, wherein the heterologous, mutant nonsegmented negative stranded RNA virus is a bovine parainfluenza virus type 3 (BPIV3), and wherein said attenuating mutation comprises an amino acid substitution at a corresponding target position Glu1711 in the HPIV 1 L protein.

93. The recombinant HPIV 1 of claim 73, wherein the recombinant HPIV 1 genome or antigenome further incorporates one or more attenuating mutation(s) identified in a mutant PIV strain, and one or more attenuating mutation(s) at an amino acid position corresponding to an amino acid position of an attenuating mutation identified in a heterologous, mutant nonsegmented negative stranded RNA virus.

94. The recombinant HPIV 1 of claim 93, wherein the one or more attenuating mutations is a combination of mutations selected from (i) $F107S_{MPIV\ 1}/Y942H/L992F_{cp45}$, or (ii) $F170S_{MPIV\ 1}/L992F/L1558I_{cp45}$.

95. The recombinant HPIV 1 of claim 73, wherein the recombinant HPIV 1 genome or antigenome further incorporates at least one attenuating mutation stabilized by multiple nucleotide changes in a codon specifying the mutation.

96. The recombinant HPIV 1 of claim 95, wherein the at least one stabilized mutation is one or any combination of mutation(s) in the L protein selected from Y942W, Y942S, Y942Q, Y942T, Y942G, Y942A, Y942V, Y942M, Y942T, Y942L, L992K, L992A, L992Y, and L992C.

97. The recombinant HPIV 1 of claim 73, wherein the recombinant HPIV 1 genome or antigenome further incorporates one or more attenuating host range mutation(s).

98. The recombinant HPIV 1 of claim 73, wherein the recombinant HPIV 1 genome or antigenome further comprises one or both of the attenuating host range mutation(s): (i) E119G in HPIV1 P and R84G in HPIV 1 C, or (ii) T553A in HPIV 1 HN.

99. The recombinant HPIV 1 of claim 73, wherein the recombinant HPIV 1 genome or antigenome further comprises a nucleotide modification that alters one or more HPIV 1 N, P, C, C', Y1, Y2, M, F, HN and/or L genes and/or a 3' leader, 5' trailer, and/or intergenic region within the HPIV 1 genome or antigenome and specifies a phenotypic change selected from a change in growth characteristics, attenuation, temperature-sensitivity, coldadaptation, plaque size, host-range restriction, or a change in immunogenicity.

100. The recombinant HPIV 1 of claim 73, wherein one or more HPIV 1 gene(s) is deleted in whole or in part or expression of the gene(s) is reduced or ablated by a mutation in an RNA editing site, by a frameshift mutation, by a mutation that alters a translation start site, by introduction of one or more stop codons in an open reading frame (ORF) of the gene, or by a mutation in a transcription signal.

101. The recombinant HPIV 1 of claim 73, wherein the recombinant HPIV 1 genome or antigenome is modified by a partial or complete deletion of one or more C, C', Y1, and/or Y2 ORF(s), or one or more nucleotide change(s) that reduces or ablates expression of said one or more C, C', Y1, and/or Y2 ORF(s).

102. The recombinant HPIV 1 of claim 73, wherein the recombinant HPIV 1 genome or antigenome is further modified to encode a non-PIV molecule selected from a cytokine, a T-helper epitope, a restriction site marker, or a protein of a microbial pathogen capable of eliciting an immune response in a mammalian host.

103. The recombinant HPIV 1 of claim 102, wherein the recombinant HPIV 1 genome or antigenome is modified to encode a cytokine.

104. The recombinant HPIV 1 of claim 73, wherein the recombinant HPIV 1 genome or antigenome comprises a partial or complete HPIV 1 genome or antigenome, wherein said genome or antigenome is combined with one or more heterologous gene(s) or genome segment(s) encoding one or more antigenic determinant(s) of one or more heterologous pathogen(s) to form a chimeric HPIV 1 genome or antigenome.

105. The recombinant HPIV 1 of claim 104, wherein said one or more heterologous gene(s) or genome segment(s) encoding the antigenic determinant(s) is/are added as supernumerary gene(s) or genome segment(s) adjacent to or within a noncoding region of the partial or complete HPIV 1 genome or antigenome, or wherein said one or more heterologous gene(s) or genome segment(s) encoding the antigenic determinant(s) is/are substituted for one or more counterpart gene(s) or genome segment(s) in a partial HPIV 1 genome or antigenome.

106. The recombinant HPIV 1 of claim 104, wherein said one or more heterologous gene(s) or genome segment(s) includes a heterologous regulatory element comprising an extragenic 3' leader or 5' trailer region, a gene-start signal, gene-end signal, editing region, intergenic region, or a 3' or 5' non-coding region.

107. The recombinant HPIV 1 of claim 104, wherein said one or more heterologous pathogens is one or more heterologous PIV(s) and said heterologous gene(s) or genome segment(s) encode(s) one or more PIV N, P, C, D, V, M, F, HN and/or L protein(s) or fragment(s) thereof.

108. The recombinant HPIV 1 of claim 104, wherein the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumoviruses, and influenza viruses.

109. The recombinant HPIV 1 of claim 104, wherein the partial or complete HPIV 1 genome or antigenome is combined with one or more supernumerary heterologous gene(s) or genome segment(s) to form the chimeric HPIV 1 genome or antigenome.

110. The recombinant HPIV 1 of claim 104, wherein said one or more heterologous gene(s) or genome segment(s) is selected from HPIV2 HN, HPIV2 F, HPIV3 HN, HPIV3 F, respiratory syncytial virus (RSV) G, RSV F, human metapneumovirus F, human metapneumovirus G and measles HA proteins, and antigenic domains, fragments and epitopes thereof.

111. The recombinant HPIV 1 of claim 104, wherein the heterologous gene or genome segment is added or substituted at a position corresponding to a wild-type gene order position of a counterpart gene or genome segment within the partial or complete HPIV 1 genome or antigenome.

112. The recombinant HPIV 1 of claim 104, wherein the heterologous gene or genome segment is added or substituted at a position that is more promoter-proximal or promoter-distal compared to a wild-type gene order position of a counterpart gene or genome segment within the partial or complete HPIV 1 genome or antigenome.

113. The recombinant HPIV 1 of claim 104, wherein the HPIV 1 genome or antigenome is modified to encode a chimeric glycoprotein incorporating one or more heterologous antigenic domains, fragments, or epitopes of a heterologous PIV or non-PIV pathogen to form the chimeric genome or antigenome.

114. The recombinant HPIV 1 of claim 113, wherein the HPIV 1 genome or antigenome is modified to encode a chimeric glycoprotein incorporating one or more antigenic domains, fragments, or epitopes from a second, antigenically distinct PIV to form the chimeric genome or antigenome.

115. The recombinant HPIV 1 of claim 113, wherein the chimeric genome or antigenome encodes a chimeric virus or chimeric glycoprotein having antigenic domains, fragments, or epitopes from two or more HPIVs.

116. The recombinant HPIV 1 of claim 113, wherein the heterologous genome segment encodes a glycoprotein cytoplasmic, transmembrane or ectodomain which is substituted for a corresponding glycoprotein domain in the HPIV 1 genome or antigenome.

117. The recombinant HPIV 1 of claim 113, wherein one or more heterologous genome segment(s) of a second, antigenically distinct HPIV encoding said one or more antigenic domains, fragments, or epitopes is/are substituted within a HPIV 1 genome or antigenome to encode said chimeric glycoprotein.

118. The recombinant HPIV 1 of claim 113, wherein said one or more heterologous genome segment(s) is selected from ectodomains of HPIV 2 and/or HPIV 3 HN and/or F glycoproteins.

119. The recombinant HPIV 1 of claim 104, wherein the chimeric HPIV 1 genome or antigenome is further modified by introduction of one or more additional attenuating mutations identified in a mutant PIV or other mutant nonsegmented negative stranded RNA virus.

120. The recombinant HPIV 1 of claim 119, wherein the additional mutation is one or any combination of mutation(s) selected from mutations specifying amino acid substitution(s) in the L protein at a position corresponding to Tyr942, Leu992, and/or Leu1558 of wild-type (wt) HPIV 1 L, amino acid substitution in the N protein at a position corresponding to residue Val99 of wt HPIV 1 N, amino acid substitution(s) in the F protein at a position corresponding to residue Ile423 and/or Ser453 of wt HPIV 1 F, amino acid substitution in the HN protein at a position corresponding to residue Arg3 86 of wt HPIV 1 HN, amino acid substitution in the C protein at a position corresponding to Ser102 of wt HPIV 1 C, amino acid substitution in the M protein at a position corresponding to residue Pro 195 of wt HPIV1 M, nucleotide substitution(s) in a 3' leader sequence of the genome or antigenome at a position corresponding to nucleotide 23 and/or nucleotide 28 of wt HPIV1, and/or nucleotide substitution in a N gene start sequence at a position corresponding to nucleotide 62 of wt HPIV 1.

121. The recombinant HPIV1 of claim 120, wherein the additional mutation is one or any combination of mutation(s) selected from C:S102$T_{cp45}$, M: P195$T_{cp45}$, F: I423$V_{cp45}$, F: S453$T_{cp45}$, HN: R386$A_{cp45}$, L: Y942$H_{cp45}$, L: Y942F, L: Y942N, L: Y942D, L: Y942C, L:Y942W, L: Y942S, L: Y942Q, L: Y942G, L: Y942T, L: Y942T, L: Y942M, L: Y942L, L: Y942A, L: L992$F_{cp45}$, L: L992I, L: L992M, L: L992H, L: L992W, L: L992A, L: L992C, L: L992K, L: L992N, L: L992V, L: L992Y and L: L1558$I_{cp45}$.

122. The recombinant HPIV1 of claim 120, wherein additional mutations are multiple mutations selected from (i) mutations specifying amino acid substitutions in the L protein at positions corresponding to Tyr942 and Leu992 of wild-type (wt) HPIV 1 L, (ii) mutations specifying amino acid substitutions in the L protein at positions corresponding to Leu992 and Leu1558 of wild-type wt HPIV1 L, (iii) mutations specifying amino acid substitutions in the L protein at positions corresponding to Tyr942, Leu992 and Leu1558 of wt HPIV1 L, (iv) mutations specifying amino acid substitutions in the F protein at positions corresponding to Ile423 and Ser453 of wt HPIV1 F, and (v) mutations specifying an amino acid substitution in the N protein at a position corresponding to residue Val99 of wt HPIV 1 N, mutations in a 3' leader sequence of the genome or antigenome at positions corresponding to nucleotide 23 and nucleotide 28 of wt HPIV 1, and a nucleotide substitution in a N gene start sequence at a position corresponding to nucleotide 62 of wt HPIV 1.

123. The recombinant HPIV1 of claim 120, wherein the polynucleotide molecule encoding the chimeric HPIV1 genome or antigenome additional mutations are multiple mutations selected from (i) 3'-N V99$A_{cp45}$, (ii) F: I423V/S453$T_{cp45}$, Y942H/L992$F_{cp45}$, (iii) L992F/L1558$I_{cp45}$, and (iv) Y942H/L992F/L1558$I_{cp45}$.

124. The recombinant HPIV 1 of claim 119, wherein the one or more additional mutation is an attenuating mutation at an amino acid position corresponding to an amino acid position of an attenuating mutation identified in a heterologous, mutant nonsegmented negative stranded RNA virus.

125. The recombinant HPIV 1 of claim 124, wherein said attenuating mutation comprises an amino acid substitution of phenylalanine at position 456 of the HPIV 1 L protein.

126. The recombinant HPIV 1 of claim 124, wherein said attenuating mutation comprises an amino acid substitution of phenylalanine at position 170 of the HPIV 1 C protein.

127. The recombinant HPIV1 of claim 124, wherein the heterologous, mutant nonsegmented negative stranded RNA virus is a bovine parainfluenza virus type 3 (BPIV3), and wherein said attenuating mutation comprises an amino acid substitution at a corresponding target position Glu1711 in the HPIV 1 L protein.

128. The recombinant HPIV 1 of claim 119, wherein one or more attenuating mutations is one or more attenuating mutation(s) identified in mutant PIV strain, and one or more attenuating mutation(s) at an amino acid position corresponding to an amino acid position of an attenuating mutation identified in a heterologous, mutant nonsegmented negative stranded RNA virus.

129. The recombinant HPIV 1 of claim 128, wherein the chimeric HPIV 1 genome or antigenome includes the combination of mutations (i) F170S$_{MPIV\ 1}$/Y942H/L992F$_{cp45}$, or (ii) F 170S$_{MPIV\ 1}$ /L992F/L1558I$_{cp45}$.

130. The recombinant HPIV 1 of claim 104, wherein s at least one attenuating mutation is stabilized by multiple nucleotide changes in a codon specifying the mutation.

131. The recombinant HPIV 1 of claim 130, wherein the stabilized mutation is one or any combination of mutation(s) in the L protein selected from Y942W, Y942S, Y942Q, Y942T, Y942G, Y942A, Y942V, Y942M, Y942T, Y942L, L992K, L992A, L992Y, and L992C.

132. The recombinant HPIV 1 of claim 104, wherein the chimeric HPIV 1 genome or antigenome further incorporates one or more attenuating host range mutation(s).

133. The recombinant HPIV 1 of claim 104, wherein the chimeric HPIV 1 genome or antigenome further comprises one or both of the attenuating host range mutation(s): (i) E119G in HPIV1 P and R84G in HPIV 1 C, or (ii) T553A in HPIV 1 HN.

134. The recombinant HPIV 1 of claim 104, wherein the chimeric HPIV 1 genome or antigenome further comprises a nucleotide modification specifying a phenotypic change selected from a change in growth characteristics, attenuation, temperature-sensitivity, cold-adaptation, plaque size, host-range restriction, or a change in immunogenicity.

135. The recombinant HPIV 1 of claim 134, wherein one or more HPIV 1 gene(s) is deleted in whole or in part or expression of the gene(s) is reduced or ablated by a mutation in an RNA editing site, by a frameshift mutation, by a mutation that alters a translation start site, by introduction of one or more stop codons in an open reading frame (ORF) of the gene, or by a mutation in a transcription signal.

136. The recombinant HPIV 1 of claim 135, wherein the chimeric HPIV 1 genome or antigenome is modified by a partial or complete deletion of one or more C, C', Y1, and/or Y2 ORF(s), or one or more nucleotide change(s) that reduces or ablates expression of said one or more C, C', Y1, and/or Y2 ORF(s).

137. The recombinant HPIV 1 of claim 136, wherein the chimeric HPIV 1 genome or antigenome is modified by one or more partial deletions corresponding to (i) codons 10-11 of the C ORF (ii) codons 12-13 of the C ORF (iii) codons 14-15 of the C ORF, (iv) codons 10-15 of the C ORF, and/or (v) codons 168-170 of the C ORF.

138. The recombinant HPIV1 of claim 104, wherein the chimeric HPIV 1 genome or antigenome is further modified to encode a non-PIV molecule selected from a cytokine, a T-helper epitope, a restriction site marker, or a protein of a microbial pathogen capable of eliciting an immune response in a mammalian host.

139. The recombinant HPIV 1 of claim 73, wherein the recombinant HPIV 1 genome or antigenome further incorporates a polynucleotide insertion of between 150 nucleotides (nts) and 4,000 nucleotides in length in a non-coding region (NCR) of the genome or antigenome or as a separate gene unit (GU), said polynucleotide insertion lacking a complete open reading frame (ORF) and specifying an attenuated phenotype in said recombinant HPIV 1.

140. The recombinant HPIV 1 of claim 139, wherein said polynucleotide insert is introduced into the HPIV 1 genome or antigenome in a reverse, non-sense orientation whereby the insert does not encode protein.

141. The recombinant HPIV 1 of claim 139, wherein said polynucleotide insert is 2,000 nts or greater in length.

142. The recombinant HPIV 1 of claim 139, wherein said polynucleotide insert is 3,000 nts or greater in length.

143. The recombinant HPIV 1 of claim 139, wherein said recombinant HPIV 1 replicates efficiently in vitro and exhibits an attenuated phenotype in vivo.

144. The recombinant HPIV 1 of claim 139, wherein said polynucleotide insertion adds a total length of foreign sequence to the recombinant HPIV 1 genome or antigenome of 30% to 50% or greater compared to the wild-type HPIV 1 genome length of 15,600 nt.

145. The recombinant HPIV1 of claim 138, wherein said polynucleotide insertion specifies an attenuation phenotype of the recombinant HPIV 1 which exhibits at least a 10-to 100-fold decrease in replication in the upper and/or lower respiratory tract.

146. An immunogenic composition comprising an immunogenically effective amount of an infectious, self-replicating, recombinant human parainfluenza virus type 1 (HPIV 1) in a pharmaceutically acceptable carrier, said HPIV 1 comprising a recombinant HPIV 1 genome or antigenome, a PIV N protein, a PIV P protein, and a PIV L protein, said recombinant HPIV1 genome or antigenome including at least one mutation selected from the group consisting of:

a mutation in the L protein Y942 to an amino acid selected from the group consisting Of F, C, N, D, W, S, Q, G, 1, V, M, L and A;

a mutation in the L protein L992 to an amino acid selected from the group consisting of H, I, M, W, A, C, K, N, V and Y;

a mutation in the L protein of E1711 to another amino acid; a mutation in the HN protein T553 to another amino acid;

a mutation in the C protein R84 to another amino acid;

a mutation in the C protein R84 to another amino acid and mutation of the P protein E119 to another amino acid;

a mutation in the P protein E119 to another amino acid;

a deletion of codons 10-15 of the C protein and codons 13-19 of the P protein;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

147. The immunogenic composition of claim 146, wherein one or more of the PIV N, P, and/or L proteinsis of a heterologous PIV.

148. The immunogenic composition of claim 146, wherein the recombinant HPIV 1 is a complete virus.

149. The immunogenic composition of claim 146, wherein the recombinant HPIV 1 genome or antigenome further incorporates one or more recombinantly-introduced attenuating mutations.

150. The immunogenic composition of claim 146, wherein the recombinant HPIV 1 genome or antigenome further incorporates one or more recombinantly introduced, temperature sensitive (ts) attenuating mutations.

151. The immunogenic composition of claim 146, wherein the recombinant HPIV 1 genome or antigenome further incorporates one or more attenuating mutation(s) identified in a mutant PIV strain or other mutant nonsegmented negative stranded RNA virus.

152. The immunogenic composition of claim 151, wherein the one or more attenuating mutations is one or any combination of mutation(s) selected from mutations specifying amino acid substitution(s) in the L protein at a position corresponding to Tyr942, Leu992, and/or Leu1558 of wild-type (wt) HPIV1 L, amino acid substitution in the N protein at a position corresponding to residue Val99 of wt HPIV 1 N, amino acid substitution(s) in the F protein at a position corresponding to residue Ile423 and/or Ser453 of wt HPIV1 F, amino acid substitution in the HN protein at a position corresponding to residue Arg386 of wt HPIV 1 FIN, amino acid substitution in the C protein at a position corresponding to Ser102 of wt HPIV1 C, amino acid substitution in the M protein at a position corresponding to residue Pro 195 of wt HPIV 1 M, nucleotide substitution(s) in a 3' leader sequence of the genome or antigenome at a position corresponding to nucleotide 23 and/or nucleotide 28 of wt HPIV 1, and/or nucleotide substitution in a N gene start sequence at a position corresponding to nucleotide 62 of wt HPIV 1.

153. The immunogenic composition of claim 152, wherein the one or more attenuating mutations is one or any combination of mutation(s) selected from C:S102$T_{cp45}$, M: P195$T_{cp45}$, F: I423$V_{cp45}$, F: S453$T_{cp45}$, FN: R386$A_{cp45}$, L: Y942$H_{cp45}$, L: Y942F, L: Y942N, L: Y942D, L: Y942C, L: Y942W, L: Y942S, L: Y942Q, L:Y942G, L: Y942T, L: Y942V, L: Y942M, L: Y942L, L: Y942A, L: L992$F_{cp45}$, L: L992I, L: L992M, L: L992H, L: L992W, L: L992A, L: L992C, L: L992K, L: L992N, L: L992V, L: L992Y and L: L1558$I_{cp45}$.

154. The immunogenic composition of claim 146, wherein the recombinant HPIV 1, genome or antigenome further incorporates multiple mutations selected from (i) mutations specifying amino acid substitutions in the L protein at positions corresponding to Tyr942 and Leu992 of wild-type (wt) HPIV 1 L, (ii) mutations specifying amino acid substitutions in the L protein at positions corresponding to Leu992 and Leu1558 of wild-type wt HPIV 1 L, (iii) mutations specifying amino acid substitutions in the L protein at positions corresponding to Tyr942, Leu992 and Leu1558 of wt HPIV1 L, (iv) mutations specifying amino acid substitutions in the F protein at positions corresponding to Ile423 and Ser453 of wt HPIV 1 F, and (v) mutations specifying an amino acid substitution in the N protein at a position corresponding to residue Val99 of wt HPIV 1 N, mutations in a 3' leader sequence of the genome or antigenome at positions corresponding to nucleotide 23 and nucleotide 28 of wt HPIV 1, and a nucleotide substitution in a N gene start sequence at a position corresponding to nucleotide 62 of wt HPIV 1.

155. The immunogenic composition of claim 154, wherein the multiple mutations are selected from (i) 3'-N V99$A_{cp45}$, (ii) F: I423V/S453$T_{cp45}$, L: Y942H/L992$F_{cp45}$, (iii) L992F/L1558$I_{cp45}$, or (iv) L: Y942H/L992F/L 1558$I_{cp45}$.

156. The immunogenic composition of claim 151, wherein the recombinant HPIV 1 genome or antigenome further incorporates one or more attenuating mutations from a different PIV or a non-PIV nonsegmented negative stranded RNA virus.

157. The immunogenic composition of claim 156, wherein one or more attenuating mutations is an attenuating mutation at an amino acid position corresponding to an amino acid position of an attenuating mutation identified in a heterologous, mutant nonsegmented negative stranded RNA virus.

158. The immunogenic composition of claim 157, wherein said attenuating mutation comprises an amino acid substitution of phenylalanine at position 456 of the HPIV 1 L protein.

159. The immunogenic composition of claim 157, wherein said attenuating mutation comprises an amino acid substitution of phenylalanine at position 170 of the HPIV 1 C protein.

160. The immunogenic composition of claim 157, wherein the heterologous, mutant nonsegmented negative stranded RNA virus is a bovine parainfluenza virus type 3 (BPIV3), and wherein said attenuating mutation comprises an amino acid substitution at a corresponding target position Glu1711 in the HPIV1 L protein.

161. The immunogenic composition of claim 151, wherein one or more attenuating mutations is one or more attenuating mutation(s) identified in a mutant PIV strain, and one or more attenuating mutation(s) at an amino acid position corresponding to an amino acid position of an attenuating mutation identified in a heterologous, mutant nonsegmented negative stranded RNA virus.

162. The immunogenic composition of claim 161, wherein the one or more attenuating mutations is a combination of mutations (i) F170$S_{MPIV\ 1}$/Y942H/L992$F_{cp45}$, or (ii) F170$S_{MPIV\ 1}$/L992F/L 1558$I_{cp45}$.

163. The immunogenic composition of claim 146, wherein at least one attenuating mutation is stabilized by multiple nucleotide changes in a codon specifying the mutation.

164. The immunogenic composition of claim 163, wherein the at least one stabilized mutation is one or any combination of mutation(s) selected from Y942W, Y942S, Y942Q, Y942T, Y942G, Y942A , Y942V, Y942M, Y942T, Y942L, L992K, L992A, L992Y, and L992C.

165. The immunogenic composition of claim 146, wherein the recombinant HPIV 1 genome or antigenome further incorporates one or more attenuating host range mutation(s).

166. The immunogenic composition of claim 146, wherein the recombinant HPIV 1 genome or antigenome further comprises one or both of the attenuating host range mutation(s): (i) E119G in HPIV1 P and R84G in HPIV 1 C, or (ii) T553A in HPIV 1 HN.

167. The immunogenic composition of claim 146, wherein the recombinant HPIV 1 genome or antigenome further comprises a nucleotide modification that alters one or more HPIV1 N, P, C, C', Y1, Y2, M, F, HN and/or L genes and/or a 3' leader, 5' trailer, and/or intergenic region within the HPIV 1 genome or antigenome and specifies a phenotypic change selected from a change in growth characteristics, attenuation, temperature-sensitivity, cold-adaptation, plaque size, host-range restriction, or a change in immunogenicity.

168. The immunogenic composition of claim 146, wherein one or more HPIV 1 gene(s) is deleted in whole or in part or expression of the gene(s) is reduced or ablated by a mutation in an RNA editing site, by a frameshift mutation, by a mutation that alters a translation start site, by introduction of one or more stop codons in an open reading frame (ORF) of the gene, or by a mutation in a transcription signal.

169. The immunogenic composition of claim 168, wherein the recombinant HPIV1 genome or antigenome is modified by a partial or complete deletion of one or more C, C', Y1, and/or Y2 ORF(s), or one or more nucleotide changes that reduces or ablates expression of said one or more C, C', Y1, and/or Y2 ORF(s).

170. The immunogenic composition of claim 169, wherein the recombinant HPIV 1 genome or antigenome is modified by one or more partial deletions corresponding to (i) codons 10-11 of the C ORF (ii) codons 12-13 of the C ORF (iii) codons 14-15 of the C ORF, (iv) codons 10-15 of the C ORF, and/or (v) codons 168-170 of the C ORF.

171. The immunogenic composition of claim 146, wherein the recombinant HPIV 1 genome or antigenome is further modified to encode a non-PIV molecule selected from a cytokine, a T-helper epitope, a restriction site marker, or a protein of a microbial pathogen capable of eliciting an immune response in a mammalian host.

172. The immunogenic composition of claim 171, wherein the recombinant HPIV 1 genome or antigenome is modified to encode a cytokine.

173. The immunogenic composition of claim 146, wherein the recombinant HPIV 1 genome or antigenome comprises a partial or complete HPIV 1 genome or antigenome, wherein said genome or antigenome is combined with one or more heterologous gene(s) or genome segment(s) encoding one or more antigenic determinant(s) of one or more heterologous pathogens) to form a chimeric HPIV 1 genome or antigenome.

174. The immunogenic composition of claim 173, wherein said one or more heterologous gene(s) or genome segment(s) encoding the antigenic determinant(s) is/are added as supernumerary gene(s) or genome segment(s) adjacent to or within a noncoding region of the partial or complete HPIV1 genome or antigenome, or wherein said one or more heterologous gene(s) or genome segment(s) encoding the antigenic determinant(s) is/are substituted for one or more counterpart gene(s) or genome segment(s) in a partial HPIV 1 genome or antigenome.

175. The immunogenic composition of claim 173, wherein said one or more heterologous gene(s) or genome segment(s) includes a heterologous regulatory elements comprising an extragenic 3' leader or 5' trailer region, a gene-staff signal, gene-end signal, editing region, intergenic region, or a 3' or 5' non-coding region.

176. The immunogenic composition of claim 173, wherein said one or more heterologous pathogens is one or more heterologous PIV(s) and said heterologous gene(s) or genome segment(s) encode(s) one or more PIV N, P, C, D, V, M, F, HN and/or L protein(s) or fragment(s) thereof.

177. The immunogenic composition of claim 173, wherein the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumoviruses, and influenza viruses.

178. The immunogenic composition of claim 173, wherein the partial or complete HPIV 1 genome or antigenome is combined with one or more supernumerary heterologous gene(s) or genome segment(s) to form the chimeric HPIV 1 genome or antigenome.

179. The immunogenic composition of claim 173, wherein said one or more heterologous gene(s) or genome segment(s) is selected from HPIV2 HN, HPIV2 F, HPIV3 HN, HPIV3 F, respiratory syncytial virus (RSV) G, RSV F protein, human metapneumovirus (HMPV) G, HMPV F and measles HA proteins, and antigenic domains, fragments and epitopes thereof.

180. The immunogenic composition of claim 173, wherein the heterologous gene or genome segment is added or substituted at a position corresponding to a wild-type gene order position of a counterpart gene or genome segment within the partial or complete HPIV 1 genome or antigenome.

181. The immunogenic composition of claim 173, wherein the heterologous gene or genome segment is added or substituted at a position that is more promoter-proximal or promoter-distal compared to a wild-type gene order position of a counterpart gene or genome segment within the partial or complete HPIV 1 genome or antigenome.

182. The immunogenic composition of claim 173, wherein the chimeric HPIV1 genome or antigenome encodes a chimeric glycoprotein incorporating one or more heterologous antigenic domains, fragments, or epitopes of a heterologous PIV or non-PIV pathogen to form the chimeric genome or antigenome.

183. The immunogenic composition of claim 182, wherein the chimeric HPIV 1 genome or antigenome encodes a chimeric glycoprotein incorporating one or more antigenic domains, fragments, or epitopes from a second, antigenically distinct PIV to form the chimeric genome or antigenome.

184. The immunogenic composition of claim 173, wherein the chimeric genome or antigenome encodes a chimeric virus or chimeric glycoprotein having antigenic domains, fragments, or epitopes from two or more HPIVs.

185. The immunogenic composition of claim 182, wherein the heterologous genome segment encodes a glycoprotein cytoplasmic, transmembrane or ectodomain which is substituted for a corresponding glycoprotein domain in the HPIV1 genome or antigenome.

186. The immunogenic composition of claim 182, wherein one or more heterologous genome segment(s) of a second, antigenically distinct HPIV encoding said one or more antigenic domains, fragments, or epitopes is/are substituted within a HPIV 1 genome or antigenome to encode said chimeric glycoprotein.

187. The immunogenic composition of claim 182, wherein said one or more heterologous genome segment(s) is selected from ectodomains of HPIV2 and/or HPIV3 HN and/or F glycoproteins.

188. The immunogenic composition of claim 173, wherein the chimeric HPIV 1 genome or antigenome is further modified by introduction of one or more attenuating mutations identified in a mutant PIV or other mutant nonsegmented negative stranded RNA virus.

189. The immunogenic composition of claim 188, wherein one or more attenuating mutations is one or any combination of mutation(s) selected from mutations specifying amino acid substitution(s) in the L protein at a position corresponding to Tyr942, Leu992, and/or Leu1558 of wild-type (wt) HPIV1 L, amino acid substitution in the N protein at a position corresponding to residue Val99 of wt HPIV 1 N, amino acid substitution(s) in the F protein at a position corresponding to residue Ile423 and/or Ser453 of wt HPIV 1 F, amino acid substitution in the HN protein at a position corresponding to residue Arg386 of wt HPIV 1 HN, amino acid substitution in the C protein at a position corresponding to Ser102 of wt HPIV 1 C, amino acid substitution in the M protein at a position corresponding to residue Pro 195 of wt HPIV 1 M, nucleotide substitution(s) in a 3' leader sequence of the genome or antigenome at a position corresponding to nucleotide 23 and/or nucleotide 28 of wt HPIV 1, and/or nucleotide substitution in a N gene start sequence at a position corresponding to nucleotide 62 of wt HPIV 1.

190. The immunogenic composition of claim 189, wherein one or more attenuating mutations is one or any combination of mutation(s) selected from C:S102$T_{cp45}$, M: P195$T_{cp45}$, F: I423$V_{cp45}$, F: S453$T_{cp45}$, HN: R386$A_{cp45}$, L: Y942$H_{cp45}$, L: Y942F, L: Y942N, L: Y942D, L: Y942C, L: Y942W, L: Y942S, L:y942Q, L: Y942G, L:Y942T, L: Y942V, L: Y942M, L: Y942L, L: Y942A, L: L992$F_{cp45}$, L: L992I, L: L992M, L: L992H, L: L992W, L: L992A, L: L992C, L: L992K, L: L992N, L: L992V, L: L992Y and L: L1558$I_{cp45}$.

191. The immunogenic composition of claim 173, wherein the chimeric HPIV1 genome or antigenome further incorporates multiple mutations selected from (i) mutations specifying amino acid substitutions in the L protein at positions corresponding to Tyr942 and Leu992 of wild-type (wt) HPIV 1 L, (ii) mutations specifying amino acid substitutions in the L protein at positions corresponding to Leu992 and Leu1558 of wild-type wt HPIV 1 L, (iii) mutations specifying amino acid substitutions in the L protein at positions corresponding to Tyr942, Leu992 and Leu1558 of wt HPIV 1 L, (iv) mutations specifying amino acid substitutions in the F protein at positions corresponding to Ile423 and Ser453 of wt HPIV 1 F, and (v) mutations specifying an amino acid substitution in the N protein at a position corresponding to residue Va199 of wt HPIV 1 N, mutations in a 3' leader sequence of the genome or antigenome at positions corresponding to nucleotide 23 and nucleotide 28 of wt HPIV 1, and a nucleotide substitution in a N gene start sequence at a position corresponding to nucleotide 62 of wt HPIV 1.

192. The immunogenic composition of claim 191, wherein the multiple mutations are selected from (i) 3'-N V99A$_{cp45}$, (ii) F: I423V/S453T$_{cp45}$, Y942H/L992F$_{cp45}$, (iii) L992F/L1558I$_{cp45}$, and (iv) Y942H/L992F/L1558I$_{cp45}$.

193. The immunogenic composition of claim 188, wherein the chimeric HPIV 1 genome or antigenome further incorporates an attenuating mutation at an amino acid position corresponding to an amino acid position of an attenuating mutation identified in a heterologous, mutant nonsegmented negative stranded RNA virus.

194. The immunogenic composition of claim 193, wherein said attenuating mutation comprises an amino acid substitution of phenylalanine at position 456 of the HPIV 1 L protein.

195. The immunogenic composition of claim 193, wherein said attenuating mutation comprises an amino acid substitution of phenylalanine at position 170 of the HPIV 1 C protein.

196. The immunogenic composition of claim 193, wherein the heterologous, mutant nonsegmented negative stranded RNA virus is a bovine parainfluenza virus type 3 (BPIV3), and wherein said attenuating mutation comprises an amino acid substitution at a corresponding target position Glu1711 in the HPIV1 L protein.

197. The immunogenic composition of claim 188, wherein one or more attenuating mutation(s) is one or more attenuating mutations identified in a mutant PIV strain, and one or more attenuating mutation(s) at an amino acid position corresponding to an amino acid position of an attenuating mutation identified in a heterologous, mutant nonsegmented negative stranded RNA virus.

198. The immunogenic composition of claim 197, wherein one or more attenuating mutations is a combination of mutations (i) F170S$_{MPIV\ 1}$/Y942H/L992F$_{cp45}$, or (ii) F170S$_{MPIV\ 1}$/L992F/L1558I$_{cp45}$.

199. The immunogenic composition of claim 173, wherein at least one attenuating mutation is stabilized by multiple nucleotide changes in a codon specifying the mutation.

200. The immunogenic composition of claim 199, wherein at least one stabilized mutation is one or any combination of mutation(s) in the L protein selected from Y942W, Y942S, Y942Q, Y942T, Y942G, Y942A, Y942V, Y942M, Y942T, Y942L, L992K, L992A, L992Y, and L992C.

201. The immunogenic composition of claim 173, wherein the chimeric HPIV 1 genome or antigenome further incorporates one or more attenuating host range mutation(s).

202. The immunogenic composition of claim 173, wherein the chimeric HPIV 1 genome or antigenome further comprises one or both of the attenuating host range mutation(s): (i) E119G in HPIV1 P and R84G in HPIV 1 C, or (ii) T553A in HPIV 1 HN.

203. The immunogenic composition of claim 173, wherein the chimeric HPIV 1 genome or antigenome further comprises a nucleotide modification specifying a phenotypic change selected from a change in growth characteristics, attenuation, temperature-sensitivity, cold-adaptation, plaque size, host-range restriction, or a change in immunogenicity.

204. The immunogenic composition of claim 173, wherein one or more HPIV 1 gene(s) is deleted in whole or in part or expression of the gene(s) is reduced or ablated by a mutation in an RNA editing site, by a frameshift mutation, by a mutation that alters a translation start site, by introduction of one or more stop codons in an open reading frame (ORF) of the gene, or by a mutation in a transcription signal.

205. The immunogenic composition of claim 204, wherein the chimeric HPIV 1 genome or antigenome is modified by a partial or complete deletion of one or more C, C', Y1, and/or Y2 ORF(s), or one or more nucleotide change(s) that reduces or ablates expression of said one or more C, C', Y1, and/or Y2 ORF(s).

206. The immunogenic composition of claim 205, wherein the chimeric HPIV 1 genome or antigenome is modified by one or more partial deletions corresponding to (i) codons 10-11 of the C ORF (ii) codons 12-13 of the C ORF (iii) codons 14-15 of the C ORF, (iv) codons 10-15 of the C ORF, and/or (v) codons 168-170 of the C ORF.

207. The immunogenic composition of claim 194, wherein the chimeric HPIV 1 genome or antigenome is further modified to encode a non-PIV molecule selected from a cytokine, a T-helper epitope, a restriction site marker, or a protein of a microbial pathogen capable of eliciting an immune response in a mammalian host.

208. The immunogenic composition of claim 146, wherein the recombinant HPIV 1 genome or antigenome further incorporates a polynucleotide insertion of between 150 nucleotides (nts) and 4,000 nucleotides in length in a non-coding region (NCR) of the genome or antigenome or as a separate gene unit (GU), said polynucleotide insertion lacking a complete open reading frame (ORF) and specifying an attenuated phenotype in said recombinant HPIV 1.

209. The immunogenic composition of claim 208, wherein said polynucleotide insert is introduced into the HPIV 1 genome or antigenome in a reverse, nonsense orientation whereby the insert does not encode protein.

210. The immunogenic composition of claim 208, wherein said polynucleotide insert is 2,000 nts or greater in length.

211. The immunogenic composition of claim 208, wherein said polynucleotide insert is 3,000 nts or greater in length.

212. The immunogenic composition of claim 208, wherein said recombinant HPIV 1 replicates efficiently in vitro and exhibits an attenuated phenotype in vivo.

213. The immunogenic composition of claim 208, wherein said polynucleotide insertion adds a total length of foreign sequence to the recombinant HPIV 1 genome or antigenome of 30% to 50% or greater compared to the wild-type HPIV 1 genome length of 15,600 nt.

214. The immunogenic composition of claim 208, wherein said polynucleotide insertion specifies an attenuation phenotype of the recombinant HPIV 1 which exhibits at least a 10-to 100-fold decrease in replication in the upper and/or lower respiratory tract.

215. The immunogenic composition of claim 146, wherein the recombinant HPIV1 is formulated in a dose of $10^3$ to $10^7$ PFU.

216. The immunogenic composition of claim 146, wherein the recombinant HPIV 1 is formulated for administration to the upper respiratory tract.

217. The immunogenic composition of claim 146, wherein the recombinant HPIV 1 is formulated for administration by spray, droplet or aerosol.

218. The infectious, self-replicating recombinant human parainfluenza virus type 1 (HPIV 1) of claim 73, in which the mutation is of the L protein Y942 to an amino acid selected from the group consisting of F, C, N, D, W, S, Q, G, T, V, M, L and A.

219. The infectious, self-replicating recombinant human parainfluenza virus type 1 (HPIV 1) of claim 73, in which the mutation is of the L protein L992 to an amino acid selected from the group consisting of H, I, M, W, A, C, K, N, V and Y.

220. The infectious, self replicating recombinant human parainfluenza virus type 1 (HPIV 1) of claim 73, in which the mutation is a mutation in the L protein of E1711 to another amino acid.

221. The infectious, self-replicating recombinant human parainfluenza virus type 1 (HPIV 1) of claim 73, in which the mutation is a mutation in the HN protein T553 to A.

222. The infectious, self-replicating recombinant human parainfluenza virus type 1 (HPIV 1) of claim 73, in which the mutation is a mutation in the C protein R84 to G.

223. The infectious, self-replicating recombinant human parainfluenza virus type 1 (HPIV 1) of claim 73, in which the mutation is a mutation in the C protein R84 to G and mutation of the P protein E119 to G.

224. The infectious, self-replicating recombinant human parainfluenza virus type 1 (HPIV 1) of claim 73, in which the mutation is a mutation in the P protein E119 to G.

225. The infectious, self-replicating recombinant human parainfluenza virus type 1 (HPIV 1) of claim 73, in which the mutation is a deletion of codons 10-15 of the C protein and codons 13-19 of the P protein that creates an alanine residue in the P protein at the deletion site.

226. The infectious, self-replicating recombinant human parainfluenza virus type 1 (HPIV 1) of claim 73, in which the mutation is a deletion of codons 10-11 of the C protein and codons 13-15 of the P protein that creates a glutamic acid residue in the P protein at the deletion site.

227. The infectious, self replicating recombinant human parainfluenza virus type 1 (HPIV 1) of claim 73, in which the mutation is a deletion of codons 12-13 of the C protein and codon 15-17 of the P protein that creates a glutamic acid residue in the P protein at the deletion site.

228. The infectious, self replicating recombinant human parainfluenza virus type 1 (HPIV 1) of claim 73, in which the mutation is a deletion of codons 14-15 of the C protein and codons 17-19 of the P protein that creates an alanine residue in the P protein at the deletion site.

229. The infectious, self replicating recombinant human parainfluenza virus type 1 (HPIV 1) of claim 73, in which the mutation is a deletion of codons 168-170 of the C protein and codons 172-173 of the P protein that creates a serine residue in the C protein at the deletion site.

230. The infectious, self replicating recombinant human parainfluenza virus type 1 (HPIV 1) of claim 73, in which the recombinant HPIV 1 genome or antigenome incorporates at least two of the mutations.

231. The infectious, self-replicating recombinant human parainfluenza virus type 1 (HPIV 1) of claim 218, in which the recombinant HPIV 1 genome or antigenome further includes at least one mutation selected from the group consisting of:

a mutation in the L protein L992 to another amino acid other than phenylalanine;

a mutation in the L protein of E1711 to another amino acid;

a mutation in the protein corresponding to F456 of RSV to another amino acid;

a mutation in the HN protein T553 to another amino acid;

a mutation in the C protein F170 to another amino acid;

a mutation in the C protein R84 to another amino acid;

a mutation in the C protein R84 to another amino acid and mutation of the P protein E119 to another amino acid;

a mutation in the P protein E119 to another amino acid;

a deletion of codons 10-15 of the C protein and codons 13-19 of the P protein;

a deletion of codons 10-11 of the C protein and codons 13-15 of the P protein.

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

232. The infectious, self-replicating recombinant human parainfluenza virus type 1 (HPIV 1) of claim 219, in which the recombinant HPIV 1 genome or antigenome further includes at least one mutation selected from the group consisting of:

a mutation in the L protein Y942 to another amino acid other than histidine;

a mutation in the L protein of E1711 to another amino acid;

a mutation in the protein corresponding to F456 of RSV to another amino acid;

a mutation in the HN protein T553 to another amino acid;

a mutation in the C protein F170 to another amino acid;

a mutation in the C protein R84 to another amino acid;

a mutation in the C protein R84 to another amino acid and mutation of the P protein E119 to another amino acid;

a mutation in the P protein E119 to another amino acid;

a deletion of codons 10-15 of the C protein and codons 13-19 of the P protein;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

233. The infectious, self-replicating recombinant human parainfluenza virus type 1 (HPIV 1) of claim 220, in which the recombinant HPIV 1 genome or antigenome further includes at least one mutation selected from the group consisting of:

a mutation in the L protein Y942 to another amino acid other than histidine;

a mutation in the L protein L992 to another amino acid other than phenylalanine;

a mutation in the protein corresponding to F456 of RSV to another amino acid;

a mutation in the HN protein T553 to another amino acid;

a mutation in the C protein F170 to another amino acid;

a mutation in the C protein R84 to another amino acid;

a mutation in the C protein R84 to another amino acid and mutation of the P protein E119 to another amino acid;

a mutation in the P protein E119 to another amino acid;

a deletion of codons 10-15 of the C protein and codons 13-19 of the P protein;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

234. The infectious, self-replicating recombinant human parainfluenza virus type 1 (HPIV 1) of claim 221, in which the recombinant HPIV 1 genome or antigenome further includes at least one mutation selected from the group consisting of:

a mutation in the L protein Y942 to another amino acid other than histidine;

a mutation in the L protein L992 to another amino acid other than phenylalanine;

a mutation in the L protein of E1711 to another amino acid;

a mutation in the protein corresponding to F456 of RSV to another amino acid;

a mutation in the C protein F170 to another amino acid;

a mutation in the C protein R84 to another amino acid;

a mutation in the C protein R84 to another amino acid and mutation of the P protein E119 to another amino acid;

a mutation in the P protein E119 to another amino acid;

a deletion of codons 10-15 of the C protein and codons 13-19 of the P protein;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

235. The infectious, self-replicating recombinant human parainfluenza virus type 1 (HPIV 1) of claim 222, in which the recombinant HPIV 1 genome or antigenome further includes at least one mutation selected from the group consisting of:

a mutation in the L protein Y942 to another amino acid other than histidine;

a mutation in the L protein L992 to another amino acid other than phenylalanine;

a mutation in the L protein of E1711 to another amino acid;

a mutation in the protein corresponding to F456 of RSV to another amino acid;

a mutation in the HN protein T553 to another amino acid;

a mutation in the C protein F170 to another amino acid;

a mutation in the C protein R84 to another amino acid and mutation of the P protein E119 to another amino acid;

a mutation in the P protein E119 to another amino acid;

a deletion of codons 10-15 of the C protein and codons 13-19 of the P protein;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

236. The infectious, self-replicating recombinant human parainfluenza virus type 1 (HPIV 1) of claim 223, in which the recombinant HPIV 1 genome or antigenome further includes at least one mutation selected from the group consisting of:

a mutation in the L protein Y942 to another amino acid other than histidine;

a mutation in the L protein L992 to another amino acid other than phenylalanine;

a mutation in the L protein of E1711 to another amino acid;

a mutation in the protein corresponding to F456 of RSV to another amino acid;

a mutation in the HN protein T553 to another amino acid;

a mutation in the C protein F170 to another amino acid;

a mutation in the C protein R84 to another amino acid;

a mutation in the P protein E119 to another amino acid;

a deletion of codons 10-15 of the C protein and codons 13-19 of the P protein;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

237. The infectious, self-replicating recombinant human parainfluenza virus type 1 (HPIV 1) of claim 224, in which the recombinant HPIV 1 genome or antigenome further includes at least one mutation selected from the group consisting of:

a mutation in the L protein Y942 to another amino acid other than histidine;

a mutation in the L protein L992 to another amino acid other than phenylalanine;

a mutation in the L protein of E1711 to another amino acid;

a mutation in the protein corresponding to F456 of RSV to another amino acid;

a mutation in the HN protein T553 to another amino acid;

a mutation in the C protein F170 to another amino acid;

a mutation in the C protein R84 to another amino acid;

a mutation in the C protein R84 to another amino acid and mutation of the P protein E119 to another amino acid;

a deletion of codons 10-15 of the C protein and codons 13-19 of the P protein;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

238. The infectious, self-replicating recombinant human parainfluenza virus type 1 (HPIV 1) of claim 225, in which the recombinant HPIV 1 genome or antigenome further includes at least one mutation selected from the group consisting of:

a mutation in the L protein Y942 to another amino acid other than histidine;

a mutation in the L protein L992 to another amino acid other than phenylalanine;

a mutation in the L protein of E1711 to another amino acid;

a mutation in the protein corresponding to F456 of RSV to another amino acid;

a mutation in the HN protein T553 to another amino acid;

a mutation in the C protein F170 to another amino acid;

a mutation in the C protein R84 to another amino acid;

a mutation in the C protein R84 to another amino acid and mutation of the P protein E119 to another amino acid;

a mutation in the P protein E119 to another amino acid;

a deletion of codons 10-11 of the C protein and codons 13-15 of the P protein;

a deletion of codons 12-13 of the C protein and codon 15-17 of the P protein;

a deletion of codons 14-15 of the C protein and codons 17-19 of the P protein; and a deletion of codons 168-170 of the C protein and codons 172-173 of the P protein.

239. The infectious, self-replicating recombinant human parainfluenza virus type 1 (HPIV 1) of claim 226, in which the recombinant HPIV 1 genome or antigenome further includes at least one mutation selected from the group consisting of:

a mutation in the L protein Y942 to another amino acid other than histidine;

a mutation in the L protein L992 to another amino acid other than phenylalanine;
a mutation in the L protein of E1711 to another amino acid;
a mutation in the protein corresponding to F456 of RSV to another amino acid;
a mutation in the HN protein T553 to another amino acid;
a mutation in the C protein F170 to another amino acid;
a mutation in the C protein R84 to another amino acid;
a mutation in the C protein R84 to another amino acid and mutation of the P protein E119 to another amino acid;
a mutation in the P protein E119 to another amino acid;
a deletion of codons 10-15 of the C protein and codons 13-19 of the P protein;
a deletion of codons 12-13 of the C protein and codon 15-17 of the P protein;
a deletion of codons 14-15 of the C protein and codons 17-19 of the P protein; and
a deletion of codons 168-170 of the C protein and codons 172-173 of the P protein.

240. The infectious, self-replicating recombinant human parainfluenza virus type 1 (HPIV 1) of claim 227, in which the recombinant HPIV 1 genome or antigenome further includes at least one mutation selected from the group consisting of:
a mutation in the L protein Y942 to another amino acid other than histidine;
a mutation in the L protein L992 to another amino acid other than phenylalanine;
a mutation in the L protein of E1711 to another amino acid;
a mutation in the protein corresponding to F456 of RSV to another amino acid;
a mutation in the HN protein T553 to another amino acid;
a mutation in the C protein F170 to another amino acid;
a mutation in the C protein R84 to another amino acid;
a mutation in the C protein R84 to another amino acid and mutation of the P protein E119 to another amino acid;
a mutation in the P protein E119 to another amino acid;
a deletion of codons 10-15 of the C protein and codons 13-19 of the P protein;
a deletion of codons 10-11 of the C protein and codons 13-15 of the P protein;
a deletion of codons 14-15 of the C protein and codons 17-19 of the P protein; and
a deletion of codons 168-170 of the C protein and codons 172-173 of the P protein.

241. The infectious, self-replicating recombinant human parainfluenza virus type 1 (HPIV 1) of claim 228, in which the recombinant HPIV 1 genome or antigenome further includes at least one mutation selected from the group consisting of:
a mutation in the L protein Y942 to another amino acid other than histidine;
a mutation in the L protein L992 to another amino acid other than phenylalanine;
a mutation in the L protein of E1711 to another amino acid;
a mutation in the protein corresponding to F456 of RSV to another amino acid;
a mutation in the HN protein T553 to another amino acid;
a mutation in the C protein F170 to another amino acid;
a mutation in the C protein R84 to another amino acid;
a mutation in the C protein R84 to another amino acid and mutation of the P protein E119 to another amino acid;
a mutation in the P protein E119 to another amino acid;
a deletion of codons 10-15 of the C protein and codons 13-19 of the P protein;
a deletion of codons 10-11 of the C protein and codons 13-15 of the P protein;
a deletion of codons 12-13 of the C protein and codon 15-17 of the P protein; and
a deletion of codons 168-170 of the C protein and codons 172-173 of the P protein.

242. The infectious, self-replicating recombinant human parainfluenza virus type 1 (HPIV 1) of claim 229, in which the recombinant HPIV 1 genome or antigenome further includes at least one mutation selected from the group consisting of:
a mutation in the L protein Y942 to another amino acid other than histidine;
a mutation in the L protein L992 to another amino acid other than phenylalanine;
a mutation in the L protein of E1711 to another amino acid;
a mutation in the protein corresponding to F456 of RSV to another amino acid;
a mutation in the HN protein T553 to another amino acid;
a mutation in the C protein F170 to another amino acid;
a mutation in the C protein R84 to another amino acid;
a mutation in the C protein R84 to another amino acid and mutation of the P protein E119 to another amino acid;
a mutation in the P protein E119 to another amino acid;
a deletion of codons 10-15 of the C protein and codons 13-19 of the P protein;
a deletion of codons 10-11 of the C protein and codons 13-15 of the P protein;
a deletion of codons 12-13 of the C protein and codon 15-17 of the P protein; and
a deletion of codons 14-15 of the C protein and codons 17-19 of the P protein.

243. The infectious, self-replicating recombinant human parainfluenza virus type 1 (HPIV 1) of claim 73, in which the recombinant HPIV 1 genome or antigenome includes a mutation in the L protein Y942 to alanine.

244. The infectious, self-replicating recombinant human parainfluenza virus type 1 (HPIV 1) of claim 73, in which the recombinant HPIV 1 genome or antigenome includes a mutation in the L protein L992to cysteine.

245. The infectious, self-replicating recombinant human parainfluenza virus type 1 (HPIV 1) of claim 73, in which the recombinant HPIV 1 genome or antigenome includes a mutation in the L protein of E1711 to another amino acid.

246. The infectious, self-replicating recombinant human parainfluenza virus type 1 (HPIV 1) of claim 73, in which the recombinant HPIV 1 genome or antigenome includes a mutation in the protein corresponding to F456 of RSV to another amino acid.

247. The infectious, self-replicating recombinant human parainfluenza virus type 1 (HPIV 1) of claim 73, in which the recombinant HPIV 1 genome or antigenome includes a mutation in the protein corresponding to F456 of RSV to another amino acid.

248. The infectious, self-replicating recombinant human parainfluenza virus type 1 (HPIV 1) of claim 73, in which the recombinant HPIV 1 genome or antigenome includes a mutation in the C protein F170 to another amino acid.

249. The infectious, self-replicating recombinant human parainfluenza virus type 1 (HPIV 1) of claim 73, in which the recombinant HPIV 1 genome or antigenome includes a mutation in the C protein R84 to another amino acid.

250. The infectious, self-replicating recombinant human parainfluenza virus type 1 (HPIV 1) of claim 73, in which the recombinant HPIV 1 genome or antigenome includes a mutation in the C protein R84 to another amino acid and mutation of the P protein E119 to another amino acid.

251. The infectious, self-replicating recombinant human parainfluenza virus type 1 (HPIV 1) of claim 73, in which the recombinant HPIV 1 genome or antigenome includes a mutation in the P protein E119 to another amino acid.

252. The infectious, self-replicating recombinant human parainfluenza virus type 1 (HPIV 1) of claim 73, in which the recombinant HPIV 1 genome or antigenome includes a deletion of codons 10-15 of the C protein and codons 13-19 of the P protein.

253. The infectious, self-replicating recombinant human parainfluenza virus type 1 (HPIV 1) of claim 73, in which the recombinant HPIV 1 genome or antigenome includes a deletion of codons 10-11 of the C protein and codons 13-15 of the P protein.

254. The infectious, self-replicating recombinant human parainfluenza virus type 1 (HPIV 1) of claim 73, in which the recombinant HPIV 1 genome or antigenome includes a deletion of codons 12-13 of the C protein and codon 15-17 of the P protein.

255. The infectious, self-replicating recombinant human parainfluenza virus type 1 (HPIV 1) of claim 73, in which the recombinant HPIV 1 genome or antigenome includes a deletion of codons 14-15 of the C protein and codons 17-19 of the P protein.

256. The infectious, self-replicating recombinant human parainfluenza virus type 1 (HPIV 1) of claim 73, in which the recombinant HPIV 1 genome or antigenome includes a deletion of codons 168-170 of the C protein and codons 172-173 of the P protein.

257. An infectious, self-replicating, recombinant human parainfluenza virus type 1 (HPIV 1) comprising a PIV major nucleocapsid (N) protein, a PIV nucleocapsid phosphoprotein (P), a PIV large polymerase protein (L), and a partial or complete recombinant HPIV 1 genome or antigenome, said recombinant HPIV 1 genome or antigenome including at least one mutation selected from the group consisting of:

- a mutation in the L protein Y942 to an amino acid selected from the group consisting of F, C, N, D, W, S, Q, G, T, V, M, L and A;
- a mutation in the L protein L992 to an amino acid selected from the group consisting of H, I, M, W, A, C, K, N, V and Y;
- a mutation in the L protein of E1711 to another amino acid
- a mutation in the HN protein T553 to A;
- a mutation in the C protein R84 to G;
- a mutation in the C protein R84 to G and mutation of the P protein E119 to G;
- a mutation in the P protein E119 to G;
- a deletion of codons 10-15 of the C protein and codons 13-19 of the P protein that creates an alanine residue in the P protein at the deletion site;
- a deletion of codons 10-11 of the C protein and codons 13-15 of the P protein that creates a glutamic acid residue in the P protein at the deletion site;
- a deletion of codons 12-13 of the C protein and codon 15-17 of the P protein that creates a glutamic acid residue in the P protein at the deletion site that creates a glutamic acid residue in the P protein at the deletion site;
- a deletion of codons 14-15 of the C protein and codons 17-19 of the P protein that creates an alanine residue in the P protein at the deletion site; and
- a deletion of codons 168-170 of the C protein and codons 172-173 of the P protein that creates a serine residue in the C protein at the deletion site.

258. The infectious, self-replicating, recombinant human parainfluenza virus type 1 (HPIV 1) of claim 257, in which the HPIV 1 recombinant genome or antigenome includes at least two of said mutations.

259. The infectious, self-replicating, recombinant human parainfluenza virus type 1 (HPIV 1) of claim 257, in which the HPIV 1 recombinant genome or antigenome includes only one of said mutations.

260. The infectious, self-replicating, recombinant human parainfluenza virus type 1 (HPIV 1) of claim 257, in which the HPIV 1 recombinant genome or antigenome contains one or more, in any combination of mutations at Y942 and L992, of a mutation in the L protein Y942 to an amino acid selected from the group consisting of F, C, N, D, W, S, Q, G, T, V, V, M, L and A; and

- a mutation in the L protein L992 to an amino acid selected from the group consisting of H, I, M, W, A, C, K, N, V and Y.

261. An infectious, self-replicating, recombinant human parainfluenza virus type 1 (HPIV 1) that is a complete virus or a sub-viral particle, comprising a PIV major nucleocapsid (N) protein, a PIV nucleocapsid phosphoprotein (P), a PIV large polymerase protein (L), and a partial or complete, recombinant HPIV 1 genome or antigenome, wherein the recombinant HPIV 1 genome or antigenome further incorporates one or both of the attenuating host range mutation(s): (i) E119G in HPIV 1 P and R84G in HPIV 1 C, or (ii) T553A in HPIV1 HN.

262. An infectious, self-replicating, recombinant human parainfluenza virus type 1 (HPIV 1) that is a complete virus or a sub-viral particle, comprising a PIV major nucleocapsid (N) protein, a PIV nucleocapsid phosphoprotein (P), a PIV large polymerase protein (L), and a partial or complete, recombinant HPIV 1 genome or antigenome, wherein said HPIV 1 genome or antigenome is combined with one or more heterologous gene(s) or genome segment(s) encoding one or more antigenic determinant(s) of one or more heterologous pathogen(s) to form a chimeric HPIV 1 genome or antigenome, and wherein the chimeric HPIV 1 genome or antigenome is modified by introduction of a further attenuating mutation that is selected from the group consisting of:

- an amino acid substitution of Glu 1711 in the HPIV 1 L protein;
- a combination of mutations selected from (i) $F170S_{MPIV\ 1}$/Y942H/$L992F_{cp45}$, and (ii) $F170S_{MPIV\ 1}$/L992F/$L1558I_{cp45}$;
- one or any combination of mutation(s) in the PIV L protein selected from Y942W, Y942S, Y942Q, Y942T, Y942G, Y942A, Y942V, Y942M, Y942T, Y942L, L992K, L992A, L992Y, L992N, L992V, and L992C;
- incorporation of one or more attenuating host range mutation(s) selected from (i) a mutation at codon 119 of the HPIV 1 P open reading frame (ORF) and corresponding mutation at codon 84 of the HPIV 1 C ORF and (ii) a mutation at codon 553 of the HPIV 1 HN ORF;
- incorporation of one or more attenuating host range mutation(s) specifying one or more amino acid change(s) selected from (i) E119G in HPIV 1 P, (ii) R84G in HPIV 1, and (iii) T553A in HPIV 1 HN; and
- one or more partial deletions corresponding to (i) codons 10-11 of the C ORF (ii) codons 12-13 of the C ORF (iii) codons 14-15 of the C ORF, (iv) codons 10-15 of the C ORF, and/or (v) codons 168-170 of the C ORF.

263. The infectious, self-replicating, recombinant human parainfluenza virus type 1 (HPIV 1) of claim 262, wherein said HPIV 1 genome or antigenome is combined with one or more heterologous gene(s) or genome segment(s) encoding one or more antigenic determinant(s) of one or more heterologous pathogen(s) to form a chimeric HPIV 1 genome or antigenome, and wherein the chimeric HPIV 1 genome or antigenome is modified by at least one attenuating mutation stabilized by multiple nucleotide changes in a codon specifying the mutation and wherein the chimeric HPIV 1 genome or antigenome further incorporates one or any combination of mutation(s) selected from Y942W, Y942S, Y942Q, Y942T, Y942G, Y942A, Y942V, Y942M, Y942T, Y942L, L992K, L992A, L992Y, L992N, L992V and L992C.

264. The infectious, self-replicating, recombinant human parainfluenza virus type 1 (HPIV 1) of claim 262, wherein said HPIV 1 genome or antigenome is combined with one or more heterologous gene(s) or genome segment(s) encoding one or more antigenic determinant(s) of one or more heterologous pathogen(s) to form a chimeric HPIV 1 genome or antigenome, and wherein the chimeric HPIV 1 genome or antigenome is further modified by incorporation of one or more attenuating host range mutation(s).

265. The recombinant HPIV 1 of claim 262, wherein the chimeric HPIV 1 genome or antigenome further comprises one or both of the attenuating host range mutation(s): (i) E119G in HPIV1 P and R84G in HPIV 1 C, or (ii) T553A in HPIV 1 HN.

266. The infectious, self-replicating, recombinant human parainfluenza virus type 1 (HPIV 1) of claim 262, wherein the chimeric HPIV 1 genome or antigenome is modified by one or more partial deletions corresponding to (i) codons 10-11 of the C ORF (ii) codons 12-13 of the C ORF (iii) codons 14-15 of the C ORF, (iv) codons 10-15 of the C ORF, and/or (v) codons 168-170 of the C ORF.

267. The infectious, self-replicating, recombinant human parainfluenza virus type 1 (HPIV 1) of claim 262, wherein the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumoviruses, and influenza viruses.

268. An immunogenic composition comprising an infectious, self-replicating human parainfluenza virus type 1 of any one of claims 218-220, 221, 222-233, 234, 235-267 and a pharmaceutically acceptable carrier.

269. The infectious, self-replicating recombinant human parainfluenza virus type 1 (HPIV 1) of claim 73, that incorporates the mutations of R84 of the C protein to another amino acid, T553 of the HN protein to another amino acid, Y942 of the L protein to alanine and deletion of the codons 168-170 of the C protein and deletion of codons 172-173 of the P protein.

270. An immunogenic composition comprising the recombinant human parainfluenza virus type 1 (HPIV 1) of claim 269, and a pharmaceutically acceptable carrier.

* * * * *